(12) United States Patent
Lowinger et al.

(10) Patent No.: US 11,786,605 B2
(45) Date of Patent: Oct. 17, 2023

(54) SITE SPECIFIC ANTIBODY-DRUG CONJUGATES WITH PEPTIDE-CONTAINING LINKERS

(71) Applicant: Mersana Therapeutics, Inc., Cambridge, MA (US)

(72) Inventors: Timothy B. Lowinger, Carlisle, MA (US); Marc I. Damelin, Needham, MA (US); Dorin Toader, Cambridge, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 91 days.

(21) Appl. No.: 17/144,378

(22) Filed: Jan. 8, 2021

(65) Prior Publication Data

US 2021/0220477 A1    Jul. 22, 2021

Related U.S. Application Data

(60) Provisional application No. 63/040,735, filed on Jun. 18, 2020, provisional application No. 62/958,916, filed on Jan. 9, 2020.

(51) Int. Cl.

| | | |
|---|---|---|
| A61K 47/68 | (2017.01) | |
| A61K 47/65 | (2017.01) | |
| A61K 47/54 | (2017.01) | |
| A61P 35/00 | (2006.01) | |
| A61K 38/07 | (2006.01) | |

(52) U.S. Cl.
CPC .......... *A61K 47/6803* (2017.08); *A61K 38/07* (2013.01); *A61K 47/545* (2017.08); *A61K 47/65* (2017.08); *A61K 47/6843* (2017.08); *A61K 47/6855* (2017.08); *A61P 35/00* (2018.01)

(58) Field of Classification Search
None
See application file for complete search history.

(56) References Cited

U.S. PATENT DOCUMENTS

| | | |
|---|---|---|
| 5,208,020 A | 5/1993 | Chari et al. |
| 5,416,064 A | 5/1995 | Chari et al. |

(Continued)

FOREIGN PATENT DOCUMENTS

| | | |
|---|---|---|
| EP | 2 911 699 B1 | 9/2015 |
| EP | 2 563 753 B9 | 1/2016 |

(Continued)

OTHER PUBLICATIONS

Boeggeman et al. "The N-terminal stem region of bovine and human β1,4-galactosyltransferase I increases the in vitro folding efficiency of their catalytic domain from inclusion bodies", Protein Expression & Purification, 2003, vol. 30, p. 219-229.

(Continued)

*Primary Examiner* — Karl J Puttlitz
(74) *Attorney, Agent, or Firm* — COOLEY LLP; Heidi A. Erlacher; Christine E. Dunne

(57) ABSTRACT

The present disclosure relates generally to antibody-drug conjugates comprising peptide-containing linkers and to methods of using these conjugates as therapeutics and/or diagnostics. Also disclosed herein are peptide-containing scaffolds useful to conjugate with a targeting moiety (e.g., an antibody), a drug, or both to produce the antibody-drug conjugates.

8 Claims, 21 Drawing Sheets
Specification includes a Sequence Listing.

(56) References Cited

U.S. PATENT DOCUMENTS

| | | |
|---|---|---|
| 5,475,092 A | 12/1995 | Chari et al. |
| 5,585,499 A | 12/1996 | Chari et al. |
| 5,846,545 A | 12/1998 | Chari et al. |
| 6,333,410 B1 | 12/2001 | Chari et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,441,163 B1 | 8/2002 | Chari et al. |
| 6,534,660 B1 | 3/2003 | Yongxin et al. |
| 6,596,757 B1 | 7/2003 | Chari et al. |
| 6,630,579 B2 | 10/2003 | Chari et al. |
| 6,756,397 B2 | 6/2004 | Zhao et al. |
| 7,276,497 B2 | 10/2007 | Chari et al. |
| 7,807,619 B2 | 10/2010 | Bertozzi et al. |
| 8,367,065 B2 | 2/2013 | Zhao et al. |
| 8,524,696 B2 | 9/2013 | Borowy-Borowski et al. |
| 8,603,474 B2 | 12/2013 | Ritter et al. |
| 8,859,629 B2 | 10/2014 | Van Delft et al. |
| 9,222,940 B2 | 12/2015 | Van Delft et al. |
| 9,260,371 B2 | 2/2016 | Bertozzi et al. |
| 9,504,758 B2 | 11/2016 | Van Delft et al. |
| 9,555,112 B2 | 1/2017 | Bodyak et al. |
| 9,738,720 B2 | 8/2017 | Bodyak et al. |
| 9,988,661 B2 | 6/2018 | Van Berkel et al. |
| 9,988,662 B2 | 6/2018 | Gomes et al. |
| 10,947,317 B2 | 3/2021 | Bergstrom et al. |
| 11,135,307 B2 | 10/2021 | Yurkovetskiy et al. |
| 11,596,694 B2 | 3/2023 | Mosher et al. |
| 2017/0266311 A1 | 9/2017 | Bergstrom et al. |
| 2018/0154018 A1 | 6/2018 | Yurkovetskiy et al. |
| 2019/0040374 A1 | 2/2019 | Geel et al. |
| 2019/0160181 A1 | 5/2019 | Mosher et al. |

FOREIGN PATENT DOCUMENTS

| | | |
|---|---|---|
| EP | 3 134 520 B1 | 3/2017 |
| WO | WO 2004/063344 A2 | 7/2004 |
| WO | WO 2009/097128 A1 | 8/2009 |
| WO | WO 2009/102820 A2 | 8/2009 |
| WO | WO 2013/037824 A1 | 3/2013 |
| WO | WO-2014062697 A2 | 4/2014 |
| WO | 2014065661 * | 5/2014 |
| WO | WO 2014/065661 A1 | 5/2014 |
| WO | WO 2014/189370 A1 | 11/2014 |
| WO | WO 2015/057065 A1 | 4/2015 |
| WO | WO-2015057699 A2 | 4/2015 |
| WO | WO 2015/195917 A1 | 12/2015 |
| WO | WO 2016/022027 A1 | 2/2016 |
| WO | WO 2016/170186 A1 | 10/2016 |
| WO | WO 2017/137457 A1 | 8/2017 |
| WO | WO 2017/137457 A9 | 8/2017 |
| WO | WO 2017/137458 A1 | 8/2017 |
| WO | WO 2017/137459 A1 | 8/2017 |
| WO | 2017160754 * | 9/2017 |
| WO | WO 2017/160754 A1 | 9/2017 |
| WO | 2018098269 * | 5/2018 |
| WO | WO 2018/160538 A1 | 9/2018 |
| WO | WO-2021142199 A1 | 7/2021 |

OTHER PUBLICATIONS

Bourgeaux et al. "Two-step enzymatic synthesis of UDP-N-acetylgalactosamine", Bioorganic & Medicinal Chemistry Letters, 2005, vol. 15, p. 5459-5462.

Collin et al. "EndoS, a novel secreted protein from *Streptococcus pyogenes* with endoglycosidase activity on human IgG", The EMBO Journal, 2001, vol. 20, No. 12, p. 3046-3055.

Fessler et al. "XMT-1592, a Site-Specific Dolasynthen-Based NaPi2b-Targeted Antibody-Drug Conjugate for the Treatment of Ovarian Cancer and Lung Adenocarcinoma", Abstract #7067, Mersana Therapeutics, Dolasynthen AACR, 2020, Poster, 1 page.

Francisco et al., "cAC10-vcMMAE, an anti-CD30-monomethyl auristatin E conjugate with potent and selective antitumor activity", Blood, 2003, vol. 102, No. 4, p. 1458-1465.

Guan et al. "Highly Efficient Synthesis of UDP-GalNAc/GlcNAc Analogues with Promiscuous Recombinant Human UDP-GalNAc Pyrophosphorylase AGX1", Chemistry, 2010, vol. 16, No. 45, p. 13343-13345.

Hoskins et al. "Sequence Finishing and Mapping of *Drosophila melanogaster* Heterochromatin", Science, 2007, vol. 316, No. 5831, p. 1625-1628.

Kabat, E.A., et al., "Sequences of Protein of immunological interest", 1991, Fifth Edition, US Department of Health and Human Services, US Government Printing Office, 4 pages.

Kawar et al. "Molecular Cloning and Enzymatic Characterization of a UDP-GalNAc:GlcNAcβ-R β1,4-N-Acetylgalactosaminyltransferase from Caenorhabditis elegans", Journal of Biological Chemistry, 2002, vol. 277, Issue 368, p. 34924-34932.

Khidekel et al. "A Chemoenzymatic Approach toward the Rapid and Sensitive Detection of O-GlcNAc Posttranslational Modifications", Journal of American Chemical Society, 2003, vol. 125, p. 16162-16163,.

Krop et al., "Phase I Study of Trastuzumab-DM1, an HER2 Antibody-Drug Conjugate, Given Every 3 Weeks to Patients with HER2-Positive Metastatic Breast Cancer", Journal of Clinical Oncology, 2010, vol. 28, p. 2698-2704.

Pouilly et al. "Evaluation of Analogues of GalNAc as Substrates for Enzymes of the Mammalian GalNAc Salvage Pathway", ACS Chemical Biology, 2012, vol. 7, p. 753-760.

Ramakrishnan et al. "Structure-based Design of β1,4-Galactosyltransferase I (β4Gal-T1) with Equally Efficient N-Acetylgalactosaminyltransferase Activity", Journal of Biological Chemistry, 2002, vol. 277, Issue 23, p. 20833-20839.

Ricart AD. et al. "Technology Insight: cytotoxic drug immunoconjugates for cancer therapy", Nature Clinical Practice, 2007, vol. 4, No. 4, p. 245-255.

Schmaltz et al. "Enzymes in the Synthesis of Glycoconjugates", Chemical Reviews, 2011, vol. 111, p. 4259-4307.

Vadaie et al. "Molecular Cloning and Functional Characterization of a Lepidopteran Insect β4-N-Acetylgalactosaminyltransferase with Broad Substrate Specificity, a Functional Role in Glycoprotein Biosynthesis, and a Potential Functional Role in Glycolipid Biosynthesis", Journal of Biological Chemistry, 2004, vol. 279, Issue 32, p. 33501-33518.

Van Geel et al. "Chemoenzymatic Conjugation of Toxic Payloads to the Globally Conserved N-Glycan of Native mAbs Provides Homogeneous and Highly Efficacious Antibody-Drug Conjugates", Bioconjugate Chemistry, 2015, vol. 26, p. 2233-2242.

Van Geel et al. "The Native Antibody Glycan as Attachment Site for Cytotoxic Payloads Contributes to the Superiority of GlycoConnect™ ADCs" Synaffix BV PowerPoint Presentation, 2019, 1 page.

Lyon et al., "Reducing Hydrophobicity of Homogeneous Antibody-drug Conjugates Improves Pharmacokinetics and Therapeutic Index", Nature Biotechnology, Jun. 2015, vol. 33, pp. 733-735.

* cited by examiner

SITE SPECIFIC ANTIBODY-DRUG CONJUGATES WITH PEPTIDE-CONTAINING LINKERS

RELATED APPLICATIONS

This application claims priority to, and the benefit of, U.S. Provisional Application Nos. 62/958,916, filed Jan. 9, 2020, and 63/040,735, filed Jun. 18, 2020. The contents of each of these applications are hereby incorporated by reference in their entireties.

INCORPORATION BY REFERENCE OF SEQUENCE LISTING

The contents of the text file named "MRSN-029_001US_SeqList.txt", which was created on Jan. 6, 2021 and is 49 KB in size, are hereby incorporated by reference in their entirety.

BACKGROUND

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, accumulate in tissues other than the target, and/or have a short half-life.

One objective in the field of drug delivery systems, therefore, is to deliver medications intact to specifically targeted areas of the body through a system that can stabilize the drug and/or extend the half-life and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents, including, but not limited to, the microtubulin inhibitors (e.g., maytansinoids, auristatins, and taxanes, see, e.g., U.S. Pat. Nos. 5,208,020; 5,416,064; 6,333,410; 6,441,163; 6,340,701; 6,372,738; 6,436,931; 6,596,757; and 7,276,497) and DNA-interacting therapeutics (e.g., calicheamicin, doxorubicin, and CC-1065 analogs; see, e.g., U.S. Pat. Nos. 5,475,092; 5,585,499; 5,846,545; 6,534,660; 6,756,397; and 6,630,579). Antibody-drug conjugates with some of these cytotoxic drugs are actively being investigated in the clinic for cancer therapy (see, e.g., Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited limitations. A major limitation is their inability to deliver a sufficient concentration of drug to the target site because of the limited number of targeted antigens and/or the relatively moderate cytotoxicity of cancer drugs like auristatins, methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and/or fast in vivo clearance from the blood stream. Therefore, there is a need to improve the ability to deliver a sufficient concentration of a drug to the target such that maximum cytotoxicity for the drug is achieved.

Conjugating a drug moiety to an antibody through covalent bonds generally leads to a heterogeneous mixture of molecules where the drug moieties are attached at a number of sites on the antibody. In some embodiments, cytotoxic drugs have typically been conjugated to antibodies through the lysine or cysteine residues of the antibody thereby generating a heterogeneous antibody-drug conjugate mixture. Depending on the reaction conditions, the heterogeneous mixture typically contains a distribution of from 0 to about 8 drug moieties attached at various sites on the antibody. Analytical and preparative methods are inadequate to separate and characterize these antibody-drug conjugate species molecules within the heterogeneous mixture resulting from a conjugation reaction. Additionally, the conjugation process may be nonreproducible due to difficulties in controlling the reaction conditions. Therefore, there is a need to reproducibly produce antibody-drug conjugates with site-specificity (regarding the conjugation site in the antibody) and/or stoichiometry (regarding the ratio between the antibody and the drug).

SUMMARY

The present disclosure features antibody-drug conjugates with site-specificity. These site-specific targeting moiety-drug conjugates exhibit controlled drug load as well as strong binding to target antigen. In some embodiments, the targeting moiety is a protein-based recognition-molecule (PBRM). The present disclosure also features a peptide-containing scaffold useful to conjugate with a PBRM, a drug, or both, so as to obtain the targeting moiety-drug conjugate.

In some aspects, the present disclosure provides an antibody-drug conjugate of Formula (I'):

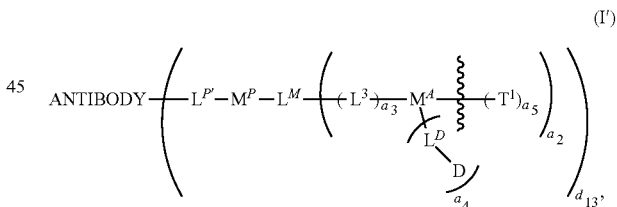

wherein
 $a_2$ is an integer from 1 to 3;
 $a_3$ is an integer from 0 to 1;
 $a_4$ is an integer from 1 to about 5;
 $a_5$ is an integer from 1 to 3;
 $d_{13}$ is an integer from 1 to about 12;
 ANTIBODY is a modified antibody;
 $L^{P'}$ is a divalent linker moiety connecting the modified antibody to $M^P$; of which the corresponding monovalent moiety $L^P$ comprises a functional group $W^P$ that is capable of forming a covalent bond with a functional group of the modified antibody;
 $M^P$ is a Stretcher unit;
 $L^M$ is a bond, or a trivalent or a tetravalent linker, and when $L^M$ is a bond, $a_2$ is 1, when $L^M$ is a trivalent linker, $a_2$ is 2, or when $L^M$ is a tetravalent linker, $a_2$ is 3;

$L^3$ is a carbonyl-containing moiety;

$M^4$ comprises a peptide moiety that comprises at least two amino acids;

$T^1$ is a hydrophilic group and the

between $T^1$ and $M^4$ denotes direct or indirect attachment of $T^1$ and $M^4$;

each occurrence of D independently is a therapeutic agent having a molecular weight ≤about 5 kDa; and each occurrence of $L^D$ independently is a divalent linker moiety connecting D to $M^4$ and comprises at least one cleavable bond such that when the bond is broken, D is released in an active form for its intended therapeutic effect.

In some aspects, the present disclosure provides an antibody-drug conjugate, being of Formula (XXX):

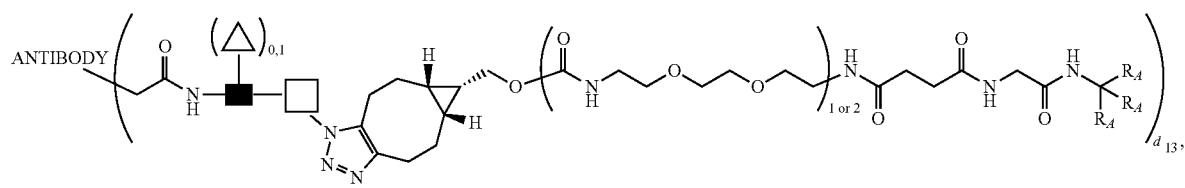

(XXX)

wherein each $R_A$ is

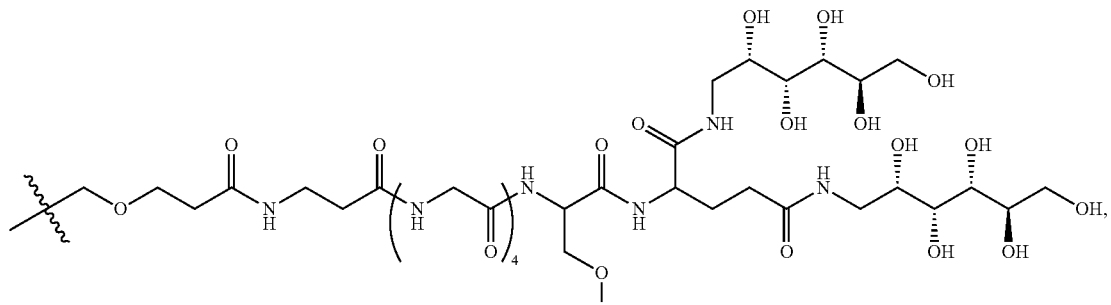

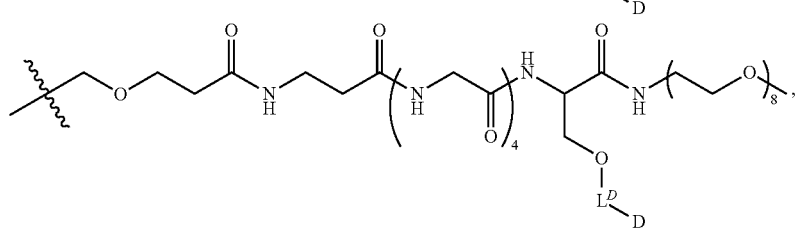

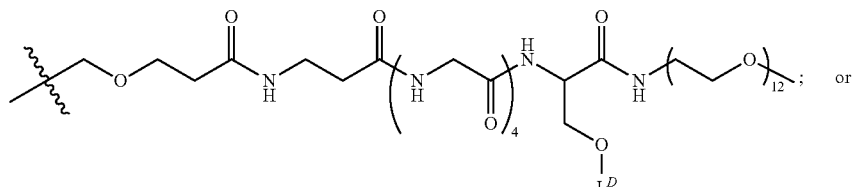

or

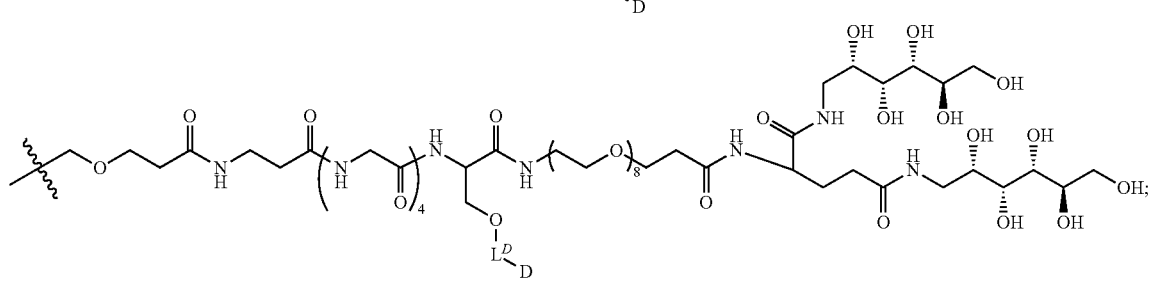

wherein $d_{13}$ is 2; and the antibody comprises one or more asparagine group at N297 being connected to the rest of the conjugate.

The disclosure also provides compositions comprising the conjugates, methods for their preparation, and methods of use thereof in the treatment of various disorders, including, but not limited to cancer.

In some embodiments, the present disclosure further relates to a pharmaceutical composition comprising a scaffold or conjugate described herein and a pharmaceutically acceptable carrier.

In some aspects, the present disclosure relates to a method for preparing an antibody-drug conjugate.

In some aspects, the present disclosure relates to a method for preparing an antibody-drug conjugate comprising one or more steps described herein.

In some embodiments, the present disclosure relates to a conjugate or method, wherein the effective amount of the conjugate is administered to the subject at a dose of about between 7 mg/m$^2$ to 162 mg/m$^2$ on the first day of treatment and every three weeks or four weeks thereafter.

In some embodiments, the present disclosure relates to a method of treating a disorder (e.g., cancer) in a subject in need thereof, comprising administering to the subject an effective amount of a conjugate disclosed herein.

In some embodiments, the present disclosure relates to a method of treating a NaPi2b expressing cancer in a subject in need thereof, comprising administering to the subject an effective amount of a conjugate disclosed herein.

In some embodiments, the present disclosure provides use of a conjugate disclosed herein in the manufacture of a medicament for treating a disorder (e.g., cancer) in a subject in need thereof.

In some embodiments, the present disclosure provides use of a conjugate disclosed herein in the manufacture of a medicament for treating a NaPi2b expressing cancer in a subject in need thereof.

In some embodiments, the present disclosure provides use of a conjugate disclosed herein for treating a disorder (e.g., cancer) in a subject in need thereof.

In some embodiments, the present disclosure provides use of a conjugate disclosed herein for treating a NaPi2b expressing cancer in a subject in need thereof.

In some embodiments, the present disclosure provides a conjugate for use in treating a disorder (e.g., cancer) in a subject in need thereof, comprising administering to the subject an effective amount of a conjugate disclosed herein.

In some embodiments, the present disclosure provides a conjugate for use in treating a NaPi2b expressing cancer in a subject in need thereof, comprising administering to the subject an effective amount of a conjugate disclosed herein.

In some embodiments, the present disclosure relates to a method of diagnosing a disorder in a subject suspected of having the disorder. The method comprises administering an effective amount of conjugate described herein to the subject suspected of having the disorder or performing an assay to detect a target antigen/receptor in a sample from the subject so as to determine whether the subject expresses target antigen or receptor.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Figure 1:
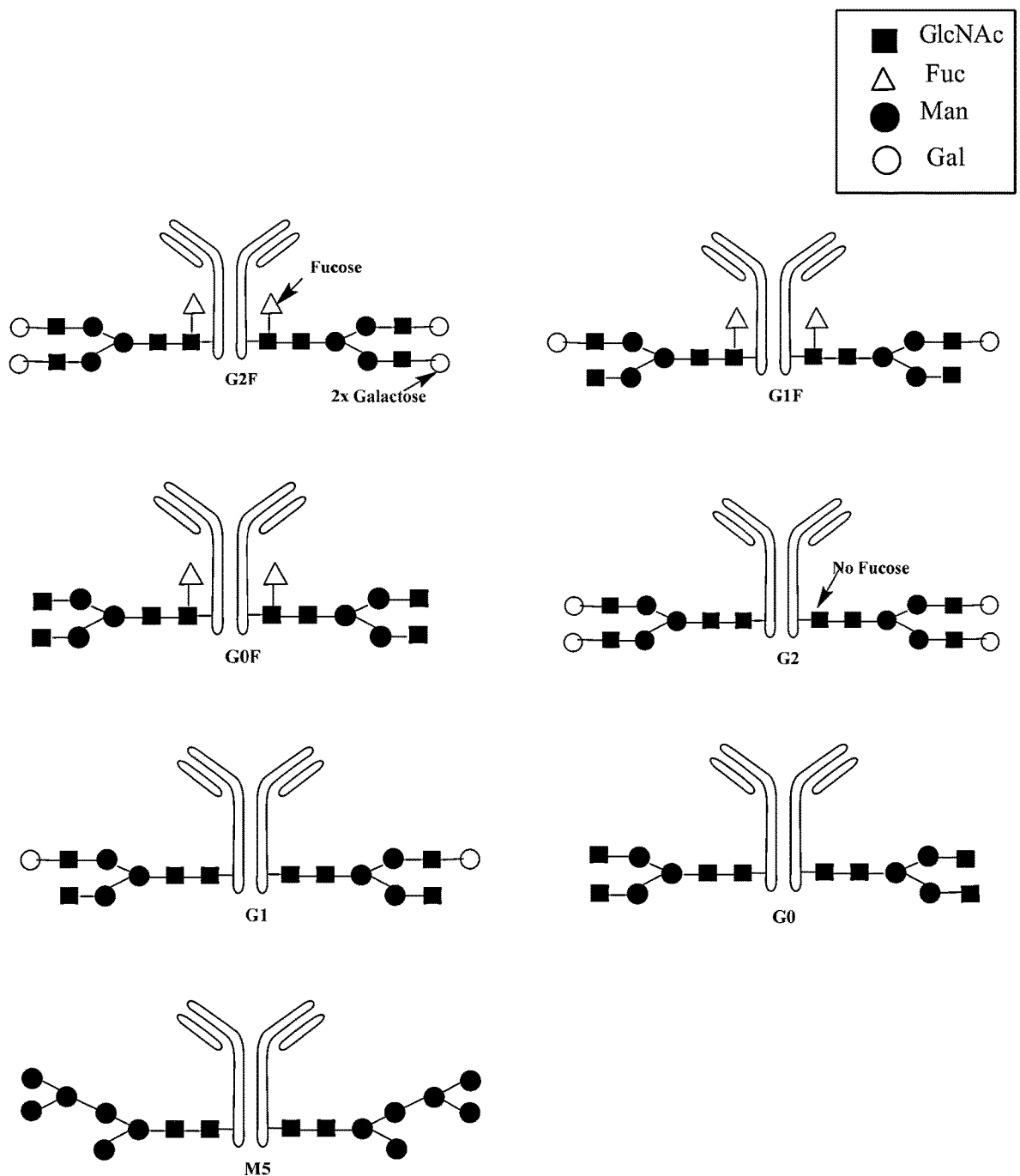
FIG. 1 is a graph showing different glycoforms of antibody glycan (G0, G1, G2, G0F, G1F, G2F, and M5).

The present disclosure provides novel targeting moiety-drug conjugates, scaffolds for preparing the conjugates, synthetic methods for preparing the conjugates or scaffolds, pharmaceutical compositions containing the scaffolds and/or conjugates, and various uses thereof.

Definitions

In some embodiments, compounds of the present disclosure and definitions of specific functional groups are also described in more detail herein. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted, permits but does not require the inclusion of additional elements or steps. In some embodiments, a scaffold of a certain formula includes all components shown in the formula and may also include additional component not shown in the formula. Additionally whenever "comprising" or another open-ended term is used in an embodiment, it is to be understood that the same embodiment can be more narrowly claimed using the intermediate term "consisting essentially of" or the closed term "consisting of."

As used herein, the expressions "one or more of A, B, or C," "one or more A, B, or C," "one or more of A, B, and C," "one or more A, B, and C" and the like are used interchangeably and all refer to a selection from A, B, and/or C, i.e., one or more As, one or more Bs, one or more Cs, or any combination thereof.

The term "about", "approximately", or "approximate", when used in connection with a numerical value, means that a collection or range of values is included. For example, "about X" includes a range of values that are ±25%, ±20%, ±15%, ±10%, ±5%, ±2%, ±1%, ±0.5%, ±0.2%, or +0.1% of X, where X is a numerical value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

"Protecting group": as used herein, the term protecting group means that a particular functional moiety, e.g., O, S, or N, is temporarily blocked so that a reaction can be carried out selectively at another reactive site in a multifunctional compound. As detailed herein, oxygen, sulfur, nitrogen and carbon protecting groups may be utilized. In some embodiments, exemplary oxygen protecting groups may be utilized. In some embodiments, nitrogen protecting groups are utilized. In some embodiments, exemplary sulphur protecting groups may be utilized. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Leaving group" refers to a molecular fragment that departs with a pair of electrons in heterolytic bond cleavage. Leaving groups can be anions or neutral molecules. Leaving groups include, but are not limited to halides such as $Cl^-$, $Br^-$, and $I^-$, sulfonate esters, such as para-toluenesulfonate ("tosylate", $TsO^-$), and RC(O)O— wherein R is H, an aliphatic, heteroaliphatic, carbocyclic, or heterocycloalkyl moiety.

"Sugar" refers to a monosaccharide, for example glucose (Glc), galactose (Gal), mannose (Man) and fucose (Fuc). The term "sugar derivative" refers to a derivative of a monosaccharide sugar, i.e. a monosaccharide sugar comprising substituents and/or functional groups. Examples of a sugar derivative include, but are not limited to, amino sugars and sugar acids. Examples of a sugar derivative also include compounds denoted as $S'(F')_{x_1}$, wherein S' is a sugar or a sugar derivative, F' is a functional group and $x_1$ indicates the number of functional groups.

The term "core-GlcNAc moiety", as used herein, refers to a monosaccharide, polysaccharide, or oligosaccharide moiety comprising a GlcNAc (e.g., a core-GlcNAc) which is attached to an antibody (e.g., via the C1 position of the GlcNAc). In some embodiments, the GlcNAc is attached to the antibody via an N-glycosidic bond to the amide nitrogen atom in the side chain of an asparagine amino acid of the antibody. In some embodiments, the core-GlcNAc moiety is present at a native glycosylation site of an antibody or is introduced on a different site on the antibody. In some embodiments, the core-GlcNAc moiety is a monosaccharide (e.g., the core-GlcNAc moiety is also a terminal-GlcNAc moiety). In some embodiments, the core-GlcNAc moiety further comprises a fucose, e.g., the core-GlcNAc moiety is a disaccharide core-GlcNAc-($\alpha$1-6-Fuc) moiety (which may be referred to as GlcNAc(Fuc)). Thus, when antibody comprises a core-GlcNAc moiety, the antibody may comprise a monosaccharide or a disaccharide core-GlcNAc moiety, and the core-GlcNAc moiety may further comprise a fucose (e.g., a disaccharide core-GlcNAc(Fuc) moiety). If the core-GlcNAc moiety further comprises a fucose, the fucose may be linked $\alpha$-1,6 to O-6 of the core-GlcNAc moiety. A core-GlcNAc moiety further comprising a fucose may be referred to as core-GlcNAc(Fuc).

The term "core-GlcNAc" refers to the inner GlcNAc that is a portion of a polysaccharide or oligosaccharide, wherein the polysaccharide or oligosaccharide is attached to an antibody via the inner GlcNAc.

The term "terminal-GlcNAc moiety", as used herein, refers to a moiety comprising a GlcNAc which is attached to an antibody and has a terminal functional group being available for further modification (e.g., with a compound of P"-S"-A"). In some embodiments, the terminal-GlcNAc moiety further comprises a fucose. In some embodiments, the terminal-GlcNAc moiety is formed by reacting the core-GlcNAc moiety of a glycoprotein (e.g., an antibody glycan) with an endoglycosidase.

"Nucleotide" is used in its normal scientific meaning and refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be referred to as a nucleoside monophosphate, a nucleoside diphosphate or a nucleoside triphosphate. The nucleobase may be adenine, guanine, cytosine, uracil or thymine.

"Protein" is used in its normal scientific meaning and includes polypeptides comprising about 10 or more amino acids. A protein may comprise natural or unnatural amino acids.

"Glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), to an amide function on the protein (N-glycoprotein), or to a carbon on the protein (C-glycoprotein). A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein.

"Glycan" is herein used in its normal scientific meaning and refers to a monosaccharide or oligosaccharide chain that is linked to a protein. Glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is also considered a glycan. A glycan of a glycoprotein may be a monosaccharide. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan, or a C-linked glycan. In a delinked glycan, a monosaccharide or oligosaccharide glycan is bonded to a C-atom in an amino acid of the protein.

"Glycosyltransferase" refers to a superfamily of enzymes that are involved in the synthesis of complex carbohydrates present on glycoproteins and glycolipids.

"N-Acetylgalactosaminyl transferase" (GalNAc-T) is a N-acetyl-D-galactosamine transferase enzyme that catalyzes the addition of N-acetyl-D-galactosamine to proteins "Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. In some embodiments, (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". Biodegradation of some conjugates (or their components, e.g., the peptide-containing scaffolds and the linkers between the scaffolds and the antibody or the drug molecule), can also be enhanced extracellularly, e.g., in low pH regions of the animal body, e.g., an inflamed area, in the close vicinity of activated macrophages or other cells releasing degradation facilitating factors. The integrity of the conjugates or scaffolds disclosed herein can be measured, for example, by size exclusion HPLC or LC/MS. Although faster degradation may be in some cases preferable, in general it may be more desirable that the conjugates or scaffolds disclosed herein degrade in cells with the rate that does not exceed the rate of metabolization or excretion of their fragments by the cells. In some embodiments, the biodegradation byproducts of conjugates or scaffolds disclosed herein are biocompatible.

"Hydrophilic": The term "hydrophilic" does not essentially differ from the common meaning of this term in the art, and denotes chemical moieties which contain ionizable, polar, or polarizable atoms, or which otherwise may be solvated by water molecules. Thus a hydrophilic moiety or group, as used herein, refers to an aliphatic, cycloalkyl, heteroaliphatic, heterocycloalkyl, aryl, or heteroaryl moiety, which falls within the definition of the term hydrophilic, as defined above. Hydrophilicity of the compounds (including drugs, conjugates and scaffolds) disclosed herein can be directly measured through determination of hydration energy, determined through investigation between two liquid phases, by HIC chromatography, or by chromatography on solid phases with known hydrophobicity.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars and/or derivatives of naturally occurring sugars.

"Drug": As used herein, the term "drug" refers to a compound which is biologically active and provides a desired physiological effect following administration to a subject in need thereof (e.g., an active pharmaceutical ingredient).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In some embodiments, the toxic effect may be a sublethal destructive effect on the cell, e.g., slowing or arresting cell growth. In order to achieve a cytotoxic effect, the drug or prodrug may be a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. In some embodiments, small molecules are biologically active in that they produce a local or systemic effect in animals, (e.g., mammals; humans). In some embodiments, the small molecule is a drug and the small molecule is referred to as "drug molecule" or "drug" or "therapeutic agent". In some embodiments, the drug molecule has MW less than or equal to about 5 kDa (e.g., less than or equal to about 1.5 kDa). In some embodiments, the drug molecule is selected from compounds found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference. In some embodiments, the drug used in this disclosure is a therapeutic agent that has antiproliferative (cytostatic and/or cytotoxic) activity against a target cell or pathway.

"Active form" as used herein refers to a form of a compound that exhibits intended pharmaceutical efficacy in vivo or in vitro. In particular, when a drug molecule intended to be delivered by the conjugate of the disclosure is released from the conjugate, the active form can be the drug itself or its derivatives, which exhibit the intended therapeutic properties. The release of the drug from the conjugate can be achieved by cleavage of a biodegradable bond of the linker which attaches the drug to the scaffold or conjugate of the disclosure.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present disclosure, such diagnostic labels permit the monitoring of the conjugate in vivo. Alternatively or additionally, constructs and compositions that include diagnostic labels can be used to monitor biological functions or structures.

"Animal": The term animal, as used herein, refers to humans as well as non-human animals, at any stage of development, including, for example, mammals, birds, reptiles, amphibians, fish, worms and single cells. In some embodiments, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc.

"Natural amino acid" as used herein refers to any one of the common, naturally occurring L-amino acids found in naturally occurring proteins or a stereoisomer thereof. Unless specified otherwise, a reference to an amino acid includes the amino acid itself and its stereoisomers.

"Unnatural amino acid" as used herein refers to any amino acid which is not a natural amino acid. This includes, for example, amino acids that comprise α-, β-, γ-, D-, L-amino acyl residues. More generally, the unnatural amino acid comprises a residue of the general formula

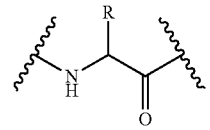

wherein the side chain R is other than the amino acid side chains occurring in nature.

"Alkyl" by itself or as part of another term, as used herein, refers to a substituted or unsubstituted straight chain or branched, saturated or unsaturated hydrocarbon having the indicated number of carbon atoms (e.g., "—$C_{1-8}$ alkyl" or "—$C_{1-10}$alkyl" refer to an alkyl group having from 1 to 8 or 1 to 10 carbon atoms, respectively). When the number of carbon atoms is not indicated, the alkyl group has from 1 to 8 carbon atoms. In some embodiments, an alkyl group is unsubstituted. An alkyl group can be substituted with one or more groups. In some embodiments, an alkyl group will be saturated.

"Alkylene" by itself or as part of another term, as used herein, refers to a substituted or unsubstituted saturated or unsaturated branched or straight chain or cyclic hydrocarbon radical of the stated number of carbon atoms, typically 2-10 carbon atoms, and having two monovalent radical centers derived by the removal of two hydrogen atoms from the same or two different carbon atoms of a parent alkane. In some embodiments, an alkylene is a branched or straight chain hydrocarbon (i.e., it is not a cyclic hydrocarbon). In any of the embodiments provided herein, the alkylene can be a saturated alkylene.

"Aryl" by itself or as part of another term, as used herein, means a substituted or unsubstituted monovalent carbocyclic aromatic hydrocarbon radical of 6-20 carbon (e.g., 6-14 carbon) atoms derived by the removal of one hydrogen atom from a single carbon atom of a parent aromatic ring system. Some aryl groups are represented in the exemplary structures as "Ar".

"Arylene" by itself or as part of another term, as used herein, is an aryl group as defined above wherein one of the aryl group's hydrogen atoms is replaced with a bond (i.e., it is divalent) and can be in the ortho, meta, or para orientations.

In some embodiments, e.g., when a Multifunctional Linker or Drug Unit, comprises an arylene, the arylene is an aryl group defined above wherein one or two of the aryl group's hydrogen atoms is replaced with a bond (i.e., the arylene can be divalent or trivalent).

"Heterocycle" by itself or as part of another term, as used herein, refers to a monovalent substituted or unsubstituted aromatic ("heteroaryl") or non-aromatic ("heterocycloalkyl") monocyclic, bicyclic, tricyclic, or tetracyclic ring system having a certain number of (e.g., from 3 to 8 or $C_{3-8}$) carbon atoms (also referred to as ring members) and one to four heteroatom ring members independently N, O, P or S, and derived by removal of one hydrogen atom from a ring atom of a parent ring system. One or more N, C or S atoms in the heterocycle can be oxidized. The ring that includes the heteroatom can be aromatic or nonaromatic. Unless otherwise noted, the heterocycle is attached to its pendant group at any heteroatom or carbon atom that results in a stable structure.

"Heterocyclo" or "Heterocyclo-" when used herein, refers to a heterocycle group (e.g., $C_{3-8}$ heterocycle) defined above wherein one or more of additional hydrogen atoms of the heterocycle are replaced with a bond (i.e., it is multivalent, such as divalent or trivalent). In some embodiments, when a hydrophilic group, Multifunctional Linker or Linker-Drug moiety comprises a heterocyclo, the heterocyclo is a heterocycle group defined above wherein one or two of the heterocycle group's hydrogen atoms is replaced with a bond (i.e., the heterocyclo can be divalent or trivalent).

"Carbocycle" by itself or as part of another term, when used herein, is monovalent, substituted or unsubstituted, aromatic ("aryl") or saturated or unsaturated non-aromatic ("cycloalkyl"), monocyclic, bicyclic, tricyclic, or tetracyclic carbocyclic ring system having a certain number of (e.g., from 3 to 8 or $C_{3-8}$) carbon atoms (also referred to as ring members) derived by the removal of one hydrogen atom from a ring atom of a parent ring system. A carbocycle can be 3-, 4-, 5-, 6-, 7- or 8-membered.

"Carbocyclo" or "Carbocyclo-" by itself or as part of another term, when used herein, refers to a $C_{3-8}$ carbocycle group defined above wherein another of the carbocycle groups' hydrogen atoms is replaced with a bond (i.e., it is divalent). In some embodiments, e.g., when a hydrophilic group, Multifunctional Linker, or Linker-Drug moiety comprises a carbocyclo, the carbocyclo is a carbocycle group defined above wherein one or two of the carbocycle group's hydrogen atoms is replaced with a bond (i.e., the carbocyclo can be divalent or trivalent).

"Heteroalkyl" by itself or in combination with another term, when used herein, means, unless otherwise stated, a stable straight or branched chain hydrocarbon, or combinations thereof, fully saturated or containing from 1 to 3 degrees of unsaturation, consisting of the stated number of carbon atoms and from one to ten, (e.g., one to three, heteroatoms O, N, Si or S), and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. In some embodiments, up to two heteroatoms may be consecutive. In some embodiments, a $C_{1-4}$ heteroalkyl or heteroalkylene has 1 to 4 carbon atoms and 1 or 2 heteroatoms and a $C_{1-3}$ heteroalkyl or heteroalkylene has 1 to 3 carbon atoms and 1 or 2 heteroatoms. In some embodiments, a heteroalkyl or heteroalkylene is saturated.

"Heteroalkylene" by itself or as part of another substituent, when used herein, means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied. In select embodiments, e.g., when a hydrophilic group, Multifunctional Linker or Linker-Drug moiety comprises a heteroalkylene, the heteroalkylene is a heteroalkyl group defined above wherein one or two of the heteroalkyl group's hydrogen atoms is replaced with a bond (i.e., the heteroalkylene can be divalent or trivalent).

"Optionally substituted" when used herein, means that a chemical moiety (such as alkyl, heteroalkyl, carbocycle, and heterocycle, etc.) is either substituted or unsubstituted. Unless otherwise specified, the chemical moieties disclosed herein are optionally substituted. When a chemical moiety is substituted, one or more hydrogen atoms are each independently replaced with a substituent. Typical substituents include, but are not limited to, —X', —R', —O, —OR', —SR', —S—, —N(R')$_2$, —N(R')$_3$, =NR', —C(X')$_3$, —CN, —OCN, —SCN, —N=C=O, —NCS, —NO, —NO$_2$, =N$_2$, —N$_3$, —NR'C(=O)R', —C(=O)R', —C(=O)N(R')$_2$, —SO$_3$—, —SO$_3$H, —S(=O)$_2$R', —OS(=O)$_2$OR', —S(=O)$_2$NR', —S(=O)R', —OP(=O)(OR')$_2$, —P(=O)(OR')$_2$, —PO$_3$—, —PO$_3$H$_2$, —AsO$_2$H$_2$, —C(=O)R', —C(=O)X', —C(=S)R', —CO$_2$R', —CO$_2$—, —C(=S)OR', —C(=O)SR', —C(=S)SR', —C(=O)N(R')$_2$, —C(=S)N(R')$_2$, or —C(=NR')N(R')$_2$, wherein each X' independently is a halogen: —F, —Cl, —Br, or —I; and each R' independently is —H, —$C_{1-20}$ alkyl, —$C_{6-20}$ aryl, —$C_3$-$C_{14}$ heterocycle, a protecting group or a prodrug moiety. Typical substituents also include oxo (=O).

"Linker-Drug moiety" as used herein, refers to the non-targeting (e.g., non-antibody) moiety portion of a conjugate disclosed herein. The Linker component of the Linker-Drug moiety has the release mechanism, which is referred to as the Releasable Assembly Unit, interposed between a Multifunctional Linker and a Drug Unit. In some embodiments, the Linker-Drug moiety is the non-antibody (e.g., non-targeting) portion of the conjugate.

"Multifunctional Linker" as used herein, refers to a linker that connects one or more hydrophilic groups, one or more Drug Units, and a targeting moiety (e.g., an antibody) to form a conjugate or scaffold as disclosed herein. The connection of these components to the Multifunctional Linker can either be parallel or serial. In some embodiments, the Multifunctional Linker comprises a peptide moiety between the targeting moiety and the hydrophilic group, wherein the peptide moiety includes at least two amino acids. In other embodiments, the Multifunctional Linker does not have to comprise a peptide moiety of at least two amino acids when the hydrophilic group is a polyalcohol or a derivative thereof. In other embodiments, the Multifunctional Linker does not have to comprise a peptide moiety of at least two amino acids when the hydrophilic group is a glucosyl-amine, a di-glucosyl-amine, a tri-glucosyl-amine or a derivative thereof.

"Free drug" as used herein, refers to a biologically active form of a drug moiety that is not covalently attached either directly or indirectly to a hydrophilic group or to a degradant product of a Ligand Unit. Free drug can refer to the drug, as it exists immediately upon cleavage from the Multifunctional Linker via the release mechanism, which is provided by the Releasable Assembly Unit in the Linker-Drug moiety, or, to subsequent intracellular conversion or metabolism. In some embodiments, the free drug will have the form H-D or may exist a as a charged moiety. In some embodiments, the pharmacologically active species may not be the parent drug and may include a component of the linker through which the drug is connected to the targeting moiety, which has not undergone subsequent intracellular metabolism.

Hydrophobicity can be measured using clogP or clogP is defined as the log of the octanol/water partition coefficient (including implicit hydrogens) and can be calculated using the program MOE™ from the Chemical Computing group (clogP values calculated using Wildman, S. A., Crippen, G. M.; Prediction of Physiochemical Parameters by Atomic Contributions; J. Chem. Inf. Comput. Sci. 39 No. 5 (1999) 868-873).

In some embodiments, the present disclosure provides a targeting moiety-drug conjugate composition comprising a population of targeting moiety-drug conjugates. The targeting moiety-drug conjugate comprises a targeting moiety unit and multiple Linker-Drug moieties attached thereto. In some embodiments, there is an average of from about 2 to about 12, about 2 to about 10, about 2 to about 8, about 2 to about 6, about 2 to about 4 or about 1 to about 2 Linker-Drug moieties (e.g., $d_{13}$ of Formula (I')) per targeting moiety in the conjugate. Exemplary attachment to specific sties on the targeting moiety is via modification of the targeting moiety N-glycan to contain an azido group, a keto group or an alkynyl group.

The present disclosure is intended to include all isotopes of atoms occurring in the present compounds (e.g., isotopes of hydrogen and isotopes of carbon).

The compound, scaffold, or conjugate of the present disclosure may exist in more than one isomeric form. It is understood that when a compound, scaffold, or conjugate is described herein, the disclosure refers to all isomers of the compound, scaffold, or conjugate. Such disclosure refers to, where applicable, regioisomers optical isomers and tautomeric isomers. The optical isomers include enantiomers and diastereomers, chiral isomers and non-chiral isomers. The optical isomers include isolated optical isomers as well as mixtures of optical isomers including racemic and non-racemic mixtures. An isomer may be in isolated form or in a mixture with one or more other isomers. Unless stated otherwise, any compound, scaffold, or conjugate described herein is meant to refer to each isomer of the compound, scaffold, or conjugate, or any mixture thereof. When a compound, scaffold, or conjugate is depicted as a specific isomer, it is understood that the present disclosure is not limited to that specific isomer, but may refer to the specific isomer as an optional embodiment.

The compound, scaffold, or conjugate of the present disclosure may exist as cis and/or trans isomers. Unless stated otherwise, any compound, scaffold, or conjugate described herein is meant to refer to the cis isomer or trans isomer of the compound, scaffold, or conjugate, as well as any mixture thereof. When a compound, scaffold, or conjugate is depicted as a cis or trans isomer, it is understood that the present disclosure is not limited to that specific cis or trans isomer, but may refer to the specific cis or trans isomer as an optional embodiment.

The compound, scaffold, or conjugate of the present disclosure may exist as regioisomers. Unless stated otherwise, any compound, scaffold, or conjugate described herein is meant to refer to each regioisomer of the compound, scaffold, or conjugate, or any mixture thereof. When a compound, scaffold, or conjugate is depicted as a specific regioisomer, it is understood that the present disclosure is not limited to that specific regioisomer, but may refer to the specific regioisomer as an optional embodiment. Recitation or depiction of a compound, scaffold, or conjugate of the present disclosure without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers.

Antibody-Drug Conjugates and Scaffolds

In some embodiments, the present disclosure provides an antibody-drug conjugate with site-specificity. In some embodiments, the conjugate is biodegradable and biocompatible, and/or exhibits high drug load and strong binding to a target antigen.

In some embodiments, the present disclosure provides an antibody-drug conjugate, comprising a targeting moiety (e.g., an antibody) and one or more Linker-Drug moieties, wherein the targeting moiety is covalently linked to the one or more Linker-Drug moieties.

In some embodiments, the present disclosure provides a scaffold useful to conjugate with a targeting moiety (e.g., an antibody) to form a conjugate disclosed herein.

In some embodiments, the targeting moiety is an antibody.

In some aspects, the present disclosure provides an antibody-drug conjugate, comprising a targeting moiety (e.g., an antibody) and one or more Linker-Drug moieties covalently linked to the targeting moiety, wherein:

each Linker-Drug moiety comprises a Multifunctional Linker that connects the targeting moiety to one or more Drug Units (e.g., one or more therapeutic agents (D)) through intermediacy of a Releasable Assembly Unit for each Drug Unit, and connects a hydrophilic group to the Drug Units of each Linker-Drug moiety;

the Releasable Assembly unit is capable of releasing free drug in proximity to a target site targeted by the targeting moiety; and the Multifunctional Linker comprises a peptide moiety between the targeting moiety and the hydrophilic group, wherein the peptide moiety comprises at least two amino acids.

In some aspects, the present disclosure provides an antibody-drug conjugate, comprising a targeting moiety (e.g., an antibody) and one or more Linker-Drug moieties covalently linked to the targeting moiety, wherein:

each Linker-Drug moiety comprises a Multifunctional Linker that connects the targeting moiety to one or more Drug Units (e.g., one or more therapeutic agents (D)) through intermediacy of a Releasable Assembly Unit for each Drug Unit, and connects a hydrophilic group to the Drug Units of each Linker-Drug moiety; and the Releasable Assembly unit is capable of releasing free drug in proximity to a target site targeted by the targeting moiety.

In some aspects, the present disclosure provides an antibody-drug conjugate of Formula (I').

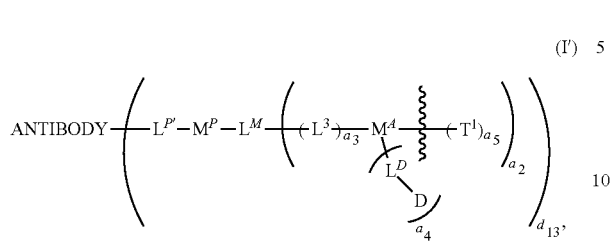

wherein
$a_2$ is an integer from 1 to 3;
$a_3$ is an integer from 0 to 1;
$a_4$ is an integer from 1 to about 5;
$a_5$ is an integer from 1 to 3;
$d_{13}$ is an integer from 1 to about 12;
ANTIBODY is a modified antibody;
$L^{P'}$ is a divalent linker moiety connecting the modified antibody to $M^P$; of which the corresponding monovalent moiety $L^P$ comprises a functional group $W^P$ that is capable of forming a covalent bond with a functional group of the modified antibody;
$M^P$ is a Stretcher unit;
$L^M$ is a bond, or a trivalent or a tetravalent linker, and when $L^M$ is a bond (i.e., a divalent linker), $a_2$ is 1, when $L^M$ is a trivalent linker, $a_2$ is 2, or when $L^M$ is a tetravalent linker, $a_2$ is 3;
$L^3$ is a carbonyl-containing moiety;
$M^A$ comprises a peptide moiety that comprises at least two amino acids;
$T^1$ is a hydrophilic group and the

between $T^1$ and $M^A$ denotes direct or indirect attachment of $T^1$ and $M^A$;
each occurrence of D independently is a therapeutic agent having a molecular weight ≤about 5 kDa; and
each occurrence of $L^D$ independently is a divalent linker moiety connecting D to $M^A$ and comprises at least one cleavable bond such that when the bond is broken, D is released in an active form for its intended therapeutic effect.

In some aspects, the present disclosure provides an antibody-drug conjugate of Formula (IV) or a scaffold of any one of Formulae (II)-(III) and (V)-(VI):

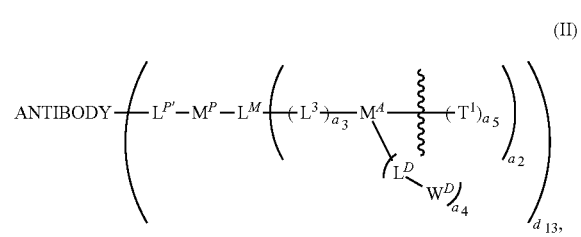

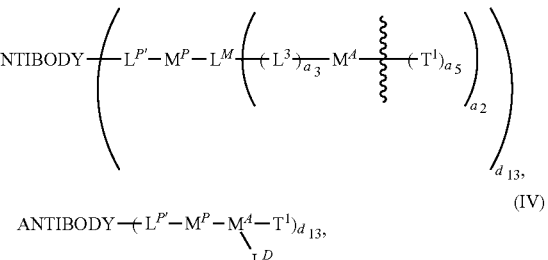

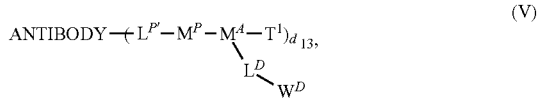

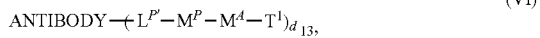

wherein
$a_2$ is an integer from 1 to 3;
$a_3$ is an integer from 0 to 1;
$a_4$ is an integer from 1 to about 5;
$a_5$ is an integer from 1 to 3;
$d_{13}$ is an integer from 1 to about 12;
ANTIBODY is a modified antibody;
$L^{P'}$ is a divalent linker moiety connecting the modified antibody to $M^P$; of which the corresponding monovalent moiety $L^P$ comprises a functional group $W^P$ that is capable of forming a covalent bond with a reactive moiety of the modified antibody;
$M^P$ is a Stretcher unit;
$L^M$, when present, is a bond, or a trivalent or a tetravalent linker, and when $L^M$ is a bond (i.e., a divalent linker), $a_2$ is 1, when $L^M$ is a trivalent linker, $a_2$ is 2, or when $L^M$ is a tetravalent linker, $a_2$ is 3;
$L^3$ is a carbonyl-containing moiety;
$M^A$ comprises a peptide moiety that comprises at least two amino acids;
$T^1$ is a hydrophilic group and the

between $T^1$ and $M^A$ denotes direct or indirect attachment of $T^1$ and $M^A$;
each occurrence of $W^D$, when present, independently is a functional group that is capable of forming a covalent bond with a functional group of a therapeutic agent ("D") having a molecular weight ≤about 5 kDa; and
each occurrence of $L^D$ independently is a divalent linker moiety connecting $W^D$ or D to $M^A$ and $L^D$ comprises at least one cleavable bond such that when the bond is broken, D is released in an active form for its intended therapeutic effect.

In some aspects, the present disclosure provides an antibody-drug conjugate of Formula (IV') or a scaffold of any one of Formulae (II')-(III') and (V')-(VI')

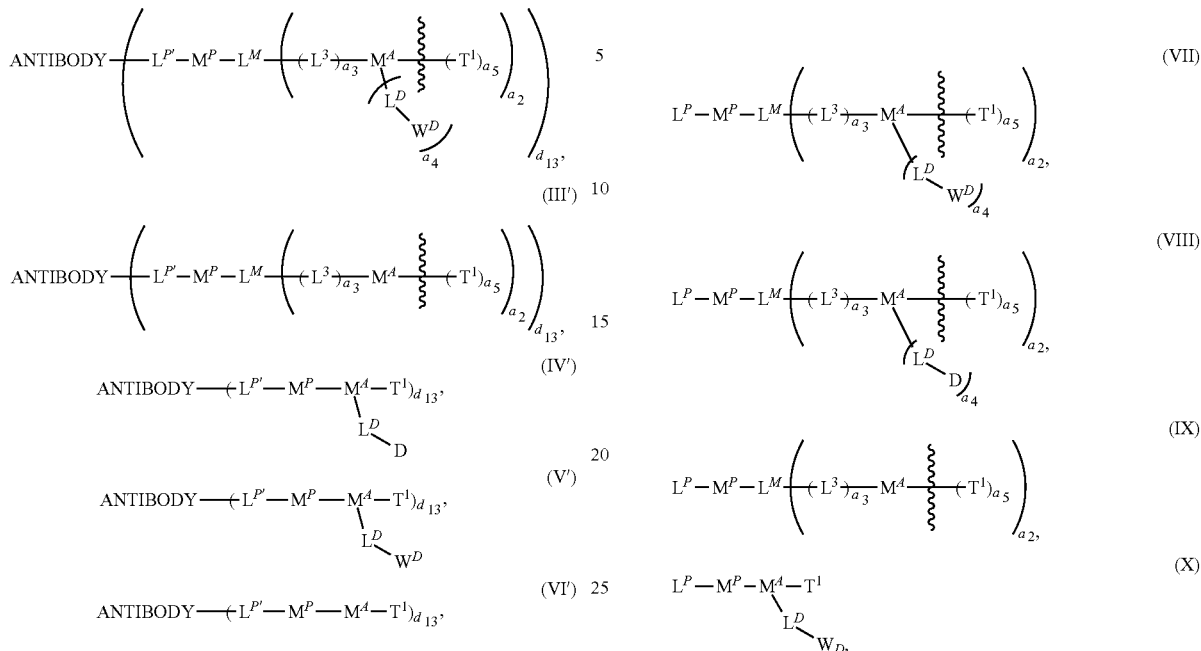

wherein
  $a_2$ is an integer from 1 to 3;
  $a_3$ is an integer from 0 to 1;
  $a_4$ is an integer from 1 to about 5;
  $a_5$ is an integer from 1 to 3;
  $d_{13}$ is an integer from 1 to about 12;
  ANTIBODY is a modified antibody;
  $L^{P'}$ is a divalent linker moiety connecting the modified antibody to $M^P$; of which the corresponding monovalent moiety $L^P$ comprises a functional group $W^P$ that is capable of forming a covalent bond with a reactive moiety of the modified antibody;
  $M^P$ is a Stretcher unit;
  $L^M$, when present, is a bond, or a trivalent or a tetravalent linker, and when $L^M$ is a bond (i.e., a divalent linker), $a_2$ is 1, when $L^M$ is a trivalent linker, $a_2$ is 2, or when $L^M$ is a tetravalent linker, $a_2$ is 3;
  $L^3$ is a carbonyl-containing moiety;
  $M^4$ comprises a peptide moiety that comprises at least two amino acids;
  $T^1$ is a hydrophilic group and the

between $T^1$ and $M^4$ denotes direct or indirect attachment of $T^1$ and $M^4$;
  each occurrence of $W^D$, when present, independently is a functional group that is capable of forming a covalent bond with a functional group of a therapeutic agent ("D") having a molecular weight ≤about 5 kDa; and
  each occurrence of $L^D$ independently is a divalent linker moiety connecting $W^D$ or D to $M^4$ and $L^D$ comprises at least one cleavable bond such that when the bond is broken, D is released in an active form for its intended therapeutic effect.

In some aspects, the present disclosure provides a peptide-containing scaffold of any one of Formulae (VII)-(XII):

wherein
  $a_2$ is an integer from 1 to 3;
  $a_3$ is an integer from 0 to 1;
  $a_4$ is an integer from 1 to about 5;
  as is an integer from 1 to 3;
  $L^P$ is a monovalent linker moiety which comprises a functional group $W^P$ that is capable of forming a covalent bond with a reactive moiety of a modified antibody;
  $M^P$ is a Stretcher unit;
  $L^M$, when present, is a bond, or a trivalent or a tetravalent linker, and when $L^M$ is a bond (i.e., a divalent linker), $a_2$ is 1, when $L^M$ is a trivalent linker, $a_2$ is 2, or when $L^M$ is a tetravalent linker, $a_2$ is 3;
  $L^3$, when present, is a carbonyl-containing moiety;
  $M^4$ comprises a peptide moiety that comprises at least two amino acids;
  $T^1$ is a hydrophilic group and the between $T^1$ and $M^4$ denotes direct or indirect attachment of $T^1$ and $M^4$;
  each occurrence of $W^D$ independently is a functional group that is capable of forming a covalent bond with a functional group of a therapeutic agent ("D") having a molecular weight ≤about 5 kDa; and
  each occurrence of $L^D$ independently is a divalent linker moiety connecting $W^D$ or D to $M^4$ and $L^D$ comprises at least one cleavable bond such that when the bond is broken, D is released in an active form for its intended therapeutic effect.

In some aspects, the present disclosure provides a peptide-containing scaffold of any one of Formulae (VII')-(XII'):

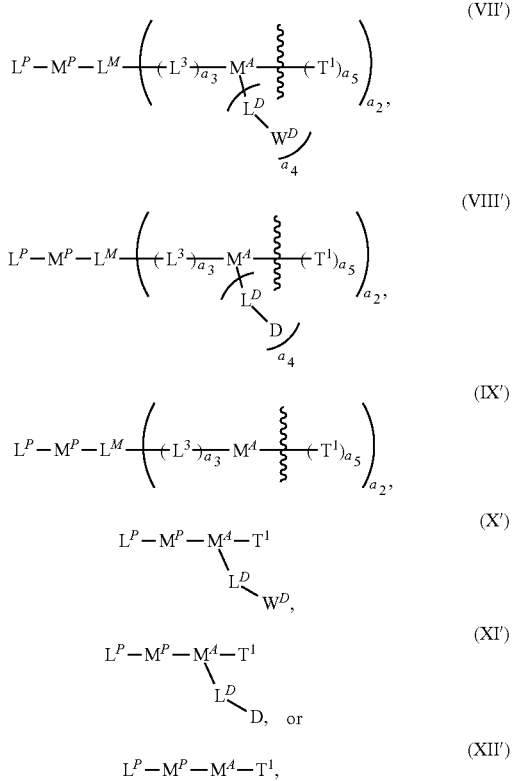

wherein
$a_2$ is an integer from 1 to 3;
$a_3$ is an integer from 0 to 1;
$a_4$, is an integer from 1 to about 5;
$a_5$ is an integer from 1 to 3;
$L^P$ is a monovalent linker moiety which comprises a functional group $W^P$ that is capable of forming a covalent bond with a reactive moiety of a modified antibody;
$M^P$ is a Stretcher unit;
$L^M$, when present, is a bond, or a trivalent or a tetravalent linker, and when $L^M$ is a bond, $a_2$ is 1, when $L^M$ is a trivalent linker, $a_2$ is 2, or when $L^M$ is a tetravalent linker, $a_2$ is 3;
$L^3$, when present, is a carbonyl-containing moiety;
$M^A$ comprises a peptide moiety that comprises at least two amino acids;
$T^1$ is a hydrophilic group and the

between $T^1$ and $M^A$ denotes direct or indirect attachment of $T^1$ and $M^A$;
each occurrence of $W^D$ independently is a functional group that is capable of forming a covalent bond with a functional group of a therapeutic agent ("D") having a molecular weight ≤about 5 kDa; and each occurrence of $L^D$ independently is a divalent linker moiety connecting $W^D$ or D to $M^A$ and $L^D$ comprises at least one cleavable bond such that when the bond is broken, D is released in an active form for its intended therapeutic effect.

The conjugates and scaffolds of the disclosure can include one or more of the following features when applicable.

In some embodiments, $d_{13}$ is an integer from 2 to 12, from 2 to 10, from 2 to 8, from 2 to 6, from 2 to 4, from 1 to 2, from 4 to 10, from 4 to 8, from 4 to 6, from 6 to 12, from 6 to 10, from 6 to 8, from 8 to 14, from 8 to 12, or from 8 to 10.

In some embodiments, $d_{13}$ is an integer ranging from 1 to 2 (e.g., $d_{13}$ is 1 or 2). In some embodiments, $d_{13}$ is an integer ranging from 2 to 4 (e.g., $d_{13}$ is 2, 3, or 4). In some embodiments, $d_{13}$ is an integer ranging from 4 to 6 (e.g., $d_{13}$ is 4, 5, or 6). In some embodiments, $d_{13}$ is an integer ranging from 6 to 8 (e.g., $d_{13}$ is 6, 7, or 8). In some embodiments, $d_{13}$ is an integer ranging from 6 to 10 (e.g., $d_{13}$ is 6, 7, 8, 9, or 10). In some embodiments, $d_{13}$ is 1 or 2. In some embodiments, $d_{13}$ is 1. In some embodiments, $d_{13}$ is 2.

In some embodiments, each $L^3$, when present, independently is *—$C_{1-12}$ alkyl-C(O)—**, *—NH—$C_{1-12}$ alkyl-C(O)—**, or *—$C_{1-12}$ alkyl-C(O)—NH—$C_{1-12}$ alkyl-C(O)—**, wherein * indicates attachment to another $L^3$ when present, or to $L^M$; and ** indicates attachment to another $L^3$ when present, or to $M^A$.

In some embodiments, at least one $L^3$ is *—CH$_2$CH$_2$—C(O)—** or is *—NH—CH$_2$CH$_2$—C(O)—** wherein * indicates attachment to another $L^3$ when present, or to $L^M$; and ** indicates attachment to another $L^3$ when present, or to $M^A$.

In some embodiments, $a_3$ is 2 or greater, at least one $L^3$ is *—$C_{1-12}$ alkyl-C(O)—**, and at least one $L^3$ is *—NH—$C_{1-12}$ alkyl-C(O)—**.

In some embodiments, $(L^3)_{a3}$ is *—CH$_2$CH$_2$—C(O)—NH—CH$_2$CH$_2$—C(O)—** or *NH—CH$_2$CH$_2$—C(O)—CH$_2$CH$_2$—C(O)—**, wherein * indicates attachment to $L^M$; and ** indicates attachment to $M^A$.

In some embodiments, $a_4$ is 1. In some embodiments, $a_4$ is 2. In some embodiments, $a_4$ is 3.

Variable $L^P$ and $L^{P'}$

In some embodiments, $L^{P'}$ is formed by the reaction between a functional group (e.g., $W^P$) of $L^P$ and a reactive moiety (e.g., the modified-GlcNAc moiety of *-GlcNAc-S"-A") of the modified antibody.

In some embodiments, $L^{P'}$ comprises a triazolyl formed between the functional group (e.g., $W^P$) of $L^P$ and the reactive moiety (e.g., the modified-GlcNAc moiety of *-GlcNAc-S"-A") of the modified antibody.

In some embodiments, each $L^P$, when not connected to an antibody, comprises a terminal group $W^P$.

In some embodiments, at least one $W^P$ is

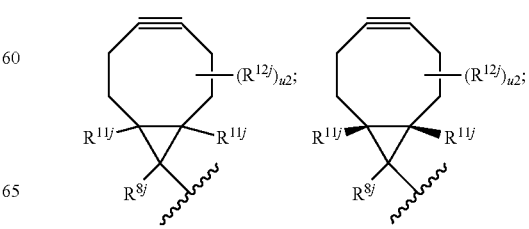

-continued

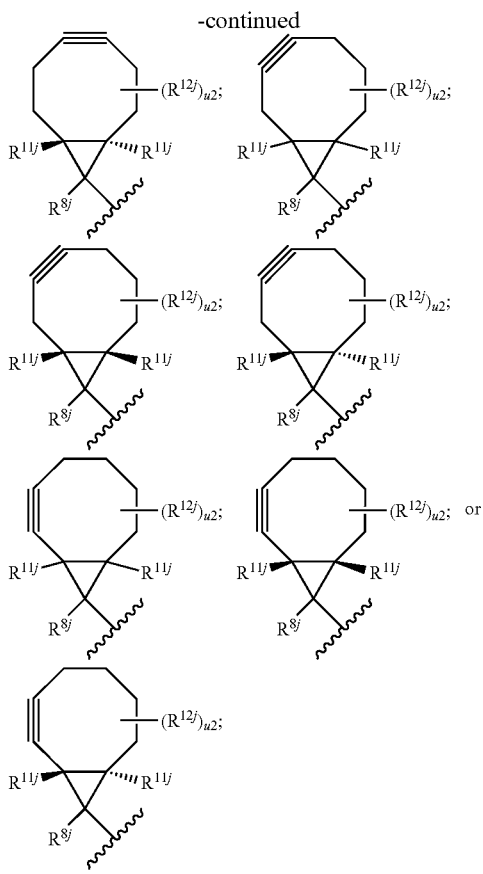

wherein

R$^{8j}$ is hydrogen, halogen, C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl), wherein the C$_{1-24}$ alkyl is optionally interrupted by one of more O, N or S, and wherein the C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl) is optionally substituted with one or more C$_1$-C$_{12}$ alkyl, C$_2$-C$_{12}$ alkenyl, C$_2$-C$_{12}$ alkynyl, C$_3$-C$_{12}$ cycloalkyl, —O(C$_1$-C$_{12}$ alkyl), —O(C$_2$-C$_{12}$ alkenyl), —O(C$_2$-C$_{12}$ alkynyl), —O(C$_3$-C$_{12}$ cycloalkyl), halogen, amino, oxo, or silyl, wherein the C$_1$-C$_{12}$ alkyl, C$_2$-C$_{12}$ alkenyl, C$_2$-C$_{12}$ alkynyl, C$_3$-C$_{12}$ cycloalkyl, —O(C$_1$-C$_{12}$ alkyl), —O(C$_2$-C$_{12}$ alkenyl), —O(C$_2$-C$_{12}$ alkynyl), —O(C$_3$-C$_{12}$ cycloalkyl) is optionally substituted, and wherein the C$_1$-C$_{12}$ alkyl, C$_3$-C$_{12}$ cycloalkyl, —O(C$_1$-C$_{12}$ alkyl), or —O(C$_3$-C$_{12}$ cycloalkyl) is optionally interrupted by one of more O, N, or S;

R$^{10j}$ is hydrogen, halogen, C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl), wherein the C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl) is optionally substituted;

each R$^{11j}$ independently is hydrogen, C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl);

each R$^{12j}$ independently is halogen, —OR$^{10j}$, —NO$_2$, —CN, —S(O)$_2$R$^{10j}$, C$_{1-24}$ alkyl (e.g., C$_{1-6}$ alkyl), C$_{6-24}$ cycloalkyl, 6- to 24-membered heterocycloalkyl, C$_{6-24}$ aryl, 6- to 24-membered heteroaryl, —(C$_{1-24}$ alkyl)-(C$_{6-24}$ cycloalkyl), —(C$_{1-24}$ alkyl)-(6- to 24-membered heterocycloalkyl), —(C$_{1-24}$ alkyl)-(C$_{6-24}$ aryl), or —(C$_{1-24}$ alkyl)-(6- to 24-membered heteroaryl); and u$_2$ is an integer ranging from 0 to 8.

In some embodiments, at least one W$^P$ is

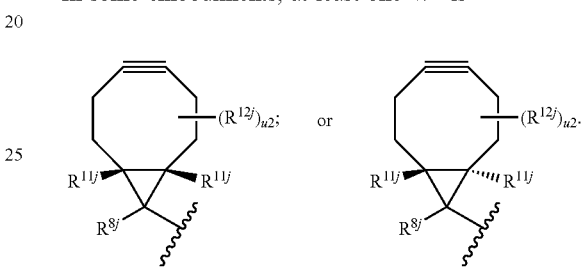

In some embodiments, at least one W$^P$ is

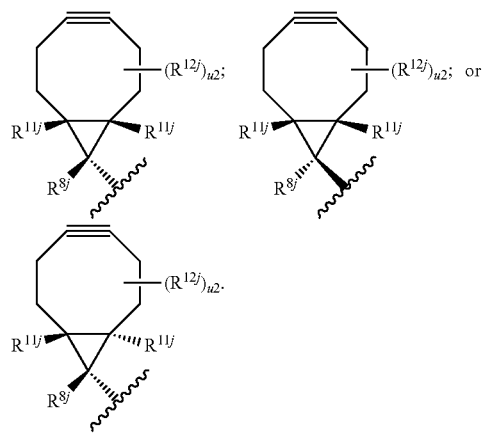

In some embodiments, each R$^{11j}$ is hydrogen. In some embodiments, u$_2$ is 0. In some embodiments, R$^{8j}$ is hydrogen.

In some embodiments, at least one W$^P$ is

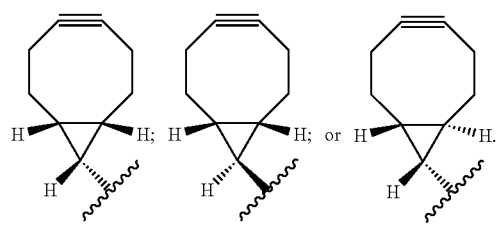

In some embodiments, at least one $W^P$ is

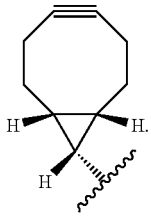

In some embodiments, at least one $R^{12j}$ is an electron-withdrawing group, e.g., a group with a positive value for the Hammett substituent constant σ. In some embodiments, suitable electron-withdrawing groups are known in the art. In some embodiments, at least one $R^{12j}$ is halogen (e.g., F or Cl), —$OR^{10j}$, —$NO_2$, —CN, —$S(O)_2R^{7j}$, substituted $C_1$-$C_{12}$ alkyl, or substituted $C_6$-$C_{12}$ aryl, wherein at least one of the substituents is an electron-withdrawing group. In some embodiments, at least one $R^{12j}$ is fluorinated $C_1$-$C_{12}$ alkyl (e.g., —$CF_3$), fluorinated $C_5$-$C_{12}$ aryl (e.g., —$C_6F_5$), or haloalkylated $C_5$-$C_{12}$ aryl (e.g., —[3,5-$(CF_3)_2(C_6H_3)$]).

In some embodiments, at least one $W^P$ is

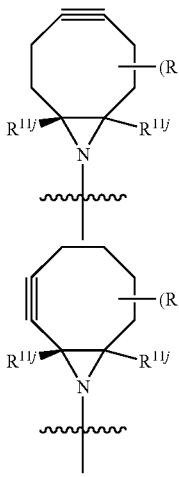

In some embodiments, at least one $W^P$ is

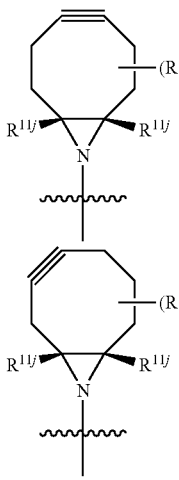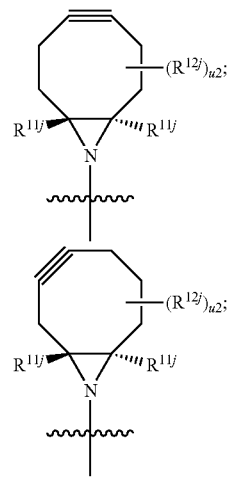

In some embodiments, at least one $W^P$ is

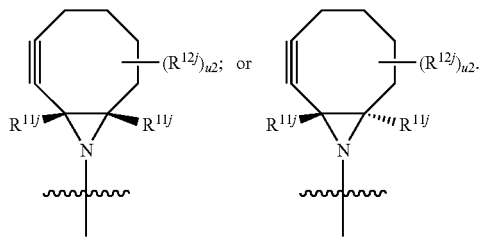

In some embodiments, at least one $W^P$ is

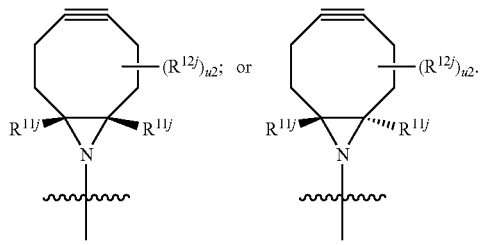

In some embodiments, each $R^{11j}$ is hydrogen. In some embodiments, $u_2$ is 0.

In some embodiments, at least one $W^P$ is

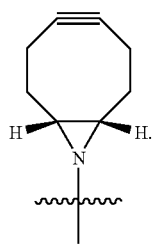

In some embodiments, each $W^P$, when present, independently is:

(a)

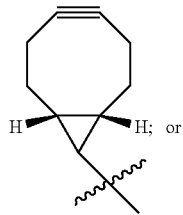

(b)

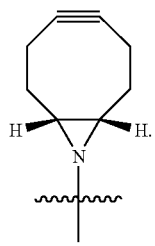

In some embodiments, each $W^P$ is
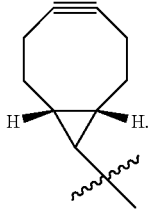
In some embodiments, each $L^{P'}$, when connected to an antibody, comprises a linking group $W^{P'}$.
In some embodiments, at least one $W^{P'}$ is
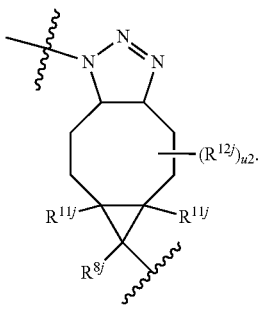
In some embodiments, at least one $W^{P'}$ is
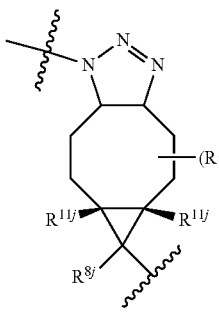 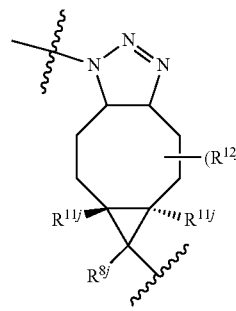
or
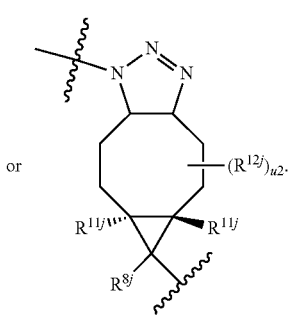
In some embodiments, at least one $W^{P'}$ is
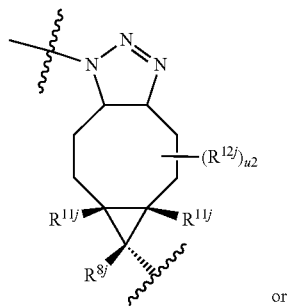
or
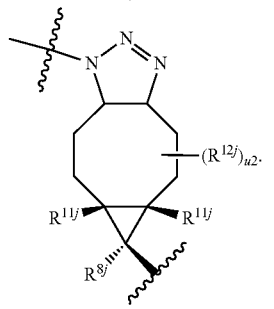
In some embodiments, at least one $W^{P'}$ is
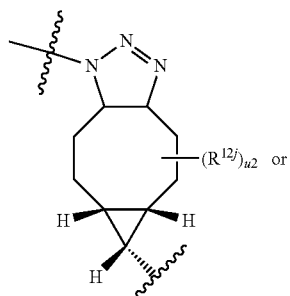
or
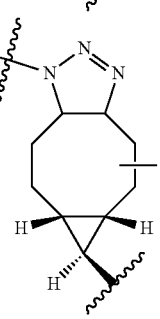
In some embodiments, at least one $W^{P'}$ is
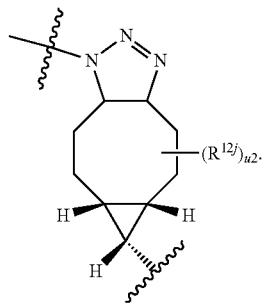

Stretcher Unit $M^P$

In some embodiments, $M^P$ is

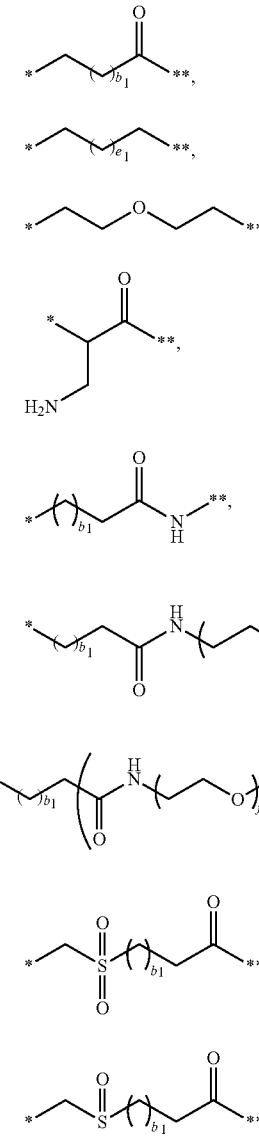

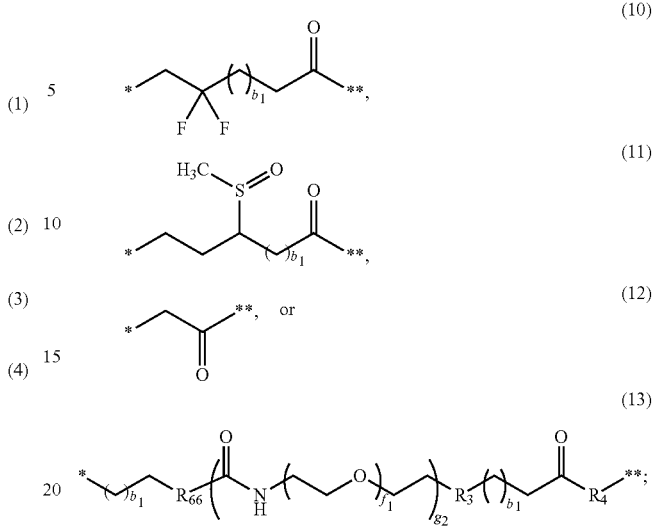

wherein * denotes attachment to $L^{P'}$ or $L^P$ and ** denotes attachment to $L^M$ or $M^A$;

each $R_{66}$ independently is NH or O; each $R_3$ independently is —C(O)—NR$_5$— or —NR$_5$—C(O)—;

each $R_5$ independently is hydrogen, $C_{1-6}$ alkyl, $C_{6-10}$ aryl, $C_{3-8}$ cycloalkyl, COOH, or COO—$C_{1-6}$ alkyl;

$R_4$ is a bond or —NR$_5$—(CR$_{20}$R$_{21}$)—C(O)—;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

each $b_1$ independently is an integer ranging from 0 to 6;
each $e_1$ independently is an integer ranging from 0 to 8;
each $f_1$ independently is an integer ranging from 1 to 6; and
each $g_2$ independently is an integer ranging from 1 to 4.

In some embodiments, $b_1$ is 0. In some embodiments, $b_1$ is 1.

In some embodiments, each $f_1$ independently is 1 or 2. In some embodiments, $f_1$ is 1. In some embodiments, $f_1$ is 2.

In some embodiments, $g_2$ is 1 or 2. In some embodiments, $g_2$ is 1. In some embodiments, $g_2$ is 2.

It is understood that for embodiments of $M^P$, * denotes attachment to $L^{P'}$ or $L^P$ and ** denotes attachment to $L^M$ or $M^A$.

In some embodiments, $M^P$ is:

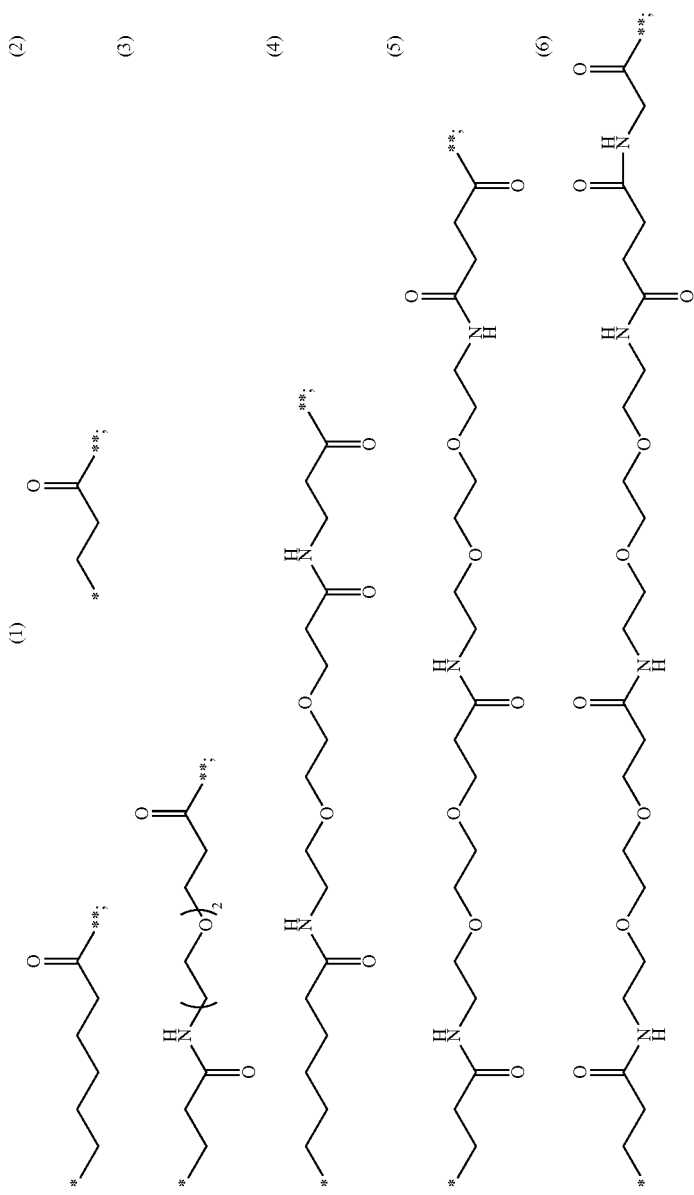

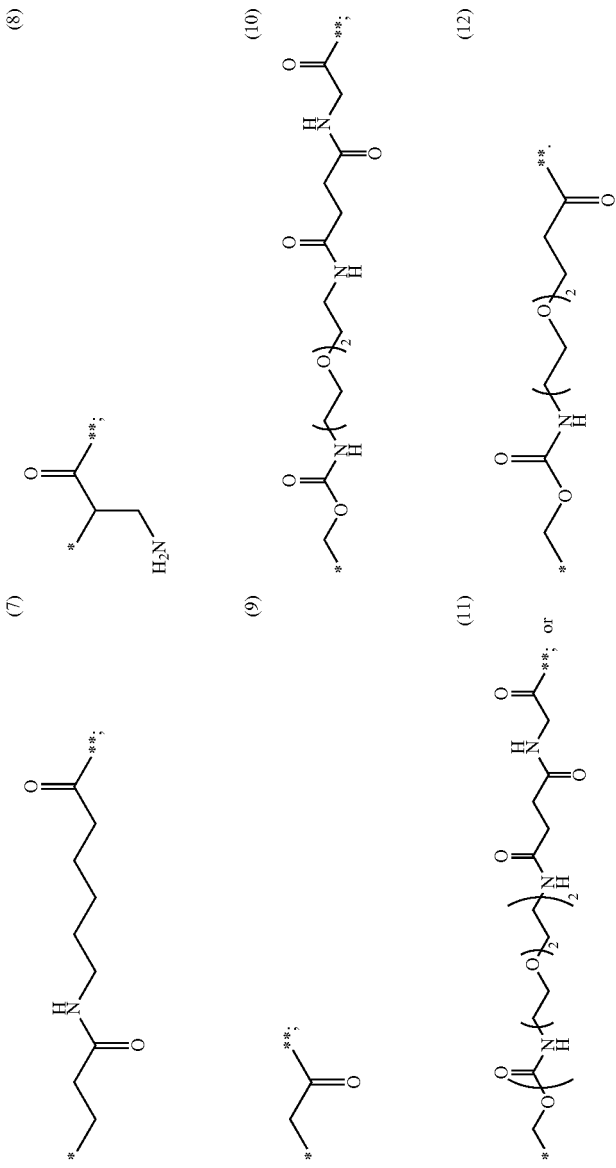

In some embodiments, $M^P$ is

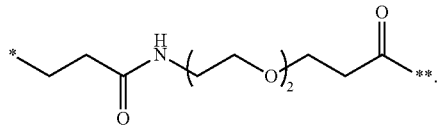

In some embodiments, $M^P$ is

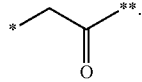

In some embodiments, $M^P$ is:

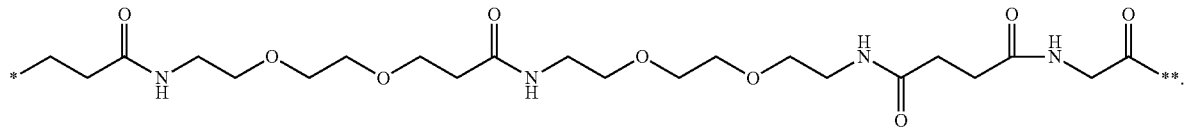

In some embodiments, $M^P$ is:

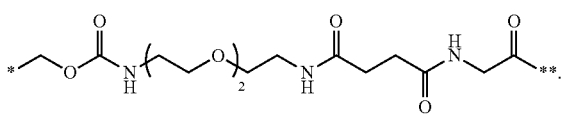

In some embodiments, $M^P$ is:

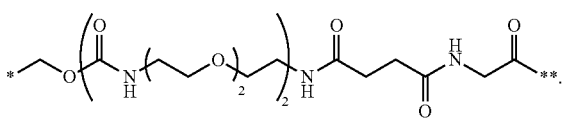

In some embodiments, $M^P$ is

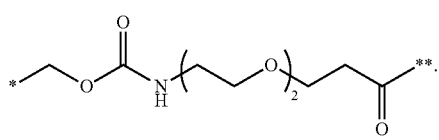

In some embodiments, $M^P$ is:

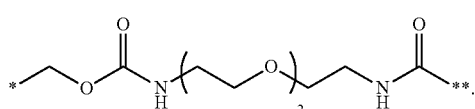

Variable $L^M$ and $W^M$

In some embodiments, $L^M$ is a bond (i.e., a divalent linker or having 2 arms), or a multi-armed linker (e.g., a trivalent or a tetravalent or having 3 or 4 arms), wherein each arm maybe the same or different.

In some embodiments, $L^M$ is a bond (i.e., a divalent linker or having 2 arms) or a multi-armed linker (e.g., a tetravalent or having 4 arms; or a trivalent having 3 arms), wherein each arm maybe the same or different.

It is understood that the term "arm", as used herein, refers to a portion of $L^M$ which is (1) attached to $M^P$ or (2) attached to $L^3$ when present or attached to $M^A$ when $L^3$ is absent;

In some embodiments, $L^M$ is a bond (i.e., a divalent linker or having 2 arms).

In some embodiments, $L^M$ is a multi-armed linker (e.g., a trivalent or a tetravalent or having 3 or 4 arms), wherein each arm maybe the same or different. In some embodiments, $L^M$ is a multi-armed linker (e.g., a trivalent or a tetravalent or having 3 or 4 arms).

In some embodiments, $L^M$ is a trivalent linker having 3 arms, wherein each arm maybe the same or different.

In some embodiments, $L^M$ is a tetravalent linker having 4 arms, wherein each arm maybe the same or different.

In some embodiments, $a_2$ is 2 and $L^M$ is

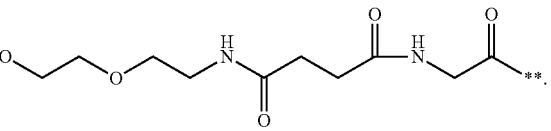

(1)

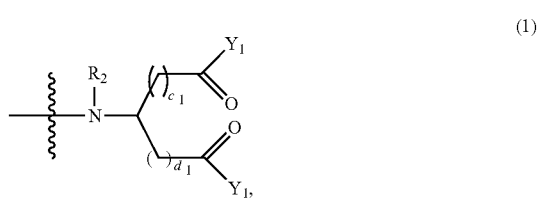

(2)

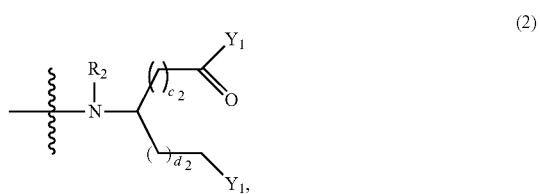

(3)

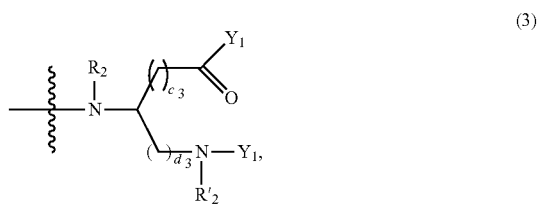

(4)

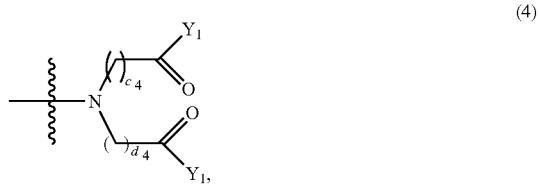

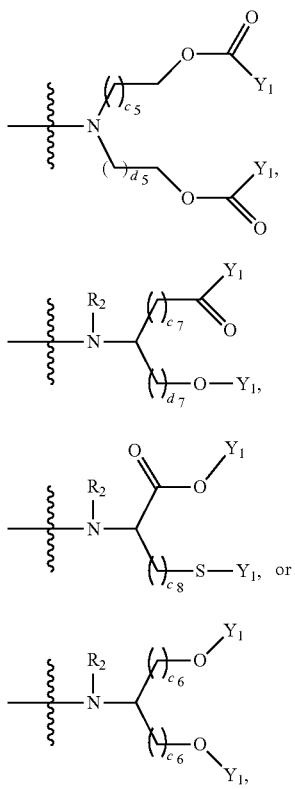

(5)

(6)

(7)

(8)

wherein:

⸹ denotes attachment to $M^P$;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_7$, and $c_8$, when present, is an integer independently ranging between 0 and 10; and each of $d_1$, $d_2$, $d_3$, $d_4$, $d_5$, and $d_7$, when present, is an integer independently ranging between 0 and 10.

In some embodiments, $a_2$ is 2 and $L^M$ is

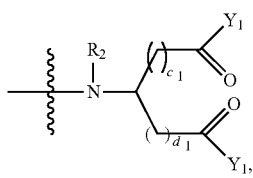

(1)

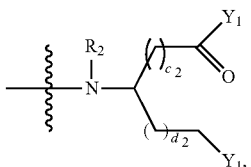

(2)

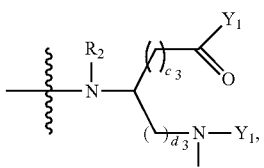

(3)

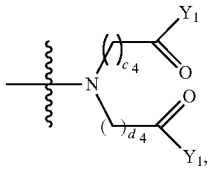

(4)

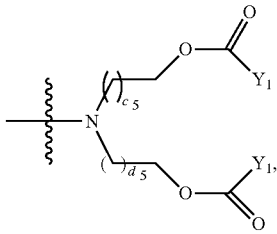

(5)

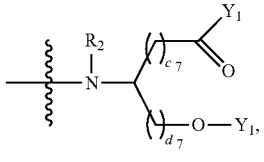

(6)

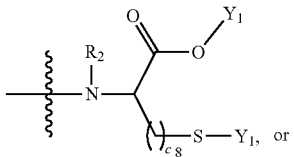

(7)

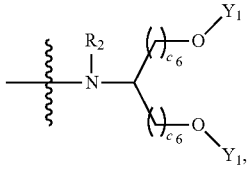

(8)

wherein:

⸹ denotes attachment to $M^P$;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_7$, and $c_8$, when present, is an integer independently ranging between 0 and 10; and each of $d_1$, $d_2$, $d_3$, $d_4$, $d_5$, and $d_7$, when present, is an integer independently ranging between 0 and 10.

In some embodiments, $a_2$ is 2 and $L^M$ is

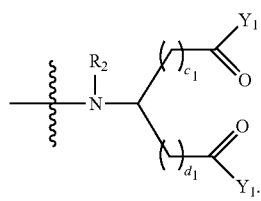

In some embodiments, $a_2$ is 2 and $L^M$ is

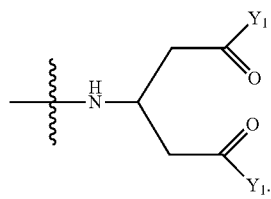

In some embodiments, $c_1$, $c_2$, $c_3$, $c_4$, $c_5$, $c_7$, and $c_8$, when present, are each independently 1, 2, 3, 4, 5, 6, 7, 8, 9, or 10. In some embodiments, $c_1$, $c_2$, $c_3$, $c_4$, $c_5$, $c_7$, and $c_8$ are each independently 0 or 1. In some embodiments, $c_1$, $c_2$, $c_3$, $c_4$, $c_5$, $c_7$, and $c_8$ are each independently 1, 2, 3, 4, 5, 6, 7, 8, 9, or 10. In some embodiments, $c_1$, $c_2$, $c_3$, $c_4$, $c_5$, $c_7$, and $c_8$ are each independently 0, 1 or 2. In some embodiments, $c_1$, $c_2$, $c_3$, $c_4$, $c_5$, $c_7$, and $c_8$ are each independently 0. In some embodiments, $c_1$, $c_2$, $c_3$, $c_4$, $c_5$, $c_7$, and $c_8$ are each independently 1. In some embodiments, $c_1$, $c_2$, $c_3$, $c_4$, $c_5$, $c_7$, and $c_8$ are each independently 2.

In some embodiments, $d_1$, $d_2$, $d_3$, $d_4$, $d_5$, and $d_7$, when present, are each independently 1, 2, 3, 4, 5, 6, 7, 8, 9, or 10. In some embodiments, $d_1$, $d_2$, $d_3$, $d_4$, $d_5$, and $d_7$ are each independently 0 or 1. In some embodiments, $d_1$, $d_2$, $d_3$, $d_4$, $d_5$, and $d_7$ are each independently 1, 2, 3, 4, 5, 6, 7, 8, 9, or 10. In some embodiments, $d_1$, $d_2$, $d_3$, $d_4$, $d_5$, and $d_7$ are each independently 1, 2, 3, or 4. In some embodiments, $d_1$, $d_2$, $d_3$, $d_4$, $d_5$, and $d_7$ are each independently 1. In some embodiments, $d_1$, $d_2$, $d_3$, $d_4$, $d_5$, and $d_7$ are each independently 2. In some embodiments, $d_1$, $d_2$, $d_3$, $d_4$, $d_5$, and $d_7$ are each independently 3. In some embodiments, $d_1$, $d_2$, $d_3$, $d_4$, $d_5$, and $d_7$ are each independently 4.

In some embodiments, $R_2$ and $R'_2$ are each independently hydrogen, $C_{1-6}$ alkyl, $C_{6-10}$ aryl, $C_{3-8}$ cycloalkyl, —COOH, or —COO—$C_{1-6}$ alkyl. In some embodiments, $R_2$ and $R'_2$ are each independently hydrogen or $C_{1-6}$ alkyl. In some embodiments, $R_2$ and $R'_2$ are each independently hydrogen. In some embodiments, $R_2$ and $R'_2$ are each independently $C_{1-6}$ alkyl.

In some embodiments, $L^M$ is:

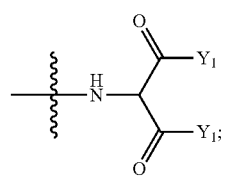

(1)

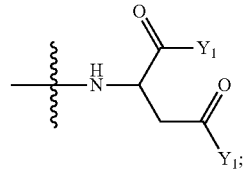

(2)

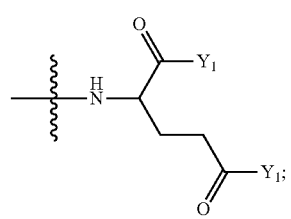

(3)

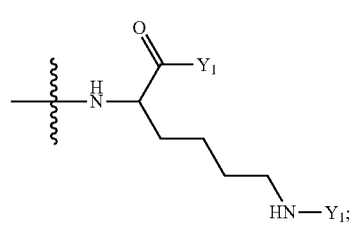

(4)

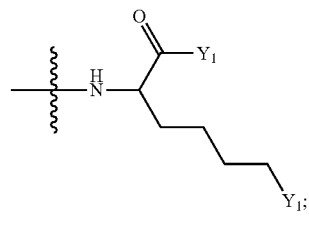

(5)

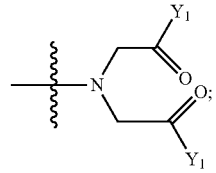

(6)

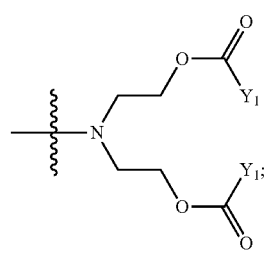

(7)

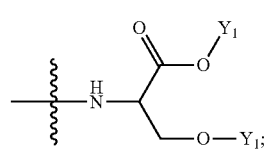

(8)

(9)
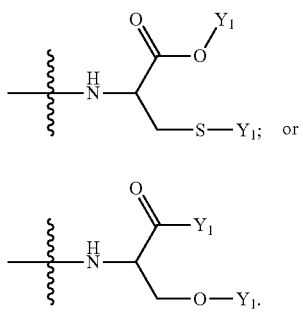
In some embodiments, $a_2$ is 3 and $L^M$ is
(1)
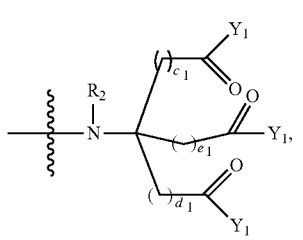
(2)
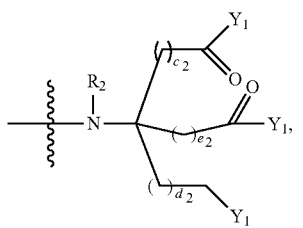
(3)
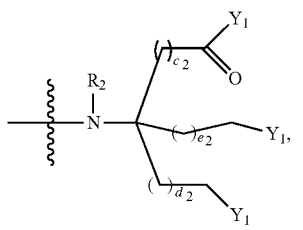
(4)
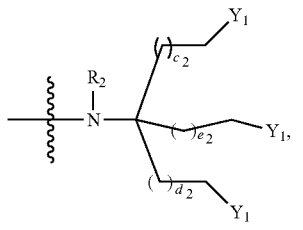
(5)
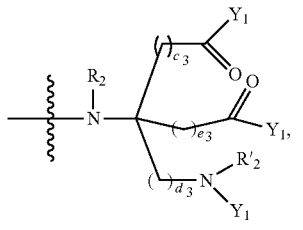
(6)
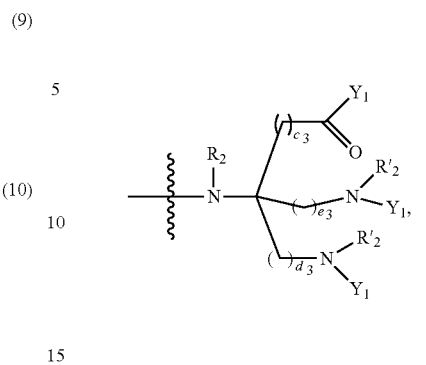
(7)
(8)
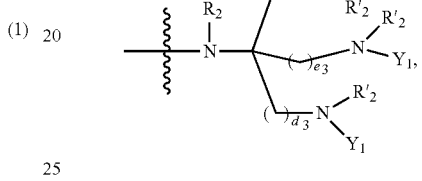
(9)
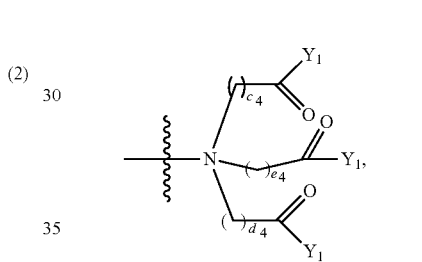
(10)
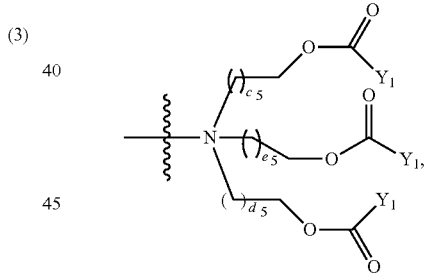
(10)
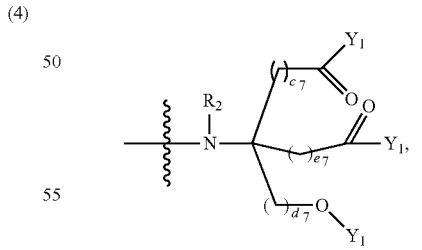
(11)
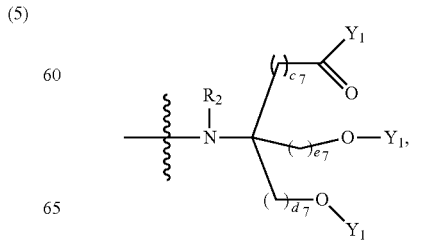

-continued

(12) 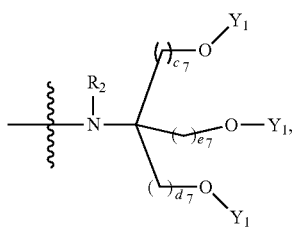

(13) 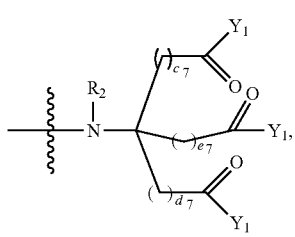

(14) 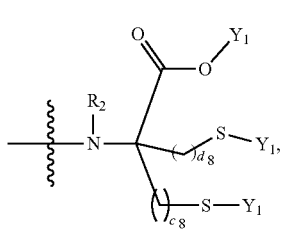

(15) 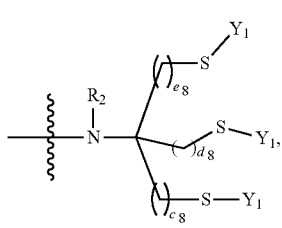

(16) 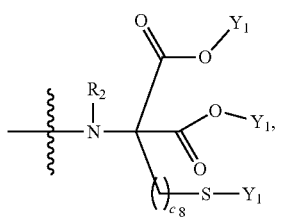

(17) 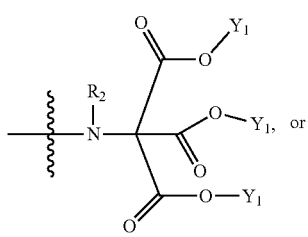

(18) 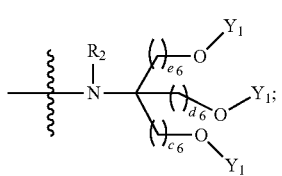

wherein:

⸞ denotes attachment to $M^P$;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_6$, $c_7$, and $c_8$ is an integer independently ranging between 0 and 10;

each of $d_1$, $d_2$, $d_3$, $d_4$, $d_5$, $d_6$, $d_7$ and $d_8$ is an integer independently ranging between 0 and 10; and each of $e_1$, $e_2$, $e_3$, $e_4$, $e_5$, $e_6$, $e_7$, and $e_8$ is an integer independently ranging between 0 and 10.

In some embodiments, $a_2$ is 3 and $L^M$ is

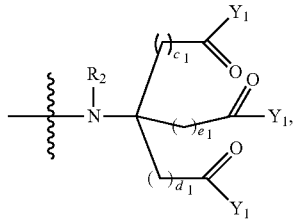 (1)

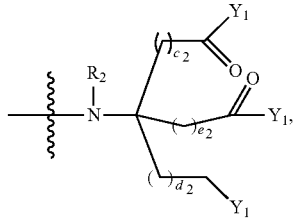 (2)

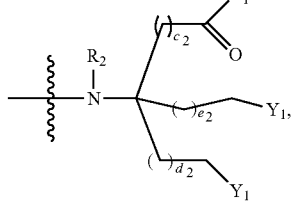 (3)

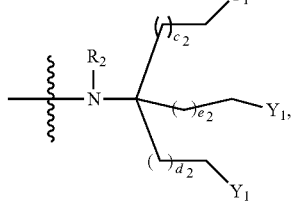 (4)

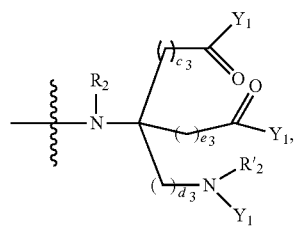
(5)
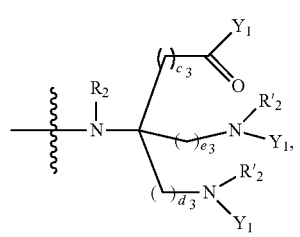
(6)
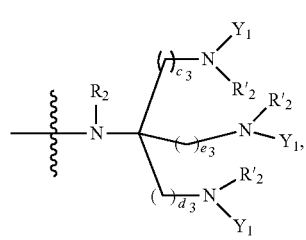
(7)
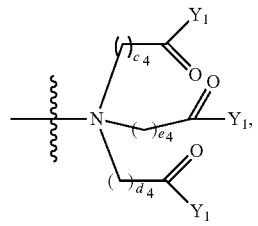
(8)
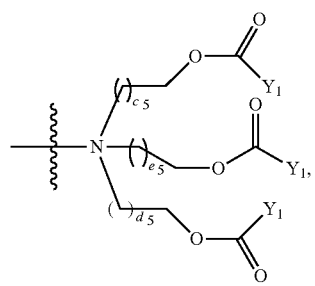
(9)
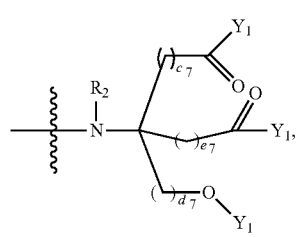
(10)
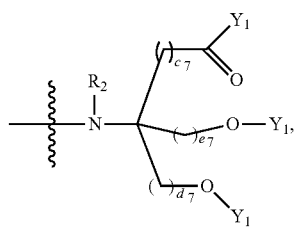
(11)
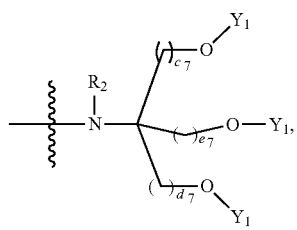
(12)
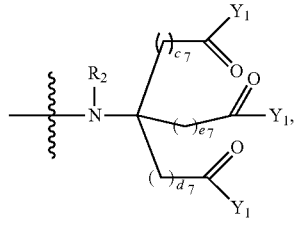
(13)
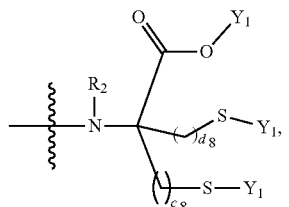
(14)
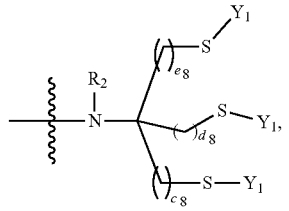
(15)
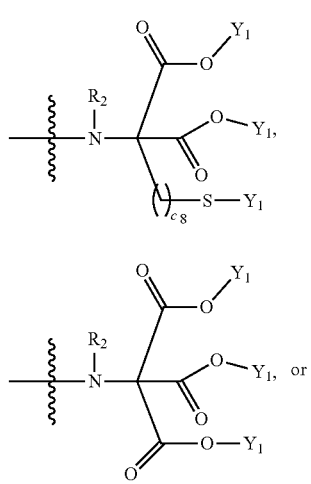
(16)
(17)

-continued

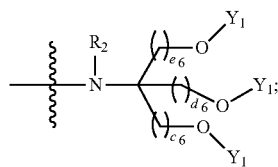

(18)

wherein:

⦃ denotes attachment to $M^P$;

$Y_1$ denotes attachment to $L^3$ when present, or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_6$, $c_7$, and $c_8$ is an integer independently ranging between 0 and 10;

each of $d_1$, $d_2$, $d_3$, $d_4$, $d_5$, $d_6$, $d_7$ and $d_8$ is an integer independently ranging between 0 and 10; and each of $e_1$, $e_2$, $e_3$, $e_4$, $e_5$, $e_6$, $e_7$, and $e_8$ is an integer independently ranging between 0 and 10.

In some embodiments, $a_2$ is 3 and $L^M$ is

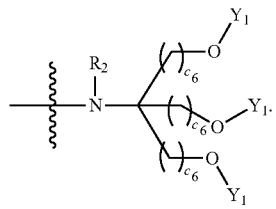

In some embodiments, $a_2$ is 3 and $L^M$ is

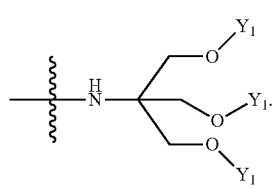

In some embodiments, $-L^M-(L^3)_{a2}-$ is

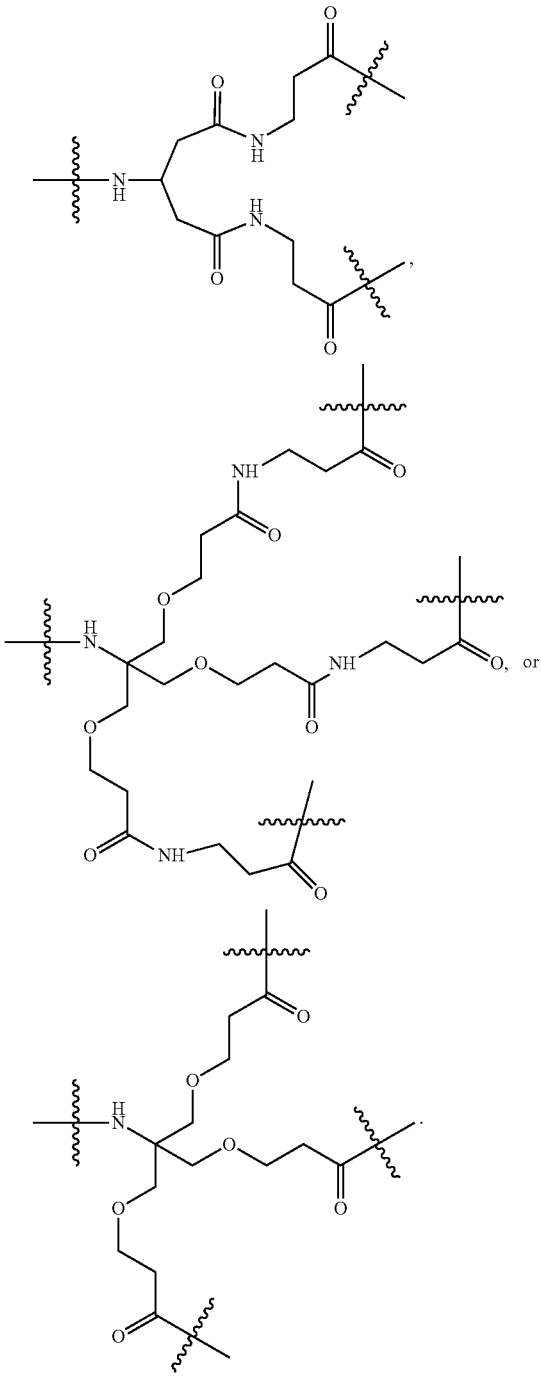 [SMILES: *NC(CC(=O)NCCC(*)=O)CC(=O)NCCC(*)=O ; *NC(COCCC(=O)NCCC(*)=O)(COCCC(=O)NCCC(*)=O)COCCC(=O)NCCC(*)=O ; "or" ; *NC(COCCC(*)=O)(COCCC(*)=O)COCCC(*)=O]

In some embodiments, wherein an amino acid unit has two attachment sites (i.e., a terminal drug unit) one of the attachment sites shown above can be replaced, for example, by H, OH, or a $C_{1-3}$ unsubstituted alkyl group.

In some embodiments, when $L^M$ is a multi-armed linker and not yet connected to the Stretcher unit $M^P$, $W^M$ is a terminus of $L^M$ and each occurrence of $W^M$ independently is hydrogen, a protecting group, a leaving group, or a functional group that is capable of connecting $L^M$ to $M^P$ by forming a covalent bond.

In some embodiments, $W^M$ is an amine protecting group. In some embodiments, $W^M$ is BOC.

In some embodiments, $W^M$ is an amine protecting group and $L^M$ is

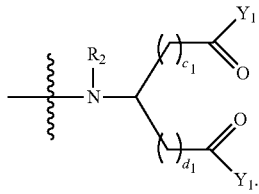

In some embodiments, $W^M$ is an amine protecting group and $L^M$ is

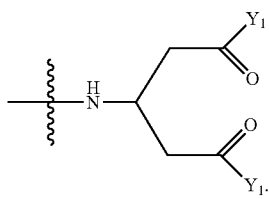

In some embodiments, $W^M$ is BOC, and $L^M$ is

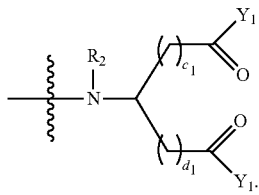

In some embodiments, $W^M$ is an amine protecting group, and $L^M$ is

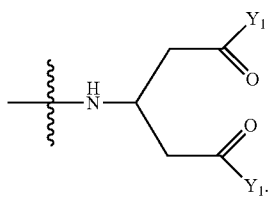

In some embodiments, $W^M$ is BOC, and $L^M$ is

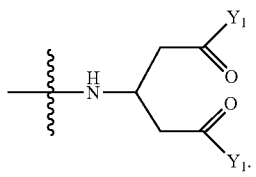

In some embodiments, $W^M$ comprises an amine group. In some embodiments, $W^M$ comprises —C(O)—(CH$_2$)$_w$—NH$_2$, wherein w is an integer from 1 to 6. In some embodiments, $W^M$ is —C(O)—CH$_2$—NH$_2$.

In some embodiments, $W^M$ is —C(O)—CH$_2$—NH$_2$ and $L^M$ is

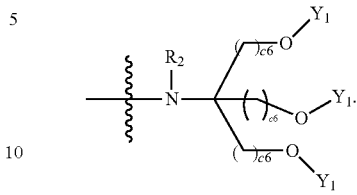

In some embodiments, $W^M$ is —C(O)—CH$_2$—NH$_2$ and $L^M$ is

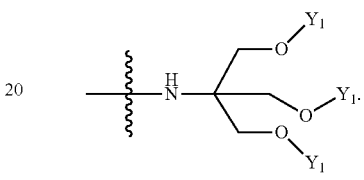

In some embodiments, $W^M$ is H.

Variable $L^3$

In some embodiments, each $L^3$, when present, is a carbonyl-containing moiety.

It is understood that for embodiments of $L^3$, * indicates attachment to another $L^3$ when present, or to $L^M$; and ** indicates attachment to another $L^3$ when present, or to $M^A$.

In some embodiments, each $L^3$, when present, independently is *—C$_{1-12}$ alkyl-C(O)—**, *—NH—C$_{1-12}$ alkyl-C(O)—**, or *—C$_{1-12}$ alkyl-C(O)—NH—C$_{1-12}$ alkyl-C(O)—**.

In some embodiments, at least one $L^3$ is *—C$_{1-12}$ alkyl-C(O)—**.

In some embodiments, at least one $L^3$ is *—CH$_2$CH$_2$—C(O)—**.

In some embodiments, $L^3$ is *—CH$_2$CH$_2$—C(O)—**.

In some embodiments, $(L^3)_{a3}$ is *—CH$_2$CH$_2$—C(O)—**.

In some embodiments, at least one $L^3$ is *—NH—C$_{1-12}$ alkyl-C(O)—**.

In some embodiments, at least one $L^3$ is *—NH—CH$_2$CH$_2$—C(O)—**.

In some embodiments, $L^3$ is *—NH—CH$_2$CH$_2$—C(O)—**.

In some embodiments, $(L^3)_{a3}$ is *—NH—CH$_2$CH$_2$—C(O)—**.

In some embodiments, at least one $L^3$ is *—C$_{1-12}$ alkyl-C(O)—NH—C$_{1-12}$ alkyl-C(O)—**.

In some embodiments, at least one $L^3$ is *—CH$_2$CH$_2$—C(O)—NH—CH$_2$CH$_2$—C(O)—**.

In some embodiments, $L^3$ is *—CH$_2$CH$_2$—C(O)—NH—CH$_2$CH$_2$—C(O)—**.

In some embodiments, $(L^3)_{a3}$ is *—CH$_2$CH$_2$—C(O)—NH—CH$_2$CH$_2$—C(O)—**.

In some embodiments, $a_3$ is 2 or greater, at least one $L^3$ is *—C$_{1-12}$ alkyl-C(O)—**, and at least one $L^3$ is *—NH—C$_{1-12}$ alkyl-C(O)—**.

In some embodiments, $(L^3)_{a3}$ is *—CH$_2$CH$_2$—C(O)—NH—CH$_2$CH$_2$—C(O)—**.

In some embodiments, $(L^3)_{a3}$ is *NH—CH$_2$CH$_2$—C(O)—CH$_2$CH$_2$—C(O)—**.

Variable $M^A$

In some embodiments, $M^A$ is a linker moiety that is capable of connecting one or more drugs and one or more hydrophilic groups to $L^P$ or $L^{P'}$. In some embodiments, $M^A$ comprises a peptide moiety of at least two amino acids. In some embodiments, amino acid is referred to herein as "AA" and amino acids as "AA's".

In some embodiments, the peptide moiety is a moiety that is capable of forming a covalent bond with a -$L^D$-D unit and allows for the attachment of multiple drugs. In some embodiments, the peptide moiety comprises a single AA unit or has two or more AA units (e.g., from 2 to 10, from 2 to 6, or 2, 3, 4, 5 or 6) wherein the AA units are each independently a natural or non-natural amino acid, an amino alcohol, an amino aldehyde, a diamine, a polyamine, or combinations thereof. In some embodiments, in order to have the requisite number of attachments, at least one of the AA units will have a functionalized side chain to provide for attachment of the -$L^D$-D unit. In some embodiments, exemplary functionalized AA units (e.g., amino acids, amino alcohols, or amino aldehydes) include, for example, azido or alkyne functionalized AA units (e.g., amino acid, amino alcohol, or amino aldehyde modified to have an azide group or alkyne group). In some embodiments, the azide group or alkyne group is for attachment using click chemistry.

In some embodiments, the peptide moiety has 2 to 12 AA units. In some embodiments, the peptide moiety has 2 to 10 AA units. In some embodiments, the peptide moiety has 2 to 6 AA units. In some embodiments, the peptide moiety has 2, 3, 4, 5 or 6 AA units.

In some embodiments, the peptide moiety has 2 AA units. In some embodiments, the peptide moiety has 3 AA units. In some embodiments, the peptide moiety has 4 AA units. In some embodiments, the peptide moiety has 5 AA units. In some embodiments, the peptide moiety has 6 AA units.

In some embodiments, attachment within the peptide moiety or with the other components of the conjugate, intermediate thereof, or scaffold, can be, for example, via amino, carboxy, or other functionalities. In some embodiments, each amino acid of the peptide moiety can be independently D or L isomer of a thiol containing amino acid. In some embodiments, each amino acid of the peptide moiety can be independently a D isomer of a thiol containing amino acid. In some embodiments, each amino acid of the peptide moiety can be independently an L isomer of a thiol containing amino acid. In some embodiments, the thiol containing amino acid can be, for example, cysteine, homocysteine, or penicillamine.

In some embodiments, each amino acid that comprises the peptide moiety can be independently the L or D isomer of the following amino acids: alanine (including β-alanine), arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, stereoisomers thereof, or derivatives thereof.

In some embodiments, each amino acid that comprises the peptide moiety is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, alanine, or a stereoisomers thereof.

In some embodiments, the peptide moiety comprises a monopeptide, a dipeptide, tripeptide, tetrapeptide, or pentapeptide. In some embodiments, the peptide moiety comprises a pentapeptide.

In some embodiments, the peptide moiety comprises at least about five amino acids (e.g., 5, 6, 7, 8, 9, or 10 amino acids). In some embodiments, the peptide moiety comprises at most about ten amino acids.

In some embodiments, each amino acid that comprises the peptide moiety independently is glycine, serine, glutamic acid, lysine, aspartic acid, and cysteine.

In some embodiments, the peptide moiety comprises at least four glycines and at least one serine, e.g., (glycine)$_4$ and serine wherein the serine is at any position along the peptide chain, such as, for example, (serine)-(glycine)$_4$; (glycine)-(serine)-(glycine)$_3$; (glycine)$_2$-(serine)-(glycine)$_2$; (glycine)$_3$-(serine)-(glycine); or (glycine)$_4$-(serine).

In some embodiments, the peptide moiety comprises (glycine)$_4$-(serine) or (serine)-(glycine)$_4$. In some embodiments, the peptide moiety comprises (glycine)$_4$-(serine). In some embodiments, the peptide moiety comprises (serine)-(glycine)$_4$.

In some embodiments, the peptide moiety comprises at least four glycines and at least one glutamic acid e.g., (glycine)$_4$ and glutamic acid, wherein the glutamic acid is at any position along the peptide chain.

In some embodiments, the peptide moiety comprises (glutamic acid)-(glycine)$_4$ or (glycine)$_4$-(glutamic acid).

In some embodiments, the peptide moiety comprises (β-alanine)-(glycine)$_4$-(serine) wherein the serine is at any position along the peptide chain.

In some embodiments, the peptide moiety comprises (glycine)$_4$-(serine)-(glutamic acid) wherein the serine is at any position along the peptide chain. In some embodiments, the peptide moiety comprises (β-alanine)-(glycine)$_4$-(serine)-(glutamic acid) wherein the serine is at any position along the peptide chain.

In some embodiments, the peptide moiety comprises (glycine)$_{1-4}$-(serine), wherein:
the peptide moiety is attached to $L^3$ when present, or to $L^M$ when $L^3$ is absent, via one of the glycine; the peptide moiety is attached to $T^1$ when present, via the serine; and the peptide moiety is attached to $L^D$ when present, via the serine.

In some embodiments, the peptide moiety comprises (serine)-(glycine)$_{1-4}$, wherein: the peptide moiety is attached to $L^3$ when present, or to $L^M$ when $L^3$ is absent, via the serine; the peptide moiety is attached to $T^1$ when present, via the glycine; and the peptide moiety is attached to $L^D$ when present, via the serine.

It is understood that for embodiments of the peptide moiety, * indicates attachment to $L^3$ when present, or to $L^M$ when $L^3$ is absent. In some embodiments,  indicates attachment to $T^1$ when present, or —OH when $T^1$ is absent. In some embodiments, * indicates attachment to $L^D$ when present, or hydrogen when $L^D$ is absent.

In some embodiments, the peptide moiety comprises

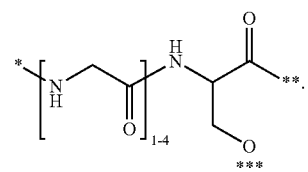

In some embodiments, the peptide moiety comprises (glycine)-(serine), wherein:
the peptide moiety is attached to $L^3$ when present, or to $L^M$ when $L^3$ is absent, via the glycine; the peptide moiety is attached to $T^1$ when present, via the serine; and the peptide moiety is attached to $L^D$ when present, via the serine.

In some embodiments, the peptide moiety comprises (glycine)-(serine), wherein: the peptide moiety is attached to $L^3$ when present, or to $L^M$ when $L^3$ is absent, via the serine; the peptide moiety is attached to $T^1$ when present, via the glycine; and the peptide moiety is attached to $L^D$ when present, via the serine.

In some embodiments, the peptide moiety comprises

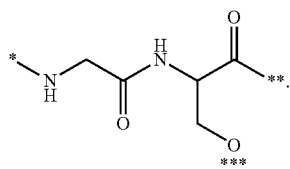

In some embodiments, the peptide moiety comprises (glycine)$_4$-(serine), wherein:
the peptide moiety is attached to $L^3$ when present, or to $L^M$ when $L^3$ is absent, via one of the glycine; the peptide moiety is attached to $T^1$ when present, via the serine; and the peptide moiety is attached to $L^D$ when present, via the serine. In some embodiments, the peptide moiety comprises

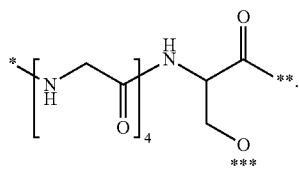

In some embodiments, the peptide moiety comprises (serine)-(glycine)$_{1-4}$, wherein:
the peptide moiety is attached to $L^3$ when present, or to $L^M$ when $L^3$ is absent, via the serine; the peptide moiety is attached to $T^1$ when present, via one of the glycine; and the peptide moiety is attached to $L^D$ when present, via the serine.

In some embodiments, the peptide moiety comprises

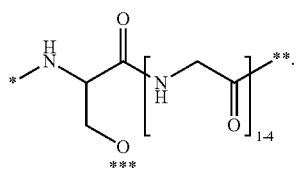

In some embodiments, the peptide moiety comprises (serine)-(glycine)-4, wherein:
the peptide moiety is attached to $L^3$ when present, or to $L^M$ when $L^3$ is absent, via the serine; the peptide moiety is attached to $T^1$ when present, via one of the glycine; and the peptide moiety is attached to $L^D$ when present, via the serine.

In some embodiments, the peptide moiety comprises

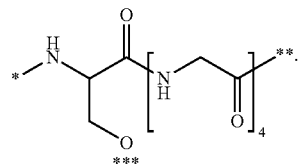

In some embodiments, the peptide moiety comprises (β-alanine)-(glycine)$_{1-4}$-(serine), wherein:
the peptide moiety is attached to $L^3$ when present, or to $L^M$ when $L^3$ is absent, via the β-alanine; the peptide moiety is attached to $T^1$ when present, via the serine; and the peptide moiety is attached to $L^D$ when present, via the serine.

In some embodiments, the peptide moiety comprises

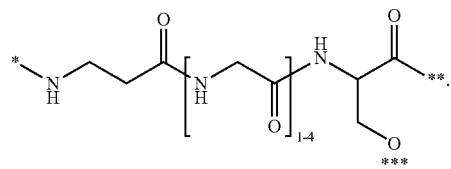

In some embodiments, the peptide moiety comprises (β-alanine)-(glycine)$_4$-(serine), wherein:
the peptide moiety is attached to $L^3$ when present, or to $L^M$ when $L^3$ is absent, via the β-alanine; the peptide moiety is attached to $T^1$ when present, via the serine; and the peptide moiety is attached to $L^D$ when present, via the serine.

In some embodiments, the peptide moiety comprises

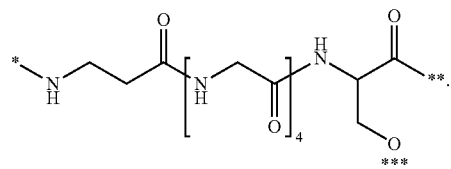

In some embodiments, the peptide moiety comprises (glycine)$_{1-4}$-(glutamic acid), wherein:
the peptide moiety is attached to $L^3$ when present, or to $L^M$ when $L^3$ is absent, via one of the glycine; the peptide moiety is attached to $T^1$ when present, via the glutamic acid; and the peptide moiety is attached to $L^D$ when present, via the glutamic acid.

In some embodiments, the peptide moiety comprises

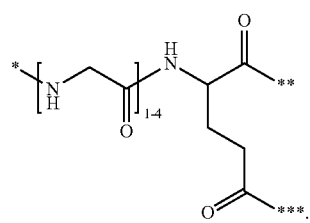

In some embodiments, the peptide moiety comprises (glycine)-(glutamic acid), wherein:
the peptide moiety is attached to $L^3$ when present, or to $L^M$ when $L^3$ is absent, via the glycine; the peptide moiety is attached to T¹ when present, via the glutamic acid; and the peptide moiety is attached to $L^D$ when present, via the glutamic acid.

In some embodiments, the peptide moiety comprises

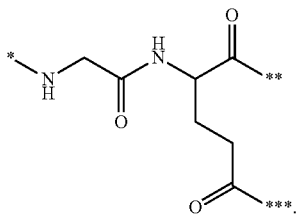

In some embodiments, the peptide moiety comprises (glycine)$_4$-(glutamic acid), wherein:

the peptide moiety is attached to $L^3$ when present, or to $L^M$ when $L^3$ is absent, via one of the glycine; the peptide moiety is attached to T¹ when present, via the glutamic acid; and the peptide moiety is attached to $L^D$ when present, via the glutamic acid.

In some embodiments, the peptide moiety comprises

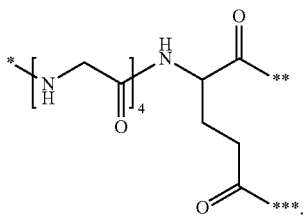

In some embodiments, the peptide moiety comprises (glutamic acid)-(glycine)$_{1-4}$, wherein:

the peptide moiety is attached to $L^3$ when present, or to $L^M$ when $L^3$ is absent, via the glutamic acid; the peptide moiety is attached to T¹ when present, via one of the glycine; and the peptide moiety is attached to $L^D$ when present, via the glutamic acid.

In some embodiments, the peptide moiety comprises

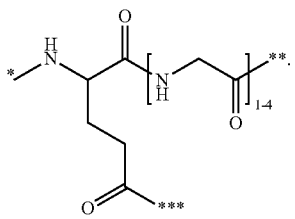

In some embodiments, the peptide moiety comprises (glutamic acid)-(glycine)$_4$, wherein:

the peptide moiety is attached to $L^3$ when present, or to $L^M$ when $L^3$ is absent, via the glutamic acid; the peptide moiety is attached to T¹ when present, via one of the glycine; and the peptide moiety is attached to $L^D$ when present, via the glutamic acid.

In some embodiments, the peptide moiety comprises

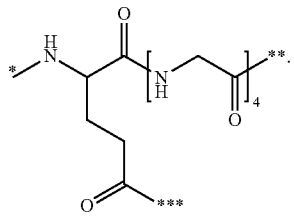

In some embodiments, the peptide moiety comprises (glutamic acid)-(glycine), wherein:

the peptide moiety is attached to $L^3$ when present, or to $L^M$ when $L^3$ is absent, via the glutamic acid; the peptide moiety is attached to T¹ when present, via one of the glycine; and the peptide moiety is attached to $L^D$ when present, via the glutamic acid.

In some embodiments, the peptide moiety comprises

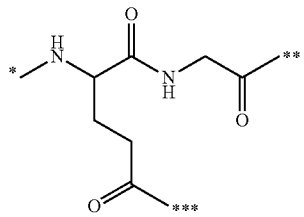

In some embodiments, the peptide moiety comprises (β-alanine)-(glycine)$_{1-4}$-(glutamic acid), wherein:

the peptide moiety is attached to $L^3$ when present, or to $L^M$ when $L^3$ is absent, via the 0-alanine; the peptide moiety is attached to T¹ when present, via the glutamic acid; and the peptide moiety is attached to $L^D$ when present, via the glutamic acid.

In some embodiments, the peptide moiety comprises

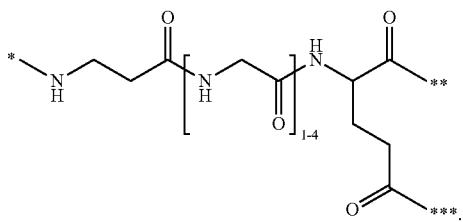

In some embodiments, the peptide moiety comprises (β-alanine)-(glycine)$_4$-(glutamic acid), wherein:

the peptide moiety is attached to $L^3$ when present, or to $L^M$ when $L^3$ is absent, via the β-alanine; the peptide moiety is attached to T¹ when present, via the glutamic acid; and the peptide moiety is attached to $L^D$ when present, via the glutamic acid.

In some embodiments, the peptide moiety comprises

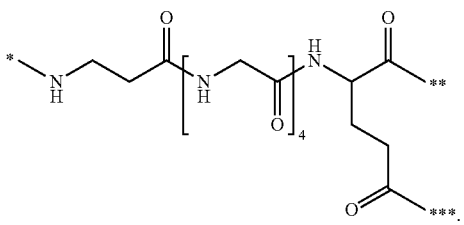

In some embodiments, the peptide moiety comprises (β-alanine)-(glycine)-(glutamic acid), wherein:
the peptide moiety is attached to $L^3$ when present, or to $L^M$ when $L^3$ is absent, via the β-alanine; the peptide moiety is attached to $T^1$ when present, via the glutamic acid; and the peptide moiety is attached to $L^D$ when present, via the glutamic acid.

In some embodiments, the peptide moiety comprises

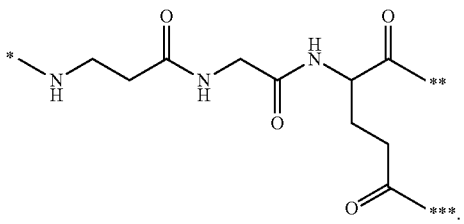 [SMILES: CNCCC(=O)NCC(=O)NC(CCC(C)=O)C(C)=O]

Variable $L^D$ and $W^D$

In some embodiments, each occurrence of $L^D$ is independently a divalent linker moiety connecting D to $M^A$ and comprises at least one cleavable bond such that when the bond is cleaved, D is released in an active form for its intended therapeutic effect.

In some embodiments, $L^D$ is a component of the Releasable Assembly Unit. In some embodiments, $L^D$ is the Releasable Assembly Unit. In some embodiments, $L^D$ comprises one cleavable bond. In some embodiments, $L^D$ comprises multiple cleavage sites or bonds.

In some embodiments, functional groups for forming a cleavable bond can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds. In some embodiments, $L^D$ comprises a disulfide bond that is cleavable through disulfide exchange, an acid-labile bond that is cleavable at acidic pH, and/or bonds that are cleavable by hydrolases. In some embodiments, $L^D$ comprises a carbamate bond (i.e., —O—C(O)—NR—, wherein R is hydrogen or alkyl or the like).

In some embodiments, the structure and sequence of the cleavable bond in $L^D$ can be such that the bond is cleaved by the action of enzymes present at the target site. In some embodiments, the cleavable bond can be cleavable by other mechanisms.

In some embodiments, the structure and sequence of the cleavable bonds in $L^D$ can be such that the bonds are cleaved by the action of enzymes present at the target site. In some embodiments, the cleavable bonds can be cleavable by other mechanisms.

In some embodiments, the cleavable bond(s) can be enzymatically cleaved by one or more enzymes, including a tumor-associated protease, to liberate the Drug unit or D, wherein the conjugate of the present disclosure, or intermediate, or scaffold thereof, is protonated in vivo upon release to provide a Drug unit or D.

In some embodiments, $L^D$ can comprise one or more amino acids. In some embodiments, each amino acid in $L^D$ can be natural or unnatural and/or a D or L isomer, provided that there is a cleavable bond. In some embodiments, $L^D$ comprises an alpha, beta, or gamma amino acid that can be natural or non-natural. In some embodiments, $L^D$ comprises 1 to 12 (e.g., 1 to 6, or 1 to 4, or 1 to 3, or 1, 2, 3, 4, 5, 6, 7, 8, 9, 10, 11, or 12) amino acids in contiguous sequence.

In some embodiments, $L^D$ can comprise natural amino acids. In some embodiments, $L^D$ can comprise non-natural amino acids. In some embodiments, $L^D$ does not comprise natural amino acids. In some embodiments, $L^D$ does not comprise non-natural amino acids. In some embodiments, $L^D$ can comprise a natural amino acid linked to a non-natural amino acid. In some embodiments, $L^D$ can comprise a natural amino acid linked to a D-isomer of a natural amino acid. In some embodiments, $L^D$ comprises a dipeptide such as -Val-Cit-, -Phe-Lys-, or -Val-Ala-.

In some embodiments, $L^D$ comprises a monopeptide, a dipeptide, a tripeptide, a tetrapeptide, a pentapeptide, a hexapeptide, a heptapeptide, an octapeptide, a nonapeptide, a decapeptide, an undecapeptide, or a dodecapeptide unit.

In some embodiments, $L^D$ comprises a peptide (e.g., of 1 to 12 amino acids), which is conjugated directly to the drug unit. In some such embodiments, the peptide is a single amino acid. In some such embodiments, the peptide is a dipeptide.

In some embodiments, each amino acid in $L^D$ is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, each amino acid is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, citrulline, and derivatives thereof.

In some embodiments, each amino acid is selected from the proteinogenic and the non-proteinogenic amino acids.

In some embodiments, each amino acid in $L^D$ can be independently selected from L or D isomers of the following amino acids: alanine, β-alanine, arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, valine, citrulline, and derivatives thereof.

In some embodiments, each amino acid in $L^D$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, citrulline, or alanine.

In some embodiments, each amino acid in $L^D$ is independently selected from L-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $L^D$ is independently selected from D-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $L^D$ is alanine, β-alanine, glutamine, glutamic acid, isoglutamic acid, isoaspartic acid, valine citrulline, or aspartic acid.

In some embodiments, $L^D$ comprises β-alanine. In some embodiments, $L^D$ comprises (β-alanine)-(alanine). In some embodiments, $L^D$ comprises (β-alanine) and optionally alanine, glutamic acid, glutamine, isoglutamic acid, aspartic acid, isoaspartic acid, valine, (valine)-(alanine), (alanine)-(alanine), or (valine)-(citruline).

In some embodiments, $L^D$ comprises (glutamic acid)-(alanine).

In some embodiments, $L^D$ comprises (β-alanine)-(glutamine).

In some embodiments, $L^D$ comprises (β-alanine)-(glutamine))-(alanine).

In some embodiments, $L^D$ comprises glutamic acid and optionally alanine, glycine, isoglutamic acid, aspartic acid, isoaspartic acid, valine, (valine)-(alanine), (alanine)-(alanine), or (valine)-(citruline).

In some embodiments, $L^D$ comprises 2,3-diaminopropanoic acid. In some embodiments, $W_w$ comprises (R)-2,3-diaminopropanoic acid. In some embodiments, $W_w$ comprises glutamic acid. In some embodiments, $W_w$ comprises (glutamic acid)-(alanine). In some embodiments, $L^D$ comprises (glutamic acid)-(glycine)-(alanine).

In some embodiments, $L^D$ comprises L-glutamic acid, D-glutamic acid, (L-glutamic acid)-(L-alanine), (L-glutamic acid)-(D-alanine), (D-glutamic acid)-(L-alanine), (D-glutamic acid)-(D-alanine), (L-glutamic acid)-(glycine)-(L-alanine), D-glutamic acid)-(glycine)-(D-alanine), (L-glutamic acid)-(glycine)-(D-alanine), or (D-glutamic acid)-(glycine)-(L-alanine). In some embodiments, $L^D$ comprises a carbamate bond in addition to one or more amino acids.

In some embodiments, $L^D$ can be designed and optimized in selectivity for enzymatic cleavage by a particular enzyme. In some embodiments, the particular enzyme is a tumor-associated protease. In some embodiments, $L^D$ comprises a bond whose cleavage is catalyzed by cathepsin B, C, and D, or a plasmin protease.

In some embodiments, $L^D$ comprises a sugar cleavage site. In some embodiments, $L^D$ comprises a sugar moiety (Su) linked via an oxygen glycosidic bond to a self-immolative group. In some embodiments, a "self-immolative group" can be a tri-functional chemical moiety that is capable of covalently linking together three spaced chemical moieties (i.e., the sugar moiety (via a glycosidic bond), a drug unit (directly or indirectly), and $M^A$ (directly or indirectly). In some embodiments, the glycosidic bond can be cleaved at the target site to initiate a self-immolative reaction sequence that leads to a release of the drug.

Therapeutic Agents, Drug Unit, or D

In some embodiments, the therapeutic agent is a small molecule having a molecular weight ≤about 5 kDa (e.g., having a molecular weight ≤about 4 kDa, ≤about 3 kDa, ≤about 1.5 kDa, or ≤about 1 kDa).

In some embodiments, the therapeutic agent has an $IC_{50}$ of about less than 1 nM. In some embodiments, the therapeutic agent has an $IC_{50}$ of less than 1 nM.

In some embodiments, the therapeutic agent has an $IC_{50}$ of about greater than 1 nM, (e.g., the therapeutic agent has an $IC_{50}$ of about 1 to 50 nM). In some embodiments, the therapeutic agent has an $IC_{50}$ of about greater than 1 nM. In some embodiments, the therapeutic agent has an $IC_{50}$ of greater than 1 nM, (e.g., the therapeutic agent has an $IC_{50}$ of 1 to 50 nM). In some embodiments, the therapeutic agent has an $IC_{50}$ of greater than 1 nM.

In some embodiments, some therapeutic agents having an $IC_{50}$ of greater than about 1 nM (e.g., "less potent drugs") are unsuitable for conjugation with an antibody using art-recognized conjugation techniques. Without wishing to be bound by theory, such therapeutic agents have a potency that is insufficient for use in targeted antibody-drug conjugates using conventional techniques as sufficient copies of the drug (i.e., more than 8) cannot be conjugated using art-recognized techniques without resulting in diminished pharmacokinetic and physiochemical properties of the conjugate. In some embodiments, sufficiently high loadings of these less potent drugs can be achieved using the conjugation strategies described herein thereby resulting in high loadings of the therapeutic agent while maintaining the desirable pharmacokinetic and physiochemical properties. In some embodiments, the disclosure relates to an antibody-drug conjugate which includes an antibody, a scaffold, and at least eight therapeutic agent moieties, wherein the therapeutic agent has an $IC_{50}$ of greater than about 1 nM.

In some embodiments, the drug is a derivative of (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase; (q) a PARP inhibitor; (r) a NAMPT inhibitor; (s) a topoisomerase inhibitor; (t) a protein synthesis inhibitor; (u) a DNA-binding drug; (v) a DNA intercalation drug; or (w) an immunomodulatory compound, as described in US 2018/0154018, the contents of which is hereby incorporated by reference in its entireties In some embodiments, the drug used in the disclosure is auristatin F-hydroxypropylamide-L-alanine.

In some embodiments the auristatin is a compound of Formula (X):

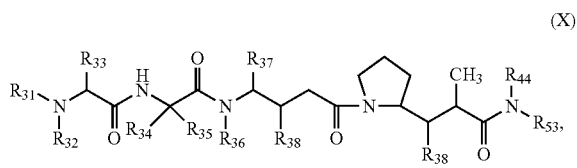

wherein:
each of $R_{31}$ and $R_{32}$ independently is hydrogen or $C_{1-8}$ alkyl and at most one of $R_{31}$ and $R_{32}$ is H;

$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle, or $X^1$—($C_{3-8}$ heterocycle);

$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle, or $X^1$—($C_{3-8}$ heterocycle);

$R_{35}$ is hydrogen or methyl;

or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;

$R_{36}$ is hydrogen or $C_{1-8}$ alkyl;

$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);

each $R_{38}$ independently is hydrogen, OH, $C_{1-8}$ alkyl, $C_{3-8}$ carbocycle or O—($C_{1-8}$ alkyl);

$R_{53}$ is:

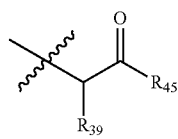

or $R_{54}$;

$R_{39}$ is hydrogen, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$;

each $X^1$ independently is $C_{1-10}$ alkylene or $C_{3-10}$ cycloalkylene;

$R_{44}$ is hydrogen or $C_{1-8}$ alkyl;

$R_{45}$ is $X^3$—$R_{42}$ or NH—$R_{19}$;

$X^3$ is O or S;

$R_{19}$ is hydrogen, OH, amino group, $C_{1-8}$ alkyl amino, or —$[C(R_{20}R_{21})]_a$—$R_{22}$;

$R_{42}$ is an amino group, $C_{1-6}$ alkyl amino, or —$[C(R_{20}R_{21})]_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

$R_{22}$ is —OH, —$NHR_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(O CH$_2$—CH$_2$)$_f$—N(H)(R$_{23}$) or —$R_{82}$—(C(O)—CH(X$^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

$R_{54}$ is —$C(R_{56})_2$—$C(R_{56})_2$—$C_{6-10}$ aryl, —$C(R_{56})_2$—$C(R_{56})_2$—$C_{3-8}$ heterocycle, or —$C(R_{56})_2$—$C(R_{56})_2$—$C_{3-8}$ carbocycle;

$R_{56}$ independently is H, OH, $C_{1-8}$ alkyl, $C_{3-8}$ carbocycle, —O—$C_{1-8}$ alkyl, —O—C(O)—$R_{29}$, or —O—$R_{23}$—O—$C_{1-6}$ alkyl-$NH_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$[C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments, in the auristatin compound of Formula (X):

$R_{39}$ is benzyl or

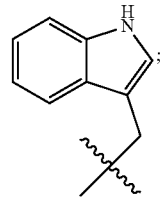 [SMILES: *Cc1c[nH]c2ccccc12]

and $R_{44}$ is hydrogen.

In some embodiments the auristatin is a compound of Formula (Xa):

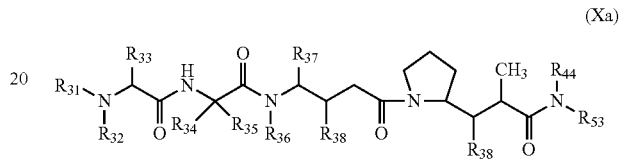

(Xa)

wherein:

$R_{33}$ through $R_{38}$, and $R_{44}$ are as defined herein, one of $R_{31}$ and $R_{32}$ is hydrogen or $C_{1-8}$ alkyl and the other is:

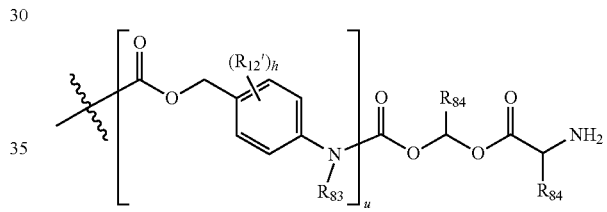

wherein:

$R_{83}$ is hydrogen or $CH_3$;

$R_{84}$ is $C_{1-6}$ alkyl or $C_{6-10}$ aryl;

each $R_{12}'$ independently is halogen, —$C_{1-8}$ alkyl, —O—$C_{1-8}$ alkyl, nitro, or cyano;

h is an integer from 0 to 4;

u is an integer 0 or 1;

$R_{53}$ is:

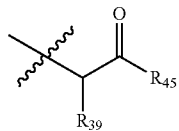

$R_{39}$ or $R_{54}$ $R_{39}$ is hydrogen, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$, each $X^1$ independently is $C_{1-10}$ alkylene or $C_{3-10}$ cycloalkylene;

$R_{45}$ is $X^3$—$R_{42}$ or NH—$R_{19}$;

$X^3$ is O or S;

$R_{19}$ is hydrogen, OH, amino group, $C_{1-8}$ alkyl amino, or —$[C(R_{20}R_{21})]_a$—$R_{22}$;

$R_{42}$ is hydrogen, an amino group, $C_{1-6}$ alkyl amino, or —$[C(R_{20}R_{21})]_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

$R_{22}$ is —OH, —$NHR_{23}$, —COOH, —$R_{82}$—C(O) $(CH_2)_c$—C(H)($R_{23}$)—N(H)($R_{23}$), —$R_{82}$—C(O)($CH_2)_d$— (O—$CH_2$—$CH_2)_f$—N(H)($R_{23}$), or —$R_{82}$—(C(O)—CH $(X^2)$—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

$R_{54}$ is —$C(R_{56})_2$—$C(R_{56})_2$—$C_{6-10}$ aryl, —$C(R_{56})_2$—C $(R_{56})_2$—$C_{3-8}$ heterocycle, or —$C(R_{56})_2$—$C(R_{56})_2$—$C_{3-8}$ carbocycle;

$R_{56}$ independently is hydrogen, OH, $C_{1-8}$ alkyl, $C_{3-8}$ carbocycle, —O—$C_{1-8}$ alkyl, —O—C(O)—$R_{29}$, or —O—$R_{23}$—O—$C_{1-6}$ alkyl-$NH_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —[C($R_{20}R_{21}$)]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments, the auristatin compound of Formula (Xa) is a compound of Formula (XIa) or Formula (XIb):

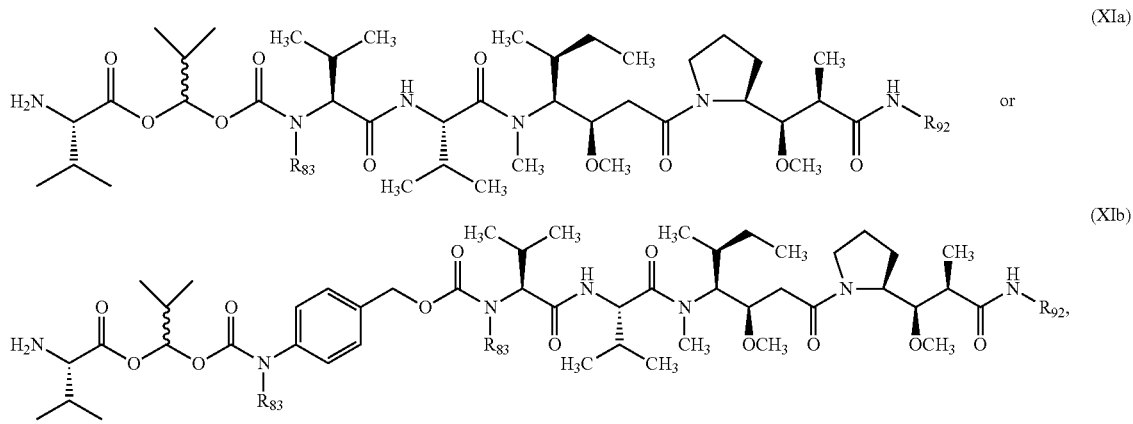

(XIa)

(XIb)

wherein:

$R_{92}$ is:

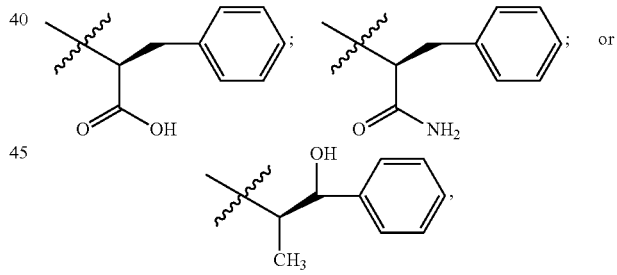

and $R_{83}$ is hydrogen or $CH_3$.

In some embodiments, the auristatin of Formula (X) is a compound of Formula (XI), Formula (XII), or Formula (XIII):

wherein the compound of Formula (XI) is:

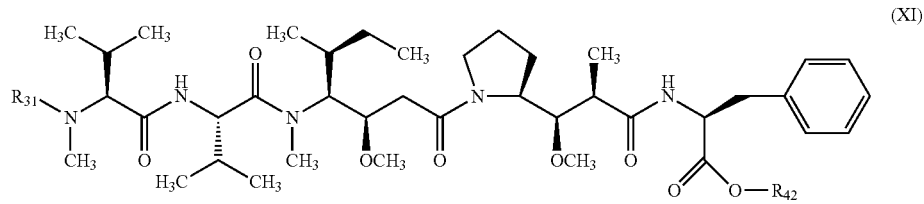

(XI)

wherein R$_{31}$ is hydrogen or CH$_3$ and R$_{42}$ is —CH$_3$ or any one of the following structures:
(1)
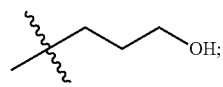
(2)
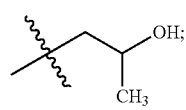
(3)
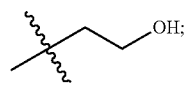
(4)
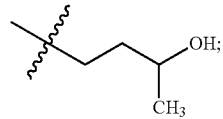
(5)
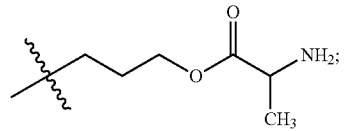
(6)
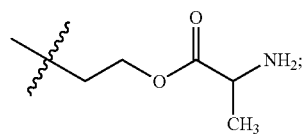
(7)
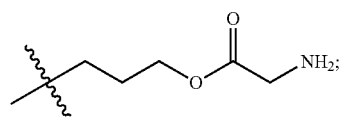
(8)
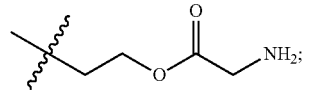
(9)
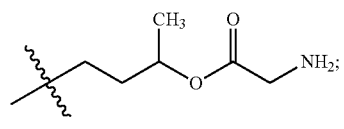
(10)
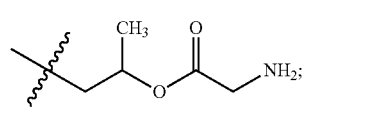
(11)
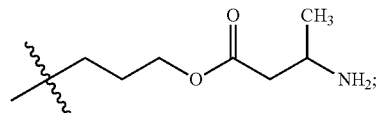
(12)
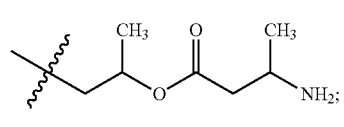
(13)
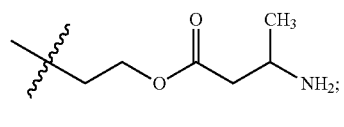
-continued
(14)
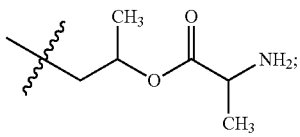
(15)
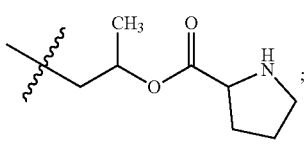
(16)
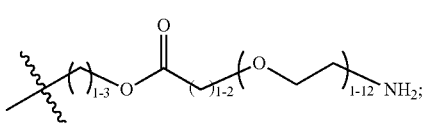
(17)
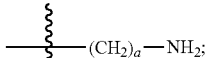
(18)
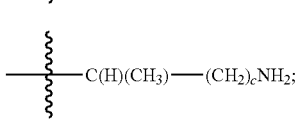
(19)
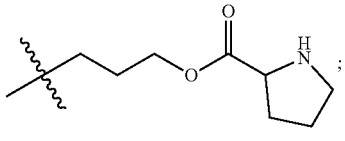
(20)
(21)
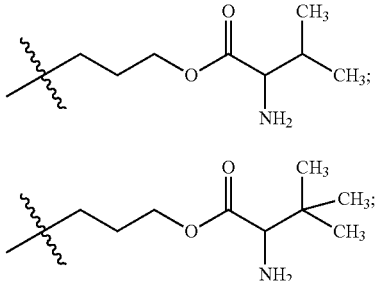
(22)
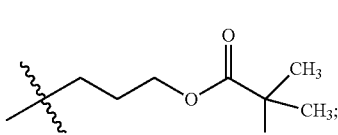
(23)
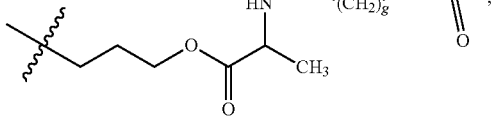
(24)
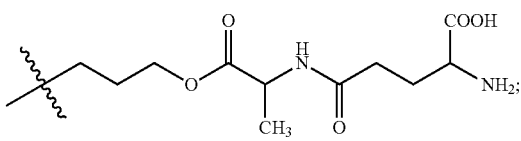

-continued
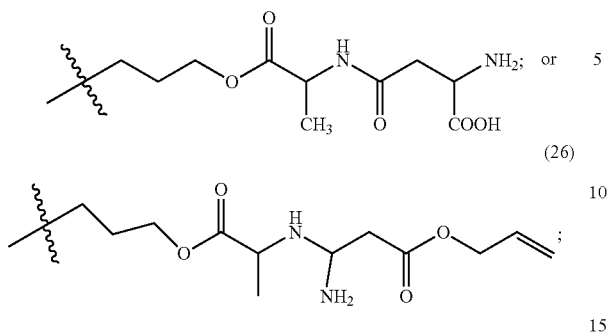
wherein:
a is an integer from 1 to 6; c is an integer from 0 to 3; and g is an integer from 2 to 6;
wherein the compound of Formula (XII) is:
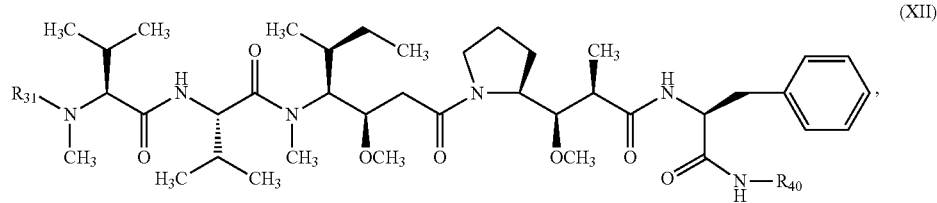
wherein $R_{31}$ is hydrogen or $CH_3$ and $R_{40}$ is hydrogen, —OH, —$NH_2$, or any of the following structures:
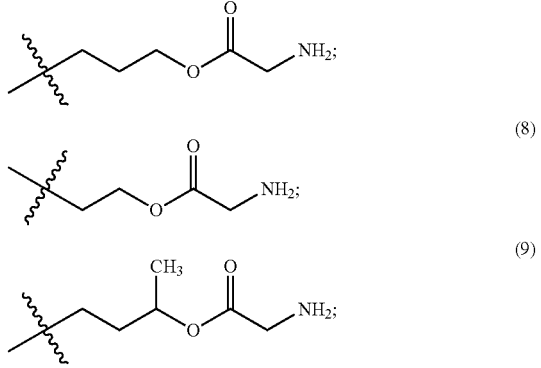
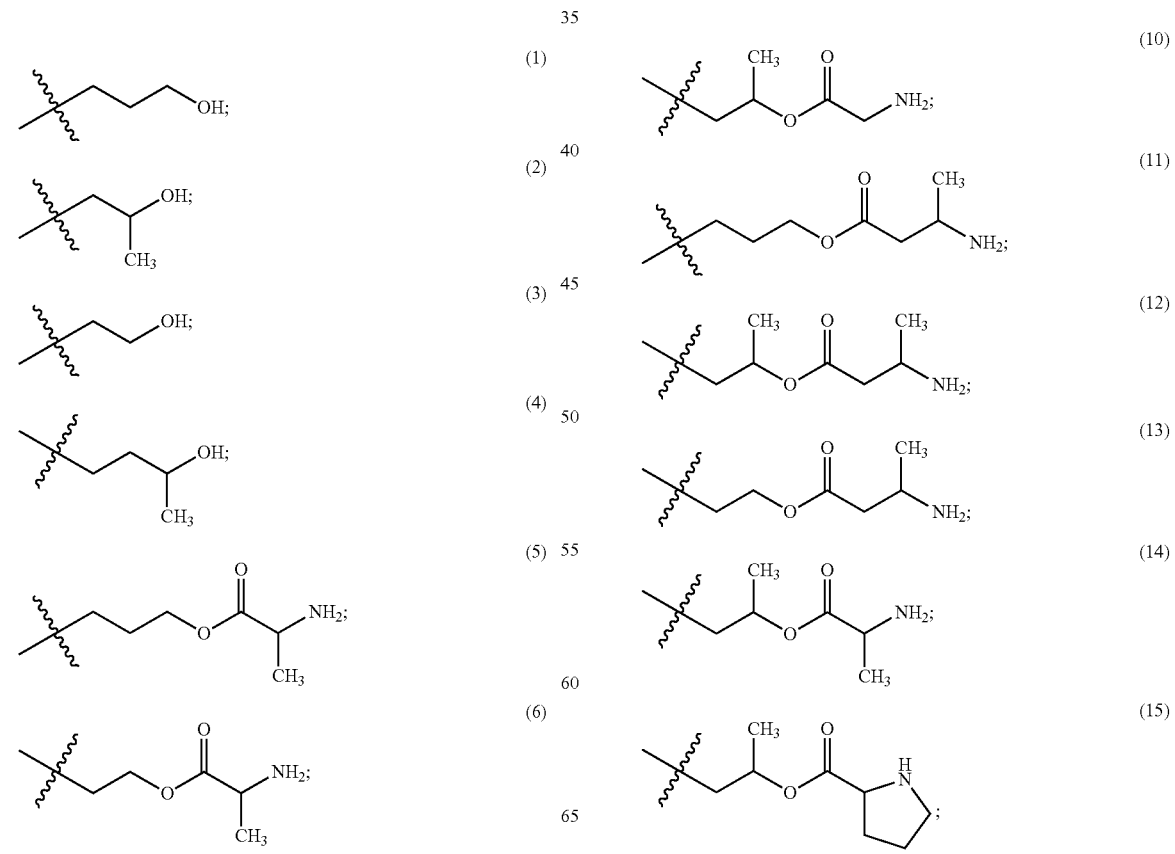

(16) 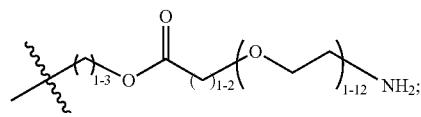
(17) 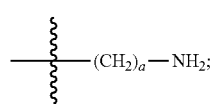
(18) 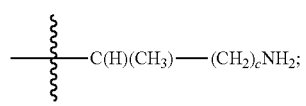
(19) 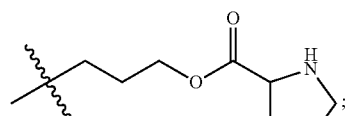
(20) 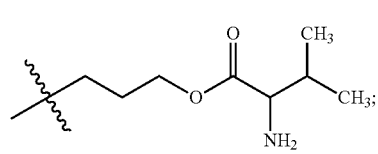
(21) 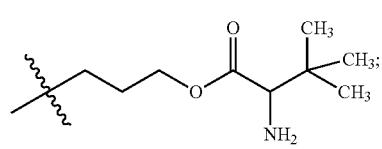
(22) 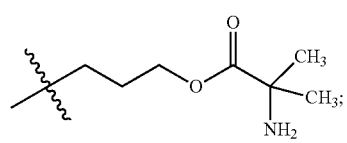
(23) 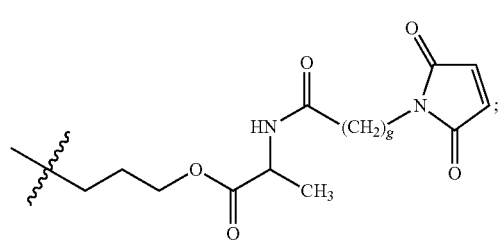
(24) 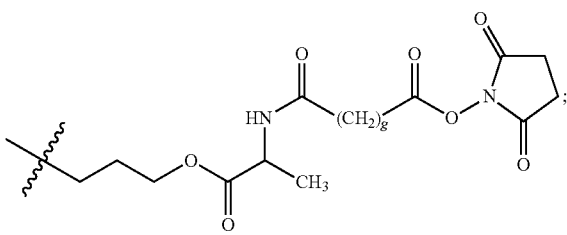
(25) 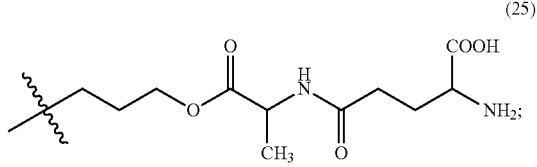
(26) 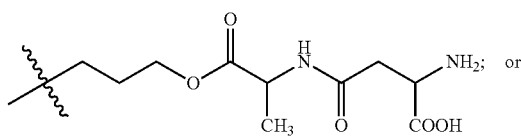
(27) 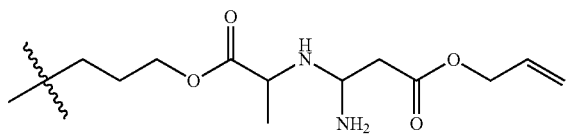
wherein:
a is an integer from 1 to 6; g is an integer from 2 to 6; and c is an integer from 0 to 3;
wherein the compound of Formula (XIII) is:
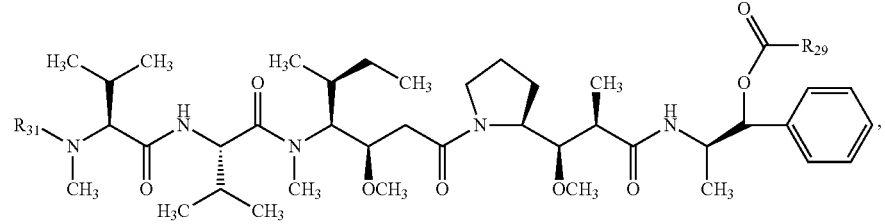
(XIII)

wherein:

$R_{31}$ is hydrogen or $CH_3$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—$[C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl, or a side chain of a natural or unnatural amino acid;

$R_{22}$ is —OH, —$NHR_{23}$, —COOH, —$R_{82}$—C(O)($CH_2$)$_c$—C(H)($R_{23}$)—N(H)($R_{23}$), —$R_{82}$—C(O)($CH_2$)$_d$—(O $CH_2$—$CH_2$)$_f$—N(H)($R_{23}$), or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

$R_{28}$ is absent, $NR_{23}$ or oxygen;

a is an integer from 1 to 6; c is an integer from 0 to 3; d is an integer from 1 to 3; and f is an integer from 1 to 12.

In some embodiments of the Formula (XII), $R_{40}$ is

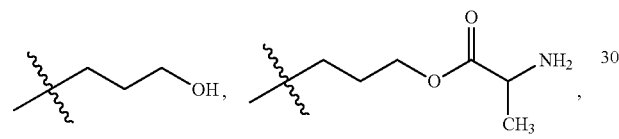

-continued

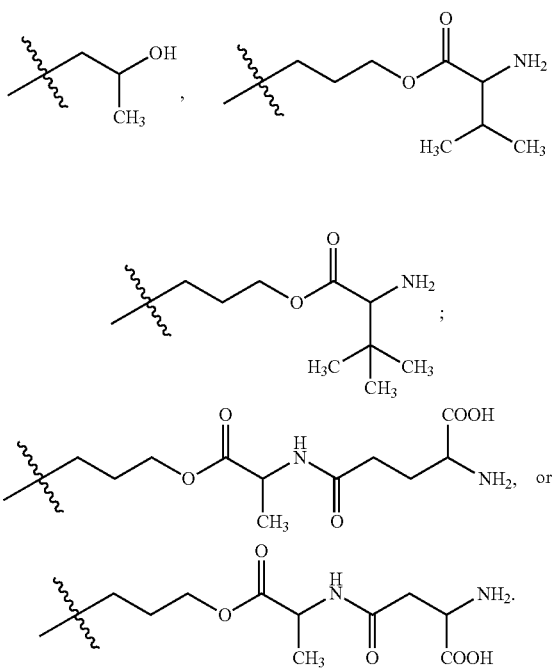

In some embodiments, the compound of Formula (XII) is a compound of Formula (XIIa), (XIIb), (XIIc), (XIId), (XIIe), (XIIf), (XIIg) or (XIIh):

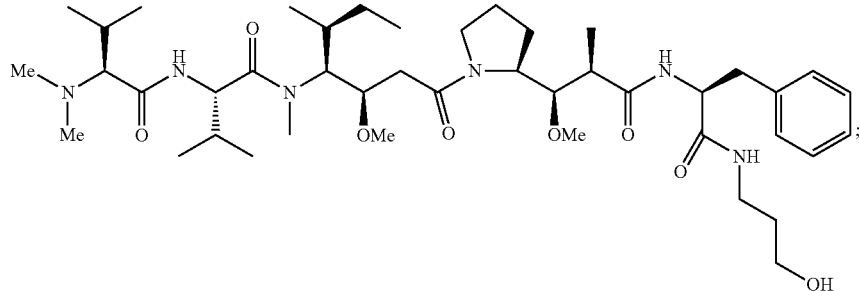

(XIIa)

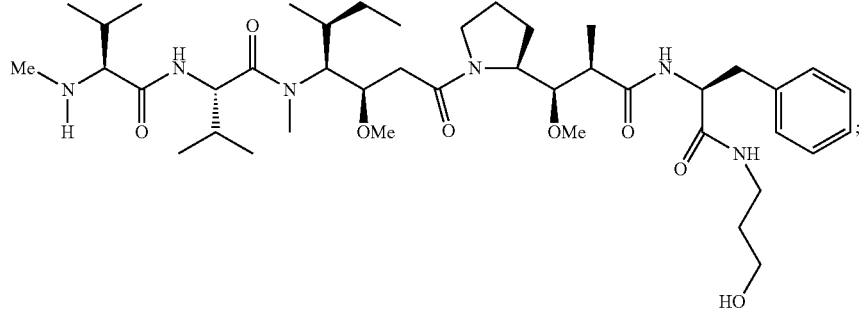

(XIIb)

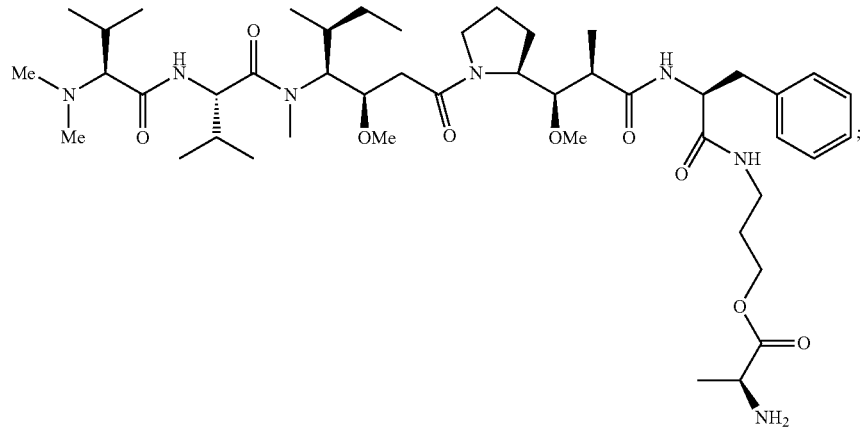
(XIIc)
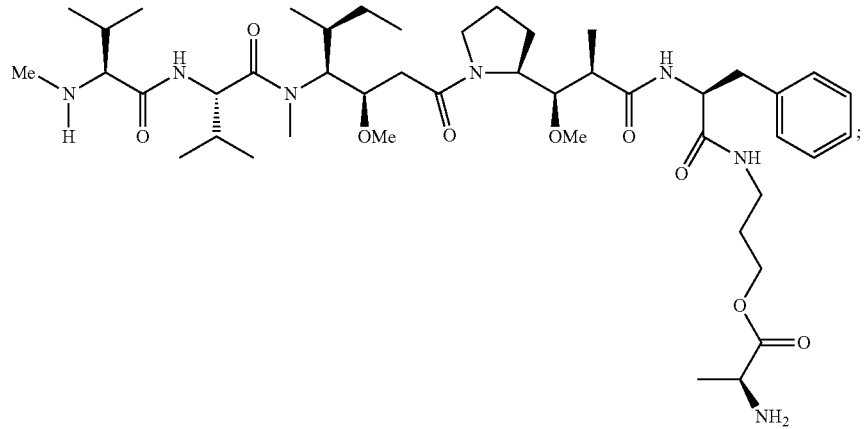
(XIId)
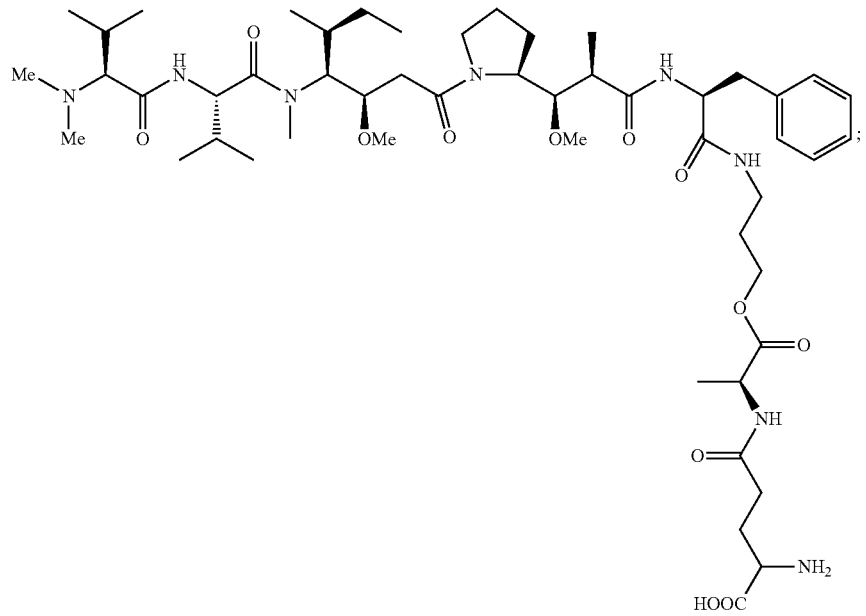
(XIIe)

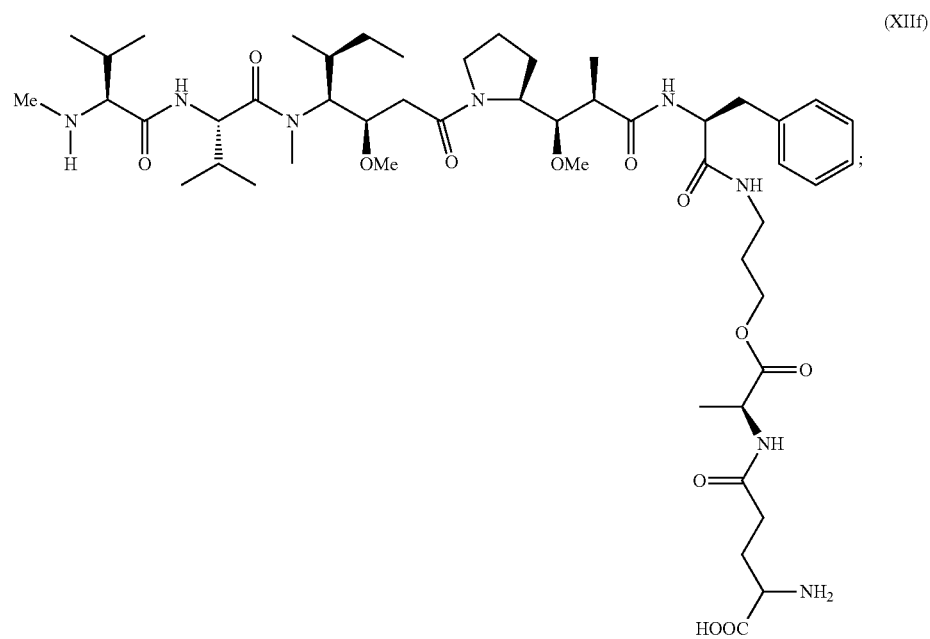
(XIIf)
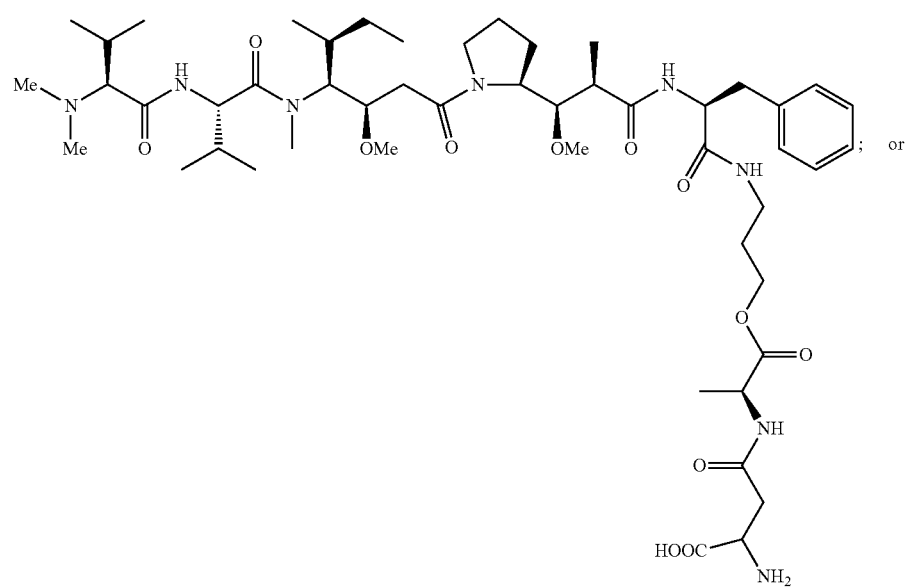
(XIIg) ; or (XIIh)

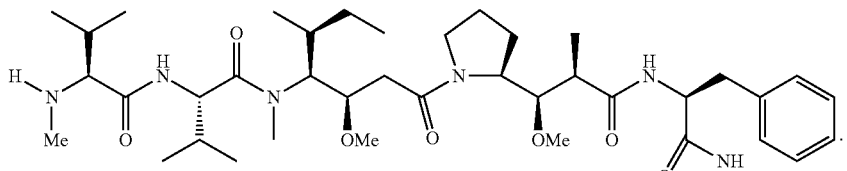
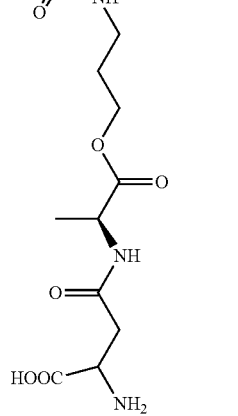

In some embodiments of the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$, or oxygen;

$R_{22}$ is —OH, —$NHR_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(O CH$_2$—CH$_2$)$_f$—N(H)(R$_{23}$) or —$R_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing cyclic compound;

$R_{82}$ is —$NR_{23}$ or oxygen;

c is an integer from 0 to 3; d is an integer from 1 to 3; and f is an integer from 1 to 12.

In some embodiments, $R_{29}$ is any one of the following structures:

(1)
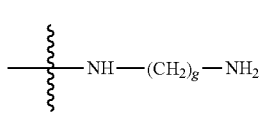

(2)
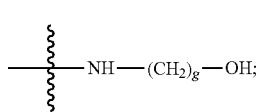

(3)
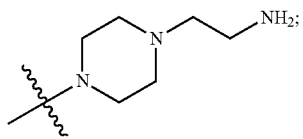

(4)
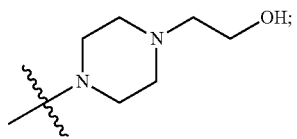

(5)
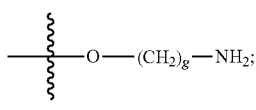

(6)
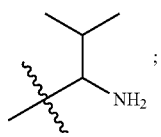

(7)
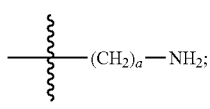

(8)
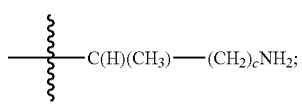

(9)
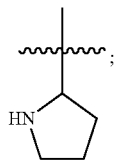

(10)
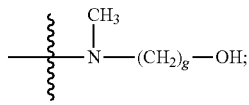

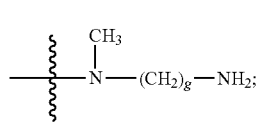 (11)
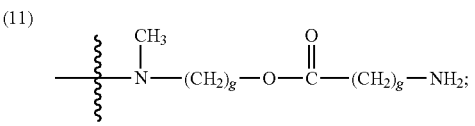 (12)
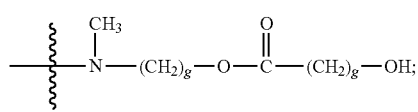 (13)
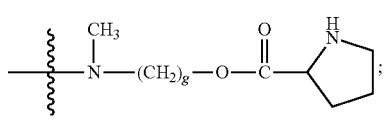 (14)
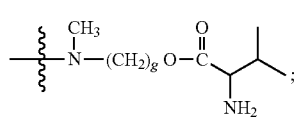 (15)
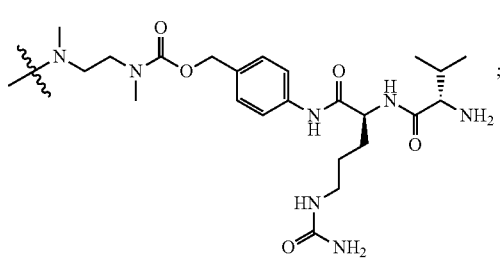 (16)
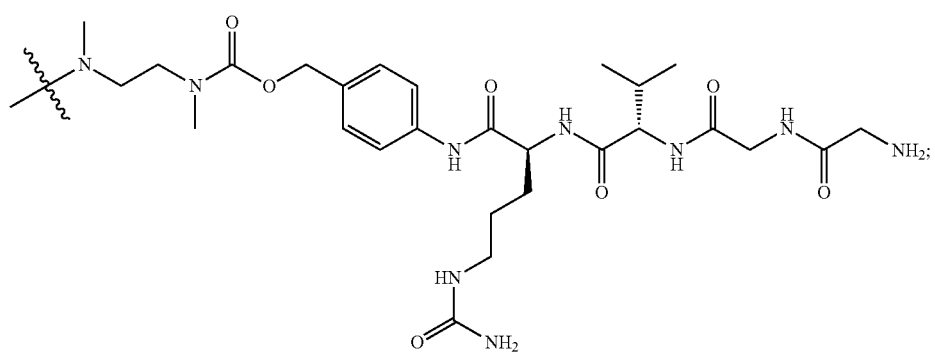 (17)
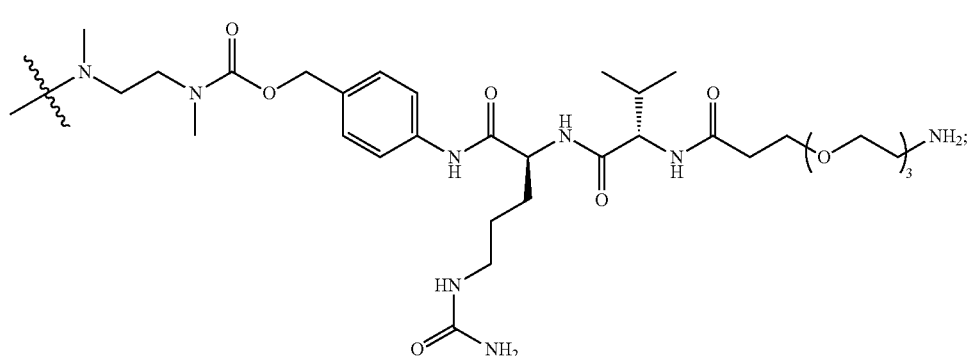 (18)
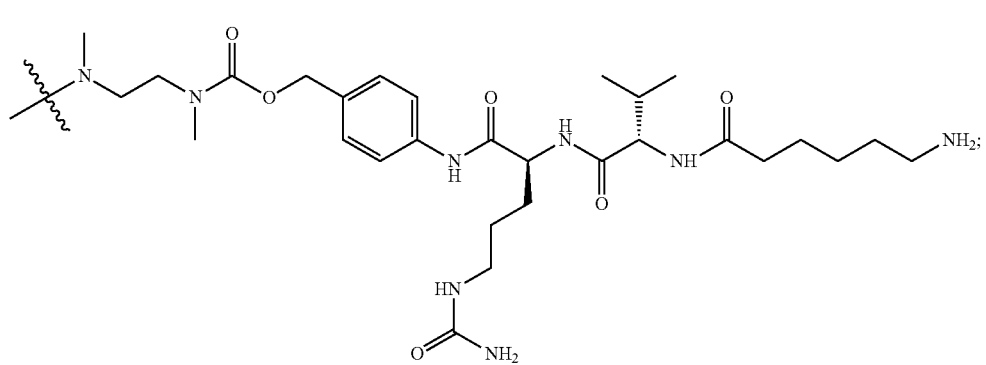 (19)

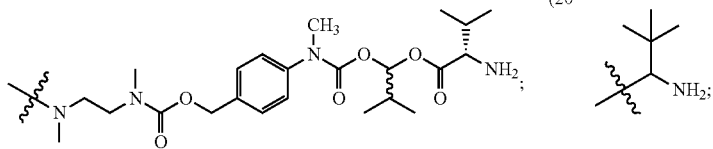
(20)
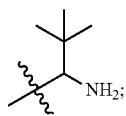
(21)
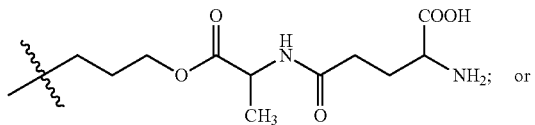
(22)
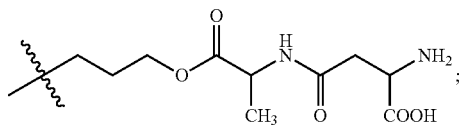
(23)
wherein:
  a is an integer from 1 to 6; c is an integer from 0 to 3; and
  g is an integer from 2 to 6.
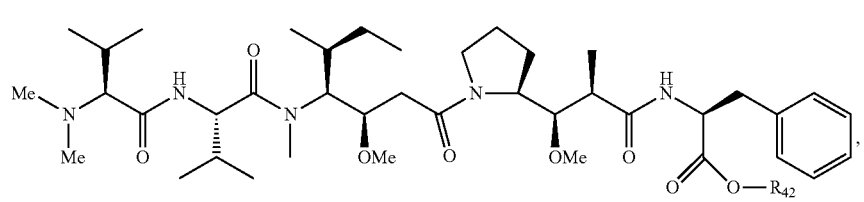
(XI)
wherein $R_{42}$ is H, —CH$_3$ (m/z=760),
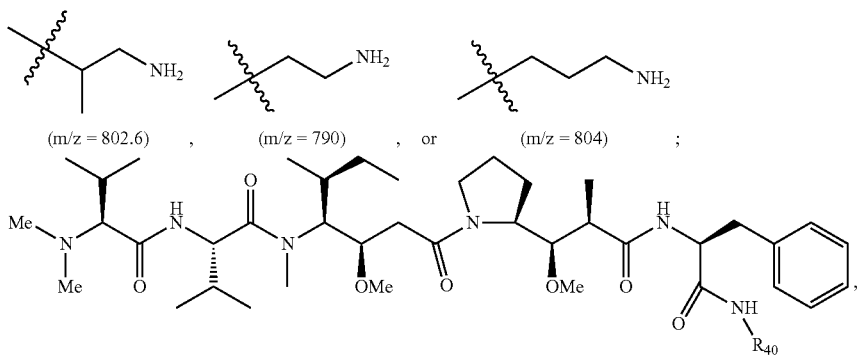
(m/z = 802.6), (m/z = 790), or (m/z = 804);
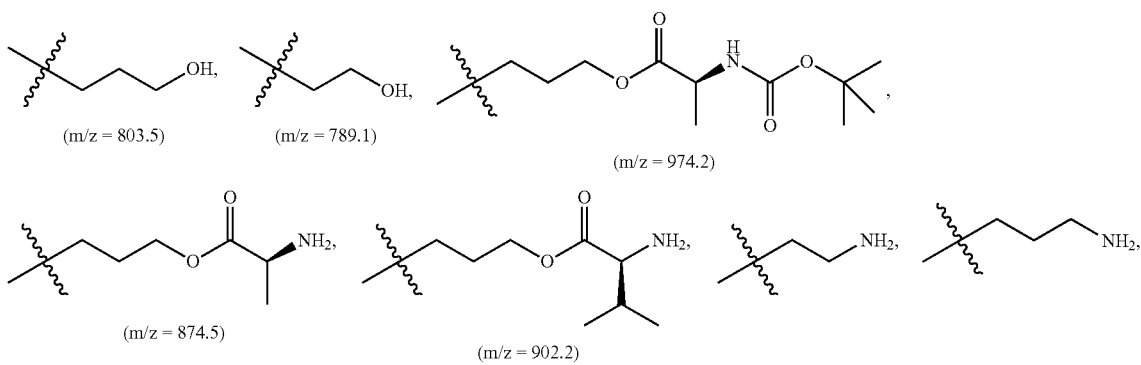
wherein $R_{40}$ is H,
(m/z = 803.5), (m/z = 789.1), (m/z = 974.2),
(m/z = 874.5), (m/z = 902.2),

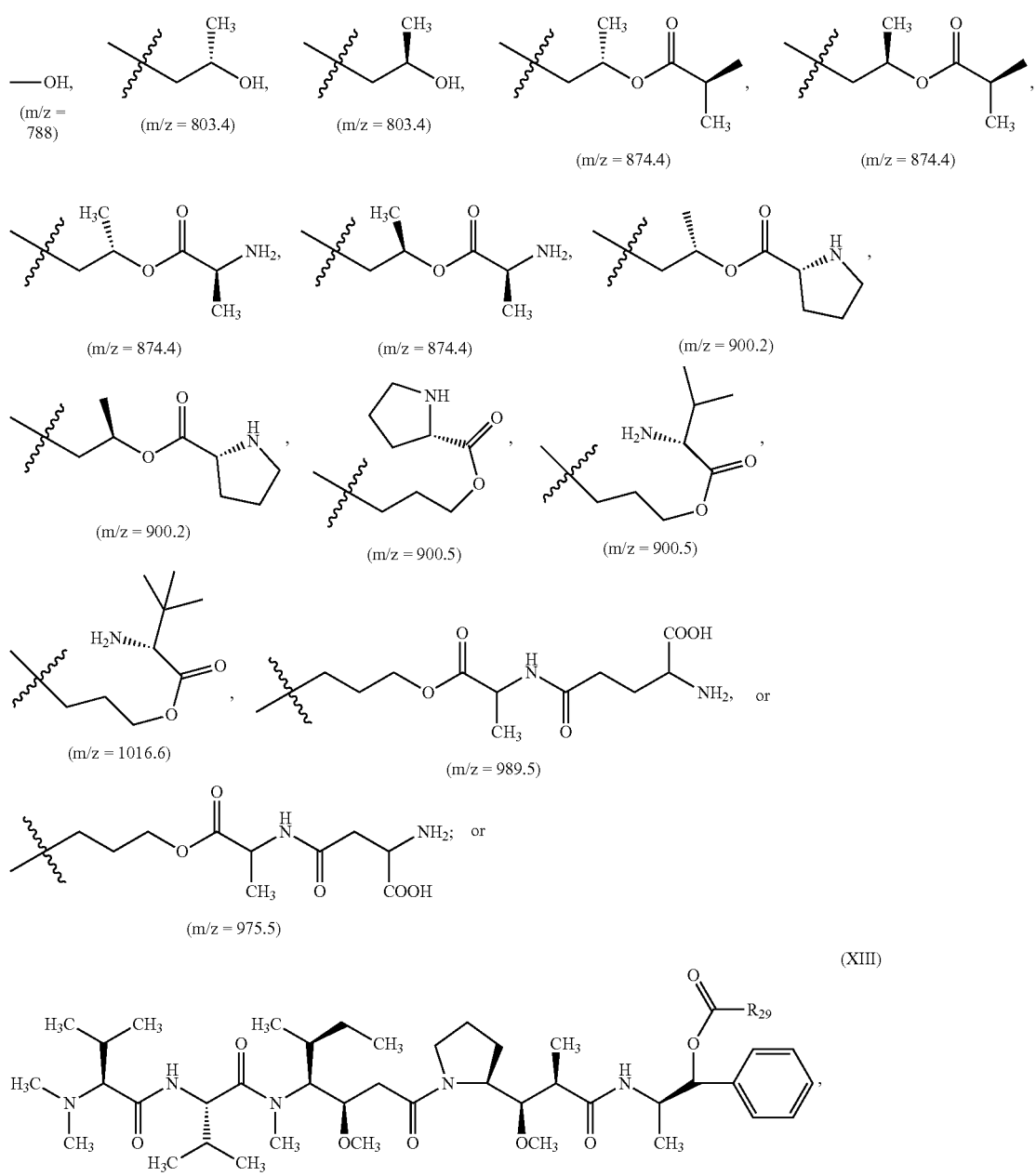
wherein —C(O)—R$_{29}$ is
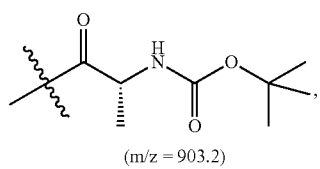
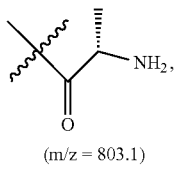
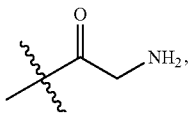
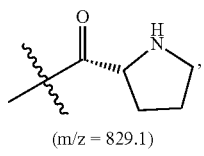
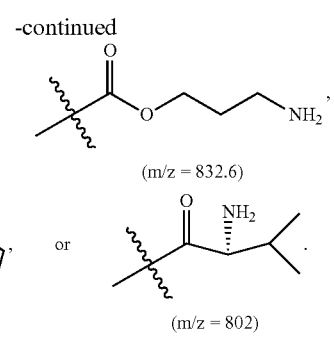

In some embodiments, D is:

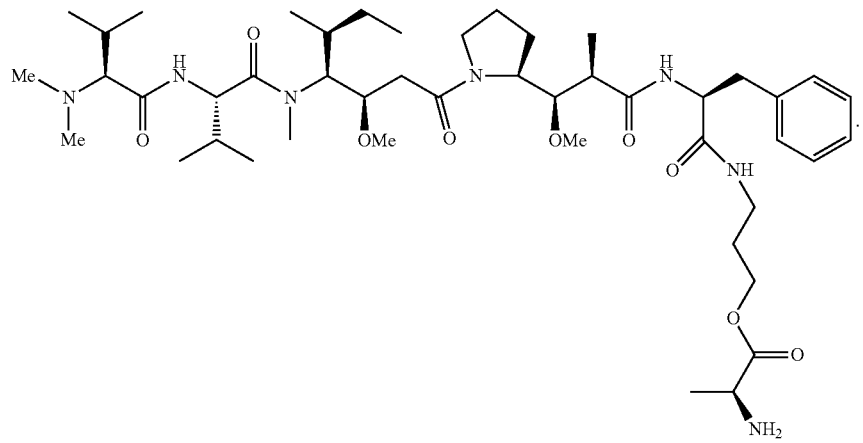 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCOC(=O)[C@H](C)N)OC)N(C)C(=O)[C@@H](NC(=O)[C@H](C(C)C)N(C)C)C(C)C]

In some embodiments, D is:

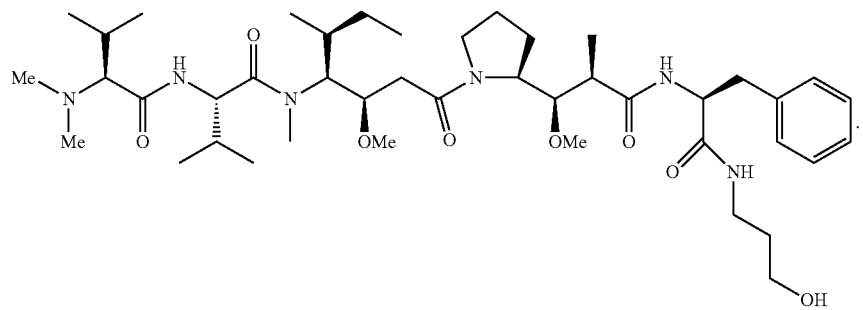 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCO)OC)N(C)C(=O)[C@@H](NC(=O)[C@H](C(C)C)N(C)C)C(C)C]

Hydrophilic Group or $T^1$

In some embodiments, the hydrophilic group included in the conjugates or scaffolds of the disclosure is a water-soluble and substantially non-antigenic polymer. In some embodiments, examples of the hydrophilic group, include, but are not limited to, polyalcohols, polyethers, polyanions, polycations, polyphosphoric acids, polyamines, polysaccharides, polyhydroxy compounds, polylysines, and derivatives thereof. In some embodiments, one end of the hydrophilic group can be functionalized so that it can be covalently attached to the Multifunctional Linker or $M^4$ linker (e.g., to an amino acid in the $M^4$ linker) by means of a non-cleavable linkage or via a cleavable linkage. In some embodiments, functionalization can be, for example, via an amine, thiol, NHS ester, maleimide, alkyne, azide, carbonyl, or other functional group. In some embodiments, the other terminus (or termini) of the hydrophilic group will be free and untethered. In some embodiments, by "untethered", it is meant that the hydrophilic group will not be attached to another moiety, such as D or a Drug Unit, Releasable Assembly Unit, or other components of the conjugates or scaffolds of the disclosure. In some embodiments, the free and untethered end of the hydrophilic group may include a methoxy, carboxylic acid, alcohol, or other suitable functional group. In some embodiments, the methoxy, carboxylic acid, alcohol, or other suitable functional group acts as a cap for the terminus or termini of the hydrophilic group.

In some embodiments, a cleavable linkage refers to a linkage that is not substantially sensitive to cleavage while circulating in the plasma but is sensitive to cleavage in an intracellular or intratumoral environment. In some embodiments, a non-cleavable linkage is not substantially sensitive to cleavage in any biological environment. In some embodiments, chemical hydrolysis of a hydrazone, reduction of a disulfide, and enzymatic cleavage of a peptide bond or glycosidic linkage are examples of cleavable linkages. In some embodiments, exemplary attachments of the hydrophilic group are via amide linkages, ether linkages, ester linkages, hydrazone linkages, oxime linkages, disulfide linkages, peptide linkages, or triazole linkages. In some embodiments, the attachment of the hydrophilic group to the Multifunctional Linker or $M^4$ linker (e.g., to an amino acid in the $M^4$ linker) is via an amide linkage.

In some embodiments wherein the conjugate or scaffold of the disclosure comprises more than one hydrophilic groups, the multiple hydrophilic groups may be the same or different chemical moieties. In some embodiments, the multiple hydrophilic groups can be attached to the Multifunctional Linker or $M^4$ linker at a single attachment site or different sites.

In some embodiments, the addition of the hydrophilic group may have two potential impacts upon the pharmacokinetics of the resulting conjugate. In some embodiments, the desired impact is the decrease in clearance (and consequent in increase in exposure) that arises from the reduction in non-specific interactions induced by the exposed hydrophobic elements of the drug or drug-linker. In some embodiments, the undesired impact is the decrease in volume and rate of distribution that may arise from the increase in the molecular weight of the conjugate. In some embodiments, increasing the molecular weight of the hydrophilic group increases the hydrodynamic radius of a conjugate, resulting in decreased diffusivity that may diminish the ability of the conjugate to penetrate into a tumor. In some embodiments, a hydrophilic group that is sufficiently large is used to decrease the conjugate clearance, thus increasing plasma exposure, but not so large as to greatly diminish its diffusivity, which may reduce the ability of the conjugate to reach the intended target cell population.

In some embodiments, the hydrophilic group, includes, but is not limited to, a sugar alcohol (also known as polyalcohol, polyhydric alcohol, alditol or glycitol) or a derivative thereof (e.g., amino polyalcohol), carbohydrate (e.g., a saccharide), a polyvinyl alcohol, a carbohydrate-based polymer (e.g., dextrans), a hydroxypropylmethacrylamide (HPMA), a polyalkylene oxide, and/or a copolymer thereof.

In some embodiments, the hydrophilic group comprises a plurality of hydroxyl groups, such as moieties that incorporate monosaccharides, oligosaccharides, polysaccharides, and the like. In some embodiments the hydrophilic group comprises a plurality of —(CR$_5$SOH)— groups, wherein R$_{58}$ is —H or C$_{1-8}$ alkyl.

In some embodiments, the hydrophilic group comprises one or more of the following fragments of the formula:

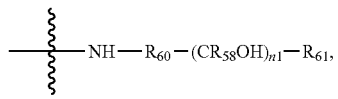

wherein n$_1$ is an integer from 0 to about 6; each R$_{58}$ independently is hydrogen or C$_{1-8}$ alkyl; R$_{60}$ is a bond, a C$_{1-6}$ alkyl linker, or —CHR$_{59}$— wherein R$_{59}$ is hydrogen, alkyl, cycloalkyl, or arylalkyl; R$_{61}$ is CH$_2$OR$_{62}$, COOR$_{62}$, —(CH$_2$)$_{n2}$COOR$_{62}$, or a heterocycloalkyl substituted with one or more hydroxyl; R$_{62}$ is hydrogen or C$_{1-8}$ alkyl; and n$_2$ is an integer from 1 to about 5.

In some embodiments, R$_{58}$ is hydrogen; R$_{60}$ is a bond or a C$_{1-6}$ alkyl linker; n$_1$ is an integer from 1 to about 6; and R$_{61}$ is CH$_2$OH or COOH. In some embodiments, R$_{58}$ is hydrogen; R$_{60}$ is —CHR$_{59}$—; n$_1$ is 0; and R$_{61}$ is a heterocycloalkyl substituted with one or more hydroxyl, e.g., a monosaccharide.

In some embodiments, the hydrophilic group comprises a glucosyl-amine, a di-amine, or a tri-amine.

In some embodiments, the hydrophilic group comprises one or more of the following fragments or a stereoisomer thereof:

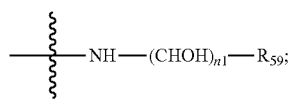

(1)

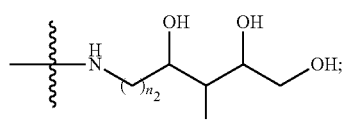

(2)

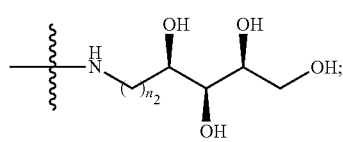

(3)

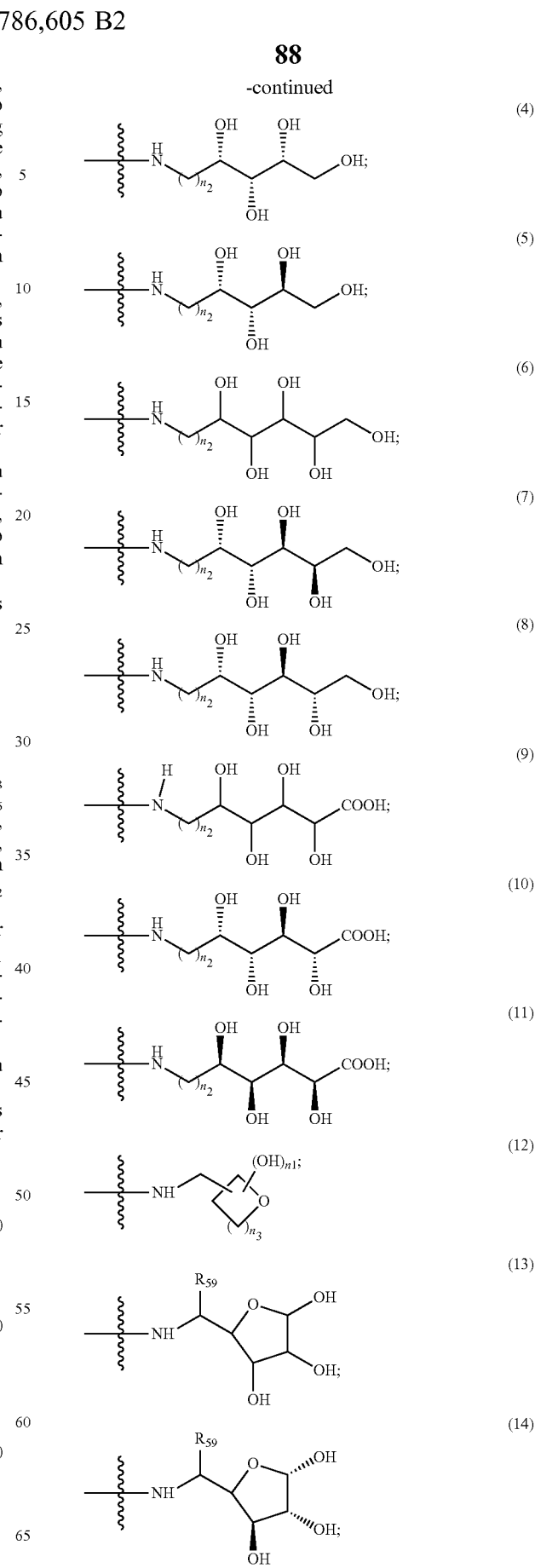

-continued

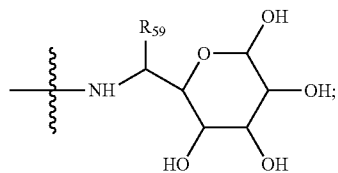
(15)

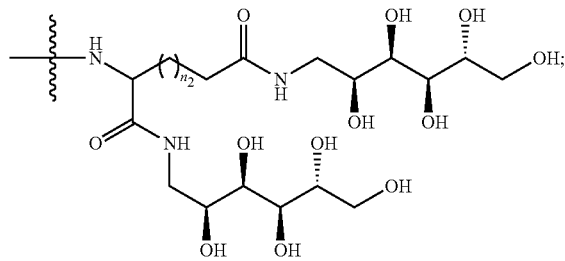
(16)

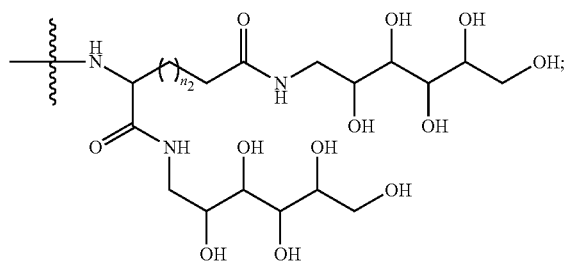
(17)

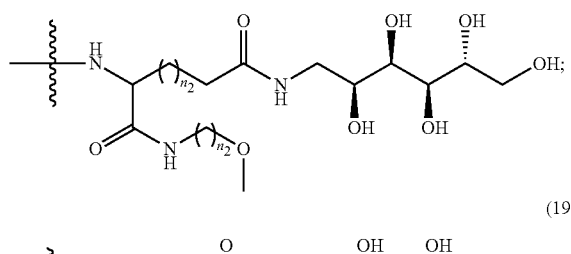
(18)

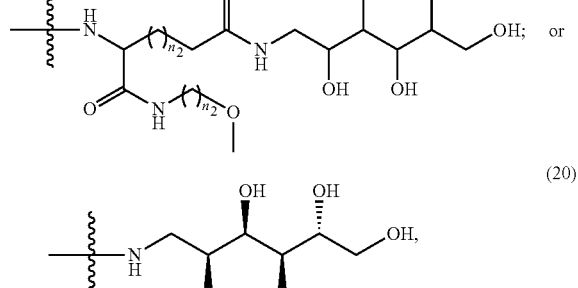
(19)

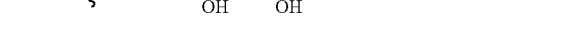
(20)

wherein:

$R_{59}$ is hydrogen, $C_{1-8}$ alkyl, cycloalkyl, or arylalkyl;

$n_1$ is an integer from 1 to about 6; $n_2$ is an integer from 1 to about 5; and $n_3$ is an integer from about 1 to about 3.

It is understood that all stereochemical forms of the hydrophilic groups are contemplated herein. In the above formula, the hydrophilic group may be derived from ribose, xylose, glucose, mannose, galactose, or other sugar and retain the stereochemical arrangements of pendant hydroxyl and alkyl groups present on those molecules. In some embodiments, it is to be understood that in the foregoing formulae, various deoxy compounds are also contemplated.

Illustratively, one or more of the following features are contemplated for the hydrophilic groups when applicable:

In some embodiments, $n_3$ is 2 or 3. In some embodiments, $n_3$ is 2. In some embodiments, $n_3$ is 3. In some embodiments, $n_1$ is 1, 2, or 3. In some embodiments, $n_1$ is 1. In some embodiments, $n_1$ is 2. In some embodiments, $n_1$ is 3. In some embodiments, $n_2$ is 1.

In some embodiments, $R_{59}$ is H.

In some embodiments, the hydrophilic group comprises:

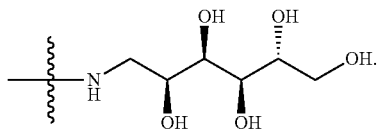 [SMILES: *NC[C@H](O)[C@@H](O)[C@H](O)[C@H](O)CO]

In some embodiments, the hydrophilic group comprises:

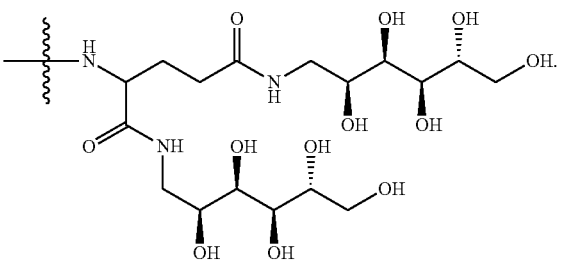 [SMILES: *NC(CCC(=O)NC[C@H](O)[C@@H](O)[C@H](O)[C@H](O)CO)C(=O)NC[C@H](O)[C@@H](O)[C@H](O)[C@H](O)CO]

In some embodiments, the hydrophilic group comprises:

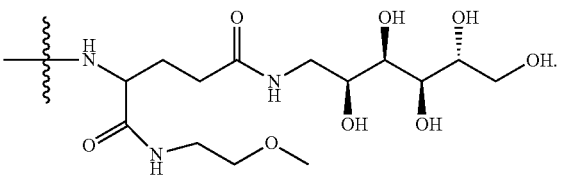 [SMILES: *NC(CCC(=O)NC[C@H](O)[C@@H](O)[C@H](O)[C@H](O)CO)C(=O)NCCOC]

In some embodiments, the hydrophilic group comprises

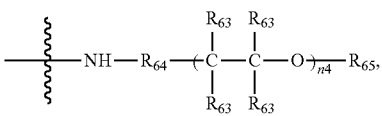

wherein $n_4$ is an integer from 1 to about 25;
each $R_{63}$ is independently hydrogen or $C_{1-8}$ alkyl;
$R_{64}$ is a bond or a $C_{1-8}$ alkyl linker;
$R_{65}$ is hydrogen, $C_{1-8}$ alkyl, or —$(CH_2)_{n2}COOR_{62}$;
$R_{62}$ is hydrogen or $C_{1-8}$ alkyl; and
$n_2$ is an integer from 1 to about 5.

In some embodiments, the hydrophilic group comprises:

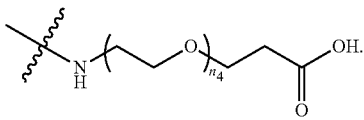

In some embodiments, $n_4$ is an integer from about 2 to about 20, from about 4 to about 16, from about 6 to about 12, or from about 8 to about 12.

In some embodiments, $n_4$ is an integer from about 2 to about 20. In some embodiments, $n_4$ is an integer from about 4 to about 16. In some embodiments, $n_4$ is an integer from about 6 to about 12. In some embodiments, $n_4$ is an integer from about 8 to about 12.

In some embodiments, $n_4$ is 6, 7, 8, 9, 10, 11, or 12.
In some embodiments, $n_4$ is 8 or 12.
In some embodiments, $n_4$ is 8.
In some embodiments, T' comprises:

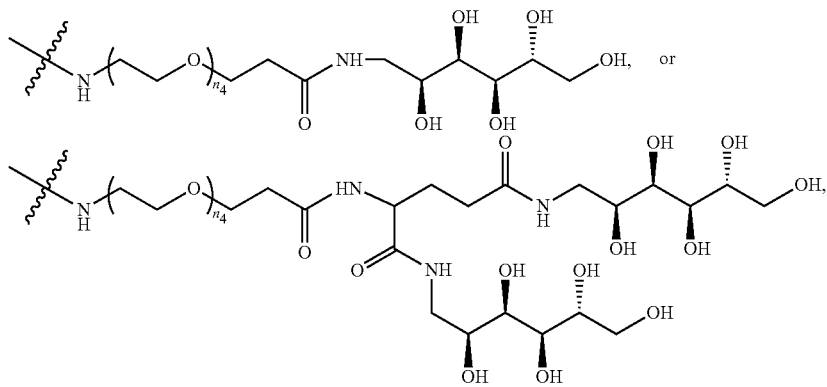

in which $n_4$ is an integer from about 2 to about 20, from about 4 to about 16, from about 6 to about 12, or from about 8 to about 12.

In some embodiments, $n_4$ is 6, 7, 8, 9, 10, 11, or 12.
In some embodiments, $n_4$ is 8 or 12.
In some embodiments, $n_4$ is 8.

In some embodiments, the hydrophilic group comprises a polyether, e.g., a polyalkylene glycol (PAO). In some embodiments, PAO includes but is not limited to, polymers of $C_{1-6}$ alkylene oxides, in particular polymers of ethylene oxide. In some embodiments, the polyalkylene glycol is a polyethylene glycol (PEG). In some embodiments, the polyethylene glycol is mPEG.

In some embodiments, the hydrophilic group comprises a PEG unit which comprises one or multiple PEG chains. In some embodiments, the PEG chains can be linked together, for example, in a linear, branched or star shaped configuration. In some embodiments, the PEG unit, in addition to comprising repeating PEG subunits, may also comprise non-PEG material (e.g., to facilitate coupling of multiple PEG chains to each other or to facilitate coupling to the amino acid).

In some embodiments, the PEG unit may be covalently bound to the Multifunctional Linker or $M^A$ linker (e.g., to an amino acid in the $M^A$ linker) via a reactive group. In some embodiments, reactive groups are those to which an activated PEG molecule may be bound (e.g., a free amino or carboxyl group). In some embodiments, N-terminal amino acids and lysines (K) have a free amino group; and C-terminal amino acid residues have a free carboxyl group. Sulfhydryl groups (e.g., as found on cysteine residues) may also be used as a reactive group for attaching PEG.

In some embodiments, the PEG unit may be attached to the Multifunctional Linker or $M^A$ linker (e.g., to an amino acid in the $M^A$ linker) by using methoxylated PEG ("mPEG") having different reactive moieties, including, but not limited to, succinimidyl succinate (SS), succinimidyl carbonate (SC), mPEG-imidate, para-nitrophenylcarbonate (NPC), succinimidyl propionate (SPA), and cyanuric chloride. In some embodiments, a variety of PEG species can be used, and substantially any suitable reactive PEG reagent can be used. In some embodiments, the reactive PEG reagent will result in formation of a carbamate or amide bond upon attachment to the Multifunctional Linker or $M^A$ linker (e.g., to an amino acid in the $M^A$ linker).

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some embodiments, the PEG unit comprises no more than about 72 subunits.

In some embodiments, the PEG unit comprises at least 6 subunits, at least 7 subunits, at least 8 subunits, at least 9 subunits, at least 10 subunits, at least 11 subunits, or at least 12 subunits.

In some embodiments, the PEG unit comprises at least 8 subunits, at least 9 subunits, at least 10 subunits, at least 11 subunits, or at least 12 subunits.

In some embodiments, the PEG unit comprises at least 6 subunits, at least 7 subunits, or at least 8 subunits.

In some embodiments, the PEG unit comprises at least 6 subunits. In some embodiments, the PEG unit comprises at least 7 subunits. In some embodiments, the PEG unit comprises at least 8 subunits.

In some embodiments, the PEG unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some embodiments, the PEG unit comprises a combined total of at least 6 subunits, at least 8, at least 10 subunits, or at least 12 subunits. In some such embodiments, the PEG unit comprises no more than a combined total of about 72 subunits. In some such embodiments, the PEG unit comprises no more than a combined total of about 36 subunits.

In some embodiments, the PEG unit comprises a combined total of from 4 to 72, 4 to 60, 4 to 48, 4 to 36, or 4 to 24 subunits; from 5 to 72, 5 to 60, 5 to 48, 5 to 36, or 5 to 24 subunits; from 6 to 72, 6 to 60, 6 to 48, 6 to 36, or from 6 to 24 subunits; from 7 to 72, 7 to 60, 7 to 48, 7 to 36, or 7 to 24 subunits; from 8 to 72, 8 to 60, 8 to 48, 8 to 36, or 8 to 24 subunits; from 9 to 72, 9 to 60, 9 to 48, 9 to 36, or 9 to 24 subunits; from 10 to 72, 10 to 60, 10 to 48, 10 to 36, or 10 to 24 subunits; from 11 to 72, 11 to 60, 11 to 48, 11 to 36, or 11 to 24 subunits; from 12 to 72, 12 to 60, 12 to 48, 12 to 36, or 12 to 24 subunits; from 13 to 72, 13 to 60, 13 to 48, 13 to 36, or 13 to 24 subunits; from 14 to 72, 14 to 60, 14 to 48, 14 to 36, or 14 to 24 subunits; from 15 to 72, 15 to 60, 15 to 48, 15 to 36, or 15 to 24 subunits; from 16 to 72, 16 to 60, 16 to 48, 16 to 36, or 16 to 24 subunits; from 17 to 72, 17 to 60, 17 to 48, 17 to 36, or 17 to 24 subunits; from 18 to 72, 18 to 60, 18 to 48, 18 to 36, or 18 to 24 subunits; from 19 to 72, 19 to 60, 19 to 48, 19 to 36, or 19 to 24 subunits; from 20 to 72, 20 to 60, 20 to 48, 20 to 36, or 20 to 24 subunits; from 21 to 72, 21 to 60, 21 to 48, 21 to 36, or 21 to 24 subunits; from 22 to 72, 22 to 60, 22 to 48, 22 to 36, or 22 to 24 subunits; from 23 to 72, 23 to 60, 23 to 48, 23 to 36, or 23 to 24 subunits; or from 24 to 72, 24 to 60, 24 to 48, 24 to 36 subunits.

In some embodiments, the PEG unit comprises one or more linear PEG chains having a combined total of from 4 to 72, 4 to 60, 4 to 48, 4 to 36, or 4 to 24 subunits; from 5 to 72, 5 to 60, 5 to 48, 5 to 36, or 5 to 24 subunits; from 6 to 72, 6 to 60, 6 to 48, 6 to 36, or 6 to 24 subunits; from 7 to 72, 7 to 60, 7 to 48, 7 to 36, or 7 to 24 subunits; from 8 to 72, 8 to 60, 8 to 48, 8 to 36, or 8 to 24 subunits; from 9 to 72, 9 to 60, 9 to 48, 9 to 36, or 9 to 24 subunits; from 10 to 72, 10 to 60, 10 to 48, 10 to 36, or 10 to 24 subunits; from 11 to 72, 11 to 60, 11 to 48, 11 to 36, or 11 to 24 subunits; from 12 to 72, 12 to 60, 12 to 48, 12 to 36, or 12 to 24 subunits; from 13 to 72, 13 to 60, 13 to 48, 13 to 36, or 13 to 24 subunits; from 14 to 72, 14 to 60, 14 to 48, 14 to 36, or 14 to 24 subunits; from 15 to 72, 15 to 60, 15 to 48, 15 to 36, or 15 to 24 subunits; from 16 to 72, 16 to 60, 16 to 48, 16 to 36, or 16 to 24 subunits; from 17 to 72, 17 to 60, 17 to 48, 17 to 36, or 17 to 24 subunits; from 18 to 72, 18 to 60, 18 to 48, 18 to 36, or 18 to 24 subunits; from 19 to 72, 19 to 60, 19 to 48, 19 to 36, or 19 to 24 subunits; from 20 to 72, 20 to 60, 20 to 48, 20 to 36, or 20 to 24 subunits; from 21 to 72, 21 to 60, 21 to 48, 21 to 36, or 21 to 24 subunits; from 22 to 72, 22 to 60, 22 to 48, 22 to 36, or 22 to 24 subunits; from 23 to 72, 23 to 60, 23 to 48, 23 to 36, or 23 to 24 subunits; or from 24 to 72, 24 to 60, 24 to 48, 24 to 36 subunits.

In some embodiments, the PEG unit is a derivatized linear single PEG chain having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In some embodiments, the PEG unit is a derivatized linear single PEG chain having from 6 to 72, 6 to 60, 6 to 48, 6 to 36, or 6 to 24 subunits; from 7 to 72, 7 to 60, 7 to 48, 7 to 36, or 7 to 24 subunits; from 8 to 72, 8 to 60, 8 to 48, 8 to 36, or 8 to 24 subunits; from 9 to 72, 9 to 60, 9 to 48, 9 to 36, or 9 to 24 subunits; from 10 to 72, 10 to 60, 10 to 48, 10 to 36, or 10 to 24 subunits; from 11 to 72, 11 to 60, 11 to 48, 11 to 36, or 11 to 24 subunits; from 12 to 72, 12 to 60, 12 to 48, 12 to 36, or 12 to 24 subunits; from 13 to 72, 13 to 60, 13 to 48, 13 to 36, or 13 to 24 subunits; from 14 to 72, 14 to 60, 14 to 48, 14 to 36, or 14 to 24 subunits; from 15 to 72, 15 to 60, 15 to 48, 15 to 36, or 15 to 24 subunits; from 16 to 72, 16 to 60, 16 to 48, 16 to 36, or 16 to 24 subunits; from 17 to 72, 17 to 60, 17 to 48, 17 to 36, or 17 to 24 subunits; from 18 to 72, 18 to 60, 18 to 48, 18 to 36, or 18 to 24 subunits; from 19 to 72, 19 to 60, 19 to 48, 19 to 36, or 19 to 24 subunits; from 20 to 72, 20 to 60, 20 to 48, 20 to 36, or 20 to 24 subunits; from 21 to 72, 21 to 60, 21 to 48, 21 to 36, or 21 to 24 subunits; from 22 to 72, 22 to 60, 22 to 48, 22 to 36, or 22 to 24 subunits; from 23 to 72, 23 to 60, 23 to 48, 23 to 36, or 23 to 24 subunits; or from 24 to 72, 24 to 60, 24 to 48, 24 to 36 subunits.

In some embodiments, examples of hydrophilic groups that are suitable for the conjugates, scaffolds, and methods disclosed herein can be found in e.g., U.S. Pat. No. 8,367,065 column 13; U.S. Pat. No. 8,524,696 column 6; WO2015/057699 and WO 2014/062697, the contents of each of which are hereby incorporated by reference in their entireties.

Antibodies

The term, "Antibody", as used herein, refers to a protein generated by the immune system that is capable of recognizing and binding to a specific antigen. In some embodiments, the antibody is a glycoprotein. In some embodiments, antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments (e.g., Fv, Fab, F(ab)$_2$, F(ab)$_3$, Fab', Fab'-SH, F(ab')$_2$), single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies.

The term, "Antibody fragment", as used herein, refers to at least a portion of the variable region of the immunoglobulin molecule that binds to its target, i.e., the antigen-binding region. As used herein, the term "antibody" refers to both the full-length antibody and antibody fragments unless otherwise specified. In some embodiments, the term includes genetically engineered antibodies, derivatives of an antibody, fragments of antibodies and may be obtained by methods that are known in the art. In some embodiments, the antibody may be engineered to comprise at least one chemically reactive group.

In some embodiments, the glycoprotein comprising a core-N-acetylglucosamine substituent (core-GlcNAc moiety) is an antibody comprising a core-N-acetylglucosamine substituent (core-GlcNAc moiety). In some embodiments, the glycoprotein is a monoclonal antibody (mAb) IgA, IgD, IgE, IgG, or IgM antibodies. In some embodiments, the antibody is an IgG antibody. In some embodiments, the antibody is an lgG1 antibody. In some embodiments, when said antibody is a whole antibody, the antibody comprises one or more (e.g., one) core-GlcNAc moiety on each heavy chain, said core-GlcNAc moiety being optionally fucosylated. In some embodiments, the whole antibody comprises two or more (e.g., two) optionally fucosylated, core-GlcNAc moieties. In some embodiments, when said antibody is a single chain antibody or an antibody fragment, e.g. a Fab or Fc fragment, the antibody comprises one or more core-GlcNAc moietys, which are optionally fucosylated. In some embodiments in the antibody comprising a core-GlcNAc moiety, said core-GlcNAc moiety may be situated anywhere on the antibody, provided that said substituent does not hinder the antigen-binding site of the antibody. In some embodiments, said core-GlcNAc moiety is present at a native N-glycosylation site of the antibody. In some embodiments, the antibody comprises, or is engineered to comprise, at least one chemically reactive group or a chemically reactive amino acid moiety or side chains.

In some embodiments, the antibody is capable of directing the conjugate to specific tissues, cells, or locations in a cell. In some embodiments, the antibody is capable of directing the conjugate in culture or in a whole organism, or both. In some embodiments, the antibody comprises a ligand that is present on the cell surface of the targeted cell(s) to which it binds with an effective specificity, affinity, and avidity. In some embodiments, the antibody directs the conjugate to tissues other than the liver. In some embodiments, the antibody directs the conjugate to a specific tissue such as the liver, kidney, lung, or pancreas. In some embodiments, the antibody directs the conjugate to a target cell (e.g., a cancer cell), a receptor expressed on a cell (e.g., a cancer cell), a matrix tissue, or a protein associated with cancer (e.g., tumor antigen). In some embodiments, cells comprising the tumor vasculature may be targeted. In some embodiments, the antibody is capable of directing the conjugate to specific types of cells, e.g., specific targeting to hepatocytes in the liver as opposed to Kupffer cells. In some embodiments, the antibody is capable of directing the conjugate to cells of the reticular endothelial or lymphatic system, or to professional phagocytic cells such as macrophages or eosinophils. In some embodiments, the conjugate itself is an effective delivery system, without the need for specific targeting.

In some embodiments, the antibody is capable of directing the conjugate to a location within the cell (e.g., the nucleus, the cytoplasm, or the endosome). In some embodiments, the antibody enhances cellular binding to receptors, or cytoplasmic transport to the nucleus and nuclear entry or release from endosomes or other intracellular vesicles.

In some embodiments, the conjugate comprises a Her-2 or NaPi2b antibody. In some embodiments, the Her-2 antibody suitable for the conjugate is trastuzumab. In some embodiments, the Her-2 antibody suitable for the conjugate include those described in WO 2015/195917 and PCT/US2018/019873, each of which is incorporated herein in its entirety by reference.

NaPi2b Antibodies

In some embodiments, the NaPi2b antibodies suitable for conjugation bind to the extracellular region of SLC34A2. In some embodiments, the present disclosure provides NaPi2b-targeted monoclonal antibodies that specifically recognizes NaPi2b, also known as sodium-dependent phosphate transport protein 2B. In some embodiments, the NaPi2b antibodies used in the conjugates disclosed herein are capable of and useful in modulating, e.g., blocking, inhibiting, reducing, antagonizing, neutralizing or otherwise interfering with at least one biological activity of NaPi2b. In some embodiments, antibodies disclosed herein also include antibodies that bind soluble NaPi2b. In some embodiments, the NaPi2b antibodies specifically bind to an epitope on an extracellular domain (ECD) of the human NaPi2b. These antibodies are collectively referred to herein as "NaPi2b" antibodies.

In some embodiments, the NaPi2b antibody-drug conjugates provided herein include antibodies that bind to a NaPi2b epitope with an equilibrium dissociation constant ($K_d$ or $K_D$) of ≤1 µM (e.g., ≤100 nM; ≤10 nM; and ≤1 nM). In some embodiments, the NaPi2b antibodies used in the antibody-drug conjugates disclosed herein exhibit a $K_d$ in the range approximately between ≤1 nM to about 1 pM.

In some embodiments, the NaPi2b antibody-drug conjugates provided herein can include antibodies that serve to modulate, block, inhibit, reduce, antagonize, neutralize, or otherwise interfere with the functional activity of NaPi2b. In some embodiments, functional activities of NaPi2b include for example, participating in the transcellular inorganic phosphate (Pi) absorption, thereby contributing to the maintenance of phosphate homeostasis in the body. In some embodiments, the NaPi2b antibodies completely or partially inhibit NaPi2b functional activity by partially or completely modulating, blocking, inhibiting, reducing antagonizing, neutralizing, or otherwise interfering with transcellular inorganic phosphate absorption.

In some embodiments, the NaPi2b antibodies are considered to completely modulate, block, inhibit, reduce, antagonize, neutralize, or otherwise interfere with NaPi2b functional activity when the level of NaPi2b functional activity in the presence of the NaPi2b antibody is decreased by at least 95%, e.g., by 96%, 97%, 98%, 99%, or 100% as compared to the level of NaPi2b functional activity in the absence of binding with a NaPi2b antibody described herein. In some embodiments, the NaPi2b antibodies are considered to partially modulate, block, inhibit, reduce, antagonize, neutralize or otherwise interfere with NaPi2b functional activity when the level of NaPi2b activity in the presence of the NaPi2b antibody is decreased by less than 95%, e.g., 10%, 20%, 25%, 30%, 40%, 50%, 60%, 75%, 80%, 85% or 90% as compared to the level of NaPi2b activity in the absence of binding with a NaPi2b antibody described herein.

In some embodiments, exemplary antibodies disclosed herein include, the XMT-1535 antibody. These antibodies show specificity for human NaPi2b and they have been shown to inhibit NaPi2b activity.

NaPi2b human or humanized monoclonal antibody, XMT-1535, includes a heavy chain (HC), heavy chain variable region (VH), light chain (LC), and a light chain variable region (VL), as shown in the amino acid and corresponding nucleic acid sequences presented in Table 1 below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDRs) for the XMT-1535 antibody are as defined by E. A. Kabat et al. (See Kabat, E. A., et al., Sequences of Protein of immunological interest, Fifth Edition, US Department of Health and Human Services, US Government Printing Office (1991)) and are disclosed in U.S. Pat. No. 8,603,474.

TABLE 1

NaPi2b human or humanized monoclonal antibody XMT-1535 sequences

| SEQ ID NO: | Sequence Description |
|---|---|
| 1 | XMT-1535 Heavy Chain Amino Acid Sequence |
| 2 | XMT-1535 Light Chain Amino Acid Sequence |

TABLE 1-continued

NaPi2b human or humanized monoclonal antibody XMT-1535 sequences

| SEQ ID NO: | Sequence Description |
|---|---|
| 3 | XMT-1535 Heavy chain variable region |
| 4 | XMT-1535 Light chain variable region |
| 5 | XMT-1535 CDRH1 |
| 6 | XMT-1535 CDRH2 |
| 7 | XMT-1535 CDRH3 |
| 8 | XMT-1535 CDRL1 |
| 9 | XMT-1535 CDRL2 |
| 10 | XMT-1535 CDRL3 |
| 11 | XMT-1535 IgG1 Heavy chain constant region |
| 12 | XMT-1535 Light chain constant region |
| 13 | XMT-1535 Heavy chain variable region nucleic acid sequence |
| 14 | XMT-1535 Light chain variable region nucleic acid sequence |
| 15 | Full-length human NaPi2b sequence |

Antibodies disclosed herein specifically bind to an epitope on an extracellular domain (ECD) of the human NaPi2b.

In some embodiments, those skilled in the art will recognize that it is possible to determine, without undue experimentation, if a monoclonal antibody has the same specificity as a monoclonal antibody disclosed herein (e.g., XMT-1535, 10H1.11.4B) by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. If the monoclonal antibody being tested is inhibited then, in all likelihood, it has the same, or functionally equivalent, epitopic specificity as the monoclonal antibody disclosed herein.

Screening of monoclonal antibodies disclosed herein, can also be carried out, e.g., by measuring NaPi2b-mediated activity, and determining whether the test monoclonal antibody is able to modulate, block, inhibit, reduce, antagonize, neutralize or otherwise interfere with NaPi2b activity.

In some embodiments, the antibodies disclosed herein comprise a heavy chain variable region having an amino acid sequence at least 85%, 86%, 87% 88%, 89%, 90%, 91%, 92%, 93%, 94%, 95%, 96%, 97% 98%, 99% or more identical to a sequence selected from SEQ ID NOs: 3 and a light chain variable region having an amino acid sequence at least 85%, 86%, 87% 88%, 89%, 90%, 91%, 92%, 93%, 94%, 95%, 96%, 97% 98%, 99% or more identical to a sequence selected from SEQ ID NOs: 4.

In some embodiments, the antibodies disclosed herein comprise a heavy chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 1 and a light chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 2.

In some embodiments, the antibodies disclosed herein comprise the heavy chain variable region amino acid sequence of SEQ ID NO: 3 and the light chain variable region amino acid sequence of SEQ ID NO: 4.

In some embodiments, the antibodies disclosed herein comprise the heavy chain amino acid sequence of SEQ ID NO: 1 and the light chain amino acid sequence of SEQ ID NO: 2.

In some embodiments, the antibodies disclosed herein comprise the CDRH1 amino acid sequence of SEQ ID NO: 5, the CDRH2 amino acid sequence of SEQ ID NO: 6, the CDRH3 amino acid sequence of SEQ ID NO: 7, the CDRL1 amino acid sequence of SEQ ID NO: 8, the CDRL2 amino acid sequence of SEQ ID NO: 9, and the CDRL3 amino acid sequence of SEQ ID NO: 10.

In some embodiments, the antibodies disclosed herein that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 5; a CDRH2 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 6; a CDRH3 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 7; a CDRL1 that comprises the amino acid sequence at 85%, 86%, 87% 88%, 89%, 90%, 91%, 92%, 93%, 94%, 95%, 96%, 97% 98%, 99% or more identical to the amino acid sequence of SEQ ID NO: 8; a CDRL2 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 9; and a CDRL3 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 10.

In some embodiments, the antibodies disclosed herein include one or more conservative amino acid substitutions in a variable domain sequence such as 1, 2, 3, 4, 5, 6, 7, 8, 9, 10, 11, 12, 13, 14, 15, or more conservative substitutions in a variable domain sequence. In some embodiments, these conservative amino acid substitutions are in a CDR region, e.g., 1, 2, 3, 4, 5, 6, 7, 8, 9, 10, 11, 12, 13, 14, 15, or more conservative substitutions are made cumulatively across all CDRs and in some particular embodiments, up to 1, 2, 3, or 4 conservative amino acid substitutions may be present in each CDR sequence, e.g., SEQ ID NOs: 5-10.

In some embodiments, those skilled in the art will recognize that it is possible to determine, without undue experimentation, if a monoclonal antibody has the same specificity as a monoclonal antibody XMT-1535, by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

In some embodiments, an alternative method for determining whether a monoclonal antibody has the specificity of a monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. In some embodiments, if the monoclonal antibody being tested is inhibited then it has the same, or functionally equivalent, epitopic specificity as the monoclonal antibody disclosed herein.

Screening of monoclonal antibodies disclosed herein, can be also carried out, e.g., by measuring NaPi2b-mediated activity, and determining whether the test monoclonal antibody is able to modulate, block, inhibit, reduce, antagonize, neutralize or otherwise interfere with NaPi2b activity.

In some embodiments, the NaPi2b antibodies suitable for conjugations can be generated and purified by well-known techniques e.g., WO 2009/097128, WO 2017/160754, and U.S. Ser. No. 16/136,706, each of which is incorporated herein in its entirety by reference.

HER2 Antibodies

In some embodiments, the HER2 antibodies suitable conjugation bind the human HER2 in soluble form, or membrane bound (i.e., when expressed on a cell surface). In some embodiments, the present disclosure provides monoclonal antibodies that bind HER2 and are humanized or fully human. In some embodiments, the present disclosure provides monoclonal antibodies that bind HER2 specifically. These antibodies are collectively referred to herein as "HER2" antibodies.

In some embodiments, the HER2 antibodies suitable for conjugation bind to a HER2 epitope with an equilibrium dissociation constant ($K_d$ or $K_D$) of ≤1 µM (e.g., ≤100 nM; ≤10 nM; ≤1 nM). In some embodiments, the present disclosure provides monoclonal antibodies that bind HER2 and are humanized or fully human. for example, the HER2 antibodies provided herein exhibit a $K_d$ in the range approximately between ≤1 nM to about 1 pM.

In some embodiments, the HER2 antibodies disclosed herein serve to modulate, block, inhibit, reduce, antagonize, neutralize, or otherwise interfere with the functional activity of HER2. HER2. In some embodiments, functional activities of HER2 include for example, modulation of PI3K-Akt pathway activity. In some embodiments, the HER2 antibodies completely or partially inhibit HER2 functional activity by partially or completely modulating, blocking, inhibiting, reducing antagonizing, neutralizing, or otherwise interfering with PI3K-Akt pathway activity. PI3K-Akt pathway activity is assessed using any art-recognized method for detecting PI3K-Akt pathway activity, including, but not limited to detecting levels of phosphorylated Akt in the presence and absence of an antibody or antigen binding fragment disclosed herein.

In some embodiments, the HER2 antibodies are considered to completely modulate, block, inhibit, reduce, antagonize, neutralize, or otherwise interfere with HER2 functional activity when the level of HER2 functional activity in the presence of the HER2 antibody is decreased by at least 80%, e.g., by 81%, 82%, 83%, 84%, 85%, 86%, 87%, 88%, 89%, 90%, 91%, 92%, 93%, 94%, 95%, 96%, 97%, 98%, 99%, or 100% as compared to the level of HER2 functional activity in the absence of binding with a HER2 antibody described herein. In some embodiments, the HER2 antibodies are considered to partially modulate, block, inhibit, reduce, antagonize, neutralize, or otherwise interfere with HER2 functional activity when the level of HER2 activity in the presence of the HER2 antibody is decreased by less than 95%, e.g., 10%, 20%, 25%, 30%, 40%, 50%, 60%, 75%, 80%, 85%, or 90% as compared to the level of HER2 activity in the absence of binding with a HER2 antibody described herein.

In some embodiments, exemplary antibodies disclosed herein include, the XMT-1519 antibody. This antibody show specificity for human HER2 and they have been shown to inhibit the functional activity of HER2 in vitro.

HER-2 monoclonal antibody XMT-1519 includes a heavy chain (HC), heavy chain variable region (VH), light chain (LC), and a light chain variable region (VL), as shown in the amino acid and corresponding nucleic acid sequences presented in Table 2 below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDR) are as defined by E. A. Kabat et al. (See Kabat, E. A., et al., Sequences of Protein of immunological interest, Fifth Edition, US Department of Health and Human Services, US Government Printing Office (1991)).

TABLE 2

HER2 human or humanized monoclonal antibody XMT-1519 sequences

| SEQ ID NO: | Sequence Description |
|---|---|
| 16 | Full-length human HER2 receptor |
| 17 | XMT-1519 Heavy chain variable region |
| 18 | XMT-1519 IgG1 Heavy chain constant region |
| 19 | XMT-1519 Heavy Chain Amino Acid Sequence |
| 20 | XMT-1519 CDRH1 |
| 21 | XMT-1519 CDRH2 |
| 22 | XMT-1519 CDRH3 |
| 23 | XMT-1519 Heavy Chain variable region nucleic acid sequence |
| 24 | XMT-1519 Light chain variable region |
| 25 | XMT-1519 Light chain constant region |
| 26 | XMT-1519 Light Chain Amino Acid Sequence |
| 27 | XMT-1519 CDRL1 |
| 28 | XMT-1519 CDRL2 |
| 29 | XMT-1519 CDRL3 |
| 30 | XMT-1519 Light Chain variable region nucleic acid sequence |
| 31 | Extracellular domain (ECD) of the human HER2 receptor |

Antibodies and antigen binding fragments thereof disclosed herein specifically bind to an epitope on the full-length human HER2 receptor comprising the amino acid sequence of SEQ ID NO: 16.

Antibodies and antigen binding fragments thereof disclosed herein specifically bind to an epitope on the extracellular domain (ECD) of the human HER2 receptor comprising the amino acid sequence of SEQ ID NO: 31.

In some embodiments, the antibodies of the present disclosure exhibit HER2 binding characteristics that differ from antibodies described in the art. In some embodiments, the antibodies disclosed herein bind to a different epitope of HER2, in that they cross-block each other but not trastuzumab, pertuzumab, Fab37, or chA21 from binding to HER2. Further, as opposed to the known antibodies, the antibodies disclosed herein can internalize efficiently into HER2-expressing cells without promoting cell proliferation.

In some embodiments, the antibodies disclosed herein are fully human monoclonal antibodies that bind to novel epitopes and/or have other favorable properties for therapeutic use. In some embodiments, exemplary properties include, but are not limited to, favorable binding characteristics to cancer cells expressing human HER2 at high or low levels, specific binding to recombinant human and cynomolgus monkey HER2, efficient internalization upon binding to HER2, high capacity for killing cancer cells expressing high or low levels of HER2 when administered as an antibody drug conjugate (ADC), no substantial agonistic effect on the proliferation of HER2-expressing cancer cells, and/or provide for effective antibody-dependent cellular cytotoxicity (ADCC)-mediated killing of HER2-expressing cells, as well as any combination of the foregoing properties.

In some embodiments, the antibodies disclosed herein also include an antibody or antigen binding fragment thereof that specifically binds to an epitope of the human HER2 receptor that includes residues 452 to 531 of the extracellular domain of the human HER2 receptor, residues 474 to 553 of SEQ ID NO: 16 or residues 452 to 531 of SEQ ID NO: 31.

In some embodiments, the antibodies disclosed herein include an antibody or an antigen binding fragment thereof that binds at least a portion of the N-terminus of domain IV of human HER2 receptor but does not cross-compete with an antibody that binds to epitope 4D5 of the human HER2 receptor. In some embodiments, the antibodies or antigen binding fragments thereof described herein do not cross-compete with trastuzumab for binding to the human HER2 receptor, as trastuzumab is known to bind epitope 4D5 of the human HER2 receptor. As used herein, the term epitope 4D5 of the human HER2 receptor refers to amino acid residues 529 to 627 of the extracellular domain of the human HER2 receptor, residues 551 to 649 of SEQ ID NO: 16 or residues 529 to 627 of SEQ ID NO: 31. In some embodiments, the antibody or antigen binding fragment thereof also binds at least one epitope on cynomolgus monkey HER2 receptor.

In some embodiments, the antibodies disclosed herein also include an antibody or antigen binding fragment thereof that specifically binds to an epitope of the human HER2 receptor that includes residues 452 to 500 of the extracellular domain of the human HER2 receptor, residues 474 to 522 of SEQ ID NO: 16 or residues 452 to 500 of SEQ ID NO: 31.

In some embodiments, the antibodies disclosed herein also include an antibody or antigen binding fragment thereof that specifically binds to an epitope of the human HER2 receptor that includes at least one of amino acid residue selected from amino acid residues E521, L525 and R530 of the extracellular domain of the human HER2 receptor, e.g., residues 543, 547, and 552 of SEQ ID NO: 16, and residues 521, 525, and 530 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues selected from amino acid residues E521, L525 and R530 of the extracellular domain of the human HER2 receptor. In some embodiments, the antibodies disclosed herein also include an antibody or antigen binding fragment thereof that specifically binds to an epitope of the human HER2 receptor that includes at least amino acid residues E521, L525 and R530 of the extracellular domain of the human HER2 receptor. In some embodiments, any or all of these antibodies or antigen binding fragments thereof also bind at least one epitope on cynomolgus monkey HER2 receptor.

In some embodiments, antibodies disclosed herein also include an antibody or an antigen binding fragment thereof that binds to at least a portion of domain III and at least a portion of the N-terminus of domain IV of human HER2 receptor but does not cross-compete with Fab37 monoclonal antibody or an antibody that binds to epitope 4D5 of the human HER2 receptor. In some embodiments, the antibodies or antigen binding fragments thereof described herein do not cross-compete with the Fab37 monoclonal antibody and/or trastuzumab for binding to the human HER2 receptor. In some embodiments, the antibody or antigen binding fragment thereof also binds at least one epitope on cynomolgus monkey HER2 receptor.

In some embodiments, the antibodies disclosed herein also include an antibody or antigen binding fragment thereof that specifically binds to an epitope of the human HER2 receptor that includes residues 520 to 531 of the extracellular domain of the human HER2 receptor, residues 542 to 553 of SEQ ID NO: 16 or residues 520 to 531 of SEQ ID NO: 31.

In some embodiments, the antibodies disclosed herein also include an antibody or antigen binding fragment thereof that specifically binds to an epitope of the human HER2 receptor that includes at least one amino acid residue selected from residues C453, H456, H473, N476, R495, G496, H497, and W499 of the extracellular domain of the human HER2 receptor, e.g., residues 475, 478, 495, 498, 517, 518, 519, and 521 of SEQ ID NO: 16 or residues 453, 456, 473, 476, 495, 496, 497 and 499 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues, at least three amino acid residues, at least four amino acid residues, at least five amino acid residues, or at least six amino acid residues selected from amino acid residues C453, H456, H473, N476, R495, G496, H497, and W499 of the extracellular domain of the human HER2 receptor. In some embodiments, the antibodies disclosed herein include an antibody or antigen binding fragment thereof that specifically binds to an epitope of the extracellular domain of the human HER2 receptor that includes at least amino acid residues C453, H456, H473, N476, R495, G496, H497, and W499 of the extracellular domain of the human HER2 receptor. In some embodiments, any or all of these antibodies or antigen binding fragments thereof also bind at least one epitope on cynomolgus monkey HER2 receptor.

In some embodiments, the antibodies disclosed herein also include an antibody or antigen binding fragment thereof that specifically binds to an epitope of the human HER2 receptor that includes at least one amino acid residue selected from residues C453, H473, N476, R495, H497, and W499 of the extracellular domain of the human HER2 receptor, e.g., residues 475, 495, 498, 517, 519, and 521 of SEQ ID NO: 16 or residues 453, 473, 476, 495, 497 and 499 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues, at least three amino acid residues, at least four amino acid residues, at least five amino acid residues, or at least six amino acid residues selected from amino acid residues C453, H473, N476, R495, H497, and W499 of the extracellular domain of the human HER2 receptor. In some embodiments, the antibodies disclosed herein include an antibody or antigen binding fragment thereof that specifically binds to an epitope of the extracellular domain of the human HER2 receptor that includes at least amino acid residues C453, H473, N476, R495, H497, and W499 of the extracellular domain of the human HER2 receptor. In some embodiments, any or all of these antibodies or antigen binding fragments thereof also bind at least one epitope on cynomolgus monkey HER2 receptor.

In some embodiments, these antibodies show specificity for human HER2, and they have been shown to modulate, e.g., block, inhibit, reduce, antagonize, neutralize, or otherwise interfere with the PI3K-Akt pathway which promotes cell survival by reducing levels of phosphorylated AKT. In some embodiments, these antibodies internalize from the cell surface of HER2-expressing cells at a rate that is the same or substantially similar to the rate at which trastuzumab or a biosimilar thereof internalizes. In some embodiments, these antibodies and antigen binding fragments have a rate of internalization that is about 50% of the total surface bound at time 0 being internalized by 4 hours.

In some embodiments the antibodies disclosed herein comprise a heavy chain variable region having an amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to a sequence selected from SEQ ID NOs: 17 and a light chain variable region having an amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to a sequence selected from SEQ ID NOs: 24.

In some embodiments, the antibodies disclosed herein comprise a heavy chain amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to the amino acid sequence of SEQ ID NO: 19 and a light chain amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to the amino acid sequence of SEQ ID NO: 26.

In some embodiments, the antibodies disclosed herein comprise the heavy chain variable region amino acid sequence of SEQ ID NO: 17 and the light chain variable region amino acid sequence of SEQ ID NO: 24.

In some embodiments, the antibodies disclosed herein comprise the heavy chain amino acid sequence of SEQ ID NO: 19 and the light chain amino acid sequence of SEQ ID NO: 26.

In some embodiments, the antibodies disclosed herein comprise the CDRH1 amino acid sequence of SEQ ID NO: 20, the CDRH2 amino acid sequence of SEQ ID NO: 21, the CDRH3 amino acid sequence of SEQ ID NO: 22, the CDRL1 amino acid sequence of SEQ ID NO: 27, the CDRL2 amino acid sequence of SEQ ID NO: 28, and the CDRL3 amino acid sequence of SEQ ID NO: 29.

In some embodiments, the antibodies disclosed herein include one or more conservative amino acid substitutions in a variable domain sequence such as 1, 2, 3, 4, 5, 6, 7, 8, 9, 10, 11, 12, 13, 14, 15, or more conservative substitutions in a variable domain sequence. In some embodiments, these conservative amino acid substitutions are in a CDR region, e.g., 1, 2, 3, 4, 5, 6, 7, 8, 9, 10, 11, 12, 13, 14, 15, or more conservative substitutions are made cumulatively across all CDRs. In some embodiments, up to 1, 2, 3, or 4 conservative amino acid substitutions may be present in each CDR sequence, e.g., SEQ ID NOs: 20-22 and 27-29.

Those skilled in the art will recognize that it is possible to determine, without undue experimentation, if a monoclonal antibody has the same specificity as a monoclonal antibody XMT-1519, by ascertaining whether the former prevents the latter from binding to a natural binding partner or other molecule known to be associated with HER2. In some embodiments, if the monoclonal antibody being tested competes with the monoclonal antibody disclosed herein, as shown by a decrease in binding by the monoclonal antibody disclosed herein, then the two monoclonal antibodies bind to the same, or a closely related, epitope.

In some embodiments, an alternative method for determining whether a monoclonal antibody has the specificity of monoclonal antibody disclosed herein is to pre-incubate the monoclonal antibody disclosed herein with soluble HER2 (with which it is normally reactive), and then add the monoclonal antibody being tested to determine if the monoclonal antibody being tested is inhibited in its ability to bind HER2. If the monoclonal antibody being tested is inhibited then, in all likelihood, it has the same, or functionally equivalent, epitopic specificity as the monoclonal antibody disclosed herein.

In some embodiments, screening of monoclonal antibodies disclosed herein, can be also carried out, e.g., by measuring HER2-mediated PI3K-Akt pathway activity, and determining whether the test monoclonal antibody is able to modulate, block, inhibit, reduce, antagonize, neutralize or otherwise interfere with PI3K-Akt pathway activity. In some embodiments, the HER2 antibodies suitable for conjugation can be generated and purified by well-known techniques e.g., WO 2015/195917 and PCT/US2018/019873, each of which is incorporated herein in its entirety by reference.

Modified Antibodies

In some embodiments, the antibody is a modified antibody.

In some embodiments of the modified antibody, * denotes a direct or indirect attachment to the rest of the modified antibody. In some embodiments, S" is a sugar or a derivatized sugar. In some embodiments, A" is a functional group being capable of forming a covalent bond with a functional group of the Linker-Drug moiety, In some embodiments, the modified antibody, prior to conjugation, comprises a sugar-derivative moiety of *-S"-A".

In some embodiments, the modified antibody comprises an asparagine group in the region 290-305 (e.g., at N297). In some embodiments, the sugar-derivative moiety is directly or indirectly attached to the asparagine group (e.g., at N297).

In some embodiments, the modified antibody, prior to conjugation, comprises a modified-GlcNAc moiety, *-GlcNAc-S"-A" wherein GlcNAc is N-acetylglucosamine.

In some embodiments, the modified-GlcNAc moiety is connected to the rest of the modified antibody via the C1 position of the GlcNAc. In some embodiments, the modified-GlcNAc moiety further comprises a fucose.

In some embodiments, the modified-GlcNAc moiety is directly or indirectly attached to the asparagine group (e.g., at N297).

In some embodiments, the modified antibody is conjugated to the Linker-Drug moiety via a covalent bond formed between A" and a functional group of the Linker-Drug moiety.

In some embodiments, the modified antibody of the present disclosure is obtained by a process comprising:

(a) contacting a glycoprotein (e.g., an antibody glycan) comprising an antibody and a core-GlcNAc moiety with an endoglycosidase, thereby forming an intermediate antibody comprising the antibody and a terminal-GlcNAc moiety and, optionally, the terminal-GlcNAc moiety further comprises a fucose; and (b) contacting the intermediate antibody with a compound having the structure of P"-S"-A", in the presence of a glycosyltransferase, thereby forming the modified antibody comprising the antibody and the modified-GlcNAc moiety, *-GcNAc-S"-A", and, optionally, the modified-GlcNAc moiety is attached to the rest of the modified antibody the C1 position of the GlcNAc; wherein
GlcNAc is N-acetylglucosamine;
S" is a sugar or a derivatized sugar;
A" is azido, keto, or alkynyl; and
P'" is uridine diphosphate (UDP), guanosine diphosphate (GDP) or cytidine diphosphate (CDP).

In some embodiments, steps (a) and (b) are conducted sequentially. In some embodiments, steps (a) and (b) are conducted concurrently.

In some embodiments, the antibody glycan comprises a mixture of glycoforms G0, G1, G2, G0F, G1F, G2F, and M5 (e.g., the glycoforms shown in FIG. 1).

In some embodiments, the antibody is a monoclonal antibody (mAb).

In some embodiments, the antibody is a IgA, IgD, IgE, IgG, or IgM antibody.

In some embodiments, the antibody is an IgG antibody, e.g., an IgG1, IgG2, IgG3, or IgG4 antibody. In some embodiments, the antibody is an IgG1 antibody.

In some embodiments, the antibody is a full-length antibody, and the antibody glycan comprises one or more core-GlcNAc moiety.

In some embodiments, the antibody is a full-length antibody, and the antibody glycan comprises one or more core-GlcNAc moiety connected to each heavy chain of the antibody.

In some embodiments, the core-GlcNAc moiety further comprises a fucose.

In some embodiments, the antibody is a full-length antibody, and the antibody glycan comprises two or more core-GlcNAc moiety connected to the full-length antibody.

In some embodiments, the antibody is a full-length antibody, and the antibody glycan comprises two core-GlcNAc moieties connected to the full-length antibody.

In some embodiments, at least one of the two or more core-GlcNAc moieties further comprises a fucose.

In some embodiments, each of the two or more core-GlcNAc moiety further comprises a fucose.

In some embodiments, the antibody is a single chain antibody or an antibody fragment (e.g., a Fab or Fc fragment), the antibody glycan comprises one or more core-GlcNAc moiety (which optionally further comprises fucose) connected to the antibody.

In some embodiments, the core-GlcNAc moiety is connected to a position of the antibody, wherein the core-GlcNAc moiety does not substantially hinder the antigen-binding site of the antibody.

In some embodiments, the core-GlcNAc moiety is connected to the Fc fragment of the antibody. In some embodiments, the core-GlcNAc moiety is connected to the CH domain. In some embodiments, the core-GlcNAc moiety is connected to the Fab or Fc fragment of the antibody. In some embodiments, the core-GlcNAc moiety is connected to the antibody via an N-glycosidic bond to the amide nitrogen atom in the side chain of an asparagine amino acid of the antibody. In some embodiments, the core-GlcNAc moiety is connected to a native N-glycosylation site of the antibody.

In some embodiments, the antibody is an IgG, antibody and the core-GlcNAc moiety is connected to a native N-glycosylation site of the IgG.

In some embodiments, the antibody is an IgG, antibody and the core-GlcNAc moiety is connected to a native N-glycosylation site of the IgG (e.g., the N297 N-glycosylation site of IgG). In some embodiments, the N297 N-glycosylation site is present in the conserved Fc region of the heavy chain of an IgG antibody at asparagine in the region 290-305 (e.g., at N297).

In some embodiments, the intermediate antibody is of Formula (XXII):

$$Ab\text{---}\left[\begin{array}{c}(Fuc)u_3\\|\\GlcNAc\end{array}\right]_{u_4}; \quad (XXII)$$

wherein:
Ab is an antibody; GlcNAc is N-acetylglucosamine; Fuc is fucose; $u_3$ is 0 or 1; and $u_4$ is an integer ranging from is 1 to 16.

In some embodiments, $u_4$ is an integer ranging from 1 to 10. In some embodiments, $u_4$ is 1, 2, 3, 4, 5, 6, 7 or 8. In some embodiments, $u_4$ is 1, 2, 3, 4, 5 or 6. In some embodiments, $u_4$ is 1, 2, 3 or 4. In some embodiments, $u_4$ is 2 or 4. In some embodiments, $u_4$ is 1 or 2. In some embodiments, $u_4$ is 1. In some embodiments, $u_4$ is 2.

In some embodiments, the antibody comprises one core-GlcNAc moiety (e.g., $u_4$ is 1).

In some embodiments, the antibody comprises two core-GlcNAc moieties (e.g., $u_4$ is 2).

In some embodiments, the modified antibody is obtained by the process outlined in Scheme 1. As shown below, contacting an intermediate antibody of Formula (XXIII) comprising one terminal-GlcNAc moiety with a compound having the structure of P'"-S"-A", in the presence of a glycosyltransferase, provides a modified antibody comprising one modified-GlcNAc moiety (e.g., the modified antibody of Formula (XXIIIa)).

In some embodiments, the modified antibody is obtained by contacting an intermediate antibody of Formula (XXIV) comprising two terminal-GlcNAc moieties with a compound having the structure of P'"-S"-A", in the presence of a glycosyltransferase, provides a modified antibody comprising two modified-GlcNAc moieties (e.g., the modified antibody of Formula (XXIVa)).

Scheme 1

$$Ab\text{---}\underset{(XXIII)}{\overset{\overset{(Fuc)u_3}{|}}{GlcNAc}} \xrightarrow{P'''\text{---}S''\text{---}A''}_{Glycosyl\ Transferase} Ab\text{---}\underset{(XXIIIa)}{\overset{\overset{(Fuc)u_3}{|}}{GlcNAc}}\text{---}S''(A'')$$

$$\underset{(XXIV)}{\overset{\overset{(Fuc)u_3}{|}}{GlcNAc}\text{---}Ab\text{---}\overset{\overset{(Fuc)u_3}{|}}{GlcNAc}} \xrightarrow{P'''\text{---}S''\text{---}A''}_{Glycosyl\ Transferase}$$

$$A''\text{---}S''\text{---}\overset{\overset{(Fuc)u_3}{|}}{GlcNAc}\text{---}Ab\text{---}\overset{\overset{(Fuc)u_3}{|}}{GlcNAc}\text{---}S''\text{---}A''$$
(XXIVa)

wherein $u_3$, Ab, S", A", and P'" are as defined herein.

In some embodiments, the antibody glycan to be modified in the process according to the present disclosure comprises a glycan, said glycan comprising a core-GlcNAc moiety, i.e., a GlcNAc moiety that is present at the non-reducing end of the glycan. In some embodiments, the glycan comprises one or more saccharide moieties and may be linear or branched.

In some embodiments, upon reacting with endoglycosidase, the intermediate antibody may be formed, which comprises a terminal GlcNAc moiety (e.g., the intermediate antibody of Formula (XXIII) or (XXIV)).

Figure 2:
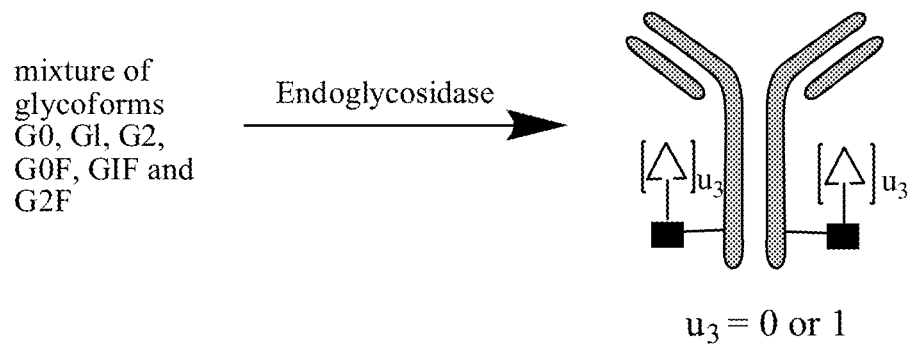
FIG. 2 is a scheme showing the deglycosylation of a mixture of glycoforms G0, G1, G2, G0F, G1F, G2F, and M5 in the presence of the endoglycosidase.

In some embodiments, step (a) of the process (the deglycosylation or trimming) is as shown in FIG. 2, wherein a mixture of antibody glycoforms G2F, G1F, G0F, G2, G1, G0, and M5 (e.g., see FIG. 1), and possibly additional glycoforms (e.g., triantennary glycans), is converted into intermediate antibodies comprising a terminal GlcNAc moiety which optionally comprises a fucose (e.g., $u_3$ is 0 or 1).

In some embodiments, the endoglycosidase is endoglycosidase Endo S, Endo SH, Endo S2, Endo S49, Endo F1, Endo F2, Endo F3, or a combination thereof.

In some embodiments, the endoglycosidase is Endo S, Endo SH, Endo S2, Endo S49, or a combination thereof.

In some embodiments the endoglycosidase is Endo S or Endo SH, or a combination thereof. In some embodiments the endoglycosidase is Endo SH.

Figure 3:
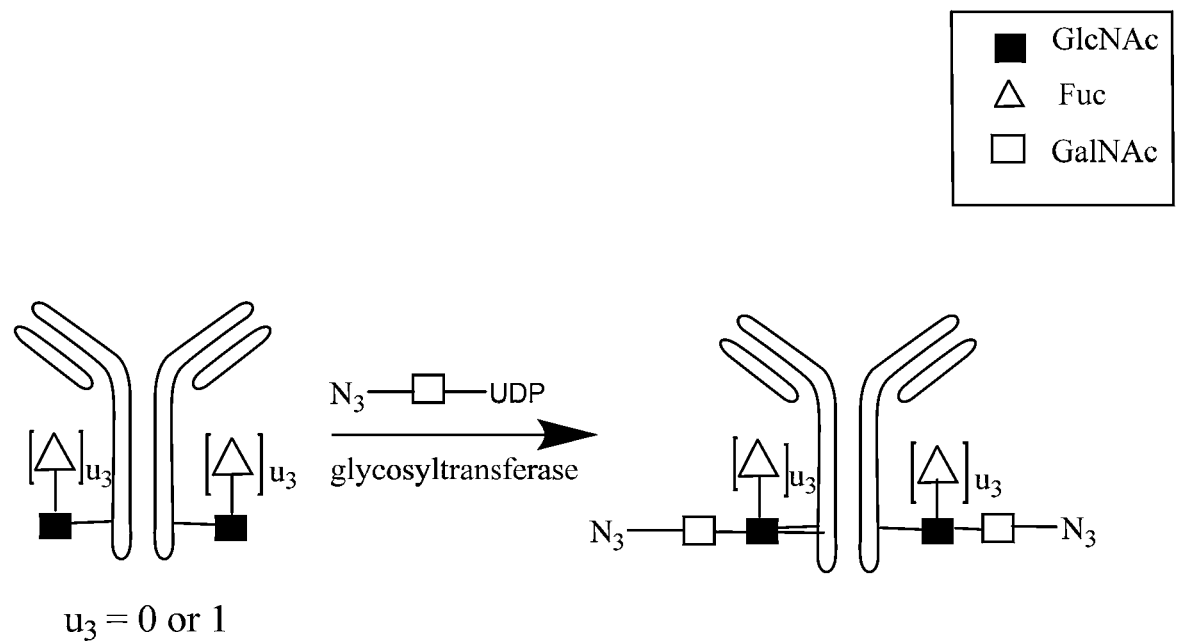
FIG. 3 is a scheme showing a process for preparing an azido-modified antibody, wherein an intermediate antibody comprising a terminal-GlcNAc moiety is reacted with an azido-modified UDP-GalNAc derivative molecule in the presence of a glycosyltransferase.

In some embodiments, step (b) of the process (the formation of the modified antibody) is as shown in FIG. 3, wherein the intermediate antibody comprises a monoclonal antibody (mAb) and a terminal terminal GlcNAc moiety (which optionally comprises a fucose (e.g., $u_3$ is 0 or 1)) on each heavy chain of the monoclonal antibody (mAb). In some embodiments, in step (b), the terminal-GlcNAc moiety is converted into modified-GlcNAc moiety. In some embodiments, said conversion may be executed via reaction of the terminal GlcNAc moiety with the compound of P'''-S''-A'' in the presence of a glycosyltransferase.

In some embodiments, the compound of P'''-S''-A'' is GalNAz-UDP (e.g., 4-AzGalNAc-UDP). In some embodiments, the terminal-GlcNAc moiety is *-GlcNAc-GalNAz or *-GlcNAc(Fuc)-GalNAz, wherein * denotes the attachment to the rest of the modified antibody.

In some embodiments, the steps of the deglycosylation/trimming step and the formation of the modified antibody are conducted sequentially.

In some embodiments, the steps of the deglycosylation/trimming step and the formation of the modified antibody are conducted simultaneously.

In some embodiments, the process for the preparation of a modified antibody is performed in a suitable buffer solution, e.g., buffered saline (e.g. phosphate-buffered saline, Tris-buffered saline), citrate, HEPES, Tris and glycine. In some embodiments, the buffer solution is phosphate-buffered saline (PBS) or Tris buffered saline. In some embodiments, the buffer solution is phosphate-buffered saline (PBS).

In some embodiments, the process is performed at a temperature ranging from about 4 to about 50° C. In some embodiments, the process is performed at a temperature ranging from about 10 to about 45° C. In some embodiments, the process is performed at a temperature ranging from about 20 to about 40° C. In some embodiments, the process is performed at a temperature ranging from about 30 to about 37° C. In some embodiments, the process is performed at a temperature of about 30° C. In some embodiments, the process is performed at a temperature of 30° C.

In some embodiments, the process is performed at a pH value ranging from about 5 to about 9 (e.g., from about 5.5 to about 8.5, from about 6 to about 8, or from about 7 to about 8). In some embodiments, the process is performed at a pH value of about 7.4.

Figure 4:
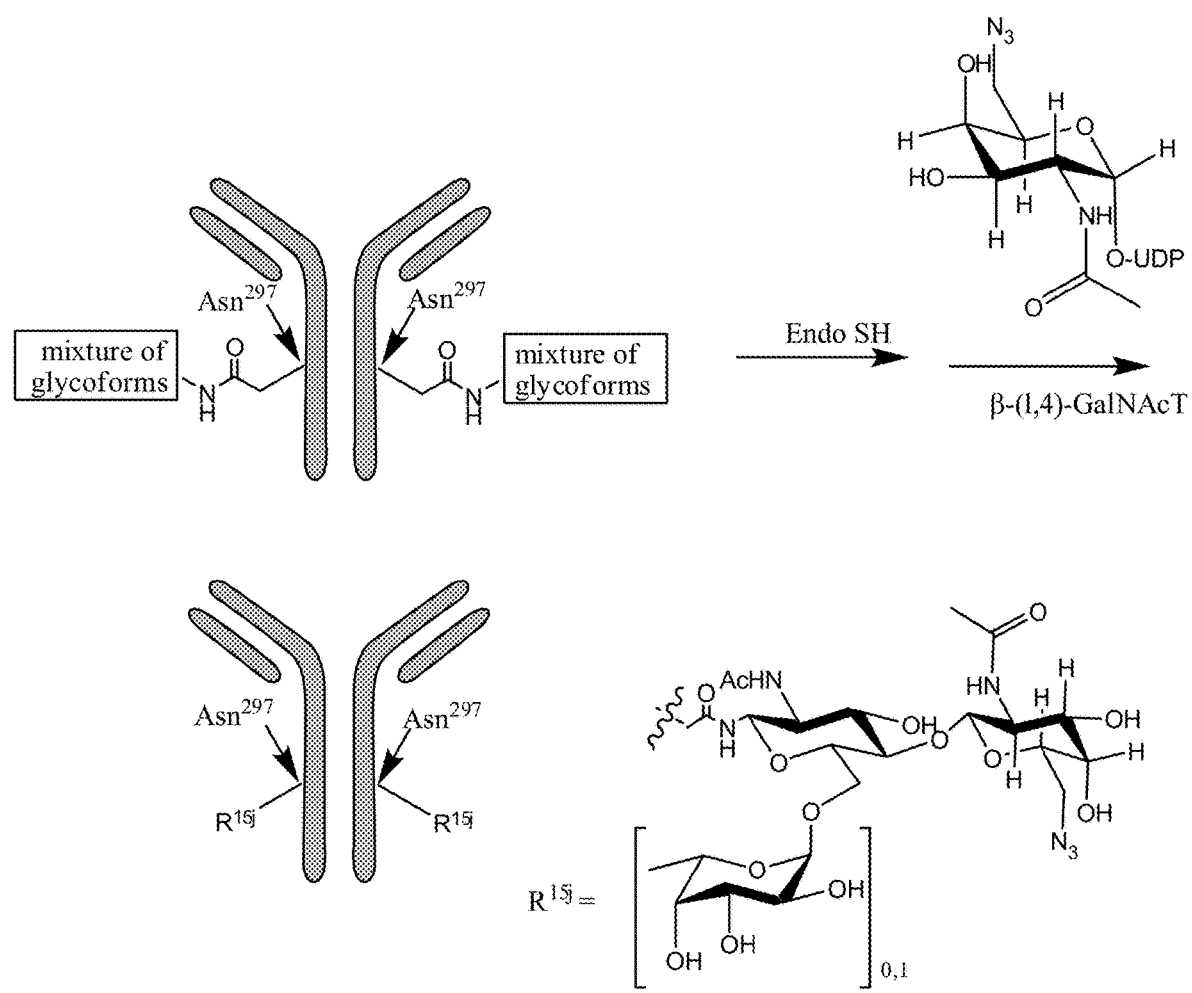
FIG. 4 is a scheme showing an embodiment of the process of preparing an azido-modified antibody.

In some embodiments, the process for the preparation of a modified antibody is as shown in FIG. 4.

In some embodiments, the process for the preparation of a modified antibody comprises:

contacting a glycoprotein (e.g., an antibody glycan) comprising an antibody and core-GlcNAc moiety connected to site N297 of the antibody, with endoglycosidase Endo SH, thereby forming an intermediate antibody comprising a terminal GlcNAc moiety; and contacting the intermediate antibody with 4-AzGalNAc-UDP in the presence of a β-(1,4)-GalNAcT enzyme, thereby forming the modified antibody comprising the modified-GlcNAc moiety;

wherein steps (a) and (b) are conducted concurrently.

In some embodiments, the endoglycosidae is Endo SH, a fusion between the two endoglycosidases, Endo S and Endo H, linked by a Gly-rich spacer comprising an internal 6×His tag resulting in an overall molecular weight of 139 kDa.

In some embodiments, the β-(1,4)-GalNAcT enzyme comprises an N-terminal 6×His tag and has an overall molecular weight of 45.7 kDa. In some embodiments, the β-(1,4)-GalNAcT enzyme containing an N-terminal 6×His tag is derived from *Trichopulsia ni*.

In some embodiments, the process is conducted in PBS buffer at pH value of about 7.4 and at a temperature of about 30° C.

Endoglycosidases

Endoglycosidases are enzymes that are capable of cleaving internal glycosidic linkages in glycan structures, thereby remodeling or trimming the glycan structure. For example, endoglycosidases can be used for the facile homogenization of heterogeneous glycan populations, when they cleave at predictable sites within conserved glycan regions. One class of endoglycosidases comprises the endo-β-N-acetylglucosaminidases (EC 3.2.1.96, commonly known as Endo S or ENGases), a class of hydrolytic enzymes that removes N-glycans from glycoproteins by hydrolyzing the β-1,4-glycosidic bond in the N,N'-diacetylchitobiose core (as described in Wong et al. Chem. Rev. 2011, 111, 4259, which is incorporated herein by reference in its entirety), leaving a single core N-linked GlcNAc residue. Endo-β-N-acetylglucosaminidases are widely found in nature with common chemoenzymatic variants including Endo D, which is specific for paucimannose; Endo A and Endo H, which are specific for high mannose; Endo F subtypes, which range from high mannose to biantennary complex; and Endo M, which can cleave most N-glycan structures (high mannose/complex-type/hybrid-type), except fucosylated glycans, and the hydrolytic activity for the high-mannose type oligosaccharides is significantly higher than that for the complex- and hybrid-type oligosaccharides. In some embodiments, these ENGases show specificity toward the distal N-glycan structure and not the protein displaying it, making them useful for cleaving most N-linked glycans from glycoproteins under native conditions.

In some embodiments, endoglycosidases F1, F2, and F3 are suitable for deglycosylation of native proteins. The linkage specificities of Endo F1, F2, and F3 suggest a general strategy for deglycosylation of proteins that may remove all classes of N-linked oligosaccharides without denaturing the protein. In some embodiments, biantennary and triantennary structures can be immediately removed by endoglycosidases F2 and F3, respectively. In some embodiments, oligo-mannose and hybrid structures can be removed by Endo F1.

Endo S is a secreted endoglycosidase from *Streptococcus pyogenes*, and also belongs to the glycoside hydrolase family 18, as disclosed by Collin et al. (EMBO J., 2001, 20, 3046), which is incorporated by reference herein in its entirety. In contrast to the ENGases mentioned above, Endo S has a more defined specificity and is specific for cleaving only the conserved N-glycan in the Fc domain of human IgGs (no other substrate has been identified to date), suggesting that a protein-protein interaction between the enzyme and IgG provides this specificity.

Endo S49, also known as Endo S2, is described in WO 2013/037824, incorporated by reference herein in its entirety, is isolated from *Streptococcus pyogenes* NZ131 and is a homologue of Endo S. Endo S49 has a specific endoglycosidase activity on native IgG and cleaves a larger variety of Fc glycans than Endo S.

Endo SH is a fusion between the two endoglycosidases, Endo S and Endo H linked by a Gly-rich spacer. Endo SH specifically cleaves the N-linked glycans between two N-acetylglucosame (GluNAc) moieties in the core region of the glycan chain.

In some embodiments, the endoglycosidase for deglycosylating the antibody is Endo S, Endo SH, Endo S2, Endo S49, Endo F1, Endo F2, Endo F3, Endo H, Endo M, Endo A, or a combination thereof. In some embodiments, the endoglycosidase for deglycosylating the antibody is Endo S, Endo SH, Endo S2, Endo S49, Endo F1, Endo F2, Endo F3, Endo H, or a combination thereof. In some embodiments, the endoglycosidase is Endo S, Endo SH, Endo S2, or Endo S49.

In some embodiments, when the glycan to be trimmed is a diantennary structure of the complex type, the endoglycosidase is Endo S, Endo SH, Endo S2, Endo S49, Endo F1, Endo F2, Endo F3, or a combination thereof.

In some embodiments, when the glycoprotein is an antibody and the oligosaccharide to be trimmed is a diantennary structure of the complex type and is present at the IgG conserved N-glycosylation site at N297, the endoglycosidase is Endo S, Endo SH, Endo S2, Endo S49, Endo F1, Endo F2, Endo F3, or a combination thereof. In some embodiments the endoglycosidase is Endo S, Endo SH, Endo S2, Endo S49, or a combination thereof.

In some embodiments, when the glycoprotein is an antibody and the glycan to be trimmed is a diantennary structure of the complex type, and is not present at the IgG conserved N-glycosylation site at N297, the endoglycosidase is Endo F1, Endo F2, Endo F3, or a combination thereof.

In some embodiments, when the glycan to be trimmed is a high mannose, the endoglycosidase is Endo H, Endo M, Endo A, Endo F1, or a combination thereof.

In some embodiments, when the glycoprotein is an antibody and the oligosaccharide to be trimmed is a high mannose in addition to having a diantennary structure of the complex type is present at the IgG conserved N-glycosylation site at N297, the endoglycosidase is Endo S, Endo SH, Endo S2, Endo S49, or a combination thereof. In some embodiments, the endoglycosidase is Endo S or Endo SH. In some embodiments, the endoglycosidase is Endo SH.

In some embodiments, the endoglycosidase enzyme as defined herein comprises a sequence encoding a tag for ease of purification. In some embodiments, said tag includes, but is not limited to, a FLAG-tag, poly(His)-tag, HA-tag, Myc-tag, SUMO-tag, GST-tag, MBP-tag, or a CBP-tag. In some embodiments, said tag is a 6×His tag. In some embodiments, said tag is covalently linked to the endoglycoside enzyme at the C-terminus of the enzyme or at an internal residue. In some embodiments, said tag is covalently linked to the endoglycoside enzyme at the N-terminus of the enzyme.

In some embodiments, the Endo SH is a fusion between the two endoglycosidases, Endo S and Endo H linked by a Gly-rich spacer comprising an internal 6×His tag resulting in an overall molecular weight of 139 kDa.

Glycosyltransferase

The process to form a modified antibody comprises treating the deglycosylated/trimmed antibody having an optionally fucosylated terminal N-acetylglucosamine (GalNAc) moiety with a compound of Formula S"(A")-P" in the presence of a glycosyltransferase to form the modified antibody having a GlcNAc-S"(A") substituent bonded to the antibody at C1 of the GalNAc moiety via a β-1,4-O-glycosidic bond.

In some embodiments, the glycosyltransferases is a β-1,4-galactosyltransferases (4Gal-T), a β-(1,4)-Acetylgalactosaminyltransferase (β-(1,4)-GalNAcT or GalNAcT) or a mutant thereof.

β-(1,4)-Acetylgalactosaminyltransferases (β-(1,4)-GalNAcTs or GalNAcTs) have been identified in a number of organisms, including humans, *Caenorhabditis elegans* (Kawar et al, J. Biol. Chem. 2002, 277, 34924, incorporated by reference herein in its entirety), *Drosophila melanogaster* (Hoskins et al. Science 2007, 316, 1625, incorporated by reference herein in its entirety) and *Trichoplusia ni* (Vadaie et al, J. Biol. Chem. 2004, 279, 33501, incorporated by reference herein in its entirety).

β-(1,4)-N-Acetylgalactosaminyltransferases (β-(1,4)-GalNAcTs) are known in the art. In some embodiments, a β-(1,4)-GalNAcT is an enzyme that catalyzes the transfer of N-acetylgalactosamine (GalNAc) from uridine diphosphate-GalNAc (UDP-GalNAc, also referred to as GalNAc-UDP) to a terminal GlcNAc moiety of a glycoprotein glycan, wherein C1 of the GalNAc moiety is attached to the antibody via a β-1,4-O-glycosidic bond. In some embodiments, the terminal GlcNAc moiety is fucosylated In some embodiments, the β-(1,4)-GalNAcT enzyme used in the process of the invention is or is derived from an invertebrate β-(1,4)-GalNAcT enzyme, such as, for example, is or is derived from a β-(1,4)-GalNAcT that originates from invertebrate animal species. The β-(1,4)-GalNAcT enzyme can be or can be derived from any invertebrate β-(1,4)-GalNAcT enzyme known by one skilled in the art. In some embodiments, the β-(1,4)-GalNAcT enzyme is or is derived from a β-(1,4)-GalNAcT enzyme that originates from the phylum of Nematoda, such as, for example, of the class of Chromadorea or Secernentea, or of the phylum of Arthropoda, such as, for example, of the class of Insecta. In some embodiments, the β-(1,4)-GalNAcT enzyme is or is derived from a β-(1,4)-GalNAcT enzyme that originates from *Caenorhabditis elegans, Caenorhabditis remanei, Caenorhabditis briggsae, Ascaris suum, Trichoplusia ni, Drosophila melanogaster, Wuchereria bancrofti, Loa loa, Cerapachys biroi, Zootermopsis nevadensis, Camponotus floridanus, Crassostrea gigas* or *Danaus plexippus*, (e.g., from *Caenorhabditis elegans, Ascaris suum, Trichoplusia ni* or *Drosophila melanogaster*). In some embodiments, the β-(1,4)-GalNAcT enzyme is, or is derived from, a β-(1,4)-GalNAcT enzyme that originates from *Caenorhabditis elegans, Ascaris suum* or *Trichoplusia ni*. In other embodiments, the β-(1,4)-GalNAcT enzyme is, or is derived from, a β-(1,4)-GalNAcT enzyme that originates from *Trichoplusia ni*.

The term "derived from" comprises e.g. truncated enzymes, mutant enzymes, enzymes comprising a tag for ease of purification or a combination of these modifications. Derived from thus refers to as having an amino acid sequence that is altered from a naturally occurring β-(1,4)-GalNAcT enzyme by substituting, inserting, deleting, or adding one or more, (e.g., 1, 2, 3, 4, 5, 6, 7, 8, 9, 10, 12, 14, 16, 18, 20 or more) amino acids, respectively. A β-(1,4)-GalNAcT enzyme that is derived from a β-(1,4)-GalNAcT enzyme is herein also referred to as a derived β-(1,4)-

GalNAcT enzyme or a modified β-(1,4)-GalNAcT enzyme or a β-(1,4)-GalNAcT mutant enzyme.

In some embodiments, the derived β-(1,4)-GalNAcT enzyme is modified by adding additional N- or C-terminal amino acids or chemical moieties or by deleting N- or C-terminal amino acids to increase stability, solubility, activity and/or ease of purification.

In some embodiments, the β-(1,4)-GalNAcT enzyme is modified by deleting the N-terminal cytoplasmic domain and transmembrane domain, referred to as a truncated enzyme.

A β-(1,4)-GalNAcT enzyme wherein one or more amino acid has been substituted, added or deleted is herein also referred to as a mutant β-(1,4)-GalNAcT enzyme or a derived β-(1,4)-GalNAcT enzyme. In some embodiments, the β-(1,4)-GalNAcT enzyme is modified by deleting the N-terminal cytoplasmic domain and transmembrane domain and mutated by substituting one or more amino acids. A substitution of one or more amino acids is herein also referred to as a mutation. An enzyme comprising one or more substituted amino acids is also referred to as a mutant enzyme.

In some embodiments, when the glycosyltransferase is a β-(1,4)-GalNAcT enzyme or truncated β-(1,4)-GalNAcT enzyme, the enzyme further comprises one or more mutations. In some embodiments, these mutations include, but are not limited to, substitution of the isoleucine (He, also referred to as I) at position 257 by leucine (Leu, also referred to as L), methionine (Met, also referred to as M), or alanine (Ala, also referred to as A). In some embodiments, substitution of the methionine (Met, also referred to as M) at position 312 by histidine (His, also referred to as H) is also included. It should be noted that the numbering of amino acid position is herein based on the numbering of amino acid position in the wild-type β-(1,4)-GalNAcT enzyme. When a β-(1,4)-GalNAcT enzyme is, for example, a truncated enzyme, the number used herein to indicate the position of an amino acid substitution corresponds to the numbering of amino acid position in the corresponding wild-type β-(1,4)-GalNAcT enzyme.

In some embodiments, the glycosyltransferase is a β(1,4)-GalT enzyme comprising a mutant catalytic domain.

A catalytic domain may have an amino acid sequence as found in a wild-type enzyme or have an amino acid sequence that is different from that of a wild-type sequence. A catalytic domain having an amino acid sequence that is different from a wild-type sequence is herein referred to as a mutant catalytic domain. In some embodiments, the mutation may comprise a single amino acid change (for example, a point mutation), or multiple amino acids changes (for example, 1 to 10, or 1 to 6, or 1, 2, 3 or 4, or 1 or 2 amino acids), or a deletion or insertion of one or more amino acids (for example, 1 to 10, or 1 to 6, or 1, 2, 3 or 4, or 1 or 2) amino acids. In some embodiments, said mutant catalytic domain may be present in a full-length enzyme, for example, β(1,4)-galactosyltransferase or α(1,3)-N-galactosyltransferase, but also in a polypeptide fragment or a recombinant polypeptide comprising said mutant catalytic domain, optionally linked to additional amino acids.

β(1,4)-galactosyltransferase I is herein referred to as GalT. Such mutant GalT catalytic domains are disclosed in, for example, WO 2004/063344, which is incorporated by reference herein in its entirety. WO 2004/063344 also discloses Tyr-289 mutants of GalT and their methods of preparation. These mutants are referred to as Y289L, Y289N or Y289I.

In some embodiments, the GalT mutant catalytic domain is Y289L, Y289N, Y289I, Y284L, or R228K. In some embodiments, the GalT mutant catalytic domain is Y289L.

In some embodiments, the GalT Y289F, GalT Y289M, GalT Y289V, GalT Y289G, GalT Y289I, GalT Y289A, GalT Y289N, and GalT Y289L mutants may be produced via site-directed mutagenesis processes, described in, for example, WO2004063344, Qasba et al, Prot. Expr. Pur. 2003, 30, 219 and Qasba et al, J. Biol. Chem. 2002, 277, 20833 (all incorporated by reference herein in their entirety). In GalT Y289F the tyrosine amino acid (Y) at position 289 is replaced by a phenyl alanine (F) amino acid, in GalT Y289M said tyrosine is replaced by a methionine (M) amino acid, in GalT Y289V by a valine (V) amino acid, in GalT Y289G by a glycine (G) amino acid, in GalT Y289I by an isoleucine (I) amino acid and in Y289A by an analine (A) amino acid.

In some embodiments, the β-(1,4)-GalNAcT enzyme comprises a sequence encoding a tag for ease of purification. In some embodiments, said tag includes, but is not limited to, a FLAG-tag, poly(His)-tag, HA-tag, Myc-tag, SUMO-tag, GST-tag, MBP-tag, or a CBP-tag. In other embodiments, said tag is a 6×His tag. In some embodiments, said tag is covalently linked to the β-(1,4)-GalNAcT enzyme at the C-terminus of the enzyme. In some embodiments, said tag is covalently linked to the β-(1,4)-GalNAcT enzyme at the N-terminus of the enzyme.

In some embodiments, β-(1,4)-GalNAcT enzyme comprises an N-terminal 6×His tag and has an overall molecular weight of 45.7 kDa. In some embodiments, the β-(1,4)-GalNAcT enzyme containing an N-terminal 6×His tag is derived from *Trichopulsia ni*.

Molecules of P"-S"-A"

In some embodiments, the molecule of P"-S"-A", for use in the process of preparing a modified antibody of the present disclosure, may be any sugar derivative nucleotide that is a substrate for a suitable galactosyltransferase catalyst.

In some embodiments, S"-A" is a sugar derivative moiety, wherein:

S" is a sugar or a derivatized sugar; and A" is a functional group being capable of forming a covalent bond with a functional group of the Linker-Drug moiety.

In some embodiments, A" is an azido, keto, or alkynyl moiety. In some embodiments, A" is an azido or keto moiety. In some embodiments, A" is an azido moiety. In some embodiments, A" is —$N^3$. In some embodiments, A" is a keto moiety.

In some embodiments, A" is —$[C(R^{8k})_2]_{x2}C(O)R^{9k}$, wherein:

$R^{9k}$ is methyl or optionally substituted $C_{2-24}$ alkyl;

each $R^{8k}$ independently is a hydrogen, halogen, or $R^{9k}$; and $x_2$ is an integer ranging from 0 to 24.

In some embodiments, $x_2$ is an integer ranging from 0 to 10. In some embodiments, $x_2$ is 0, 1, 2, 3, 4, 5, or 6.

In some embodiments, each $R^{8k}$ is hydrogen.

In some embodiments, A" is an alkynyl moiety. In some embodiments, A" is terminal alkynyl, cycloalkynyl, or heterocycloalkynyl moiety. In some embodiments, A" is terminal alkynyl moiety. In some embodiments, A" is cycloalkynyl moiety. In some embodiments, A" is heterocycloalkynyl moiety.

In some embodiments, A" is —$[C(R^{8k})_2]_{x2}$—C≡C—$R^{8k}$ group, wherein $R^{8k}$ and $x_2$ are as defined herein. In some embodiments, A" is —$[CH_2]_{x2}$—C≡CH.

In some embodiments, S"-A" is derived from a sugar or a derivatized sugar, e.g., an amino sugar or an otherwise derivatized sugar. In some embodiments, examples of sugars and derivatized sugars include, but are not limited to, galactose (Gal), mannose (Man), glucose (Glc), glucuronic acid (Gcu), and fucose (Fuc). It is understood that an amino sugar is a sugar wherein a hydroxyl (OH) group is replaced by an amine group. Examples of amino sugars include, but are not limited to, N-acetylglucosamine (GlcNAc), and N-acetylgalactosamine (GalNAc). Examples of otherwise derivatized sugars include, but are not limited to, glucuronic acid (Gcu), and N-acetylneuraminic acid (sialic acid).

In some embodiments, S"-A" is derived from galactose (Gal), mannose (Man), N-acetylglucosamine (GlcNAc), glucose (Glc), N-acetylgalactosamine (GalNAc), glucuronic acid (Gcu), fucose (Fuc), or N-acetylneuraminic acid (sialic acid). In some embodiments, S"-A" is derived from GlcNAc, Glc, Gal, or GalNAc. In some embodiments, S"-A" is derived from GlcNAc. In some embodiments, S"-A" is derived from Glc. In some embodiments, S"-A" is derived from Gal or GalNAc. In some embodiments, S"-A" is derived from Gal. In some embodiments, S"-A" is derived from GalNAc.

In some embodiments, the functional group A" may be attached to S" in various ways.

In some embodiments, A" is directly attached to the carbon atom at C2, C3, C4, or C6 position of the sugar or derivatized sugar of S" (e.g., instead of the hydroxyl at the corresponding position).

In some embodiments, S" is a fucose or a derivatized fucose, which lacks any hydroxyl C6 position. In some embodiments, when A" is attached to C6 position of the fucose or derivatized fucose, A" is directly attached to the carbon atom at the C6 position.

In some embodiments, A" is an azido moiety, and A" is attached to C2, C4, or C6 position of the sugar or derivatized sugar of S".

In some embodiments, A" is an azido moiety, and A" is directly attached to the carbon atom at C2, C3, C4 or C6 position of the sugar or derivatized sugar of S" (e.g., instead of the hydroxyl at the corresponding position). In some embodiments, S"-A" is 6-azidofucose (6-AzFuc). In some embodiments, A" is an azido moiety, and A" is attached to the N-acetyl moiety of an amino sugar or a derivatized amino sugar (e.g., by replacing the acetyl moiety with an azidoacetyl moiety). In some embodiments, S"-A" is 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc), or 6-azido-6-deoxy-2-azidoacetamidoglucose (6-AzGlcNAz). In some embodiments, S"-A" is GalNAz, 4-AzGalNAc, GlcNAz, or 6-AzGlcNAc.

In some embodiments, P"-S"-A" is a compound of Formula (XXIVb), (XXXIVc), or (XXIVd), or a salt thereof.

In some embodiments, A" keto, and A" is directly attached to the carbon atom at C2 position of the sugar or derivatized sugar of S" (e.g., instead of the hydroxyl at the corresponding position).

In some embodiments, A" is attached to the nitrogen atom of an amino sugar or derivatized amino sugar, e.g., a C2-derivatized amino sugar. In some embodiments, the derivatized amino sugar comprises a moiety of —NC(O)—$R^{9k}$, wherein $R^{9k}$ is methyl or optionally substituted $C_{2-24}$ alkyl (e.g., ethyl).

In some embodiments, $R^{9k}$ is ethyl.

In some embodiments, S"-A" is 2-deoxy-(2-oxopropyl)-galactose (2-keto-Gal), 2-N-propionyl-galactosamine (2-N-propionylGal-NAc), 2-N-(4-oxopentanoyl)-galactosamine (2-N-Lev-Gal), or 2-N-butyryl-galactosamine (2-N-butyryl-GalNAc). In some embodiments, S"-A" is 2-ketoGalNAc or 2-N-propionyl-GalNAc.

In some embodiments, P"-S"-A" is a compound of Formula (XXIVe) or (XXIVf), or a salt thereof.

In some embodiments, A" is terminal alkynyl, cycloalkynyl, or heterocycloalkynyl. In some embodiments, A" is attached to a C2-derivatized amino sugar of S".

In some embodiments, S"-A" is 2-(but-3-ynoic acid amido)-2-deoxy-galactose.

In some embodiments, P"-S"-A" is a compound of Formula (XXIVg) or a salt thereof. In some embodiments, P"-S"-A" is a compound of Formula (XXIVd) or a salt thereof.

In some embodiments, compounds of P"-S"-A" may be synthesized according to various methods known in the art. In some embodiments, the compound is synthesized by linking a nucleoside monophosphate or a nucleoside diphosphate P" to a sugar derivative S"-A", e.g., as disclosed in Wang et al. (*Chem. Eur. J.* 16:13343-13345 (2010)), Piller et al. (*ACS Chem. Biol.* 7:753 (2012)), Piller et al. (Bioorg. Med. Chem. Lett. 15:5459-5462 (2005), and PCT Appl'n Pub. No. WO/2009/102820, each of which are incorporated by reference herein in their entireties.

In some embodiments, P" is a nucleoside mono- or diphosphate. In some embodiments, P" is uridine diphosphate (UDP), guanosine diphosphate (GDP), thymidine diphosphate (TDP), cytidine diphosphate (CDP), or cytidine monophosphate (CMP). In some embodiments, P" is uridine diphosphate (UDP).

In some embodiments, P"-S"-A" is a compound of Formula (XXIVb), (XXIVc), (XXIVd), (XXIVe), (XXIVf), or (XXIVg):

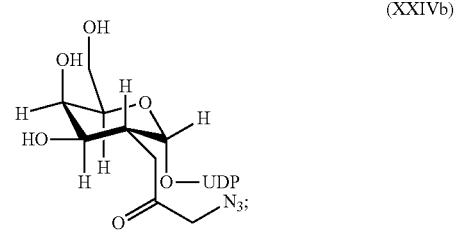
(XXIVb)

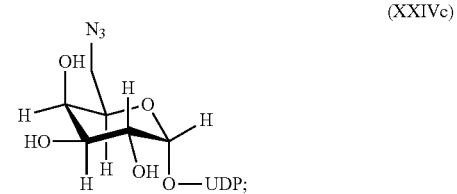
(XXIVc)

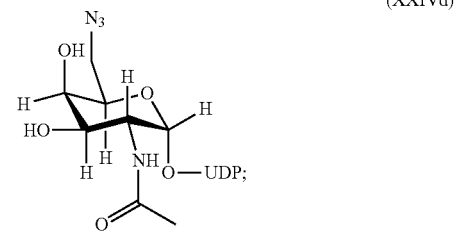
(XXIVd)

-continued

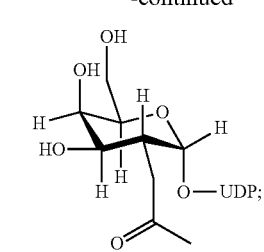

(XXIVe)

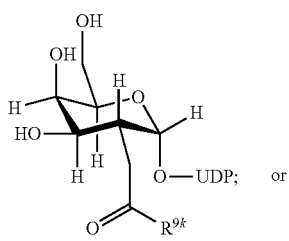

(XXIVf)

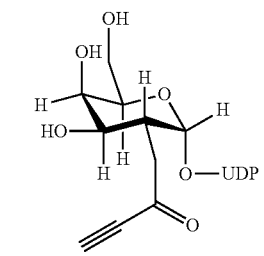

(XXIVg)

or a salt thereof, wherein: $R^{9k}$ is a $C_{2-24}$ alkyl group.

In some embodiments, P"-S"-A" is GalNAz-UDP (e.g., Formula (XXIVb)), 6-AzGal-UDP (e.g., Formula (XXIVc)), 6-AzGalNAc-UDP (e.g., Formula (XXIVd)), 4-AzGalNAz-UDP, 6-AzGalNAz-UDP, 6-AzGlc-UDP, 6-AzGlcNAz-UDP, 2-ketoGal-UDP (e.g., Formula (XXIVe)), 2-N-propionylGalNAc-UDP (e.g., Formula (XXIVf), wherein $R^{9k}$ is ethyl), or 2-(but-3-ynoic acid amido)-2-deoxy-galactose-UDP (e.g., Formula (XXIVg)).

In some embodiments, P"-S"-A" is GalNAz-UDP or 4-AzGalNAc-UDP. In some embodiments, P"-S"-A" is a compound of Formula (XXIVb) or (XXIVd). The syntheses of GalNAz-UDP (e.g., Formula (XXIVb)) and 6-AzGal-NAc-UDP (e.g., Formula (XXIVd)) are disclosed in Piller et al. (Bioorg. Med. Chem. Lett. 15:5459-5462 (2005)) and Wang et al. (*Chem. Eur. J.* 16:13343-13345 (2010)), each of which is incorporated by reference herein in its entirety.

In some embodiments, P"-S"-A" is 4-AzGalNAc-UDP. In some embodiments, P"-S"-A" is a compound of Formula (XXIVd) or a salt thereof. The synthesis of 2-ketoGal-UDP (XXIVe) is disclosed in Qasba et al. (*J. Am. Chem. Soc.* 125:16162 (2003)), and in the supporting information thereof, both of which are incorporated by reference herein in their entireties.

The synthesis of 2-(but-3-ynoic acid amido)-2-deoxy-galactose-UDP is disclosed in PCT Appl'n Pub. No. WO/2009/102820, which is incorporated by reference herein in its entirety.

Antibody Drug Conjugates

In some embodiments, antibody-drug conjugates of the present disclosure may be obtained by reacting the modified antibody of the present disclosure with a Linker-Drug moiety comprising a functional group (e.g., $W^P$), which is capable of forming a covalent bond with the functional group A" of the modified-GlcNAc moiety, *-GlcNAc-S"-A", in the modified antibody.

In some embodiments, $W^P$ comprises alkynyl e.g., cycloalkynyl, heterocycloalkynyl, or terminal alkynyl.

In some embodiments, the functional group A" of the modified antibody is azido, keto, or alkynyl. In some embodiments, the functional group A" of the modified antibody is azido. In some embodiments, the azido functional group A" of the modified antibody reacts with the alkynyl of $W^P$ (e.g., the cycloalkynyl, heterocycloalkynyl, or terminal alkynyl) of the Linker-Drug moiety to form a triazole moiety (e.g., via a cycloaddition reaction). The cycloaddition reaction of an azido group and an alkynyl group is known in the art as "click chemistry".

In some embodiments, $W^P$ of the Linker-Drug moiety comprises a terminal alkynyl, and the cycloaddition reaction may be performed in the presence of a catalyst (e.g., a Cu(I) catalyst).

In some embodiments, $W^P$ of the Linker-Drug moiety comprises cycloalkynyl or heterocycloalkynyl (e.g., strained cycloalkynyl or heterocycloalkynyl).

In some embodiments, $W^P$ of the Linker-Drug moiety comprises a strained cycloalkynyl or heterocycloalkynyl, and the cycloaddition reaction may be performed in the presence or absence of a catalyst. In some embodiments, the cycloaddition reaction may occur spontaneously by a reaction called strain-promoted azide-alkyne cycloaddition (SPAAC), which is known in the art as "metal-free click chemistry". In some embodiments, the strained cycloalkynyl or heterocycloalkynyl is as described herein.

In some embodiments, upon conjugation, the functional group A" of the modified antibody and $W^P$ of the Linker-Drug moiety forms a triazole moiety.

In some embodiments, upon conjugation, the functional group A" of the modified antibody and $W^P$ of the Linker-Drug moiety forms a triazole moiety of Formula (XXXV):

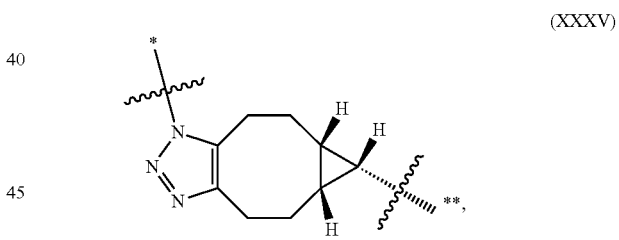

(XXXV)

wherein * denotes a direct or indirect attachment to the rest of the modified antibody; and ** indicates attachment to $N^P$.

In some embodiments, when an azide-modified antibody of the present disclosure is reacted with a Linker-Drug moiety comprising an alkynyl group to form an antibody-drug conjugate via a cycloaddition reaction, the formed triazole moiety in the antibody-drug conjugate may be resistant to hydrolysis and/or other degradation pathways.

In some embodiments, when an aldehyde or ketone-modified antibody of the present disclosure is reacted with a Linker-Drug moiety comprising a hydroxylamine or a hydrazine, the resulting oxime or hydrazone moiety in the antibody-drug conjugate may be relatively inert at neutral conditions.

In some embodiments, the antibody-drug conjugate of the present disclosure may be of high stability.

In some embodiments, the modified antibody and antibody-drug conjugate of the present disclosure may be synthesized by practical synthetic routes, as the process for introducing the functional group A" (e.g., azido, keto, or alkynyl) into the antibody is straightforward and generally applicable.

In some embodiments, a site-specific antibody-drug conjugate of the present disclosure is obtained by a process comprising reacting a modified antibody with a Linker-Drug moiety, wherein:

the Linker-Drug moiety comprises cycloalkynyl or heterocycloalkynyl, the modified antibody, prior to conjugation, comprises an antibody and a modified GlcNAc moiety of *-GlcNAc-S"-A" attached to an antibody via the C1 position of the GlcNAc; GlcNAc is N-acetylglucosamine; S" is a sugar or a derivatized sugar; and A" is azido.

In some embodiments, A" is cycloalkynyl or heterocycloalkynyl. In some embodiments, A" is cycloalkynyl. In some embodiments, A" is heterocycloalkynyl.

In some embodiments, A" is strained cycloalkynyl or heterocycloalkynyl. In some embodiments, A" is strained cycloalkynyl. In some embodiments, A" is strained heterocycloalkynyl.

In some embodiments, a site-specific antibody-drug conjugate of the present disclosure is obtained by a process comprising the steps of:

(a) contacting an intermediate antibody of Formula (XXII):

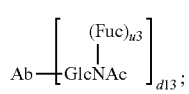
(XXII)

wherein:

Ab is an antibody; GlcNAc is N-acetylglucosamine; Fuc is fucose; $u_3$ is 0 or 1; and $d_{13}$ is an integer ranging from 1 to 12;

with a compound P"-S"-A", wherein:

S" is a sugar or a derivatized sugar; A" is azido; and P is uridine diphosphate (UDP), guanosine diphosphate (GDP), or cytidine diphosphate (CDP);

in the presence of an galactosyltransferase, thereby forming a modified antibody comprising the modified-GlcNAc moiety, *-GlcNAc-S"-A" (optionally, the modified-GlcNAc moiety is attached to the rest of the modified antibody the C1 position of the GlcNAc); and (b) reacting the modified antibody with a Linker-Drug moiety comprising a strained cycloalkynyl or heterocycloalkynyl, thereby forming the antibody-drug conjugate.

Figure 5:
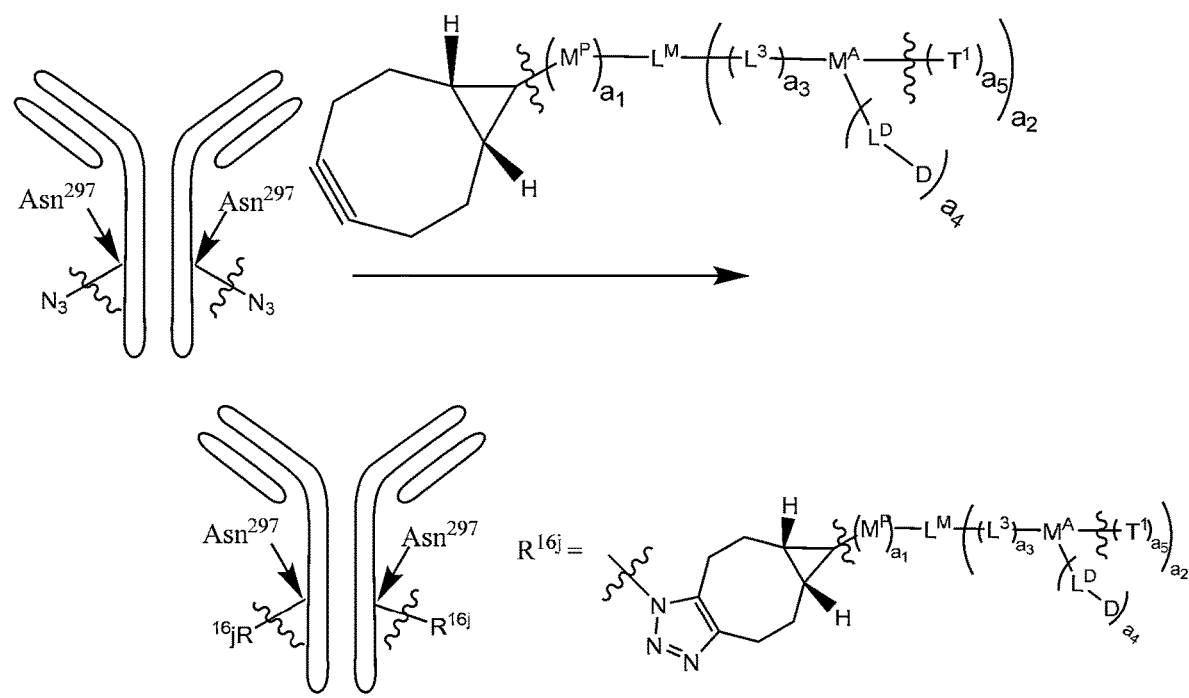
FIG. 5 is a scheme showing an embodiment of the process of preparing an antibody-drug conjugate, wherein an azido-modified antibody is conjugated to a Linker-Drug moiety comprising strained cycloalkynyl group.
Figure 6:
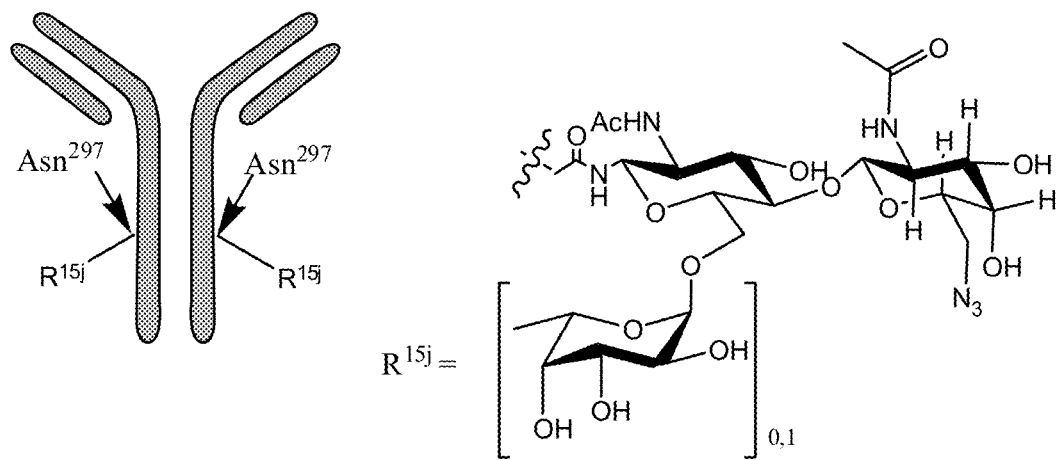
FIG. 6 is a graph showing a modified antibody.

In some embodiments, the process for preparing a site-specific antibody-drug conjugate is as depicted in FIG. 5.

In some embodiments, the modified antibody comprising an azido at each amino acid N297 of the antibody is conjugated with a Linker-drug moiety comprising strained cycloalkynyl or heterocycloalkynyl by metal-free click chemistry to form the site-specific antibody-drug conjugate of the present disclosure.

In some embodiments, when the modified antibody comprises at least one azido moiety and the Linker-drug moiety comprises a strained cycloalkynyl, the presence of a copper catalyst is not necessary for the cycloaddition reaction between the azido in the motified antibody and the strained cycloalkynyl or heterocycloalkynyl of the Linker-Drug moiety. In some embodiments, the cycloaddition reaction proceeds in the absence of a copper catalyst, which may alleviate several possible disadvantages of using a copper catalyst in the process.

In some embodiments, a Cu(I) catalyst is generally required in the cycloaddition of an azido moiety of an antibody and a terminal alkyne moiety. In some embodiments, extensive optimization and fine-tuning of conditions may be required to find the optimal parameters for efficient conversion. Nevertheless, even under such conditions, the concomitant formation of reactive oxygen species cannot always be fully avoided, which in turn may induce oxidative damage to the antibody/protein (e.g., oxidation of methionine, histidine, cysteine or disulfide bonds). Other protocols have employed Cu(I) sources such as CuBr for labeling fixed cells and synthesizing glycoproteins. In these cases, the instability of Cu(I) in air imposes a requirement for large excesses of Cu (e.g., greater than 4 mm) and ligand for efficient reactions, which could also raise the risk of antibody/protein damage or precipitation, plus the presence of residual metal after purification. Thus, the conjugation of an azido-containing antibody to a terminal alkyne in the presence of a copper catalyst can lead to extensive side-product formation by undesired amino acid oxidation.

In some embodiments, the modified antibody comprising an azido (e.g., at each amino acid N297 of the antibody) is conjugated with a Linker-Drug moiety comprising strained cycloalkynyl or heterocycloalkynyl (e.g., by metal-free click chemistry).

In some embodiments, upon conjugation, the azido moiety of the modified antibody and the strained cycloalkynyl or heterocycloalkynyl of the Linker-Drug moiety forms a triazole moiety of Formula (XXXV):

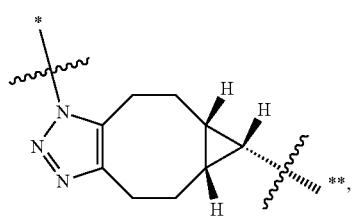
(XXXV)

wherein * denotes a direct or indirect attachment to the rest of the modified antibody; and ** indicates attachment to $N^P$.

In some embodiments, the antibody-drug conjugate of the present disclosure comprises one or more occurrences of D, wherein each D independently is a therapeutic agent (e.g., a drug), wherein the one or more occurrences of D may be the same or different.

In some embodiments, one or more specific sites of the antibody is attached to the Linker-Drug moiety, wherein the Linker-Drug moieties attached to the one or more specific sites may be the same or different. In some embodiments, one or more Linker-Drug moieties that comprises one or more occurrences of D are attached to one antibody.

In some embodiments, D is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase; (q) a PARP inhibitor; (r) a NAMPT inhibitor; (s) a topoisomerase inhibitor; (t) a protein synthesis inhibitor; (u) a DNA-binding drug; (v) a DNA intercalation drug; or (w) an immunomodulatory compound.

In some embodiments, D is (a) an auristatin compound; (b) a calicheamicin compound; (c) a duocarmycin compound; (d) a camptothecin compound, (e) a pyrrolobenzodiazepine compound; (f) a vinca compound; or an analog thereof.

In some embodiments, the auristatin compound is auristatin, dolastatin, monomethylauristatin E (MMAE), monomethylauristatin F (MMAF), auristatin F, AF-HPA, MMAF-HPA, or phenylenediamine (AFP).

In some embodiments, the duocarmycin or an analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

In some embodiments, the camptothecin compound is camptothecin, CPT-11 (irinotecan), SN-38, or topotecan.

In some embodiments, the pyrrolobenzodiazepine compound is a pyrrolobenzodiazepine monomer, a symmetrical pyrrolobenzodiazepine dimer, or an unsymmetrical pyrrolobenzodiazepine dimer.

In some embodiments, the antibody-drug conjugate of the present disclosure comprises an modified antibody that has a molecular weight about 40 kDa or greater (e.g., about 60 kDa or greater; about 80 kDa or greater; about 100 kDa or greater; about 120 kDa or greater; about 140 kDa or greater; about 160 kDa or greater; about 180 kDa or greater; or about 200 kDa or greater, or about 40-200 kDa, about 40-180 kDa, about 40-140 kDa, about 60-200 kDa, about 60-180 kDa, about 60-140 kDa, about 80-200 kDa, about 80-180 kDa, about 80-140 kDa, about 100-200 kDa, about 100-180 kDa, or about 100-140 kDa).

In some embodiments, the modified antibody has a molecular weight of about 40 kDa or greater (e.g., about 60 kDa or greater; about 80 kDa or greater; about 100 kDa or greater; about 120 kDa or greater; about 140 kDa or greater; about 160 kDa or greater; about 180 kDa or greater; or about 200 kDa or greater; or about 40-200 kDa, about 40-180 kDa, about 40-140 kDa, about 60-200 kDa, about 60-180 kDa, about 60-140 kDa, about 80-200 kDa, about 80-180 kDa, about 80-140 kDa, about 100-200 kDa, about 100-180 kDa, or about 100-140 kDa) and is modified at the amino acid N297.

In some embodiments, the total number of specific bonds formed between the Linker-Drug moiety and the antibody (or total number of attachment points) is 12 or less. In some embodiments, the total number of specific bonds formed between the Linker-Drug moiety and the antibody (or total number of attachment points) is 10 or less. In some embodiments, the total number of specific bonds formed between the Linker-Drug moiety and the antibody (or total number of attachment points) is 8 or less. In some embodiments, the total number of specific bonds formed between the Linker-Drug moiety and the antibody (or total number of attachment points) is 6 or less. In some embodiments, the total number of specific bonds formed between the Linker-Drug moiety and the antibody (or total number of attachment points) is 4 or less. In some embodiments, the total number of specific bonds formed between the Linker-Drug moiety and the antibody (or total number of attachment points) is 2 or less.

In some embodiments, the total number of specific bonds formed between the Linker-Drug moiety and the antibody (or total number of attachment points) is 2.

In some embodiments (e.g., for conjugation with one or more Linker-Drug moieties), the modified antibody has a molecular weight of about 140 kDa to about 180 kDa. In some embodiments for conjugation with one or more Linker-Drug moieties, the modified antibody has a molecular weight of 140 kDa to 180 kDa.

In some embodiments, antibodies in this molecular weight range include, but are not limited to, for example, full length antibodies, such as, IgG or IgM.

In some embodiments, the modified antibody, linker, or therapeutic agent described herein may be assembled into the conjugate or scaffold of the present disclosure according to various techniques and methods known in the art. The conjugate of the present disclosure, and method for producing the conjugate, are described herein (e.g., by way of non-limiting embodiments and examples).

In some embodiments, the total number of bonds formed between the Linker-Drug moiety and the modified antibody (or total number of attachment points) is 12 or less.

In some embodiments, the ratio between the Linker-Drug moiety and the modified antibody is greater than 1:1 and less than or equal to 12:1. In some embodiments, the ratio between Linker-Drug moiety and the modified antibody is about 12:1, about 11:1, about 10:1, about 9:1, about 8:1, about 7:1, about 6:1, about 5:1, about 4:1, about 3:1, about 2:1, or about 1:1. In some embodiments, the ratio between Linker-Drug moiety and the modified antibody is between 2:1 and 10:1. In some embodiments, the ratio between Linker-Drug moiety and the modified antibody is about 10:1, about 9:1, about 8:1, about 7:1, about 6:1, about 5:1, about 4:1, about 3:1, or about 2:1. In some embodiments, the ratio between Linker-Drug moiety and the modified antibody is between about 2:1 and about 4:1. In some embodiments, the ratio between Linker-Drug moiety and the modified antibody is about 4:1, about 3:1, or about 2:1. In some embodiments, the ratio between Linker-Drug moiety and the modified antibody is about 2:1, or 1:1.

In some embodiments, $a_2$ is 3, the ratio between the Linker-Drug moiety and the modified antibody is 2:1, and the ratio between the therapeutic agent (D) and the modified antibody is about 8:1, about 7:1, about 6:1, about 5:1, about 4:1, about 3:1, about 2:1 or about 1:1. In some embodiments, $a_2$ is 3, the ratio between the Linker-Drug moiety and the modified antibody is 2:1, and the ratio between the therapeutic agent (D) and the modified antibody is about 6:1, about 5:1, about 4:1, about 3:1, about 2:1 or about 1:1. In some embodiments, $a_2$ is 3, the ratio between the Linker-Drug moiety and the modified antibody is 2:1, and the ratio between the therapeutic agent (D) and the modified antibody is about 6:1, about 5:1, about 4:1 or about 3:1. In some embodiments, $a_2$ is 3, the ratio between the Linker-Drug moiety and the modified antibody is 1:1, and the ratio between the therapeutic agent (D) and the modified antibody is about 3:1, about 2:1 or about 1:1.

In some embodiments, $a_2$ is 3, the ratio between the Linker-Drug moiety and the modified antibody is 2:1, and the ratio between the therapeutic agent (D) and the modified antibody is about 8:1. In some embodiments, $a_2$ is 3, the ratio between the Linker-Drug moiety and the modified antibody is 2:1, and the ratio between the therapeutic agent (D) and the modified antibody is about 6:1. In some embodiments, $a_2$ is 3, the ratio between the Linker-Drug moiety and the modified antibody is 2:1, and the ratio between the therapeutic agent (D) and the modified antibody is about 5:1. In some embodiments, $a_2$ is 3, the ratio between the Linker-Drug moiety and the modified antibody is 2:1, and the ratio between the therapeutic agent (D) and the modified antibody is about 4:1. In some embodiments, $a_2$ is 3, the ratio between the Linker-Drug moiety and the modified antibody is 2:1, and the ratio between the therapeutic agent (D) and the modified antibody is about 3:1. In some embodiments, $a_2$ is 3, the ratio between the Linker-Drug moiety and the modified antibody is 2:1, and the ratio between the therapeutic agent (D) and the modified antibody is about 2:1. In some embodiments, $a_2$ is 3, the ratio between the Linker-Drug moiety and the modified antibody is 2:1, and the ratio between the therapeutic agent (D) and the modified antibody is about 1:1.

In some embodiments, the ratio between Linker-Drug moiety and the modified antibody is about 2:1.

In some embodiments, the antibody comprises an asparagine group in the region 290-305 (e.g., at N297) attached to the sugar-derivative moiety, which comprises a functional group A"; and the modified antibody is conjugated to the Linker-Drug moiety by a covalent bond formed between A" and a functional group of the Linker-Drug moiety.

In some embodiments, the Linker-Drug moiety comprises at least two functional groups, each of which is capable of forming a covalent bond with a functional group A" of the sugar-derivative moiety of the modified antibody (e.g., at amino acid N297 of the antibody) to form an antibody-drug conjugate.

In some embodiments (e.g., for conjugating to the Linker-Drug moiety), the modified antibody has a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In some embodiments, the ratio between the modified antibody and the Linker-Drug moiety is between about 1:1 and about 1:2.

In some embodiments, antibodies in this molecular weight range include, but are not limited to, full length antibodies (e.g., IgG and IgM).

In some embodiments (e.g., for conjugation with one or more Linker-Drug moieties), the modified antibody has a molecular weight of 60 kDa to 120 kDa. In some embodiments, the ratio between the modified antibody and the Linker-Drug moiety is between about 1:1 and about 1:2.

In some embodiments, antibodies in this molecular weight range include, but are not limited to, antibody fragments (e.g., Fab2, scFcFv, and camelids).

In some embodiments (e.g., for conjugation with one or more Linker-Drug moieties), the modified antibody has a molecular weight of 40 kDa to 80 kDa. In some embodiments, the ratio between the modified antibody and the Linker-Drug moiety is between about 1:1 and about 1:2.

In some embodiments, the antibody drug conjugate and scaffold of the present disclosure can be purified (e.g., to remove any starting materials) by extensive diafiltration. If necessary, additional purification by size exclusion chromatography can be conducted to remove any aggregated conjugates. In some embodiments, the purified conjugate or scaffold comprises less than 500 w/w (e.g., <2% w/w) aggregated conjugates as determined by SEC; less than 0.5% w/w (e.g., <0.100 w/w) free (unconjugated) drug as determined by RP-HIPLC; less than 1% w/w drug carrying-peptide-containing scaffolds as determined by SEC; and/or less than 2% w/w (e.g., <1% w/w) unconjugated antibodies as determined by HIC-TIPLC.

In some embodiments, the Linker-Drug moiety is selected from the scaffolds described in Tables B below.

TABLE B

| Drug linker No. | Structure |
|---|---|
| | 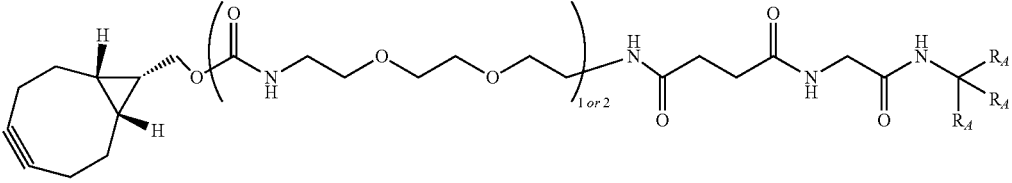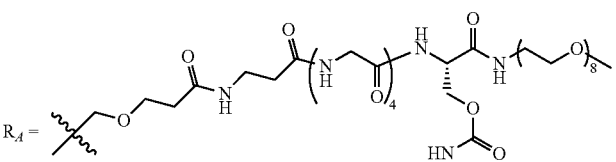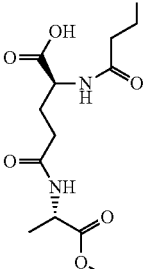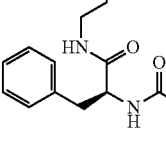 |

| Drug linker No. | Structure |
|---|---|
| | 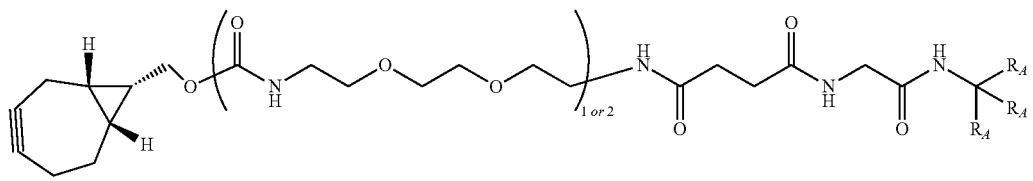<br>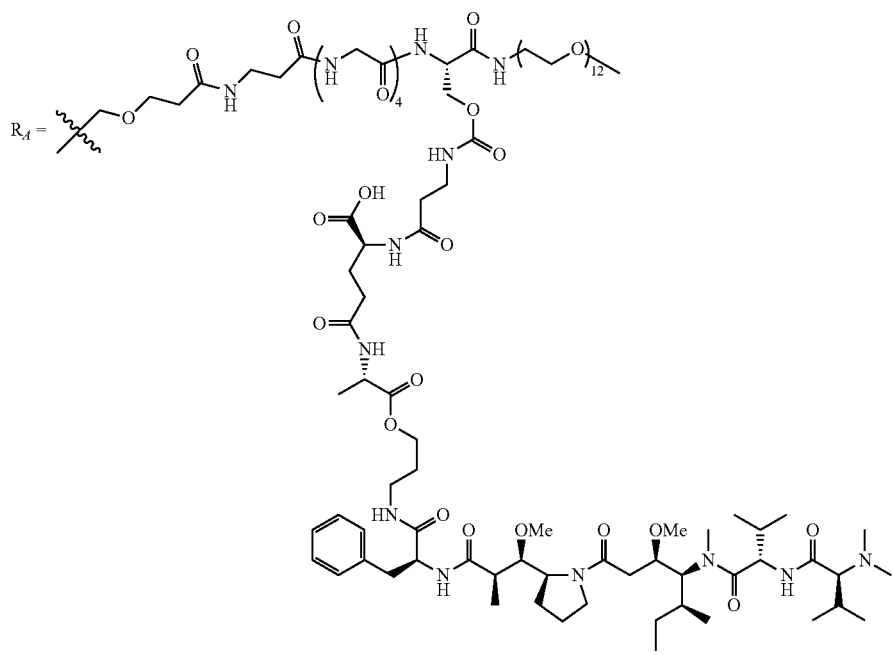<br>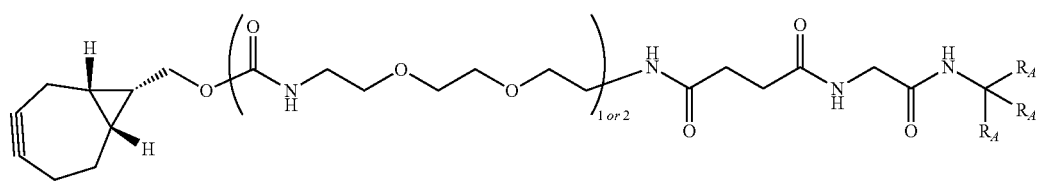 |

125 126
TABLE B-continued
| Drug linker No. | Structure |
|---|---|
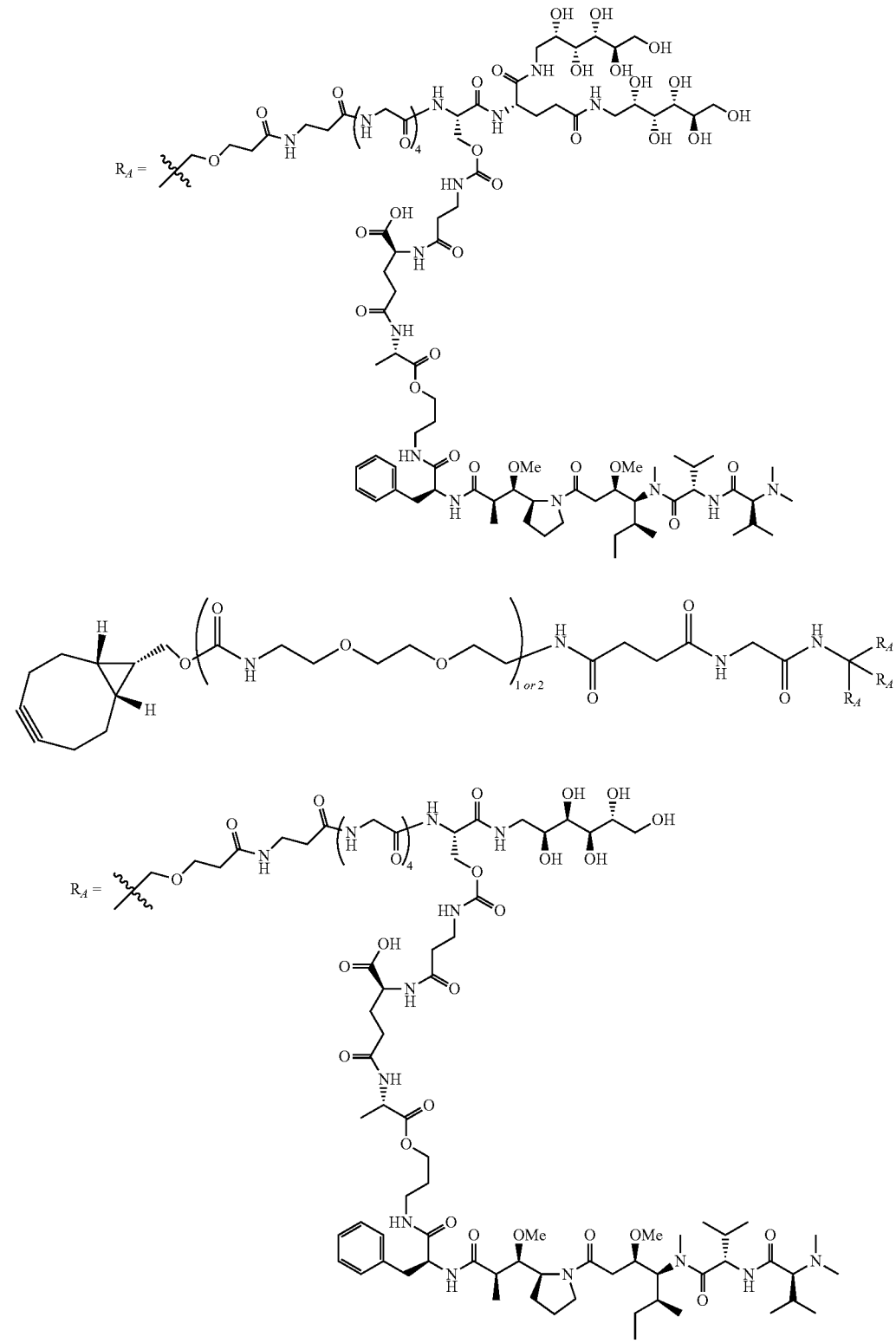

TABLE B-continued
| Drug linker No. | Structure |
|---|---|
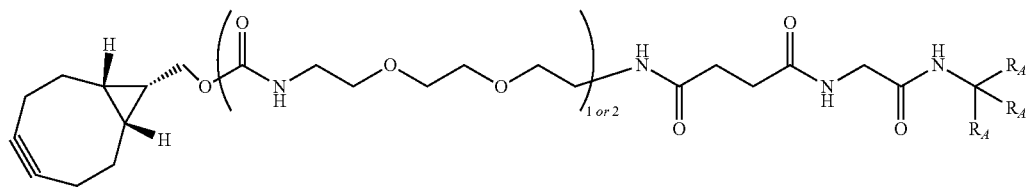
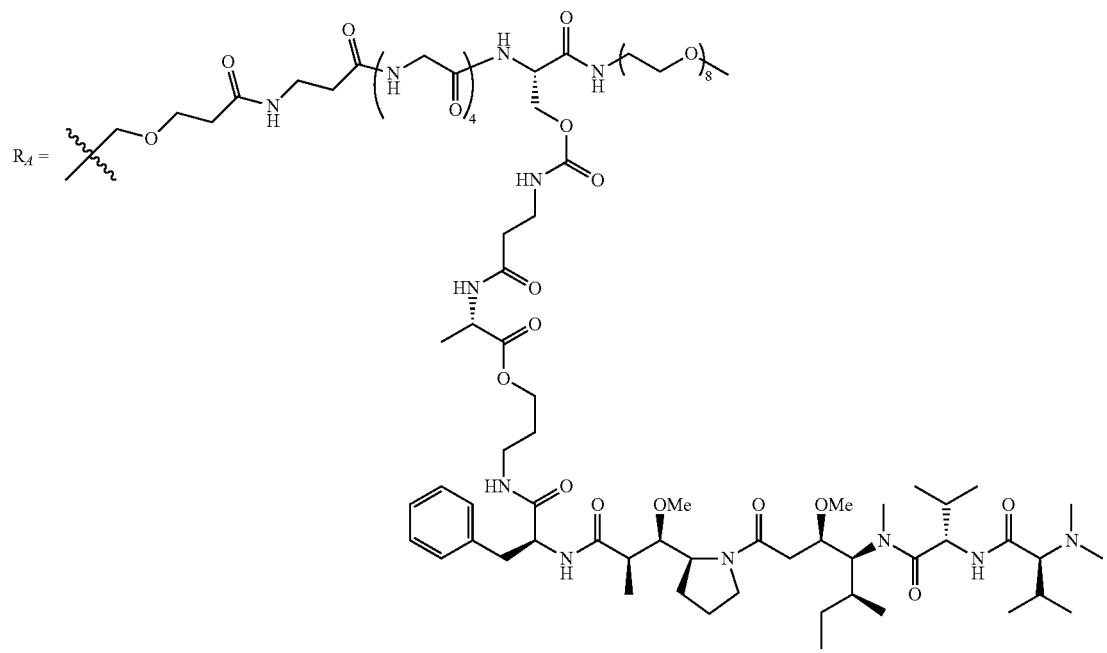
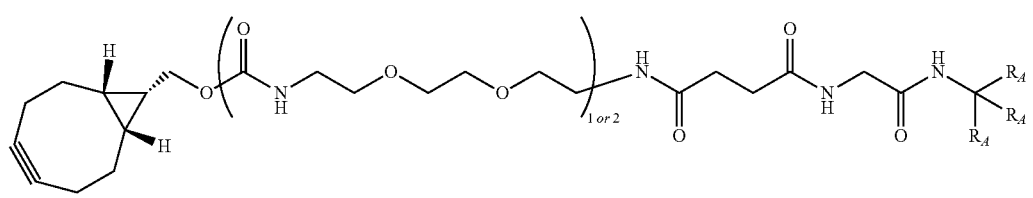

US 11,786,605 B2
129                                                                        130
TABLE B-continued
Drug
linker
No.                                   Structure
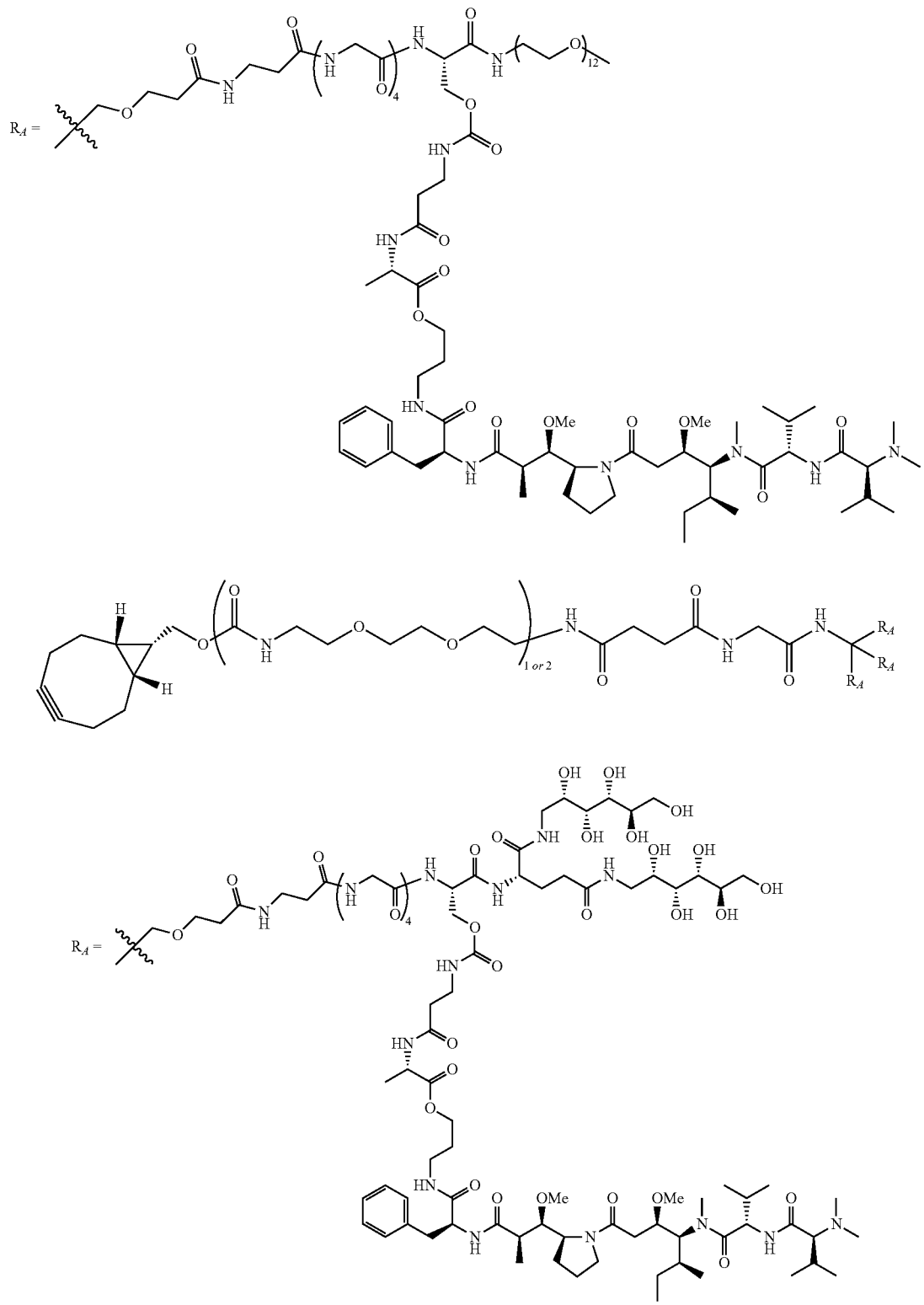

TABLE B-continued
| Drug linker No. | Structure |
|---|---|
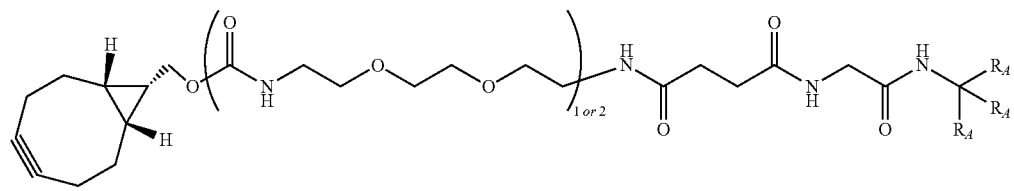
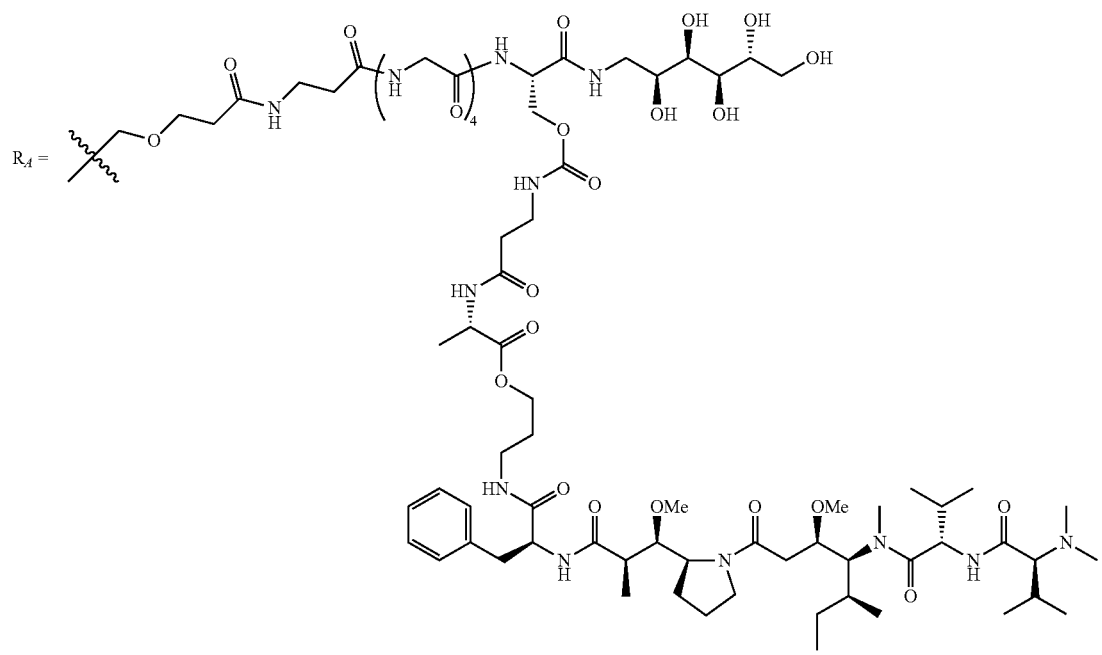
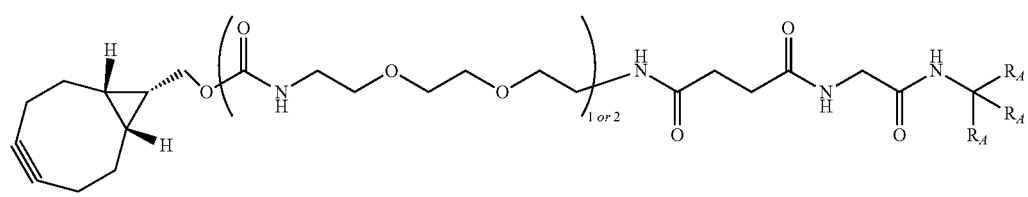

TABLE B-continued

| Drug linker No. | Structure |
|---|---|

TABLE B-continued
| Drug linker No. | Structure |
|---|---|
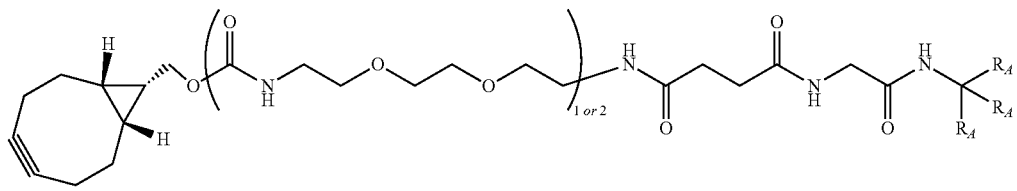
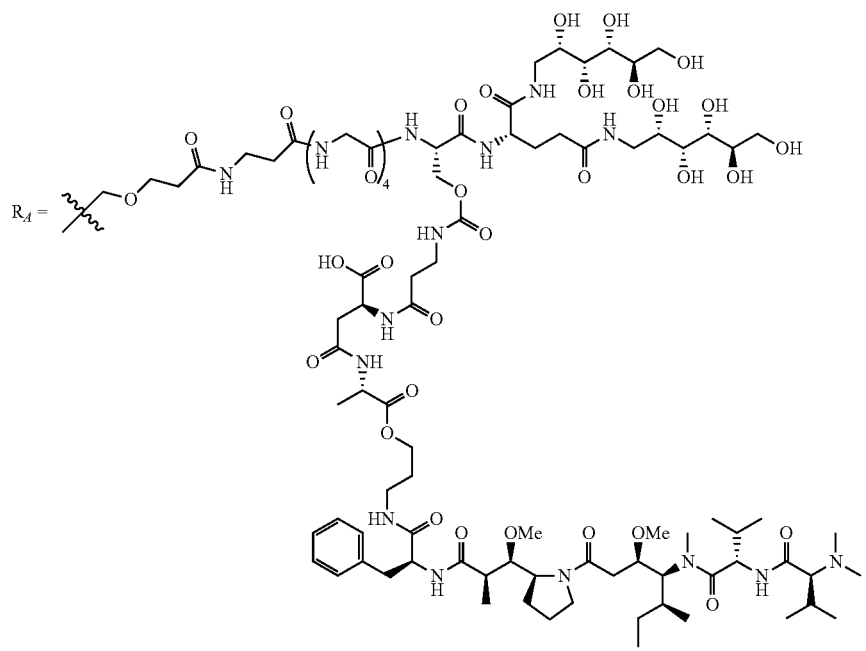
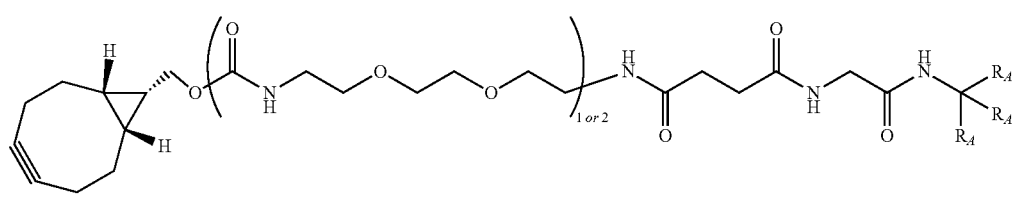

TABLE B-continued
| Drug linker No. | Structure |
|---|---|
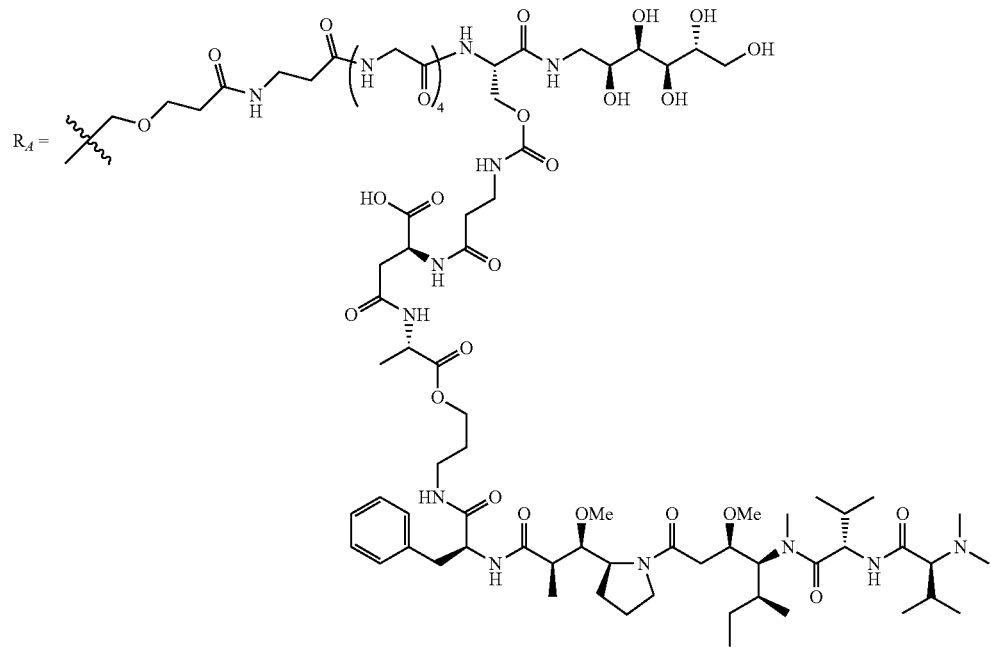
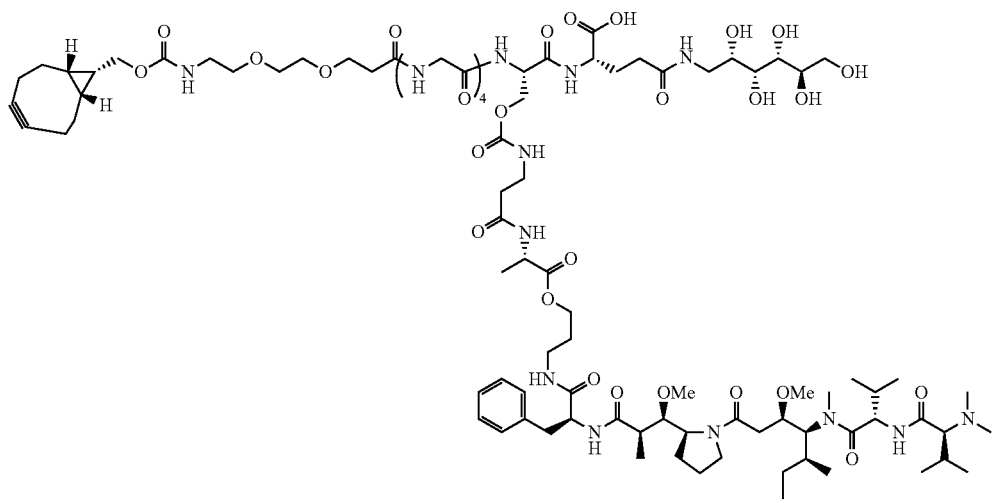

TABLE B-continued
| Drug linker No. | Structure |
|---|---|
| | 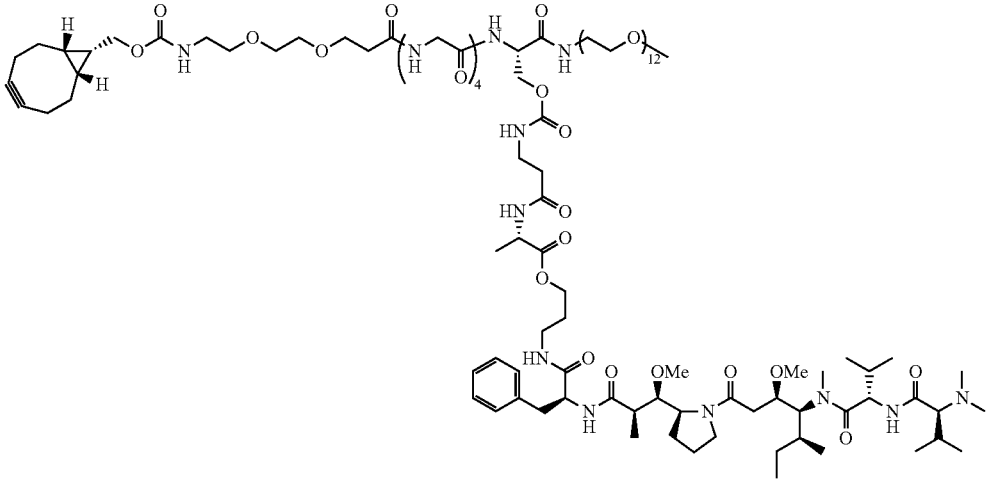 |
| | 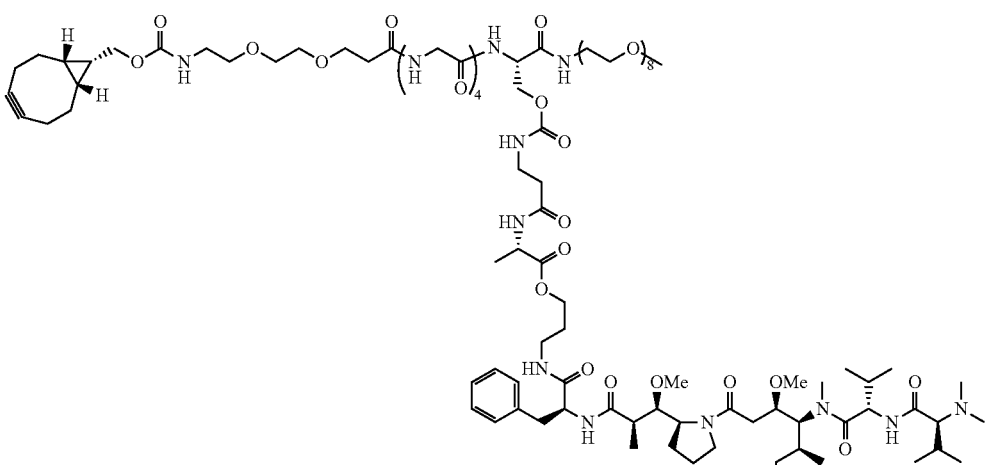 |
| | 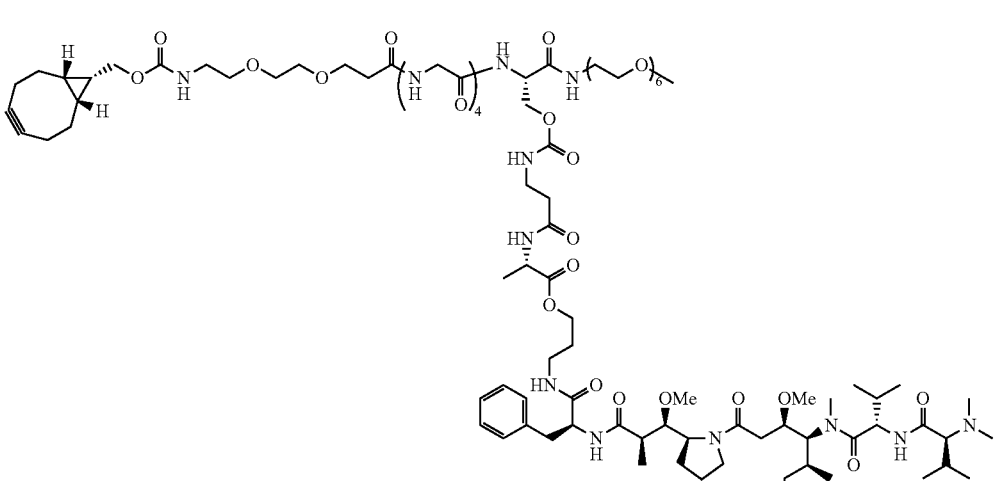 |

| Drug linker No. | Structure |
|---|---|
| | 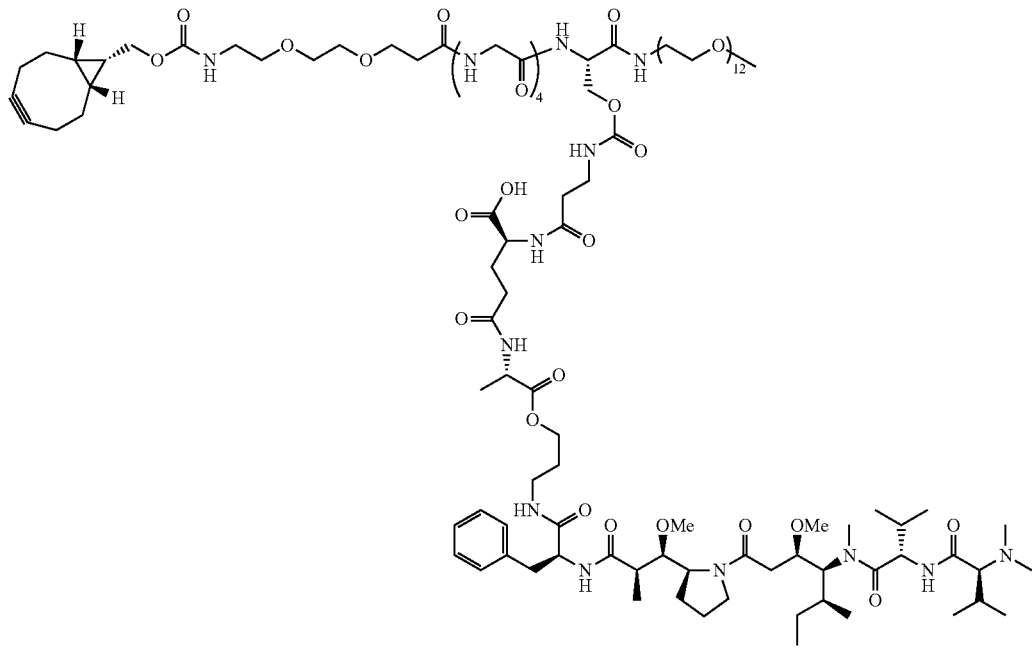 |
| | 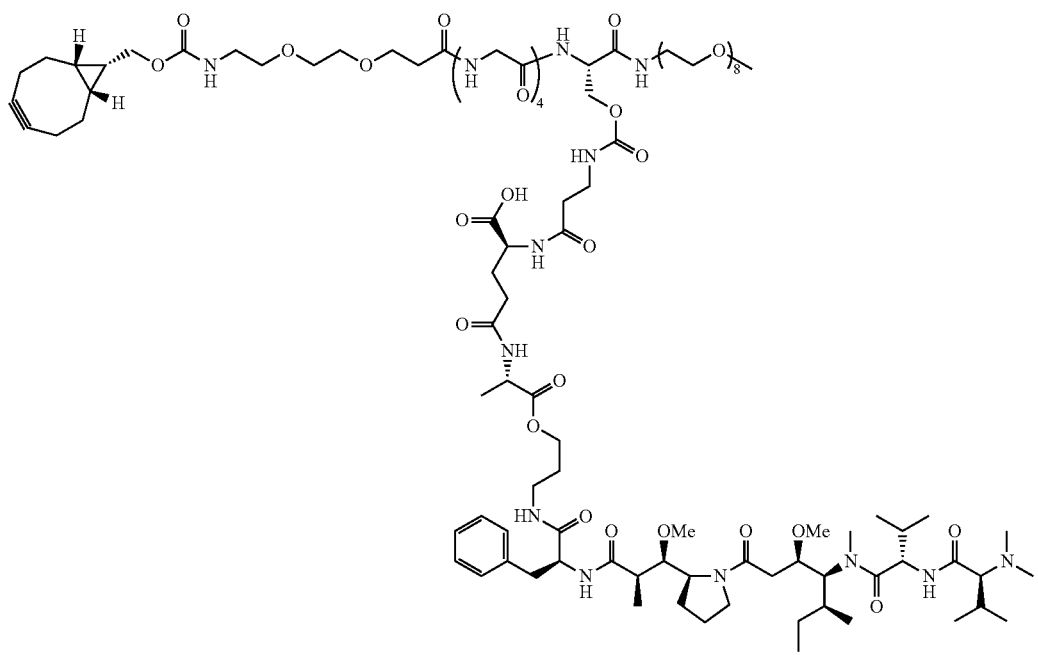 |
In some embodiments, the antibody-drug conjugate is selected from conjugates described in Table C below.

TABLE C

| Conjugate No. | Structure |
|---|---|
| | |

TABLE C-continued

| Conjugate No. | Structure |
|---|---|
| | (chemical structure) |

TABLE C-continued

| Conjugate No. | Structure |
|---|---|

TABLE C-continued
| Conjugate No. | Structure |
|---|---|
| | 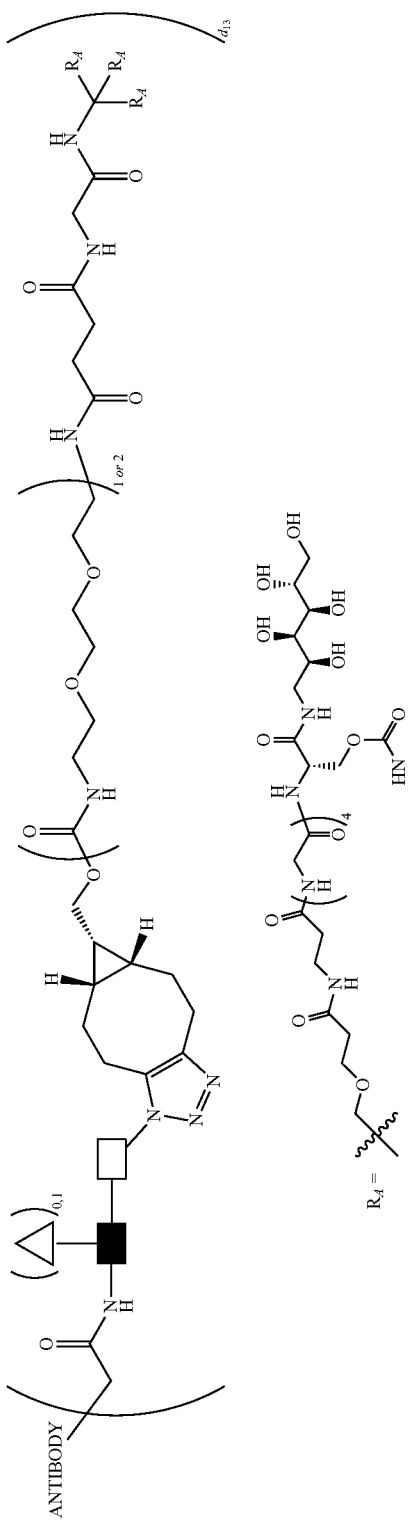 |

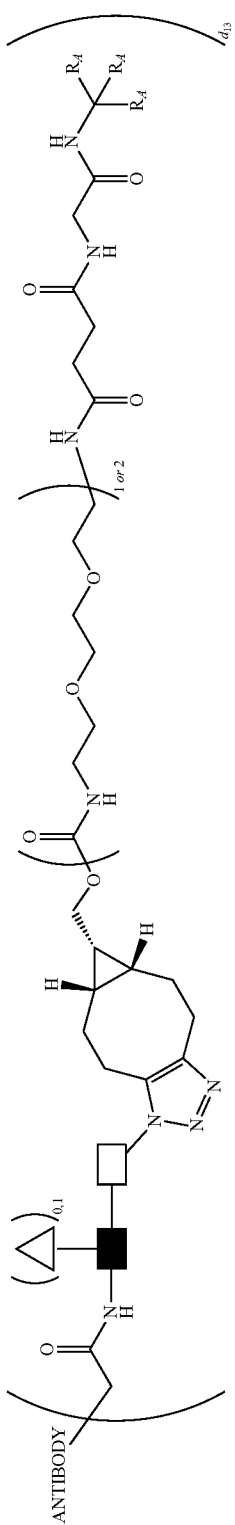

TABLE C-continued
| Conjugate No. | Structure |
|---|---|
| | 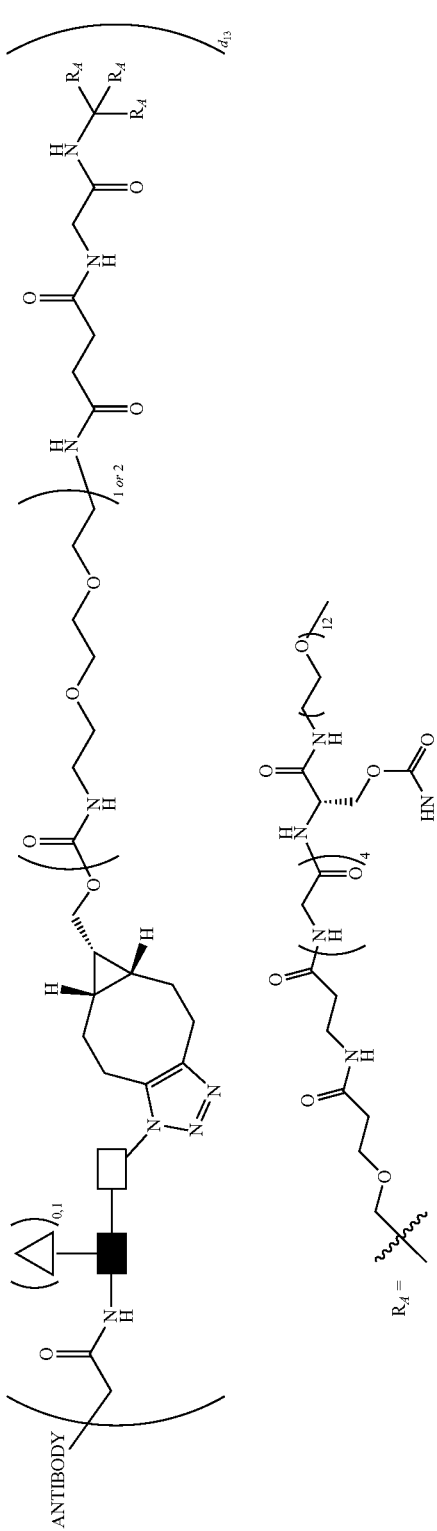 |

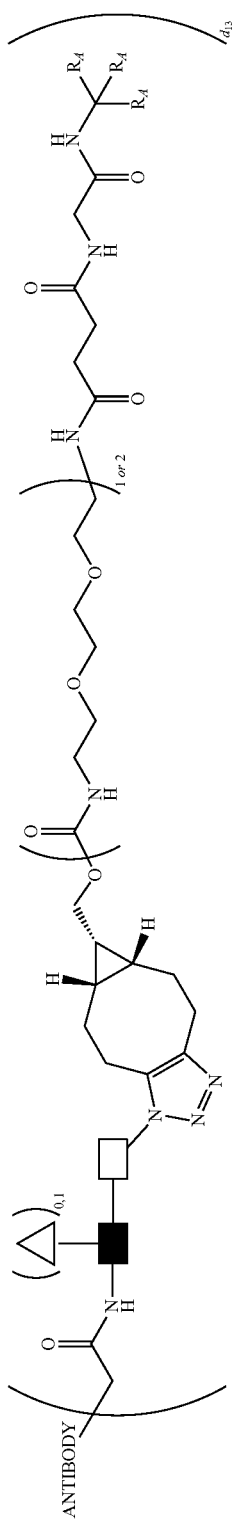

TABLE C-continued

| Conjugate No. | Structure |
|---|---|

TABLE C-continued

| Conjugate No. | Structure |
|---|---|
| | (chemical structure) |

TABLE C-continued

| Conjugate No. | Structure |
|---|---|
| | (chemical structure) |

TABLE C-continued

Conjugate No. | Structure

TABLE C-continued
| Conjugate No. | Structure |
|---|---|
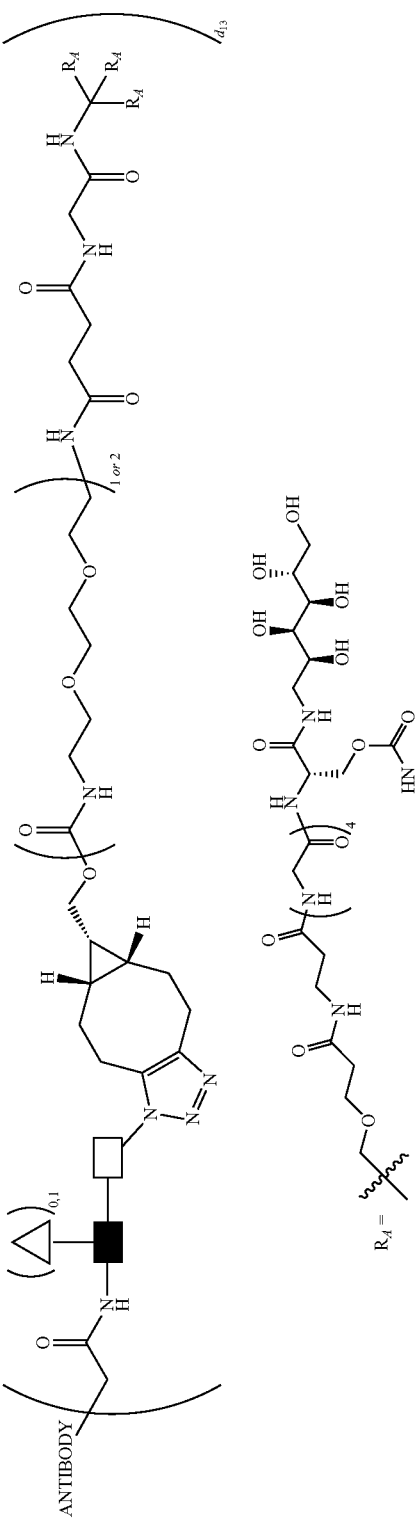

TABLE C-continued
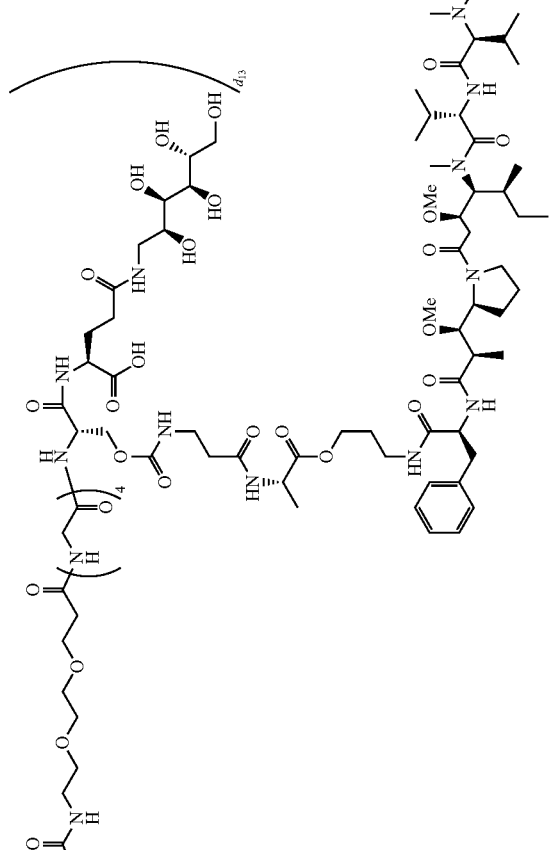

TABLE C-continued
| Conjugate No. | Structure |
|---|---|
| | 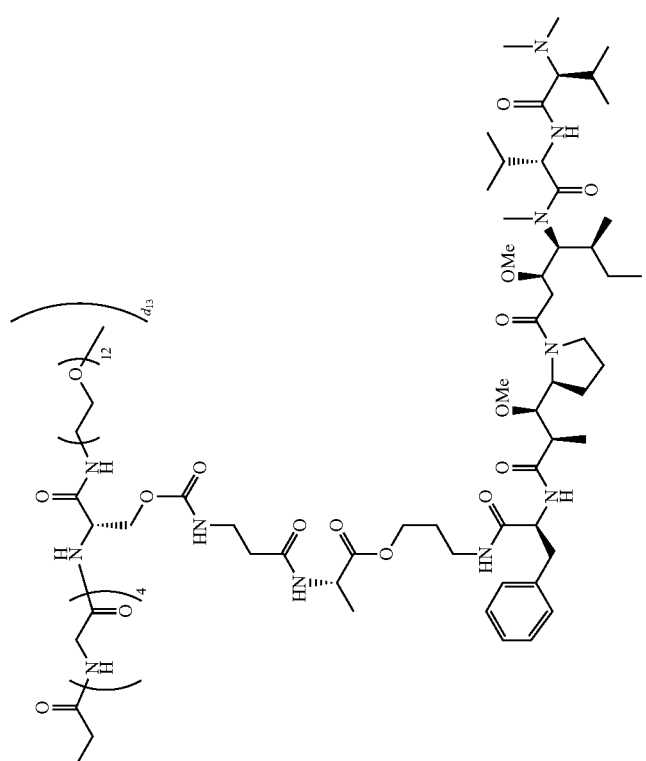 |

TABLE C-continued
| Conjugate No. | Structure |
|---|---|
|  | 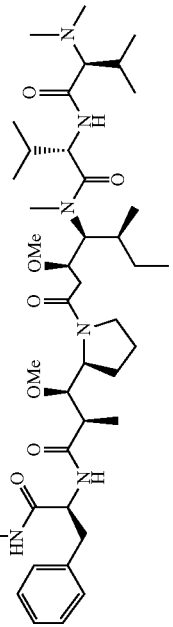 |

TABLE C-continued

| Conjugate No. | Structure |
|---|---|
| | |

TABLE C-continued
Conjugate No. | Structure
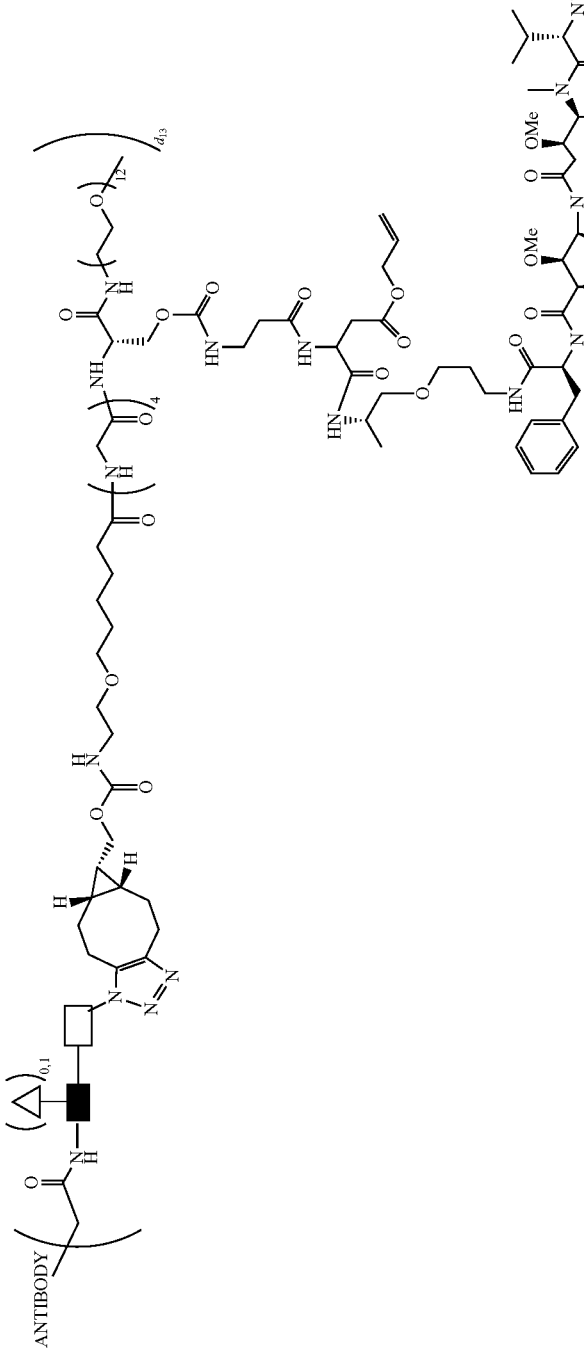

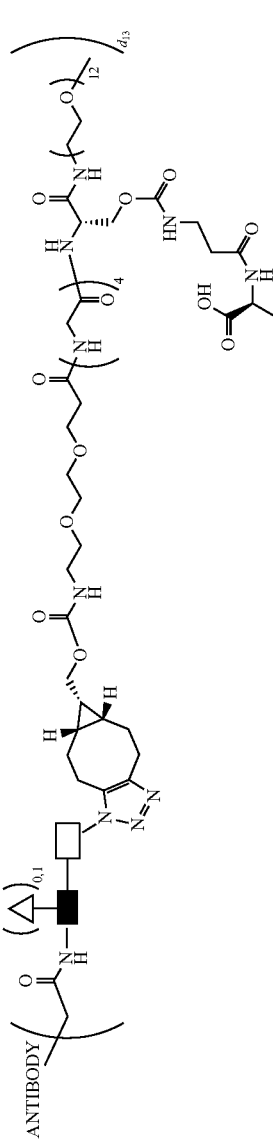

TABLE C-continued
| Conjugate No. | Structure |
|---|---|
| | 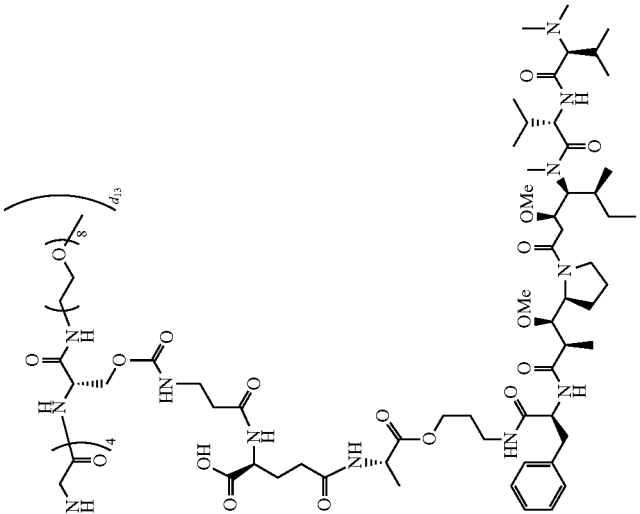 | wherein:
■ is GlcNAc; Δ is Fuc; ☐ is GalNAc; and $d_{13}$ is as defined herein.

It is understood that, unless stated otherwise, the symbol of ■ refers to GlcNAc in the present disclosure. It is understood that, unless stated otherwise, the symbol of Δ refers to fucose in the present disclosure. It is understood that, unless stated otherwise, the symbol of • refers to GalNAc in the present disclosure.

In some embodiments, the antibody-drug conjugate is of Formula (XXX):

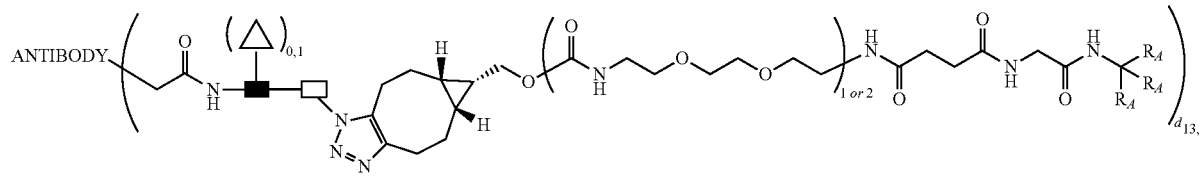

(XXX)

wherein:
each $R_A$ is

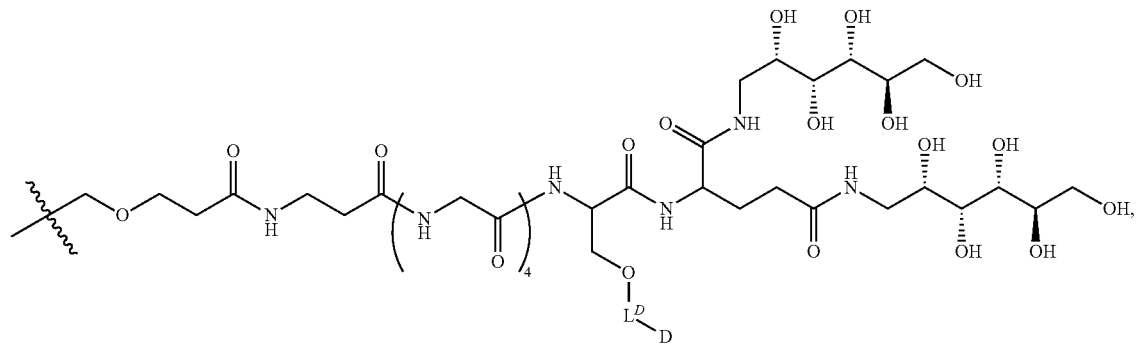

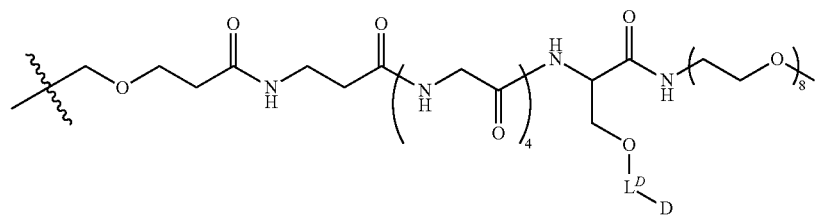

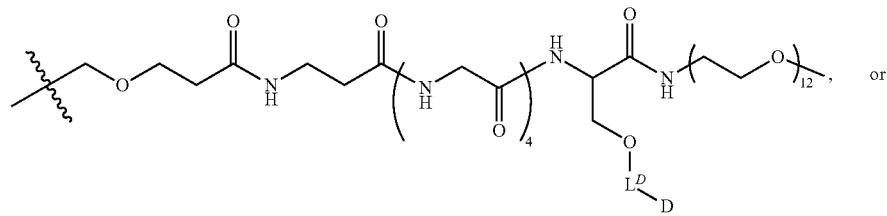

or

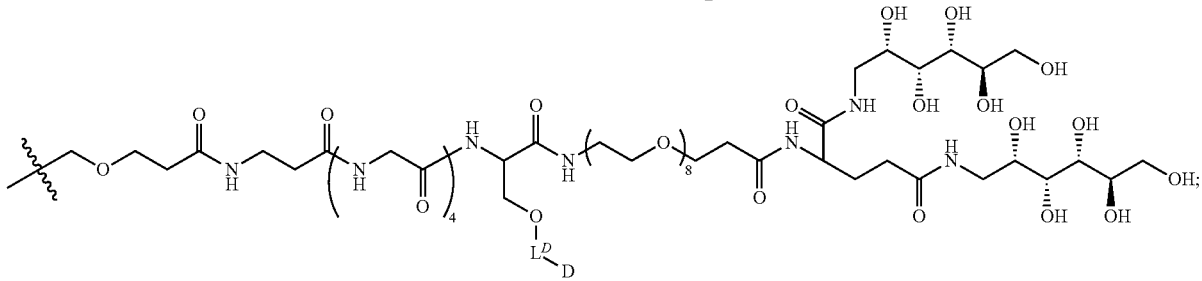

$d_{13}$ is 2; and the one or more Linker-Drug moiety is attached to the asparagine group at N297 of the antibody.
In some embodiments, the antibody-drug conjugate is of Formula (XXX):
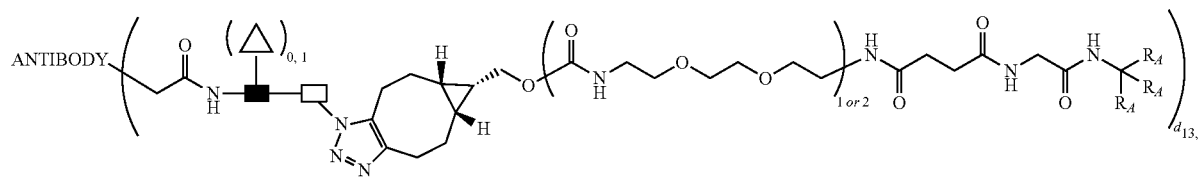
(XXX)
wherein each $R_A$ is:
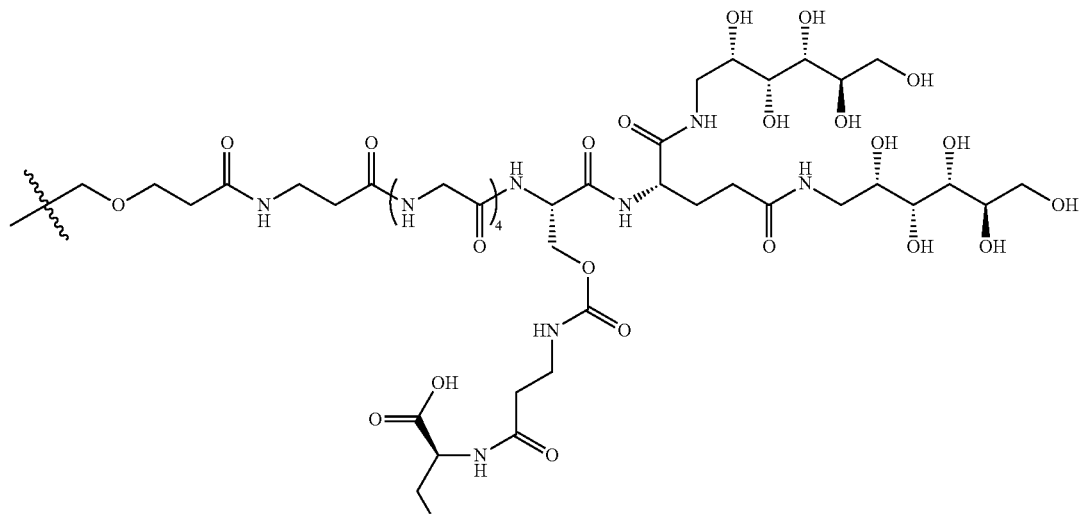
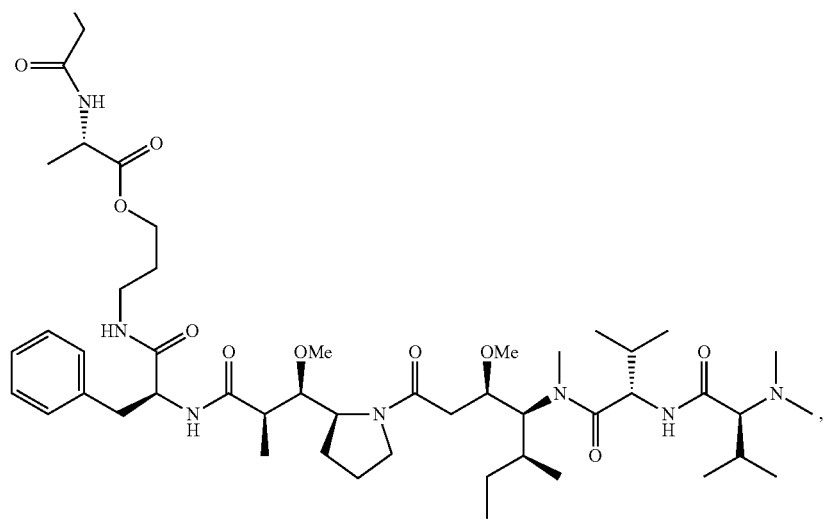

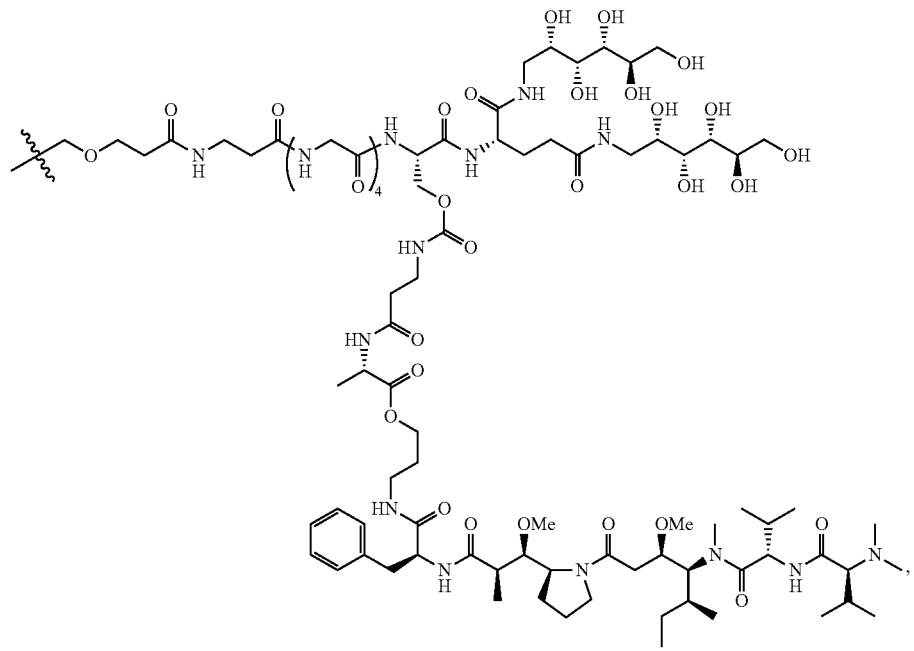
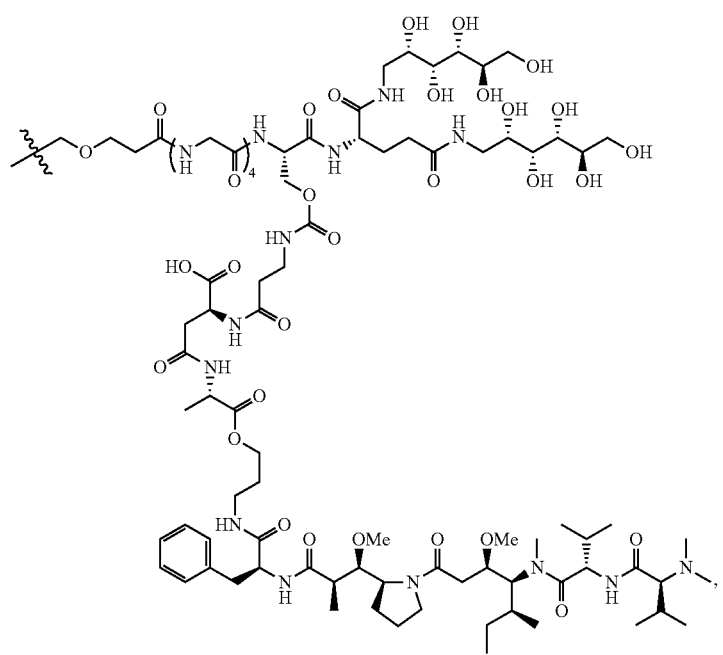

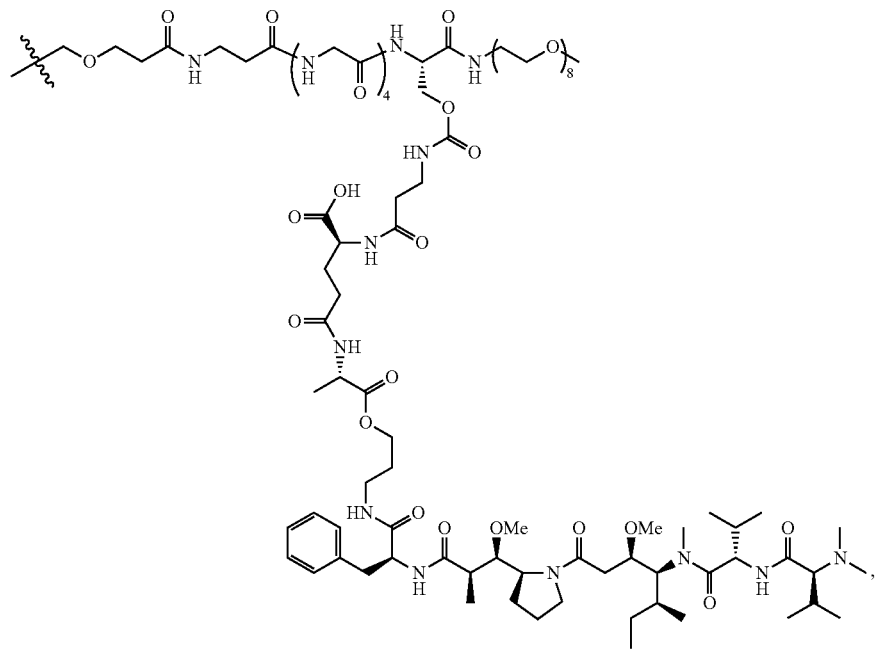
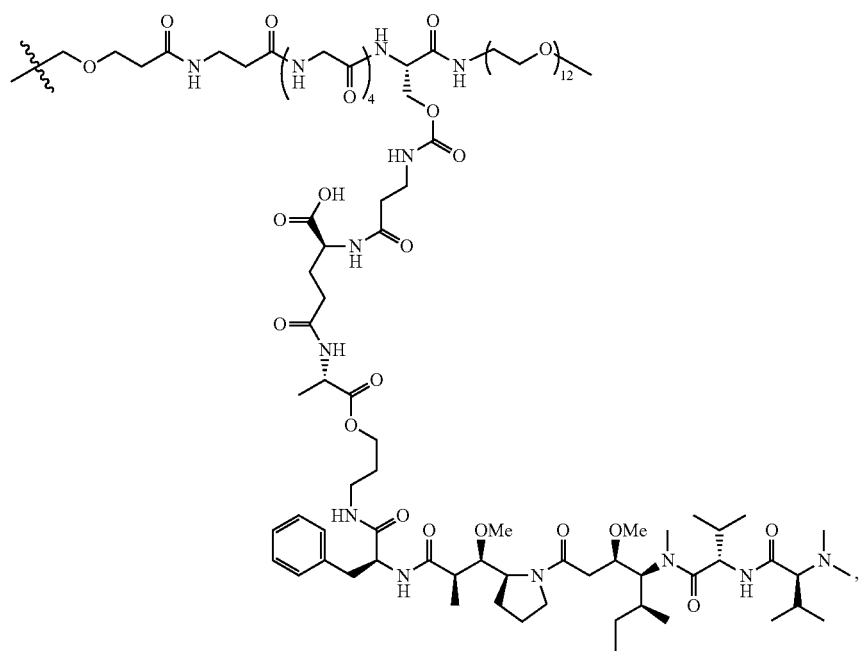

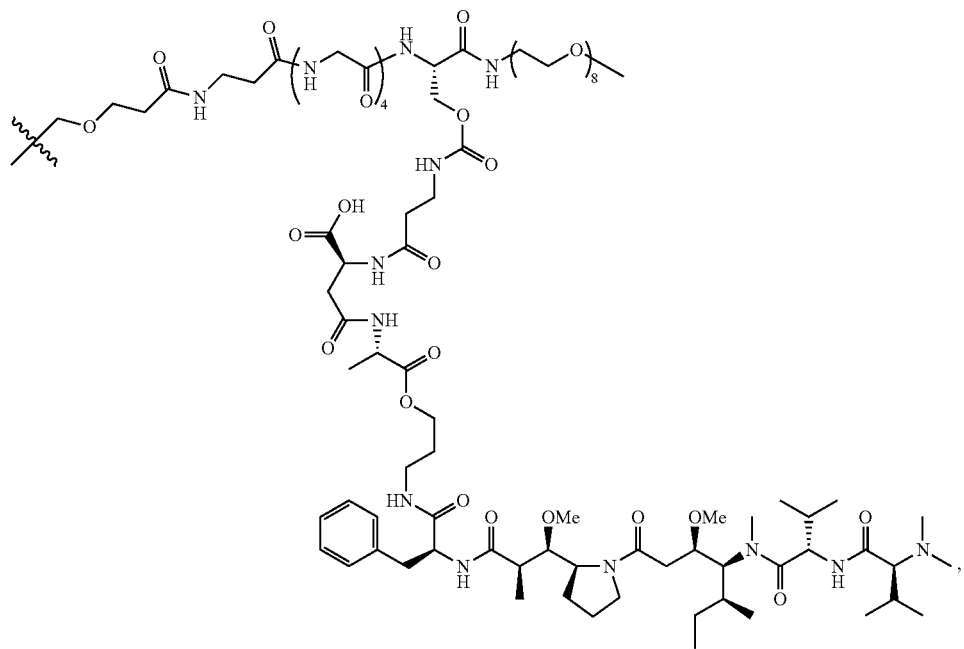
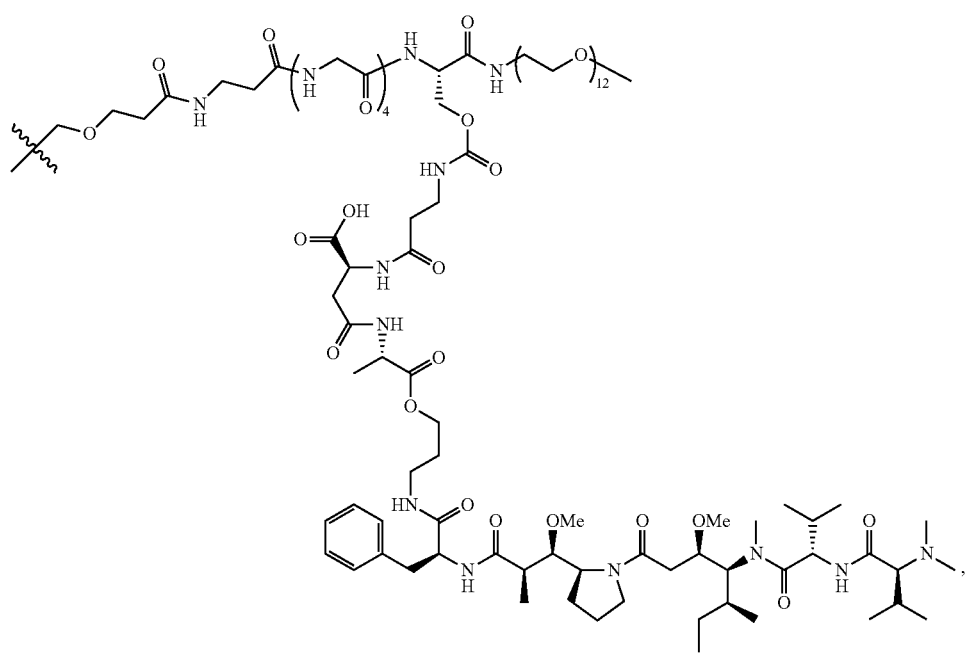

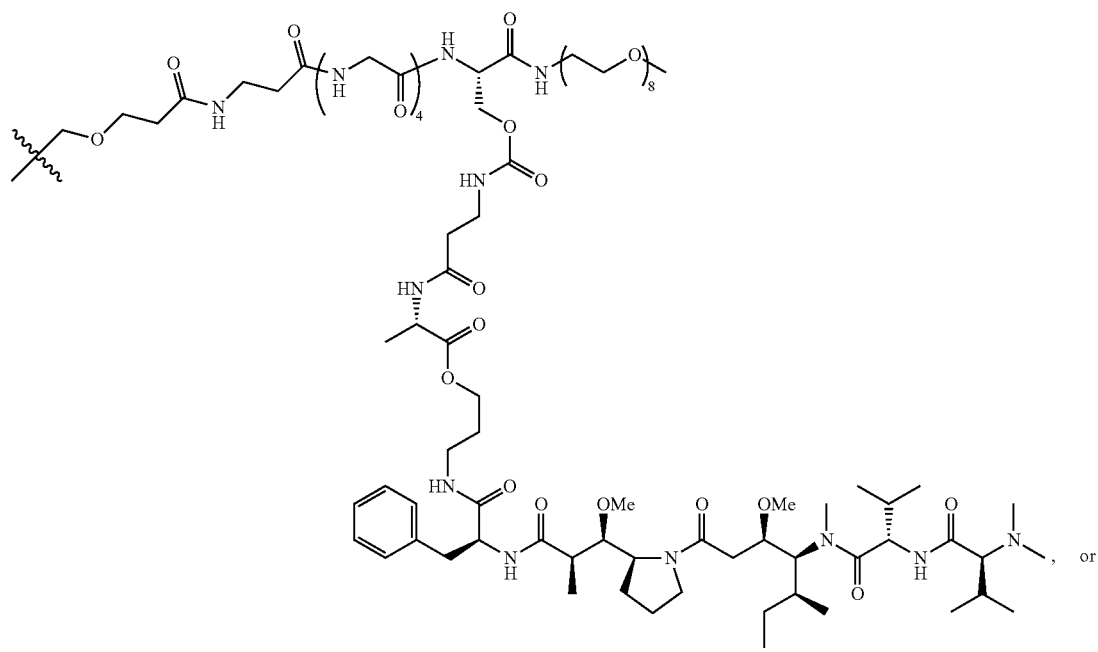
, or
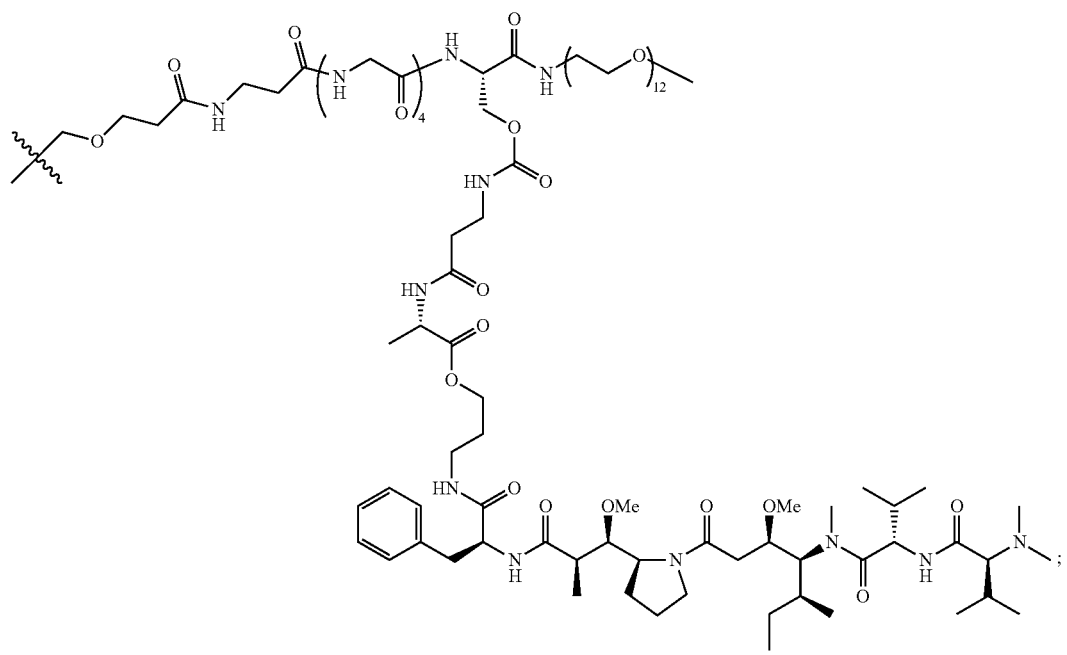
;
$d_{13}$ is 2; and the antibody comprises one or more asparagine group at N297 being connected to the rest of the conjugate.

In some embodiments, the antibody-drug conjugate is of Formula (XXX), wherein each $R_A$ is
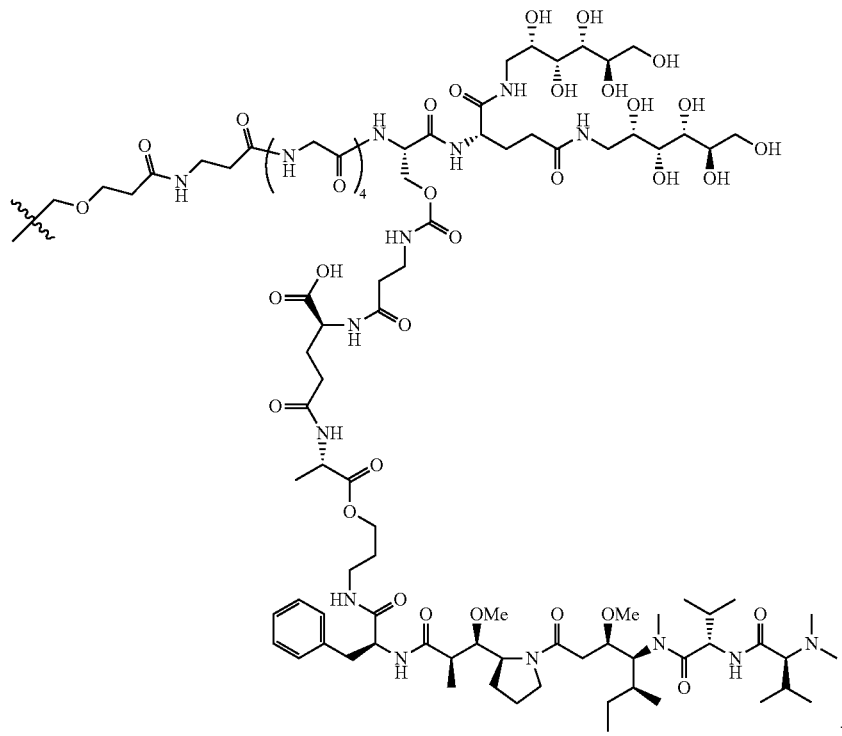
In some embodiments, the antibody-drug conjugate is of Formula (XXX), wherein each $R_A$ is
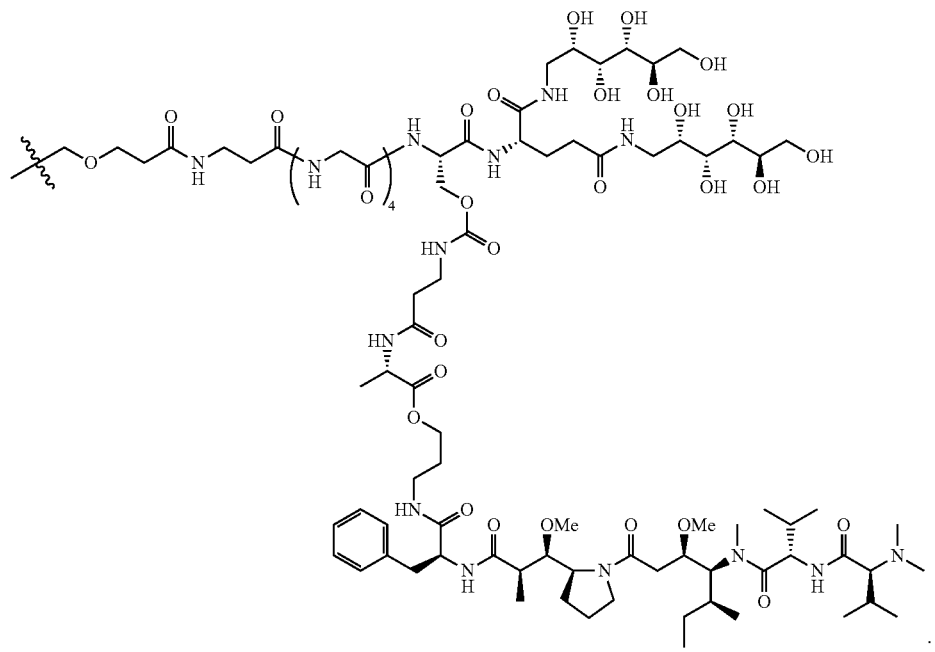

In some embodiments, the antibody-drug conjugate is of Formula (XXX), wherein each $R_A$ is
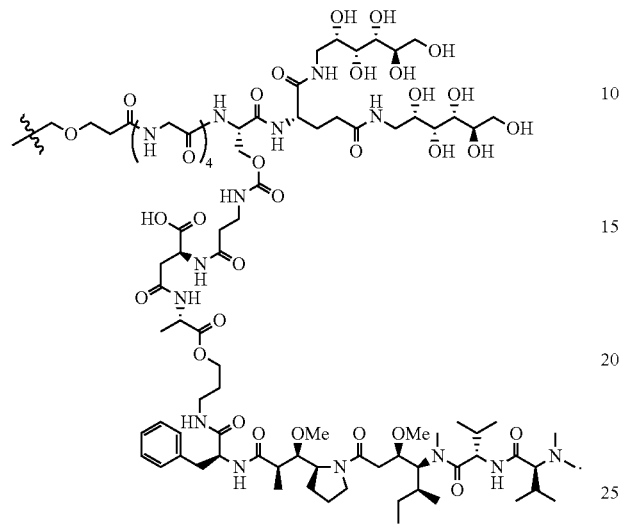
In some embodiments, the antibody-drug conjugate is of Formula (XXX), wherein each $R_A$ is
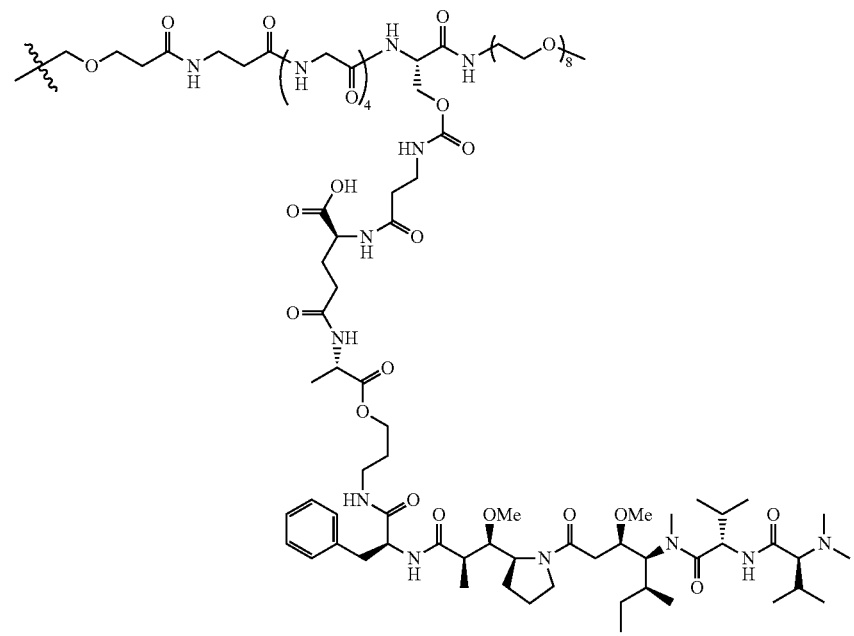

In some embodiments, the antibody-drug conjugate is of Formula (XXX), wherein each $R_A$ is
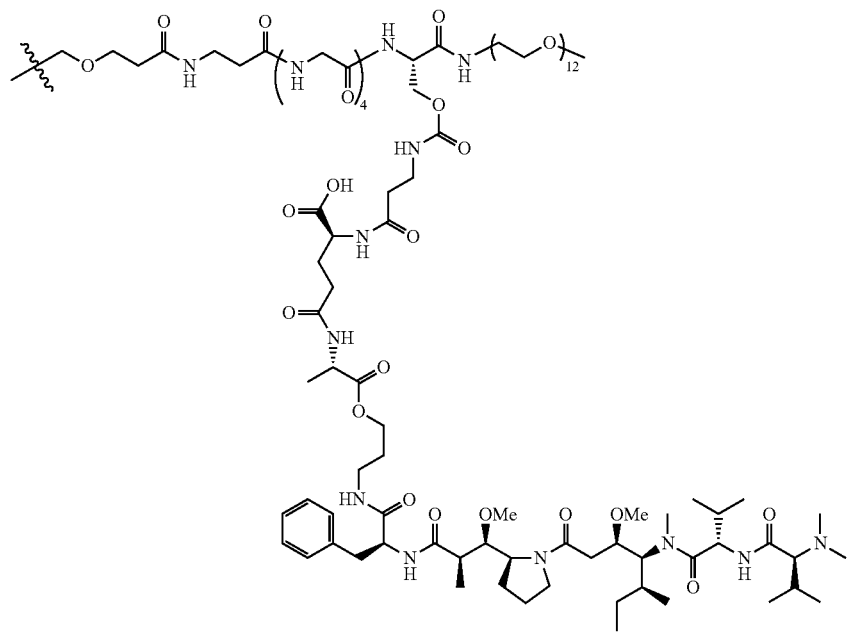
In some embodiments, the p antibody-drug conjugate is of Formula (XXX), wherein each $R_A$ is
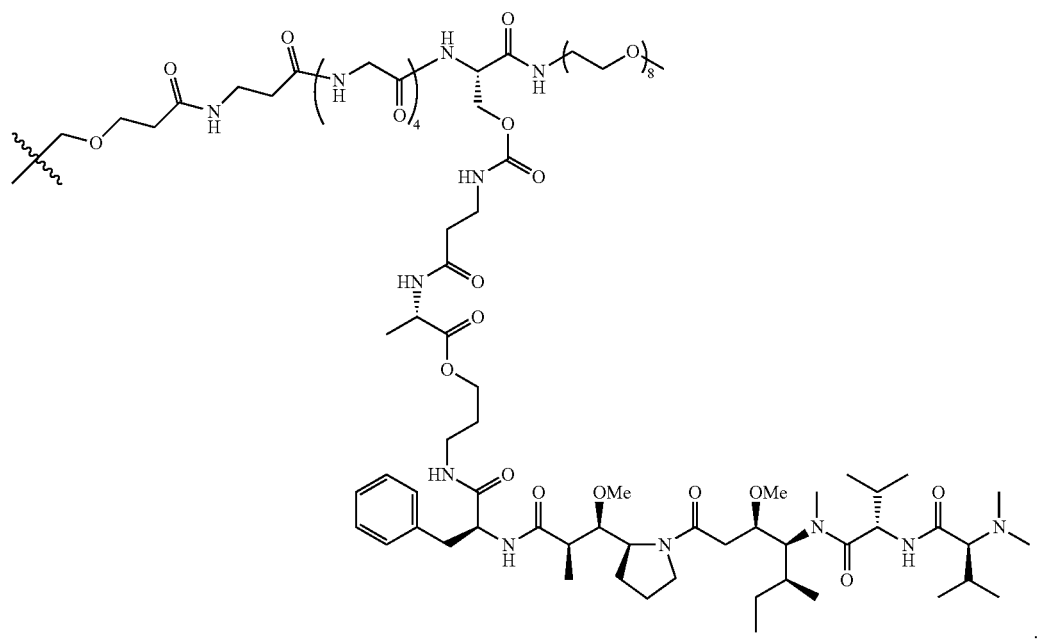

In some embodiments, the antibody-drug conjugate is of Formula (XXX), wherein each $R_A$ is
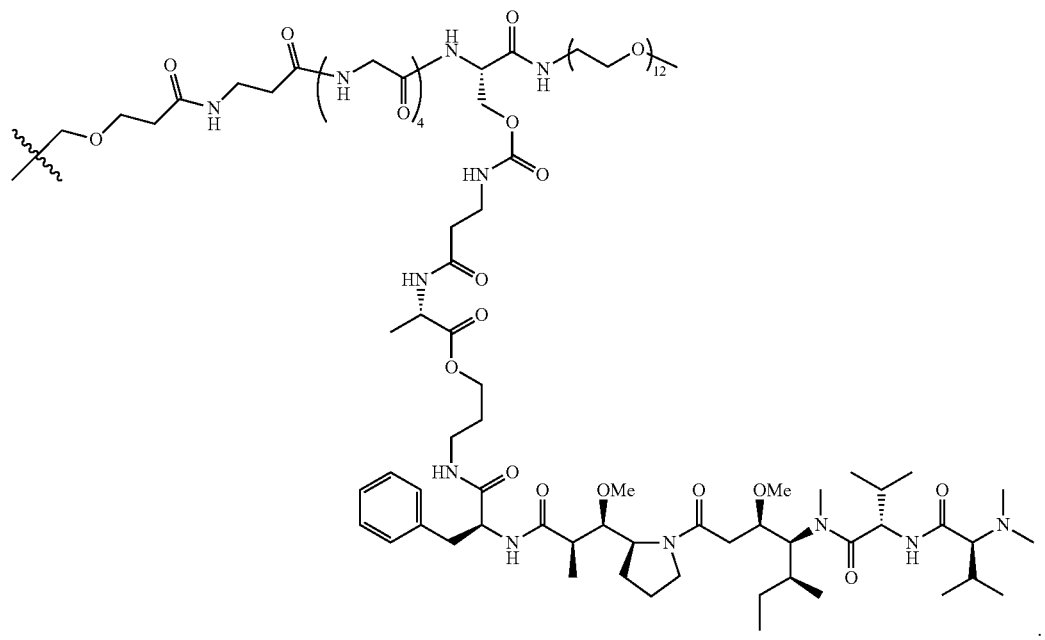
In some embodiments, the antibody-drug conjugate is of Formula (XXX), wherein each $R_A$ is:
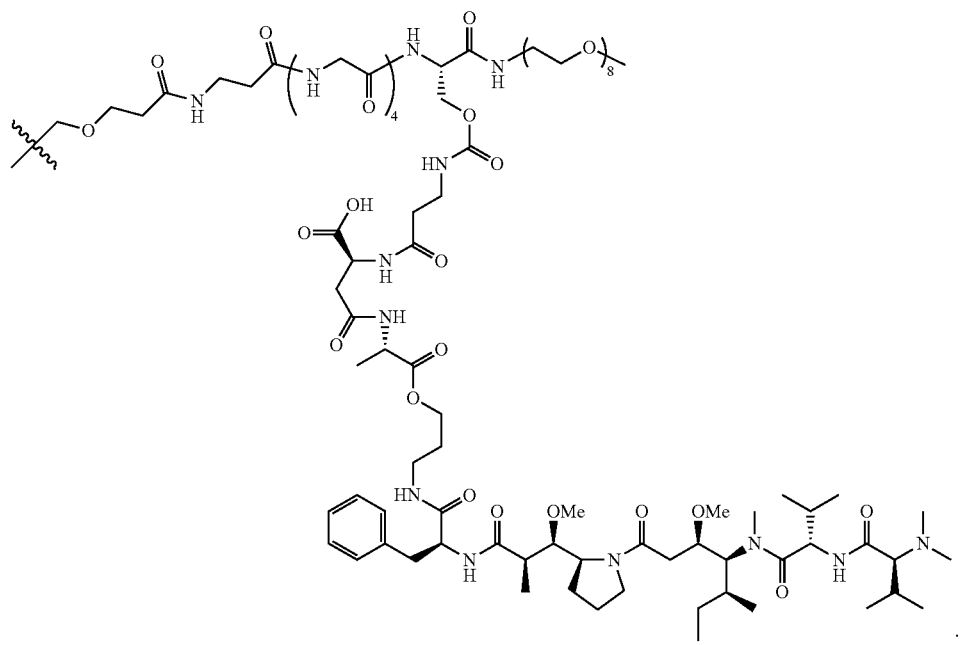

In some embodiments, the antibody-drug conjugate is of Formula (XXX), wherein each $R_A$ is
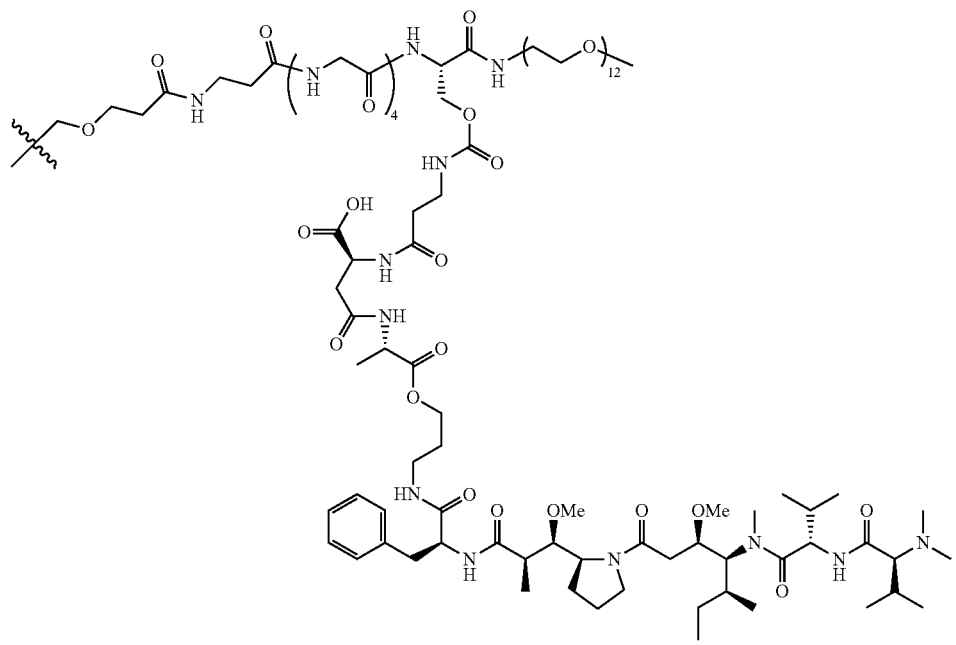
In some embodiments, the antibody-drug conjugate is of Formula (XXXII-1), (XXXII-2) (XXXII-3) or (XXXII-4):
(XXXII-1)
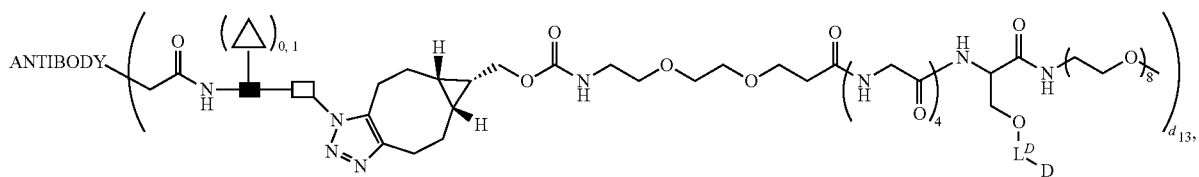
(XXXII-2)
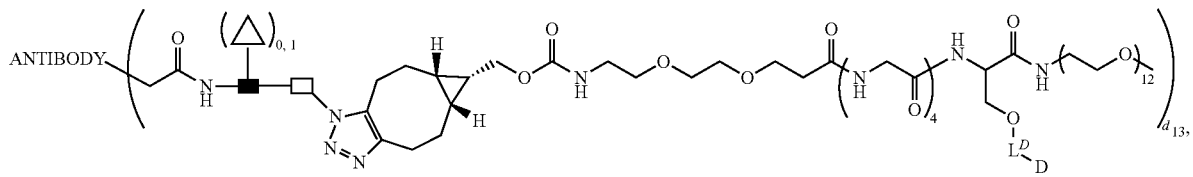
(XXXII-3)
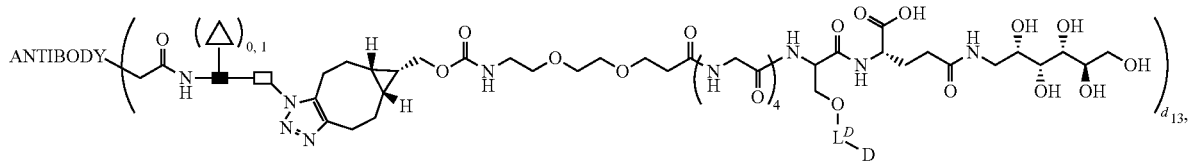

or
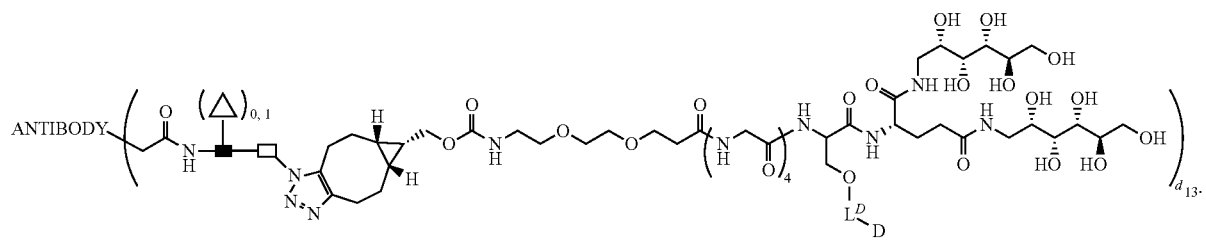
(XXXII-4)
In some embodiments, the antibody-drug conjugate is of Formula (XXXIII):
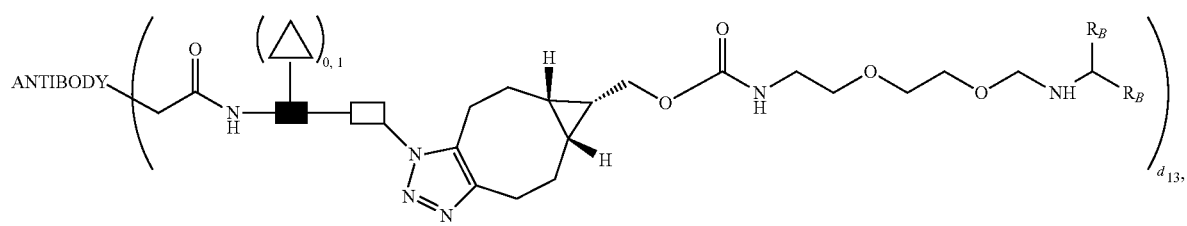
(XXXIII)
wherein each $R_B$ is:
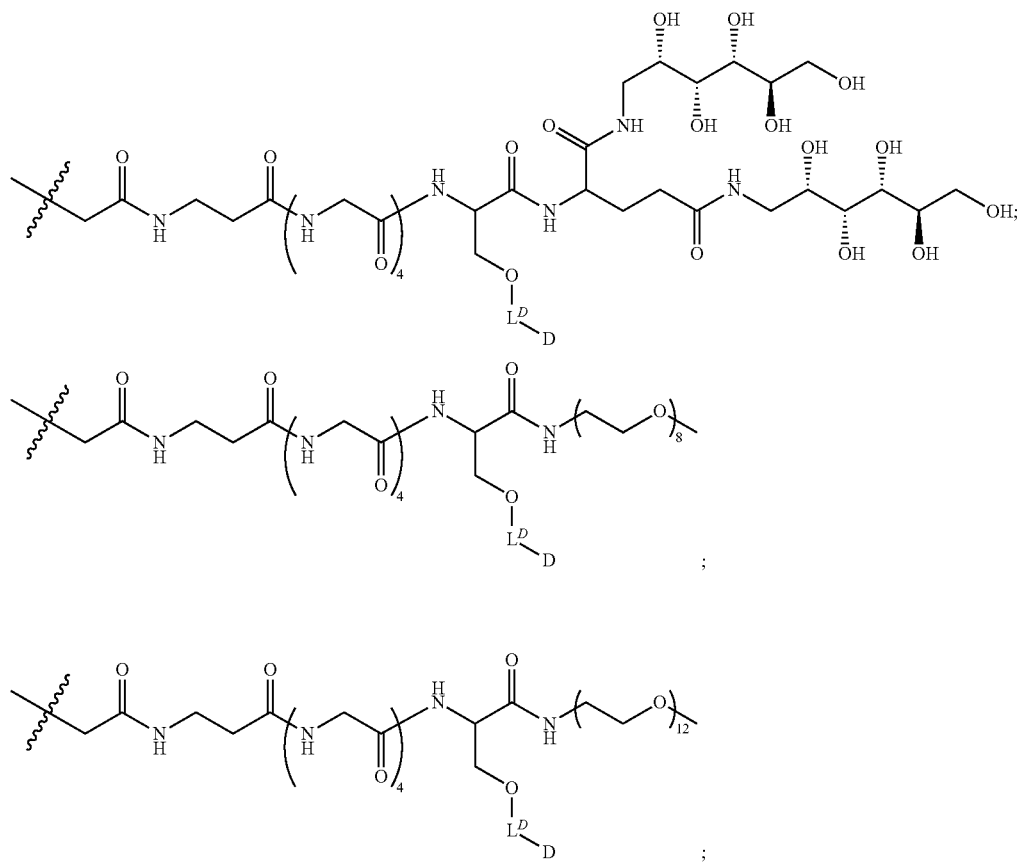

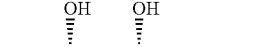
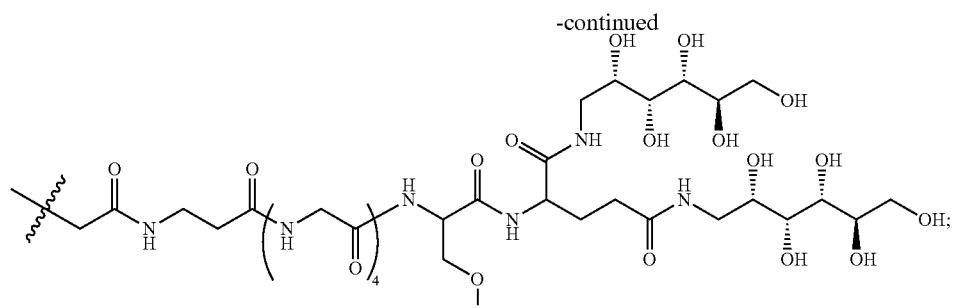
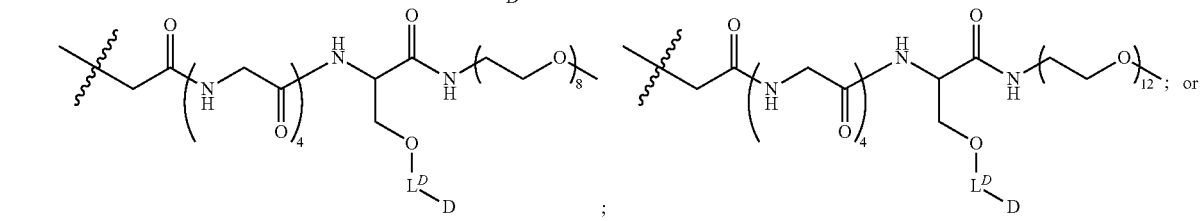
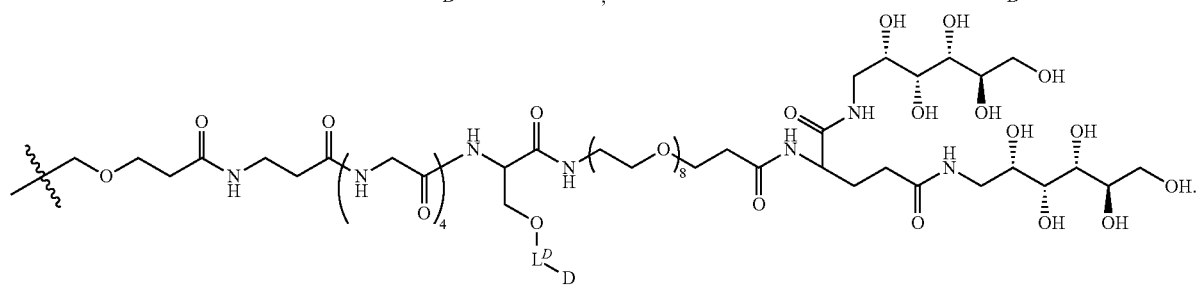
In some embodiments, the antibody-drug conjugate is of Formula (XXXII-1), (XXXII-2), (XXXII-3), (XXXII-4), or (XXXIII), wherein the moiety of -L$^D$-D is:
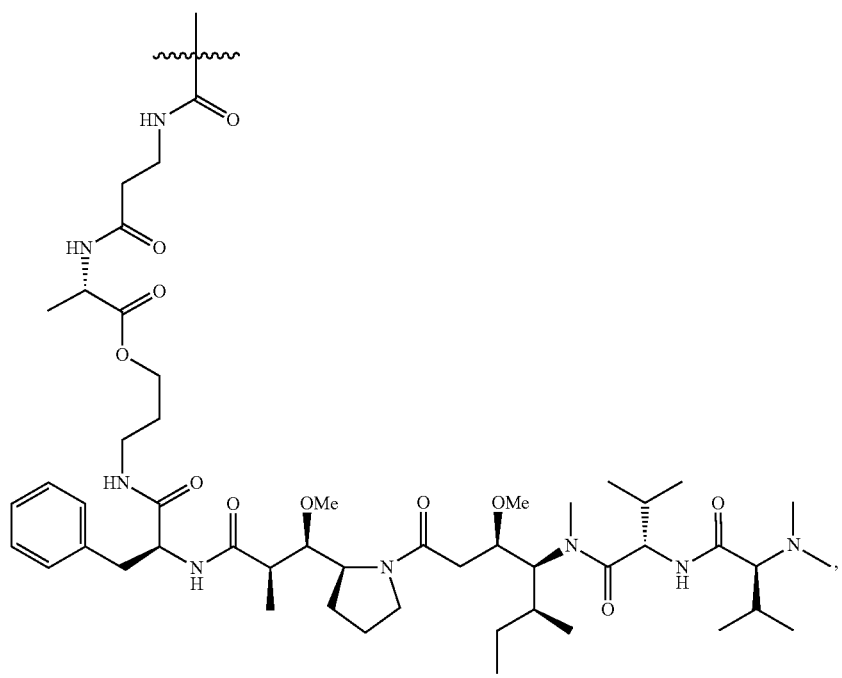

-continued
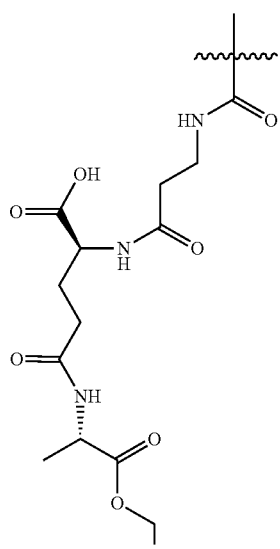
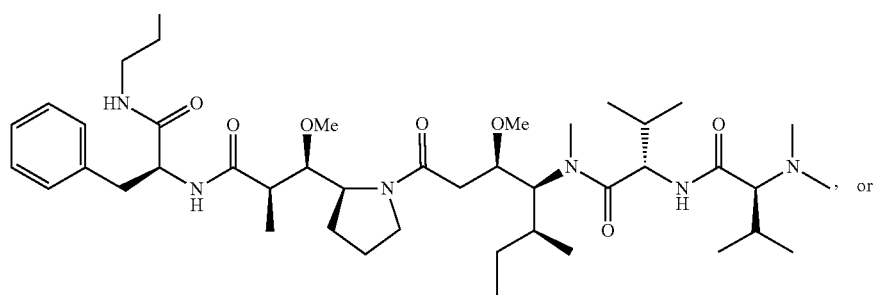
, or
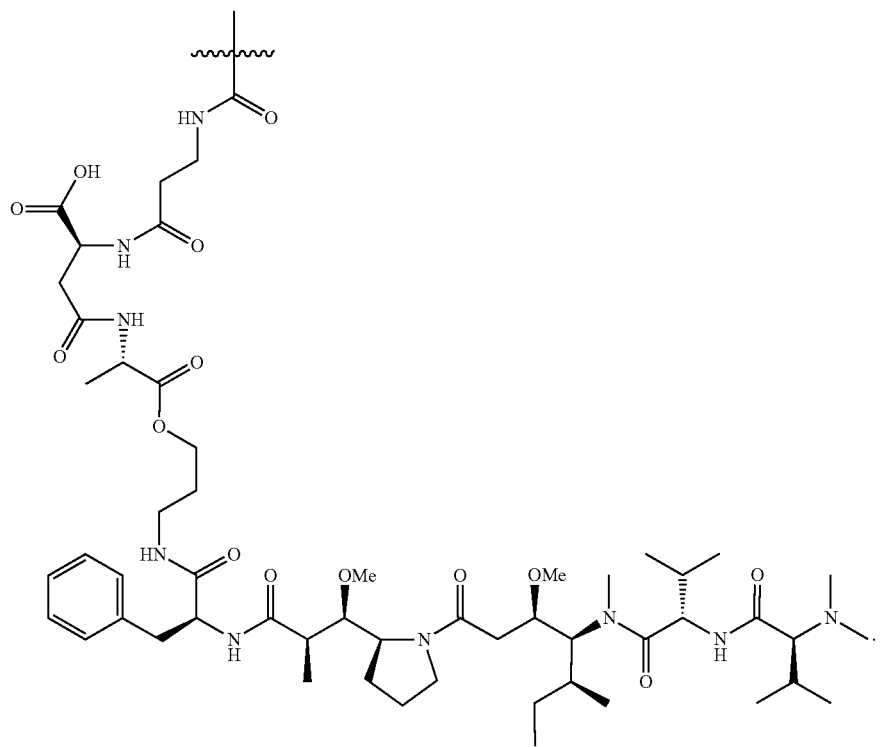 [SMILES: *C(=O)NCCC(=O)N[C@@H](CC(=O)N[C@@H](C)C(=O)OCCCNC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C)C(=O)O]

In some embodiments, the antibody-drug conjugate is of Formula (XXXII-1), (XXXII-2), (XXXII-3), (XXXII-4), or (XXXIII), wherein the moiety of -L$^D$-D is:
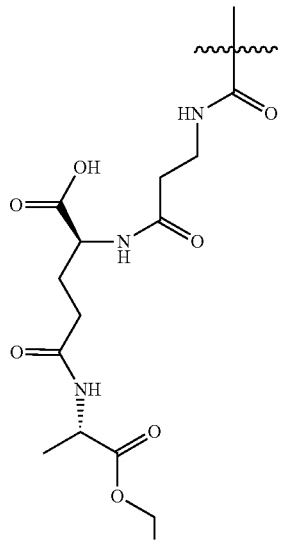
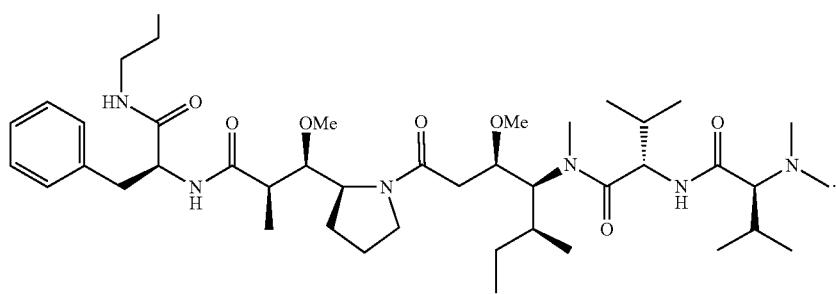
In some embodiments, the antibody-drug conjugate is of Formula (XXXIV):
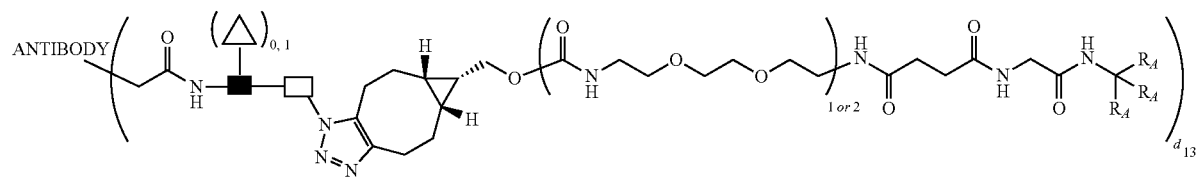

wherein each $R_A$ is
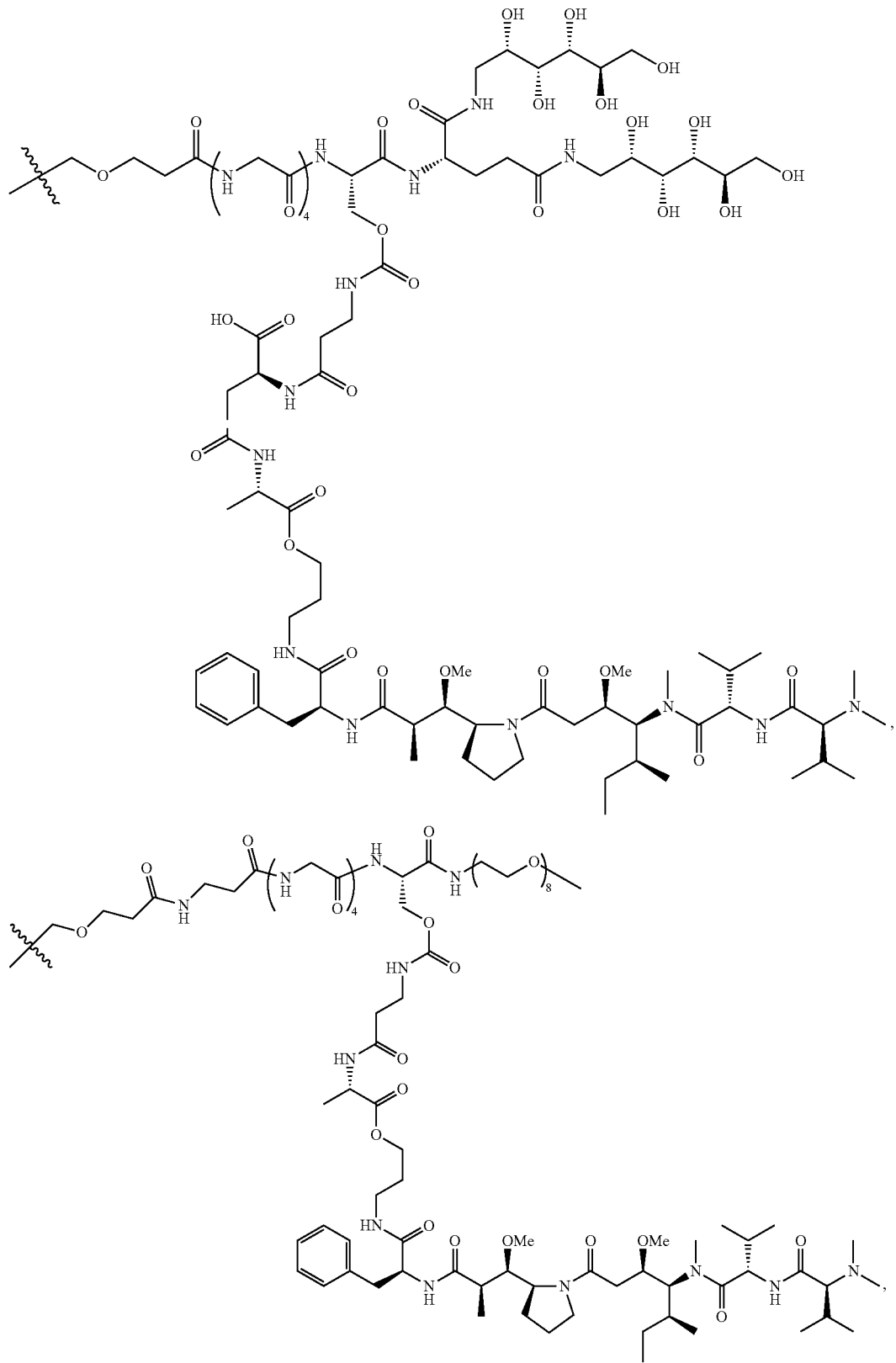

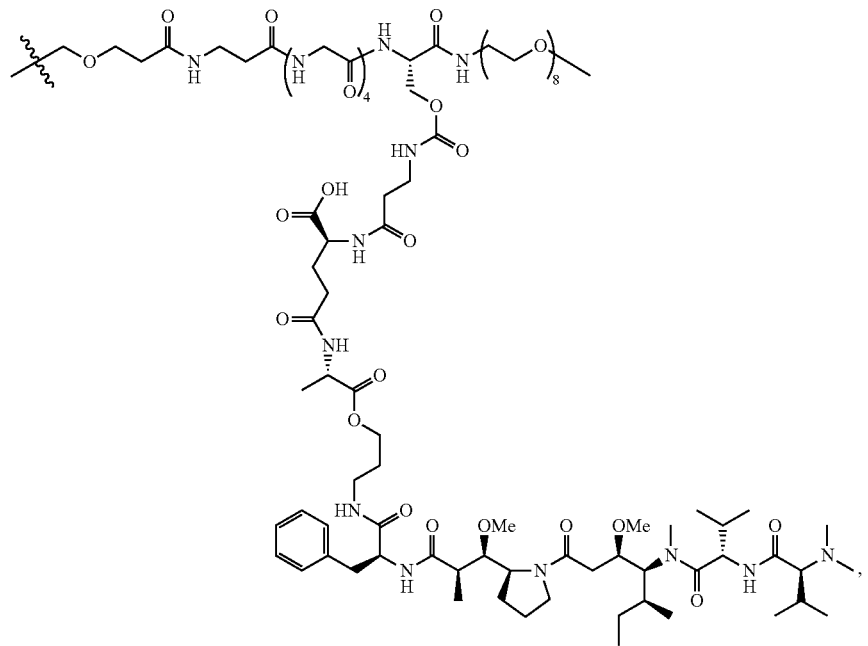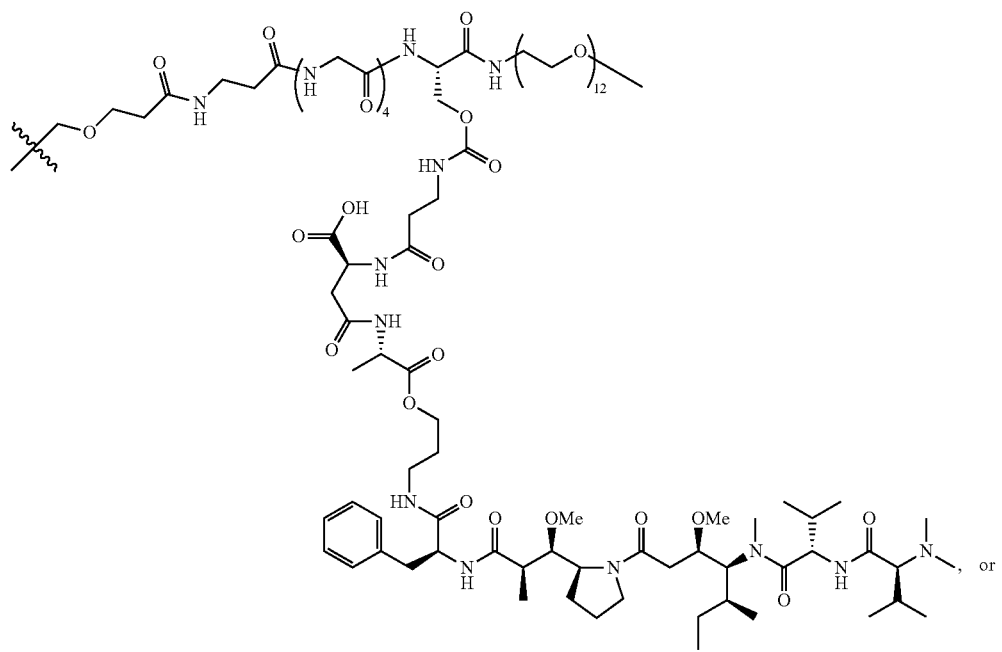

-continued
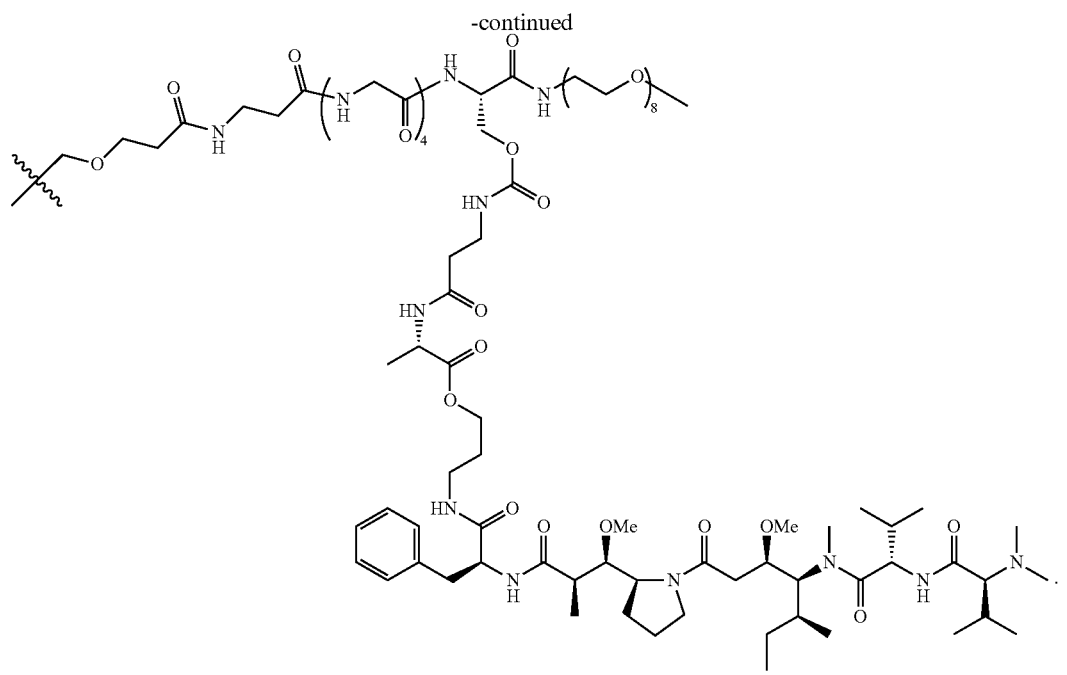
In some embodiments, the antibody-drug conjugate is a conjugate of Formula (XXXIV), wherein each $R_A$ is
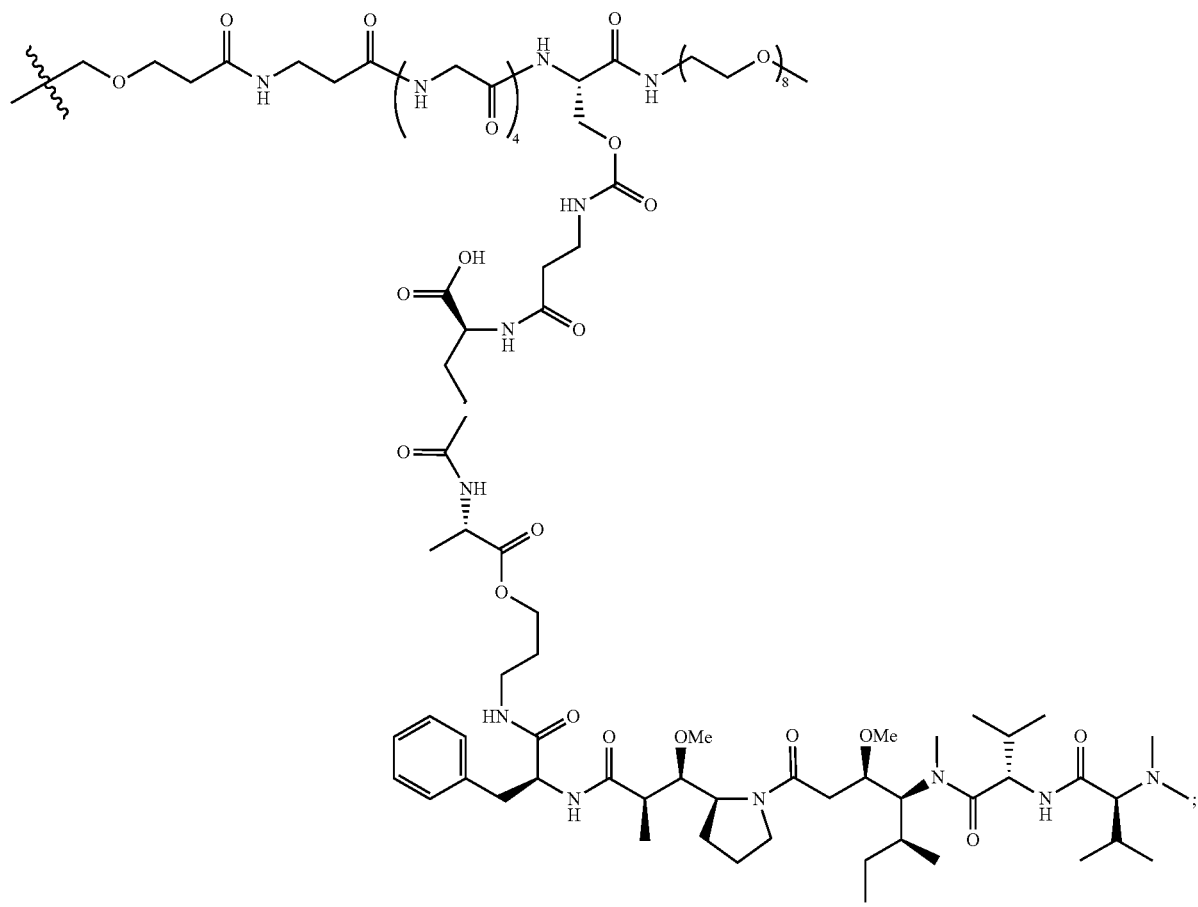

optionally, the antibody comprises one or more asparagine group at N297 being connected to the rest of the conjugate; and optionally, the antibody prior to modification is the NaPi2b antibody, XMT-1535, which is disclosed in U.S. application Ser. No. 15/457,574.

In some embodiments, the antibody-drug conjugate is a conjugate of Formula (XXXV):

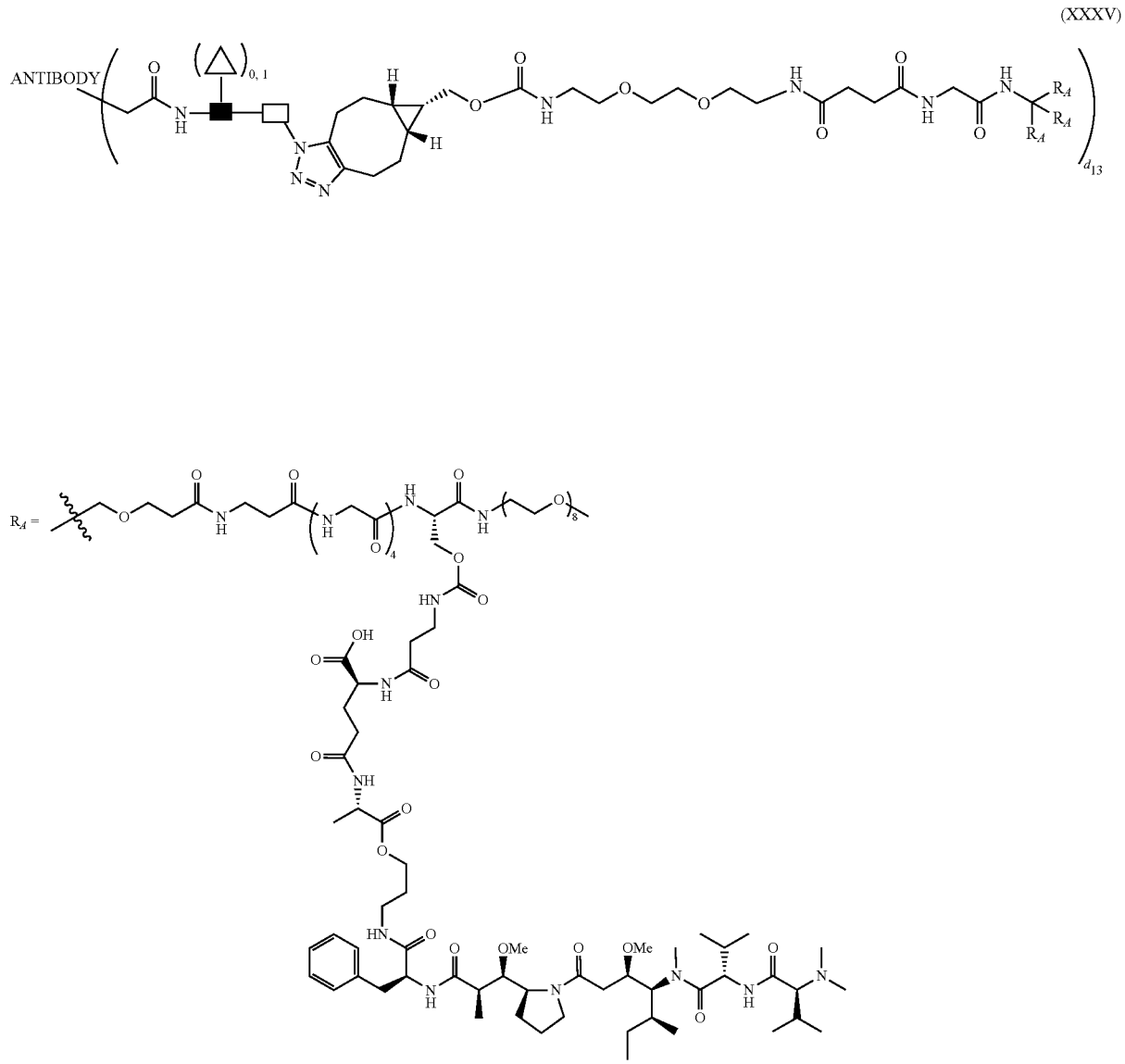

wherein $d_{13}$ is 2;

ANTIBODY is a NaPi2b antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); a CDRL3 comprising the amino acid sequence QQYSKLPLT (SEQ ID NO: 10); a heavy chain comprising the amino acid sequence of SEQ ID NO: 1; and a light chain comprising the amino acid sequence of SEQ ID NO: 2;

the Linker-Drug moiety is attached to the asparagine group at N297 of the antibody;

■ is GlcNAc; Δ is Fuc; and □ is GalNAc.

In some embodiments, the antibody-drug conjugate is a conjugate of Formula (XXXVI):

(XXXVI)

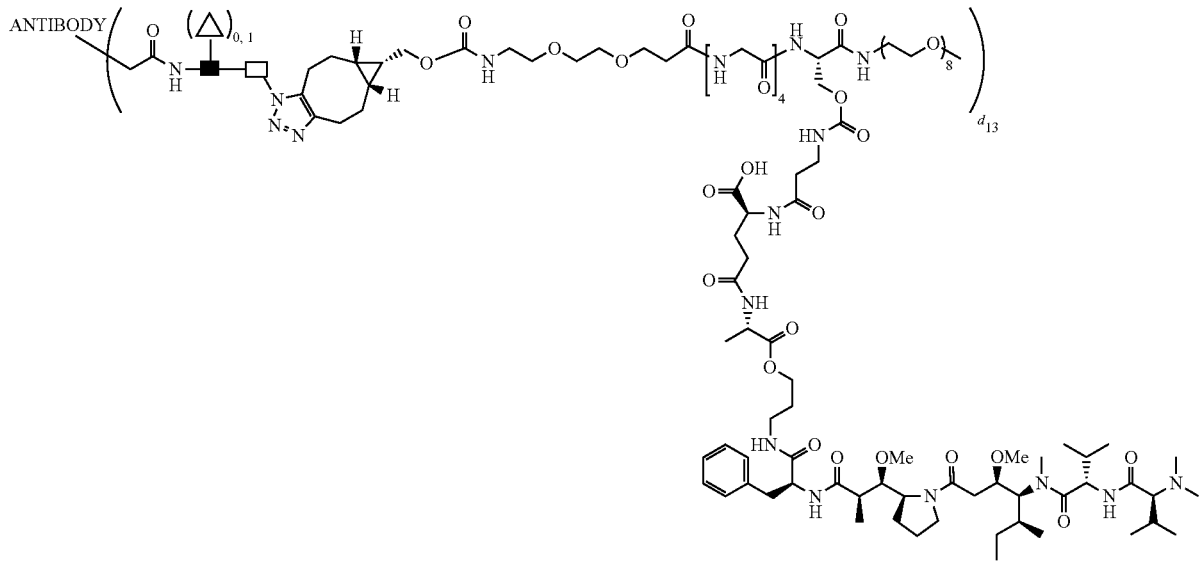

wherein $d_{13}$ is an integer 2;

ANTIBODY is a NaPi2b antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); a CDRL3 comprising the amino acid sequence QQYSKLPLT (SEQ ID NO: 10); a heavy chain comprising the amino acid sequence of SEQ ID NO: 1; and a light chain comprising the amino acid sequence of SEQ ID NO: 2;

the Linker-Drug moiety is attached to the asparagine group at N297 of the antibody;

■ is GlcNAc; Δ is Fuc; and □ is GalNAc.

Pharmaceutical Compositions

In some embodiments of the present disclosure are included pharmaceutical compositions comprising one or more conjugates as disclosed herein in an acceptable carrier, such as a stabilizer, buffer, and the like. In some embodiments, the conjugates can be administered and introduced into a subject by standard means, with or without stabilizers, buffers, and the like, to form a pharmaceutical composition. In some embodiments, administration may be parenteral administration including intravenous, intraarterial, subcutaneous, intraperitoneal, or intramuscular injection or infusion or intracranial, e.g., intrathecal or intraventricular, administration. In some embodiments, the conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery).

By "systemic administration" is meant in vivo systemic absorption or accumulation of the conjugate in the blood stream followed by distribution throughout the entire body. Administration routes that lead to systemic absorption include, without limitation: intravenous, subcutaneous, intraperitoneal, inhalation, oral, intrapulmonary, and intramuscular. The use of a conjugate of this disclosure can localize the drug delivery in certain cells, such as cancer cells via the specificity of antibodies.

A "pharmaceutically acceptable formulation" means a composition or formulation that allows for the effective distribution of the conjugates in the physical location most suitable for their desired activity. In some embodiments, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

In some embodiments of the present disclosure are pharmaceutical compositions prepared for storage or administration, which include a pharmaceutically effective amount of the desired conjugates in a pharmaceutically acceptable carrier or diluent. In some embodiments, acceptable carriers, diluents, and/or excipients for therapeutic use are well known in the pharmaceutical art. In some embodiments, buffers, preservatives, bulking agents, dispersants, stabilizers, or dyes, can be provided. In some embodiments, antioxidants and suspending agents can be used.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration.

In some embodiments, for any conjugate, the pharmaceutically effective amount can be estimated initially either in cell culture assays, e.g., of neoplastic cells, or in animal models, usually rats, mice, rabbits, dogs, or pigs. In some embodiments, the animal model may also be used to determine the appropriate concentration range and route of administration. In some embodiments, such information can then be used to determine useful doses and routes for administration in humans. In some embodiments, therapeutic and/or prophylactic efficacy and toxicity may be determined by standard pharmaceutical procedures in cell cultures or experimental animals, e.g., $ED_{50}$ (the dose therapeutically effective in 50% of the population) and $L^D_{50}$ (the dose lethal to 50% of the population). In some embodiments, the dose ratio between toxic and therapeutic and/or prophylactic effects is the therapeutic index, and it can be expressed as the ratio, $L^D_{50}/ED_{50}$. In some embodiments, pharmaceutical compositions exhibit large therapeutic indices. In some embodiments, the dosage may vary within this range depending upon the dosage form employed, sensitivity of the patient, and the route of administration.

In some embodiments, a drug or its derivatives, drug-conjugates or PBRM-drug conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In some embodiments, the conjugates are formulated for parenteral administration by injection including using conventional catheterization techniques or infusion. In some embodiments, formulations for injection may be presented in unit dosage form, e.g., in ampules or in multi-dose containers, with an added preservative. In some embodiments, the conjugates can be administered parenterally in a sterile medium. In some embodiments, the conjugate, depending on the vehicle and concentration used, can either be suspended or dissolved in the vehicle. In some embodiments, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

In some embodiments, the sterile injectable preparation can also be a sterile injectable solution or suspension in a non-toxic parentally acceptable diluent or solvent. In some embodiments, among the acceptable vehicles and solvents that can be employed are water, Ringer's solution, and isotonic sodium chloride solution. In some embodiments, sterile, fixed oils are conventionally employed as a solvent or suspending medium. In some embodiments, a bland fixed oil can be employed including synthetic mono- or diglycerides. In some embodiments, fatty acids such as oleic acid find use in the preparation of injectables.

In some embodiments, the conjugates and compositions described herein may be administered in appropriate form (e.g., parenterally or intravenously).

In some embodiments, the conjugates can be administered once a week for six weeks or longer. In some embodiments, the conjugates can be administered once every two, three or four weeks. In some embodiments, bolus doses are given in about 50 to about 400 mL of normal saline to which about 5 to about 10 mL of human serum albumin can be added. In some embodiments, continuous infusions are given in about 250 to about 500 mL of normal saline, to which about 25 to about 50 mL of human serum albumin can be added, per 24 hour period.

In some embodiments, about one to about four weeks after treatment, the patient can receive a second course of treatment (e.g., about three weeks after treatment or about four weeks after treatment).

In some embodiments, the therapeutically effective amount may be provided on another regular schedule, i.e., daily, weekly, monthly, or yearly basis or on an irregular schedule with varying administration days, weeks, months, etc. In some embodiments, the therapeutically effective amount to be administered may vary. In some embodiments, the therapeutically effective amount for the first dose is higher than the therapeutically effective amount for one or more of the subsequent doses. In some embodiments, the therapeutically effective amount for the first dose is lower than the therapeutically effective amount for one or more of the subsequent doses. In some embodiments, equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. In some embodiments, the number and frequency of dosages corresponding to a completed course of therapy will be determined according to the recommendations of the relevant regulatory bodies and judgment of a health-care practitioner. In some embodiments, the therapeutically effective amounts described herein refer to total amounts administered for a given time period; that is, if more than one different conjugate described herein is administered, the therapeutically effective amounts correspond to the total amount administered. It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

In some embodiments, a therapeutically effective amount of a conjugate disclosed herein relates generally to the amount needed to achieve a therapeutic objective. In some embodiments, this may be a binding interaction between the antibody and its target antigen that, in certain cases, interferes with the functioning of the target. In some embodiments, the amount required to be administered will furthermore depend on the binding affinity of the antibody for its specific antigen, and will also depend on the rate at which an administered antibody is depleted from the free volume other subject to which it is administered. In some embodiments, ranges for therapeutically effective dosing of conjugates disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. In some embodiments, dosing frequencies may range, for example, from twice daily to once a month (e.g., once daily, once weekly; once every other week; once every 3 weeks or monthly). In some embodiments, conjugates disclosed herein can be administered intravenously by an infusion (e.g., as a single dose weekly, every 2 weeks, every 3 weeks, or 4 weeks) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). In some embodiments, conjugates disclosed herein can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 19 mg/kg, or 20 mg/kg) for treating cancer.

In some embodiments, conjugates disclosed herein can be administered intravenously by an infusion (e.g., as a single dose weekly, every 2 weeks, every 3 weeks, or every four weeks) at about 7 mg/m$^2$ to about 162 mg/m$^2$ (e.g., 7 mg/m$^2$, 14 mg/m$^2$, 28 mg/m$^2$, 56 mg/m$^2$, 84 mg/m$^2$, 112 mg/m$^2$, 135 mg/m$^2$, or 162 mg/m$^2$). A number of packages or kits are known in the art for dispensing pharmaceutical agents for periodic oral use. In some embodiments, the package has indicators for each period. In some embodiments, the package is a labeled blister package, dial dispenser package, or bottle. In some embodiments, the packaging means of a kit may itself be geared for administration, such as a syringe, pipette, eye dropper, or other such apparatus, from which the formulation may be applied to an affected area of the body, injected into a subject, or even applied to and mixed with the other components of the kit.

Methods of Use

In some embodiments, the present disclosure provides a method of treating or preventing a disease or disorder in a subject in need thereof, comprising administering to the subject a therapeutically effective amount of a conjugate disclosed herein.

In some embodiments, the present disclosure provides a method of treating a disease or disorder in a subject in need thereof, comprising administering to the subject a therapeutically effective amount of a conjugate disclosed herein.

In some embodiments, the present disclosure relates to a method of treating a cancer in a subject in need thereof, comprising administering to the subject an effective amount of a conjugate disclosed herein. In some embodiments, the present disclosure relates to a method of treating a NaPi2b expressing cancer in a subject in need thereof, comprising administering to the subject an effective amount of a conjugate disclosed herein.

In some embodiments, the present disclosure provides a conjugate disclosed herein for use in treating or preventing a disease or disorder in a subject in need thereof.

In some embodiments, the present disclosure provides a conjugate disclosed herein for use in treating a disease or disorder in a subject in need thereof.

In some embodiments, the present disclosure provides use of a conjugate disclosed herein for treating a cancer in a subject in need thereof. In some embodiments, the present disclosure provides use of a conjugate disclosed herein for treating a NaPi2b expressing cancer in a subject in need thereof.

In some embodiments, the present disclosure provides use of a conjugate disclosed herein in the manufacture of a medicament for treating a disease or disorder in a subject in need thereof.

In some embodiments, the present disclosure provides use of a conjugate disclosed herein in the manufacture of a medicament for treating or preventing a disease or disorder in a subject in need thereof.

In some embodiments, the present disclosure provides use of a conjugate disclosed herein in the manufacture of a medicament for treating a cancer in a subject in need thereof. In some embodiments, the present disclosure provides use of a conjugate disclosed herein in the manufacture of a medicament for treating a NaPi2b expressing cancer in a subject in need thereof.

In some embodiments, the present disclosure provides a conjugate for use in treating a disease or disorder in a subject in need thereof.

In some embodiments, the present disclosure provides a conjugate for use in treating or preventing a disease or disorder in a subject in need thereof.

In some embodiments, the present disclosure provides a conjugate for use in treating a cancer in a subject in need thereof, comprising administering to the subject an effective amount of a conjugate disclosed herein. In some embodiments, the present disclosure provides a conjugate for use in treating a NaPi2b expressing cancer in a subject in need thereof, comprising administering to the subject an effective amount of a conjugate disclosed herein.

In some embodiments, the present disclosure provides a method of treating or preventing a disease or disorder in a subject in need thereof, comprising administering to the subject an efficient amount of at least one conjugate of the disclosure; wherein said conjugate releases one or more therapeutic agents upon biodegradation.

In some embodiments, the present disclosure provides a method of treating a disease or disorder in a subject in need thereof, comprising administering to the subject an efficient amount of at least one conjugate of the disclosure; wherein said conjugate releases one or more therapeutic agents upon biodegradation.

In some embodiments, the disease is a cancer.

In some embodiments, the cancer therapy provided herein, containing a NaPi2b-targeted antibody-drug conjugate, is administered in an amount sufficient to exert a therapeutically useful effect. Typically, the active agents are administered in an amount that does not result in undesirable side effects of the patient being treated, or that minimizes or reduces the observed side effects. NaPi2b expressing cancers include for example, of ovarian cancer, non-small cell lung cancer (NSCLC), endometrial cancer, papillary renal cell cancer, salivary duct cancer, papillary thyroid cancer, clear cell renal cancer, breast cancer, kidney cancer, cervical cancer and cholangiocarcinoma, It is within the level of one of skill in the art to determine the precise amounts of active agents, including NaPi2b-targeted polymer antibody-drug conjugates to be administered to a subject. For example, such agents and uses for treating cancers and solid tumors, are well-known in the art. Thus, dosages of such agents can be chosen based on standard dosing regimens for that agent under a given route of administration.

It is understood that the precise dosage and duration of treatment is a function of the tissue or tumor being treated and may be determined empirically using known testing protocols or by extrapolation from in vivo or in vitro test data and/or can be determined from known dosing regimens of the particular agent. It is to be noted that concentrations and dosage values may also vary with the age of the individual treated, the weight of the individual, the route of administration and/or the extent or severity of the disease and other factors that are within the level of a skilled medical practitioner to consider. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects). It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof.

For example, the NaPi2b-targeted polymer antibody-drug conjugate, is administered in a therapeutically effective amount to decrease the tumor volume.

The amount of a NaPi2b-targeted polymer antibody-drug conjugate is administered for the treatment of a disease or condition, for example a cancer or solid tumor can be determined by standard clinical techniques. In addition, in vitro assays and animal models can be employed to help identify optimal dosage ranges. The precise dosage, which can be determined empirically, can depend on the route of administration, the type of disease to be treated and the seriousness of the disease.

In some embodiments, the conjugates provided herein are administered intravenously. In some embodiments for intravenous administration, the conjugate can be administered by push or bolus, by infusion, or via a combination thereof. In some embodiments, the infusion time can be about 1 minute to three hours, such as about 1 minute to about two hours, or about 1 minute to about 60 minutes, or at least 10 minutes, 40 minutes, or 60 minutes.

In some embodiments, the dosage amount is between about 7 mg/m$^2$ to 162 mg/m$^2$ (e.g. 7 mg/m$^2$, 14 mg/m$^2$, 28 mg/m$^2$, 56 mg/m$^2$, 84 mg/m$^2$, 112 mg/m$^2$, 135 mg/m$^2$ or 162 mg/m$^2$). In some embodiments, the dosage amount is between about 6.5 mg/m$^2$ to about 7.5 mg/m$^2$, about 13.5 mg/m$^2$ to about 14.5 mg/m$^2$, about 27.5 mg/m$^2$ to about 28.5 mg/m$^2$, about 55.5 mg/m$^2$ to about 56.5 mg/m$^2$, about 83.5 mg/m$^2$ to about 84.5 mg/m$^2$, about 111.5 mg/m$^2$ to about 112.5 mg/m$^2$, about 134.5 mg/m$^2$ to about 135.5 mg/m$^2$, or about 161.5 mg/m$^2$ to about 162 mg/m$^2$). In some embodiments, the dosage amounts are administered intravenously once every three weeks (i.e., 21-day cycle) or once every four weeks (i.e., 28-day cycle).

The frequency and timing of administration, and the dosage amounts, can be administered periodically over a cycle of administration to maintain a continuous and/or long term effect of the active agents for a desired length of time. The provided compositions of a NaPi2b-targeted antibody-drug conjugate can be administered hourly, daily, weekly, monthly, yearly or once. The length of time of the cycle of administration can be empirically determined, and is dependent on the disease to be treated, the severity of the disease, the particular patient, and other considerations within the level of skill of the treating physician. The length of time of treatment with a combination therapy provided herein can be one week, two weeks, one months, several months, one year, several years or more.

In some embodiments, the frequency of administration of the NaPi2b-targeted antibody-drug conjugate is once a day, every other day, twice weekly, once weekly, once every 2 weeks, once every 3 weeks, or once every 4 weeks. The dosage can be divided into a plurality of cycles of administration during the course of treatment. For example, the NaPi2b-targeted antibody-drug conjugate can be administered at the frequency over a period of about a month, 2 months, 3 months, 4 months, 5 months, 6 months, a year or more. The frequency of administration can be the same throughout the period of the cycle or can differ. In some embodiments, the NaPi2b-targeted antibody-drug conjugate is administer at least two times a week for a first week of a cycle of administration. After the first week, the frequency can continue at twice a week, can increase to more than twice a week, or can be reduced to no more than once a week. It is within the level of a skilled person to determine the particular dosage frequency and cycle of administration based on the particular dosage being administered, the disease or condition being treated, the severity of the disease or condition, the age of the subject and other similar factors.

In some embodiments, if disease symptoms persist in the absence of discontinued treatment, treatment can be continued for an additional length of time. Over the course of treatment, evidence of disease and/or treatment-related toxicity or side effects can be monitored.

The cycle of administration of the NaPi2b-targeted antibody-drug conjugate can be tailored to add periods of discontinued treatment in order to provide a rest period from exposure to the agents. The length of time for the discontinuation of treatment can be for a predetermined time or can be empirically determined depending on how the patient is responding or depending on observed side effects. For example, the treatment can be discontinued for one week, two weeks, three weeks, one month or several months. In some embodiments, the period of discontinued treatment is built into a cycle of dosing regimen for a patient.

An exemplary dosing regimen is a treatment cycle or cycle of administration of 21 days or 28 days. In some embodiments, the dosing regimen is a treatment cycle or cycle of administration is 28 days. In some embodiments, the NaPi2b-targeted antibody-drug conjugate disclosed herein, is administered on day 1, followed by 20 days without dosing or is administered on day 1, followed by 27 days without dosing. It is within the level of one of skill in the art to determine the precise cycle of administration and dosing schedule.

In some embodiments, the cycle of administration can be for any desired length of time (e.g., the 21-day cycle or 28-day cycle of administration can be repeated for any length of time). For example, the 21-day cycle or 28-day cycle of administration can be repeated for 2 months, 3, months, 4 months, 5, months, 6 months, 7 months, 8 months, 9 months, 10 months, 11 months, 12 months, 1.5 years, 2 years, 2.5 years, 3 years or more.

In some embodiments, the NaPi2b expressing cancers include for example, ovarian cancer, non-small cell lung cancer (NSCLC), endometrial cancer, papillary renal cell cancer, salivary duct cancer, papillary thyroid cancer, clear cell renal cancer, breast cancer, kidney cancer, cervical cancer, and cholangiocarcinoma, In some embodiments, the NaPi2b expressing cancers include for example, ovarian cancer, non-small cell lung cancer (NSCLC), endometrial cancer, papillary renal cell cancer, salivary duct cancer, and papillary thyroid cancer.

In some embodiments, the present disclosure relates to a method of treating ovarian cancer or non-small cell lung cancer (NSCLC) in a subject in need thereof, comprising administering to the subject an effective amount of a conjugate disclosed herein.

In some embodiments, the present disclosure provides use of a conjugate disclosed herein in the manufacture of a medicament for treating ovarian cancer or non-small cell lung cancer (NSCLC) in a subject in need thereof.

In some embodiments, the present disclosure provides use of a conjugate disclosed herein for treating ovarian cancer or non-small cell lung cancer (NSCLC) in a subject in need thereof.

In some embodiments, the present disclosure provides a conjugate for use in treating ovarian cancer or non-small cell lung cancer (NSCLC) in a subject in need thereof, comprising administering to the subject an effective amount of a conjugate disclosed herein.

In some embodiments, the cancer is non-small cell lung cancer (NSCLC). In some embodiments, the NSCLC is sub-typed as adenocarcinoma.

In some embodiments, the ovarian cancer is platinum resistant ovarian cancer. In some embodiments, the ovarian cancer is high-grade serous ovarian carcinoma. In some embodiments, the ovarian cancer is platinum resistant, high-grade serous ovarian cancer.

In some embodiments, the cancer is endometrial cancer. In some embodiments, the cancer is papillary renal cell cancer. In some embodiments, the cancer is salivary duct cancer. In some embodiments, the cancer is papillary thyroid cancer.

In some embodiments, the subject has epithelial ovarian cancer, fallopian tube cancer, primary peritoneal cancer, platinum resistant ovarian cancer, non-squamous NSCLC cancer, progressive, radioactive iodine-refractory, loco-regional recurrent or metastatic disease papillary thyroid cancer, or epithelial endometrial cancer.

In some embodiments, the subject having epithelial ovarian cancer is subtyped as high-grade ovarian cancer, low-grade serous ovarian cancer or clear cell ovarian cancer.

In some embodiments, the subject having ovarian cancer has received prior treatment with a chemotherapeutic agent, such as, for example, docetaxel, doxorubicin, cyclophosphamide, carboplatin, paclitaxel, nab-paclitaxel, gemcitabine, and cisplatin; an angiogenesis inhibitors, such as, for example, bevacizumab (Avastin); a PARP inhibitor, such as, for example, niraparib (Zejula), olaparib (Lynparza), and veliparib; olaparib (Lynparza) in combination with bevacizumab; or a combination thereof.

In some embodiments, the subject having ovarian cancer has received prior single agent chemotherapy such as, for example, pegylated liposomal doxorubicin, weekly treatment with paclitaxel topotecan gemcitabine, PARP inhibitor and the like.

In some embodiments, the subject having ovarian cancer has received no more than 3 lines of prior lines of therapy such as, for example, chemotherapy combination, such as, for example, carboplatin plus paclitaxel, pegylated liposomal doxorubicin, weekly treatment with paclitaxel, docetaxel, topotecan, gemcitabine, PARP inhibitor and the like.

In some embodiments, the subject having ovarian cancer has received no more than 3 lines of prior lines of therapy including at least one line of platinum-containing regimen. In some embodiments, the subject having ovarian cancer has received no more than 4 lines of prior lines of therapy with or without at least one line of platinum-containing regimen.

In some embodiments, the subject having NSCLC cancer is subtyped as adenocarcinoma. In some embodiments, the subject having adenocarcinoma NSCLC cancer maybe metastatic or recurrent.

In some embodiments, the subject has NSCLC and has received prior treatment, such as for example, with a platinum-based chemotherapy (cisplatin or carboplatin) and a PD-1 or PD-L1 monoclonal antibody. In some embodiments, the subject has NSCLC and has received prior treatment with carboplatin/paclitaxel, abraxane nab-paclitaxel, docetaxel, premetrexed, gemcitabine or a combination of docetaxel and ramucirumab.

In some embodiments, the subject has NSCLC and has received up to 2 prior lines of chemotherapy.

In some embodiments, the subject has NSCLC and has not received additional prior treatment with a cytotoxic agent or has not received immunotherapy. In another embodiment the subject having NSCLC has documented intolerance or disease progression with known oncogenic mutations for which there are approved therapies (e.g. ALK translocation, EGFR mutation or KRAS mutation).

In some embodiments, the subject having NSCLC cancer is treated with a NaPi2b antibody-drug conjugate and a PD-1 or PD-L1 monoclonal antibody, such as, for example, nivolumab, pembrolizumab, atezolizumab or avelumab.

In some embodiments, the subject having NSCLC cancer is treated with a NaPi2b antibody-drug conjugate and the PD-1 or PD-L1 monoclonal antibody, pembrolizumab.

In some embodiments, the subject is treated with a NaPi2b antibody-drug conjugate in combination with a PARP inhibitor, such as, for example, olaparib, niraparib, rucaparib, talazoparib, and the like; a PD1/PDL-1 inhibitor, such as, for example, nivolumab, pembrolizumab, atezolizumab, avelumab, and the like; chemotherapy, such as, for example, carboplatin, cisplatin, oxaliplatin, doxil, cyclophosphamide, gemcitabine, topotecan, premetrexe, and the like; a VEGF inhibitor, such as, for example, bevacizumab, ramucirumab, and the like; a tyrosine kinase inhibitor, such as, for example, gefitinib, afatinib, erlotinib, dacomitinib, osimertinib, pazopanib, and the like; an ALK inhibitor, such as, for example, alectinib, crizotinib, ceritinib, brigatinib, and the like; or a BRAF inhibitor, such as, for example, dabrafenib, trametinib, and the like.

In some embodiments, the immune checkpoint inhibitor is pembrolizumab.

In some embodiments, the subject is treated with a NaPi2b antibody-drug conjugate in combination with pembrolizumab, carboplatin, doxil, bevacizumab or a PARP inhibitor.

In some embodiments, the subject has papillary thyroid cancer with resistance or intolerance to prior kinase inhibitor therapy or has received prior treatment for low-grade, hormone receptor-positive endometroid adenocarcinoma.

In some embodiments, the endometrial cancer is not a stromal tumor or a carcinosarcoma. In some embodiments, the subject has endometrial cancer and has received prior treatment with a carboplatin/paclitaxel or a similar regimen.

In some embodiments, the subject has papillary renal cell cancer or clear cell renal cancer that has a predominantly papillary growth pattern. In one embodiment the subject has a histologic diagnosis of salivary duct cancer has progressed after standard systemic therapy.

In some embodiments, the subject is refractory to chemotherapy, including standard, front-line chemotherapeutic agents.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Throughout the description, where compounds, scaffolds, and compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

Synthetic Methods

Any available techniques can be used to make the conjugates or compositions thereof, and intermediates and components (e.g., scaffolds) useful for making them. In some embodiments, semi-synthetic and fully synthetic methods may be used.

The general methods of producing the conjugates or scaffolds disclosed herein are illustrated in Schemes 2 and 3 below and in co-pending U.S. Ser. No. 15/819,650, the disclosure of which is incorporated herein in its entirety. The variables (e.g., $M^P$, $M^A$ $L^3$, $W^D$, $W^M$ $L^D$, and $L^{P'}$, etc.) in these schemes have the same definitions as described herein unless otherwise specified.

Scheme 2

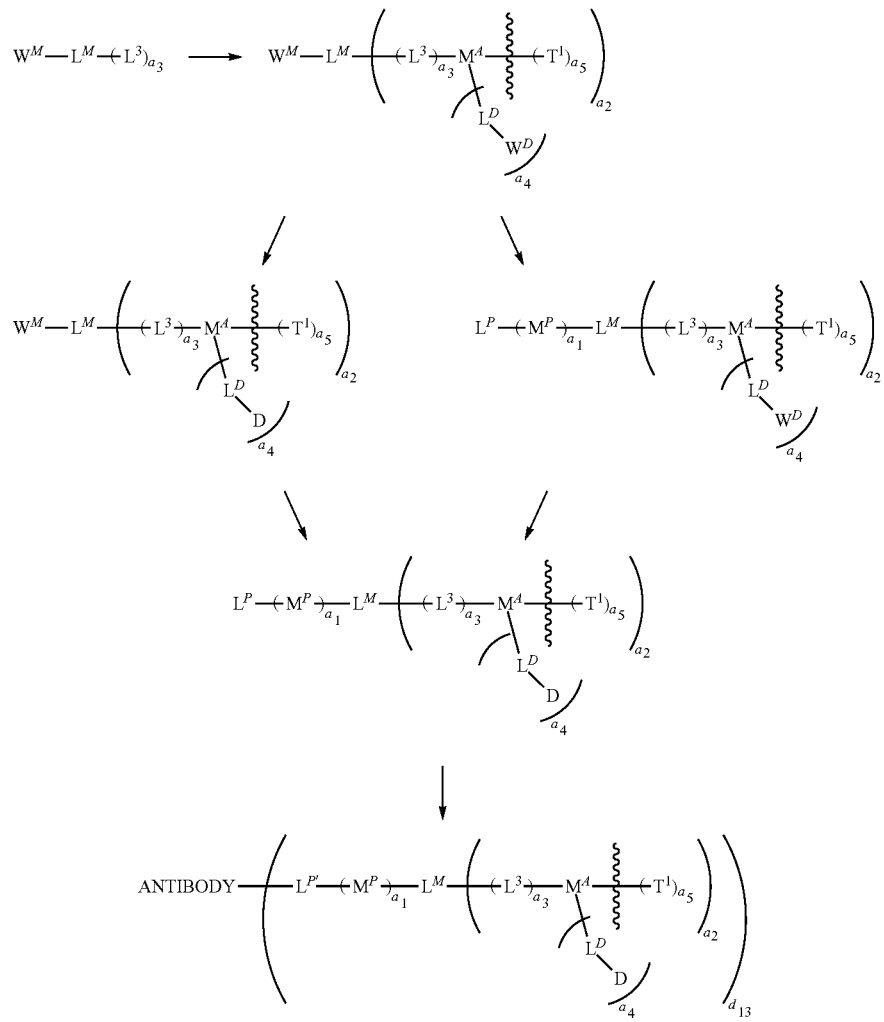

Scheme 3

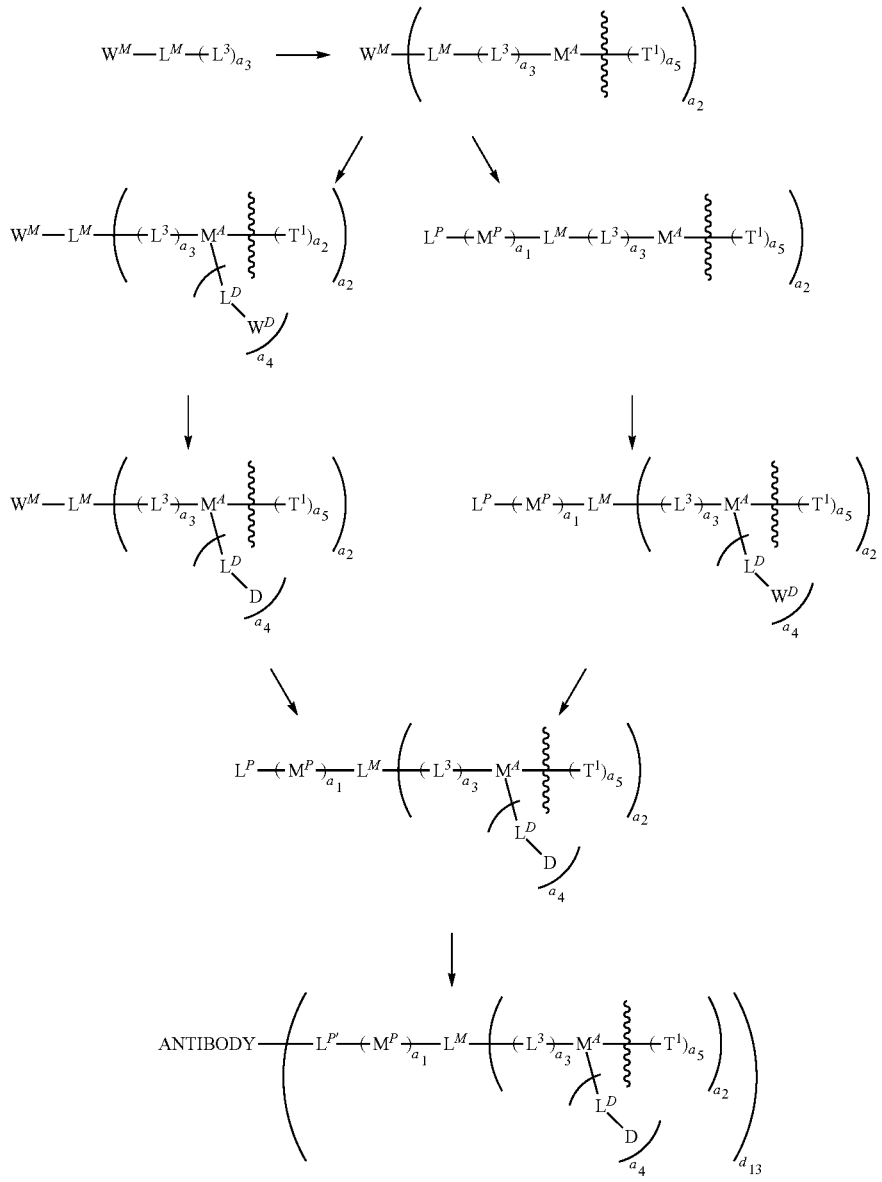

wherein the antibody is a modified antibody of the present disclosure.

The synthetic processes of the disclosure can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

Conjugates of the present disclosure and the drug compounds included therein can be prepared by a variety of methods familiar to those skilled in the art. The conjugates or compounds of the disclosure with each of the formulae described herein may be prepared according to the following procedures from commercially available starting materials or starting materials which can be prepared using literature procedures. These procedures show the preparation of representative conjugates of this disclosure.

Conjugates designed, selected and/or optimized by methods described above, once produced, can be characterized using a variety of assays known to those skilled in the art to determine whether the conjugates have biological activity. In some embodiments, the conjugates can be characterized by conventional assays, including but not limited to those assays described below, to determine whether they have a predicted activity, binding activity and/or binding specificity.

Furthermore, high-throughput screening can be used to speed up analysis using such assays. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Examples

The following working examples are illustrative of the linkers, drug molecules and antibodies or antibody fragments, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples Abbreviations ACN Acetonitrile
AF Auristatin F
AF-HPA Auristatin F hydroxypropyl amide
ALP Alkaline phosphatase
ALT Alanine aminotransferase
AST Aspartate Aminotransferase
aq Aqueous
CE Capillary electrophoresis
CR Complete regression
DAD Diode array detector
DAR Drug-to-antibody ratio
DCM Dichloromethane
DIPEA N,N-Diisopropylethylamine
DMEM Dulbecco's Modified Eagle Medium
DMF Dimethylformamide
EDC 1-Ethyl-3-[3-dimethylaminopropyl]carbodiimide
EDTA Ethylenediaminetetraacetic acid
ELISA Enzyme-linked immunosorbent assay
Endo SH Endoglycosidase SH
FBS Fetal bovine serum
Fuc Fucose
GalNAcT Glycosyltransferase
HIC Hydrophobic interaction chromatography
HOAt 1-Hydroxy-7-azabenzotriazole
HRP Horse-radish peroxidase
IV Intravenous
LC Liquid chromatography
MS Mass spectrometry
MTV Median tumor volume
NMP N-Methyl-2-pyrrolidone
NMR Nuclear magnetic resonance
PBS Phosphate buffered saline
PBST Phosphate-buffered saline containing Tween
PR Partial regression
RBC Red Blood Cells
RP-HPLC Reverse-phase high performance liquid chromatography
SDS Sodium dodecyl sulfate
SEC Size exclusion chromatography
TBS Tris buffered saline
TFS Tumor free survival
TGI Tumor growth inhibition
TCEP Tris[2-carboxyethyl] phosphine
TEAA Triethylammonium acetate
TFA Trifluoroacetic acid
THF Tetrahydrofuran
TMB Tetramethylbenzidine
UDP Uridine diphosphate
UF/DF Ultrafiltration/diafiltration
WBC White Blood Cells
WCX Weak cation exchange chromatography General Information All reagents were purchased from relevant providers unless otherwise stated.

XMT-1535 (anti-NaPi2b antibody) is disclosed in co-pending application U.S. Ser. No. 15/457,574, filed Mar. 13, 2017, the entire contents of which are incorporated herein by reference. XMT-1519 (anti-Her2 antibody) is disclosed in U.S. Pat. No. 9,555,112, issued Jan. 31, 2017 and U.S. Pat. No. 9,738,720, issued Aug. 22, 2017, the entire contents of which are incorporated herein by reference.

Endo SH was prepared as described in PCT application WO 2017137459, the entire contents of which are incorporated herein by reference. UDP-azido sugar and GalNAcT were prepared as described in U.S. Pat. No. 9,988,662, the entire contents of which are incorporated herein by reference.

Tumor growth inhibition (% TGI) was defined as the percent difference in median tumor volumes (MTVs) between treated and control groups. Tumor size was measured throughout each efficacy study to determine tumor growth inhibition (TGI).

HPLC purification was performed on a Phenomenex Gemini 5 μm C18 110 Å, 250×10 mm, semi-preparative column. When applicable, the drug content of the conjugates was determined spectrophotometrically, otherwise RP-HPLC, LC/MS or $^1$H-NMR was performed for quantitative determination of the drug content.

The protein content of the antibody-drug conjugates was determined spectrophotometrically at 280 nm or by ELISA.

Antibody-drug conjugates, drug carrying scaffolds, or antibody scaffolds were purified (i.e., removal of residual unreacted drug, unconjugated antibody, enzymes or starting materials) by extensive diafiltration, IC, or protein A as required. If necessary, additional purification by SEC or HIC were conducted to remove aggregated antibody-drug conjugates. In general, the antibody-drug conjugates, as purified, contained <5% (w/w) (e.g., <2% (w/w)) aggregated antibody-drug conjugates as determined by SEC; <0.5% (w/w) (e.g., <0.1% (w/w)) free (unconjugated) drug as determined by RP-HPLC and/or LC-MS/MS; <1% (w/w) of free drug conjugate as determined by SEC and/or RP-HPLC; and <2% (w/w) (e.g., <1% (w/w)) unconjugated antibody or antibody fragments as determined by HIC-HPLC and/or RP-HPLC. Reduced or partially reduced antibodies were prepared using procedures described in the literature, see, for example, Francisco et al., Blood 102 (4): 1458-1465 (2003). The total drug (conjugated and unconjugated) concentration was determined by RP-HPLC or back-calculation from DAR as measured by CE-SDS.

To determine the concentration of the free AF-HPA drug in a biological sample, an acidified sample was treated with ACN. The free drug was extracted and the ACN supernatant was analyzed. To determine the concentration of conjugated AF-HPA in a non-clinical sample, the sample was subjected to immunocapture using anti-IgG1 antibody-coated magnetic beads followed by exhaustive basic hydrolysis. The ACN supernatant containing the released AF-HPA drug was analyzed by LC-MS/MS. The total antibody concentration in non-clinical samples was measured by LC-MS/MS after immunocapture using an anti-IgG1 antibody via detection of a peptide sequence unique for the antibody after tryptic digestion. For clinical samples, the same procedure could be followed except that an anti-idiotype antibody would be used for immunocapture to avoid the interference of endogenous antibodies.

Analysis of free AF and AF-HPA was conducted by RP-HPLC using a C4 column, an ACN gradient, and UV detection. Peak areas are integrated and compared to AF and AF-HPA standards. The method is quantitative for AF and AF-HPA in plasma and tissue homogenates and linear over the concentration ranges of 0.1 ng/mL to 150 ng/mL. The total drug (AF-HPA) released after hydrolysis with NaOH (aq) was measured under the same condition with the dynamic range from 1 ng/mL to 5,000 ng/mL. The total antibody standards range from 0.1 µg/mL to 100 µg/mL.

The hydrophobicity of the antibody-drug conjugate was determined by HIC-HPLC on a Shimadzu Prominence HPLC system equipped with a diode array detector (DAD). A TSK gel butyl-NPR column (2.5 µm particle size) was held at 35° C. for these analyses. Mobile phase A was 1.5 M ammonium sulfate, 25 mM sodium phosphate, and pH 7.0, and mobile phase B was 25 mM sodium phosphate, 10% isopropyl alcohol, and pH 7.0. Separations were performed with a 0-100% linear gradient of mobile phase B over 25 minutes. The flow rate was 1 mL/min. Sample injections ranged from ~10 µg to 100 µg.

The drug to antibody ratio (DAR) was determined by subjecting the antibody-drug conjugates to exhaustive base hydrolysis. The released AF-HPA was then quantified from a standard curve with RP-HPLC. The measured AF-HPA concentrations were correlated to the antibody content to determine DAR.

Example 1: Synthesis of Scaffold 6

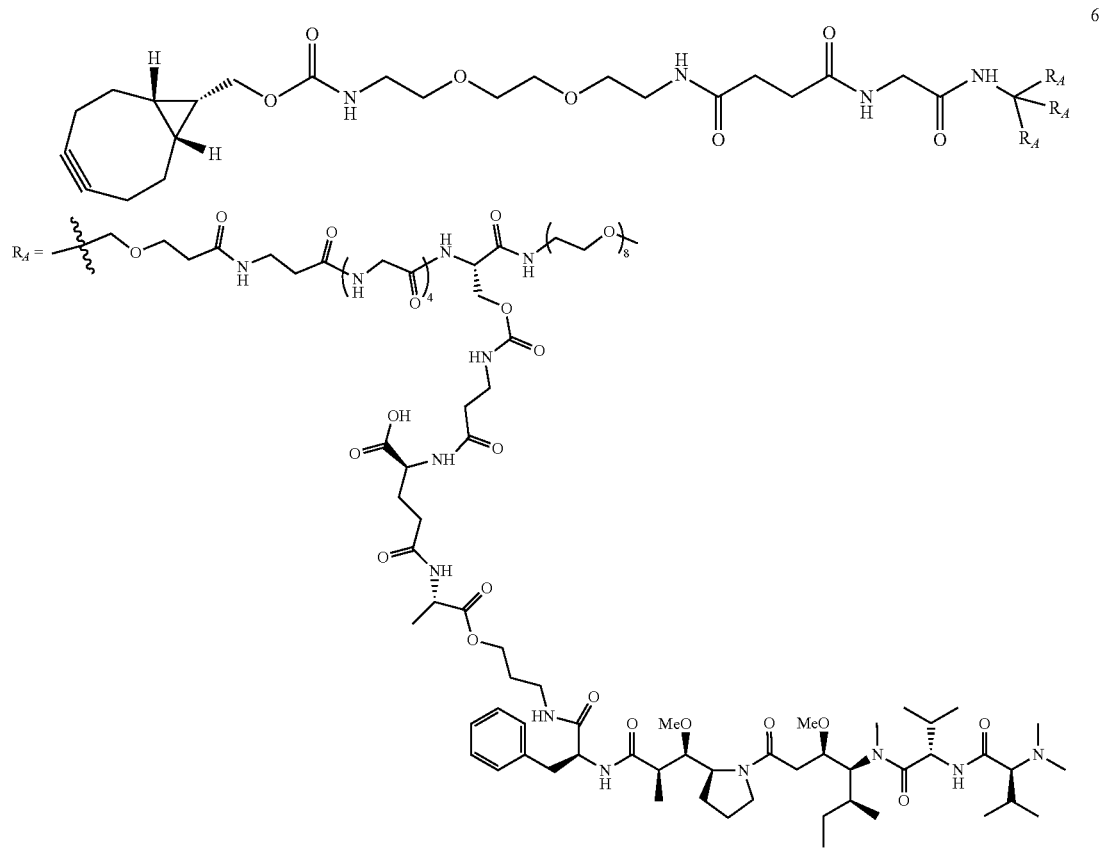

Step 1. Compound 3

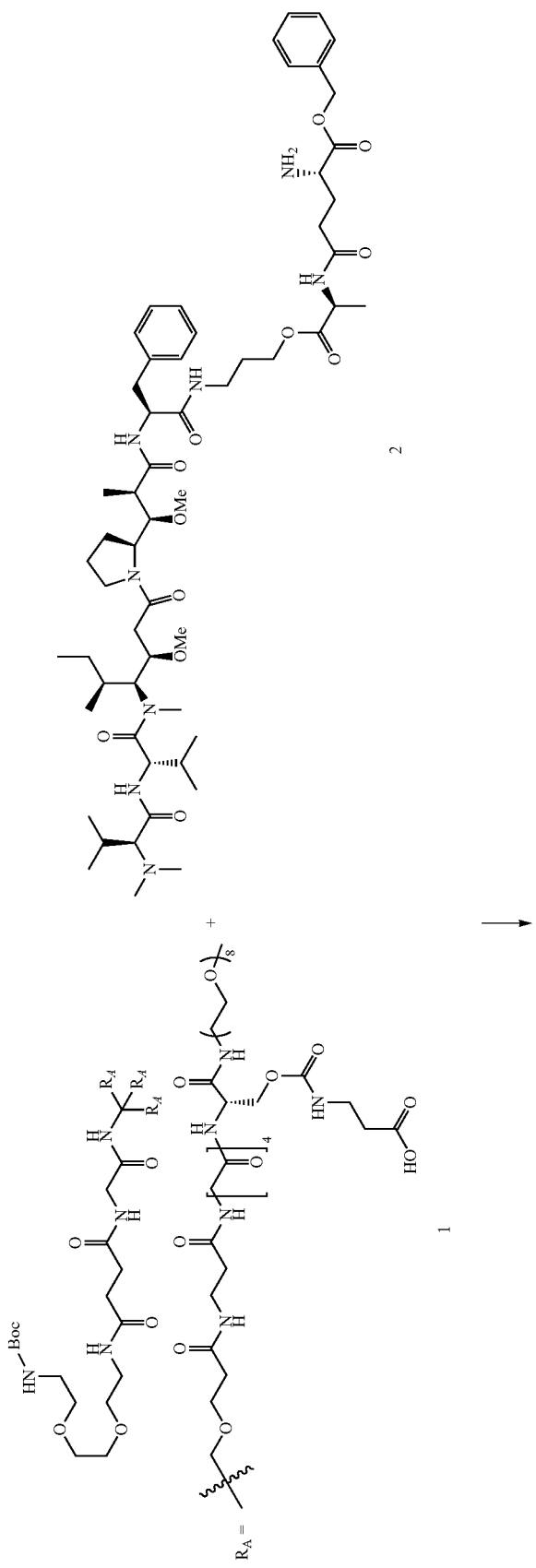

-continued
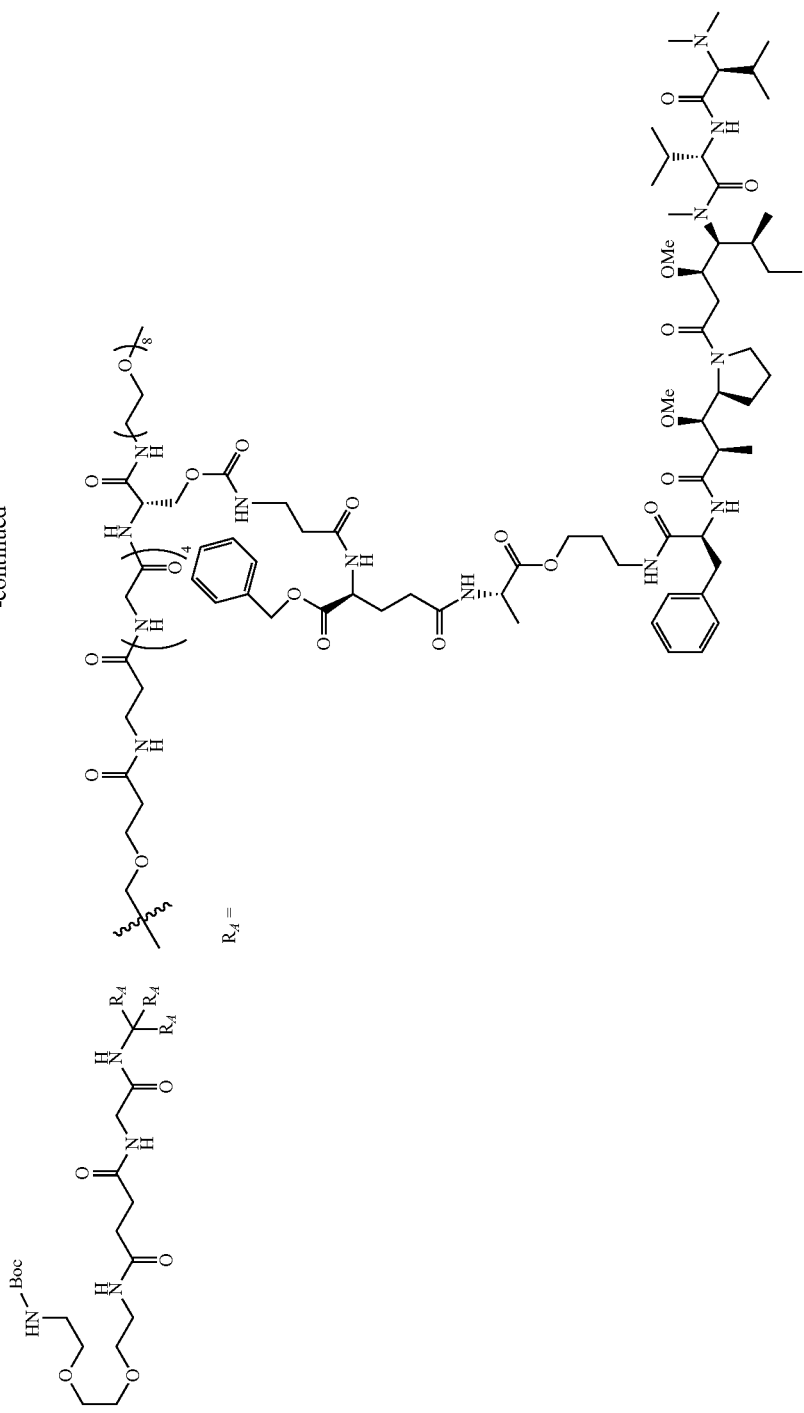

Compound 1 (548 mg, 0.165 mmol, prepared as described in U.S. Ser. No. 15/819,650, the entire contents of which are incorporated herein by reference), water (14 mL), NMP (1.4 mL), EDC (158 mg, 0.824 mmol), and HOAt (112 mg, 0.824 mmol) were stirred in an ice-bath, and the pH was adjusted to ~6.5 with 1N NaHCO$_3$(aq). Compound 2 (696 mg, 0.577 mmol) was added, followed by pH adjustment to ~6.5. The resulting mixture was stirred cold for 3 h. Additional EDC, HOAt, and compound 2 (198 mg, 0.164 mmol) were added and the stirring continued overnight. The reaction mixture was purified on a C18 cartridge (275 g) with a step gradient of ACN/H$_2$O (0.1% TFA) from 10% to 50% to 90% v/v ACN/H$_2$O (0.1% TFA). The desired fractions were lyophilized to give compound 3 as a white amorphous solid (825 mg, 76% yield). MS: 2120.04 (3$^+$), 1590.27 (4$^+$), 1272.41 (5$^+$).

Step 2. Compound 4

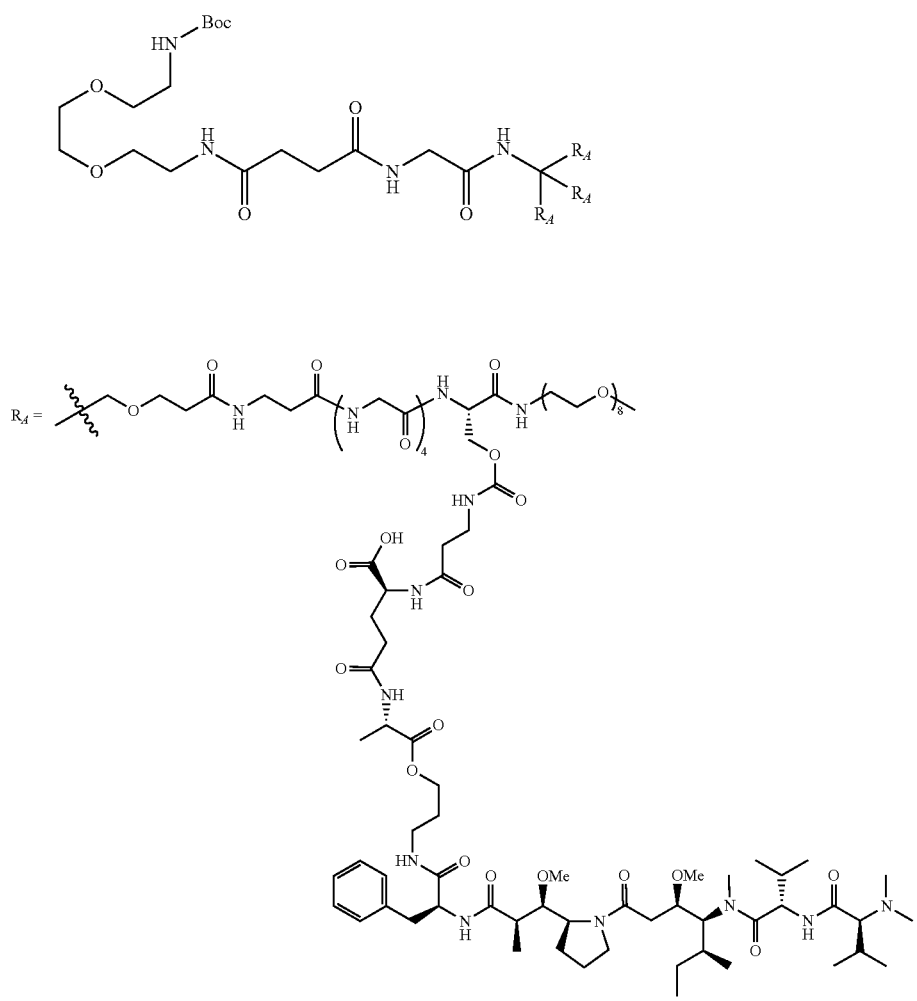

To a mixture of compound 3 (825 mg, 0.126 mmol), EtOH (90 mL), and water (9.00 mL) in a glass Parr bottle, was added acetic acid (0.288 mL, 5.04 mmol). Argon was bubbled through the mixture, followed by the addition of Pd/C (134 mg, 0.126 mmol). The bottle was attached to the hydrogenation equipment then successively vacuum pumped, filled with argon, then filled with hydrogen (0.762 mg, 0.378 mmol) to 30 psi, and the mixture was stirred vigorously overnight. The reaction mixture was filtered through a plug of silica gel and concentrated to an oil. The oil was dissolved in ACN/H$_2$O (0.1% TFA) and lyophilized to obtain compound 4 as a white amorphous solid (790 mg, 100% yield). MS: 2094.65 (3$^+$), 1570.98 (4$^+$), 1257.18 (5$^+$).

Step 3. Compound 5

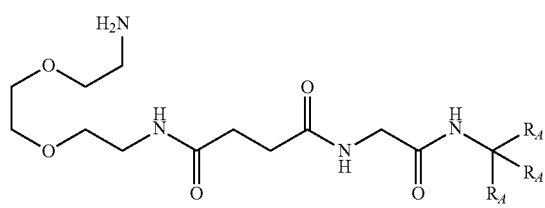

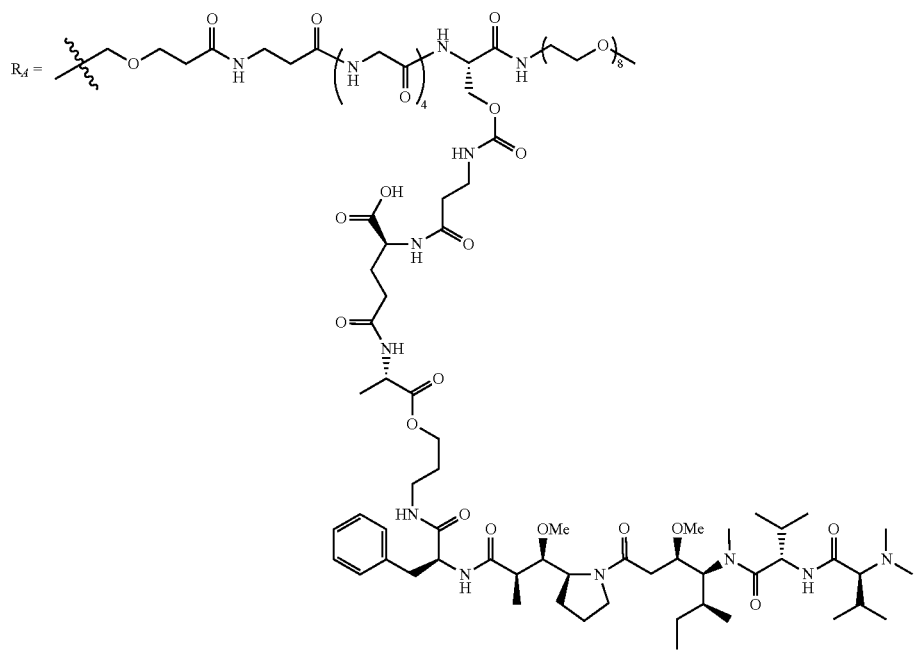

To an ice-cold solution of compound 4 (100 mg, 0.016 mmol) dissolved in THF (1.5 mL) and water (1.5 mL), was added formic acid (4.5 mL, 117 mmol). The solution was stirred cold for 15 minutes, then overnight at room temperature. THF was removed and the resulting mixture was diluted with water and purified on a C18 cartridge (150 g) using ACN/H$_2$O (0.1% TFA) as the mobile phase. The desired fractions were lyophilized to give compound 5 as a white amorphous solid (71 mg, 72% yield). MS: 2060.97 (3$^+$), 1545.98 (4$^+$), 1236.99 (5$^+$).

Step 4. Scaffold 6

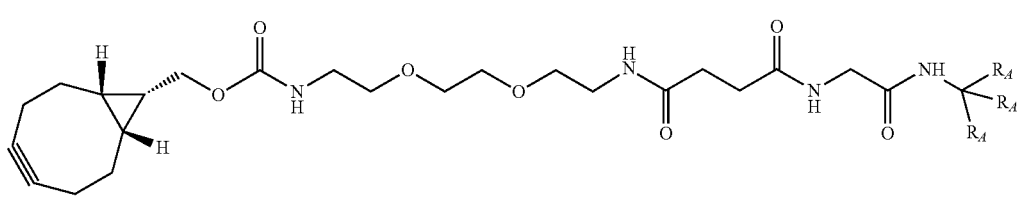

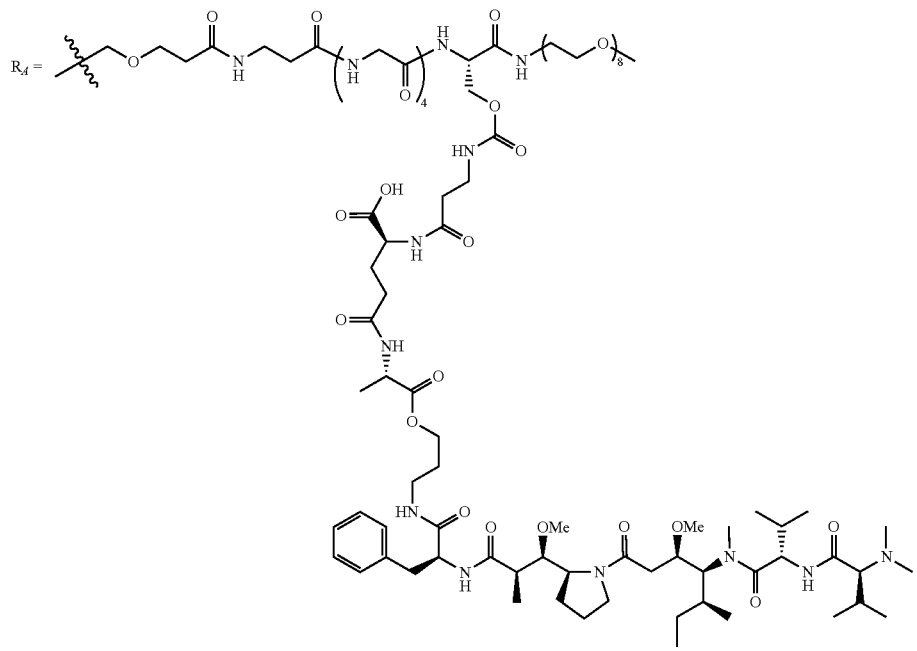

To an ice-cold solution of compound 5 (71 mg, 0.011 mmol) in DCM (5 mL) and DMF (0.500 mL) was added ((1R,8S,9s)-bicyclo[6.1.0]non-4-yn-9-yl)methyl (2,5-dioxopyrrolidin-1-yl) carbonate (5.02 mg, 0.017 mmol) and DIPEA (0.018 mL, 0.103 mmol), final pH ~8-9. After 18 h, DMF (1.5 mL) was added to the reaction mixture and the mixture was stirred at room temperature for 2 h, then concentrated and purified on a preparative HPLC using ACN/H$_2$O (0.1% AcOH) as the mobile phase. The desired fractions were lyophilized to give Scaffold 6 as a white amorphous solid (34 mg, 47% yield). MS: 2120.04 (3$^+$), 1590.27 (4$^+$), 1272.41 (5$^+$).

Example 2: Synthesis of XMT-1535 Drug Conjugate of Scaffold 6 (Conjugate 7, DAR 6.0)

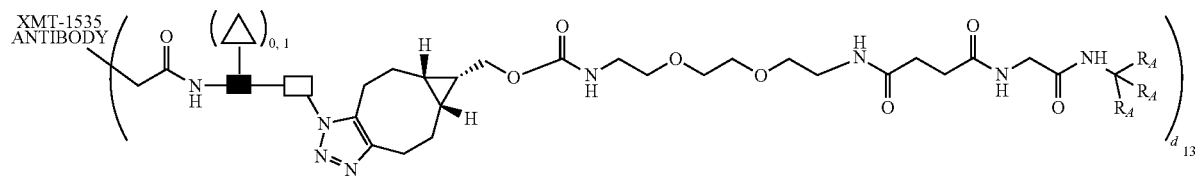

-continued

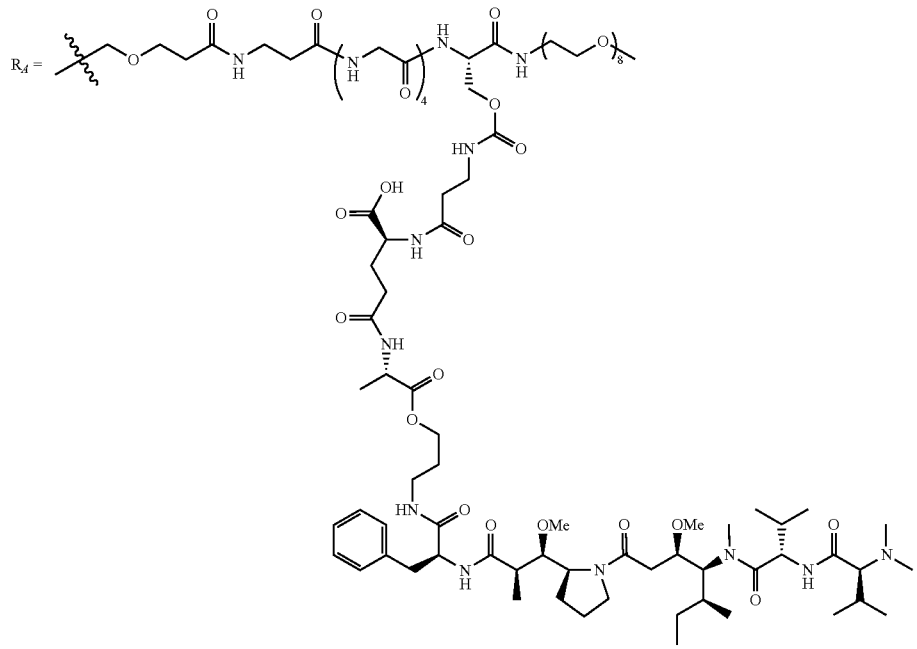

wherein: is GlcNAc; 0 is Fuc; and is GalNAc.

Step 1. Azido modified XMT-1535 antibody

To XMT-1535 antibody (910.6 mg, 6.22 μmole) in TBS, pH 7.6, was added in the following order: TBS (249 μL, pH 7.6), Endo SH (9.10 mg, 0.065 μmole), GalNAcT (77.9 mg, 1.69 μmole), UDP-azido sugar (144 mg, 227 μmole), and MnCl$_2$ (76 mg, 604 μmole), to achieve a final antibody concentration of 15 g/L. The reaction was stirred at 30 rpm overnight at 30° C. The crude azido modified XMT-1535 antibody was purified by Protein A chromatography and dialysis to give the azido modified XMT-1535 antibody (880 mg, 97% yield).

Step 2. MiT-1535 Drug Conjugate of Scaffold 6 (Conjugate 7, DAR 6.0)

Azido modified XMT-1535 antibody (300 mg, 2.05 μmole) in PBS, pH 7.4 (5.5 mL) and Scaffold 6 (127.2 mg, 20.0 μmole) in water, were gently mixed, then left for 20 hours at 30° C. without shaking or rocking. The crude product was purified by UF/DF and HIC to give Conjugate 7 (132 mg, 44% yield), that had a DAR of 6.6 as determined by hydrolysis followed by RP-HIPLC.

Example 3: Synthesis of XMT-1519 Conjugate of Scaffold 6 (Conjugate 8, DAR 7.3)

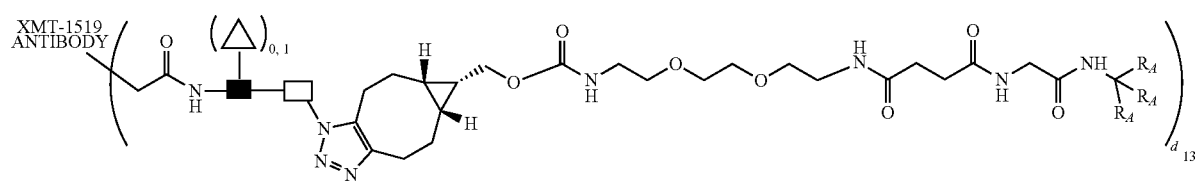

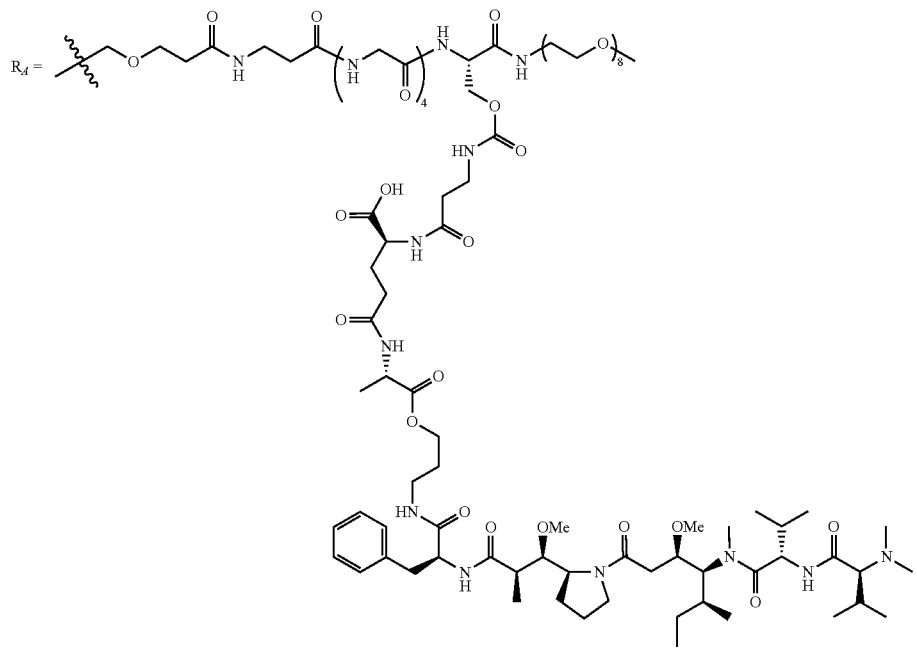
wherein: ■ is GlcNAc; Δ is Fuc; and □ is GalNAc.
Conjugate 8 was synthesized as described in Example 2, except azido-modified XMT-1519 (400 mg, 2.78 μmole) was used in Step 2 instead of azido-modified XMT-1535 antibody. The purified Conjugate 8 (163 mg, 41% yield) had a drug to DAR of 7.3 as determined by hydrolysis followed by RP-HPLC.
Example 4: Synthesis of Trastuzumab Conjugate of Scaffold 6 (Conjugate 9, DAR 7.3)
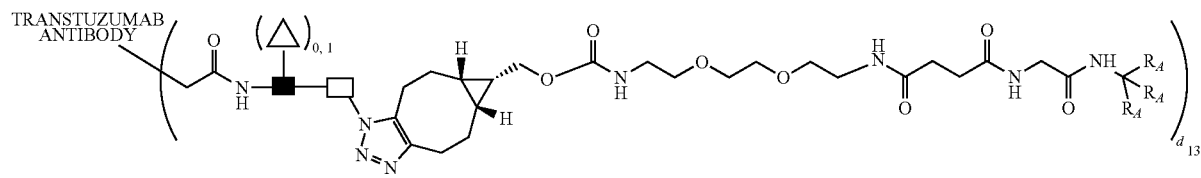

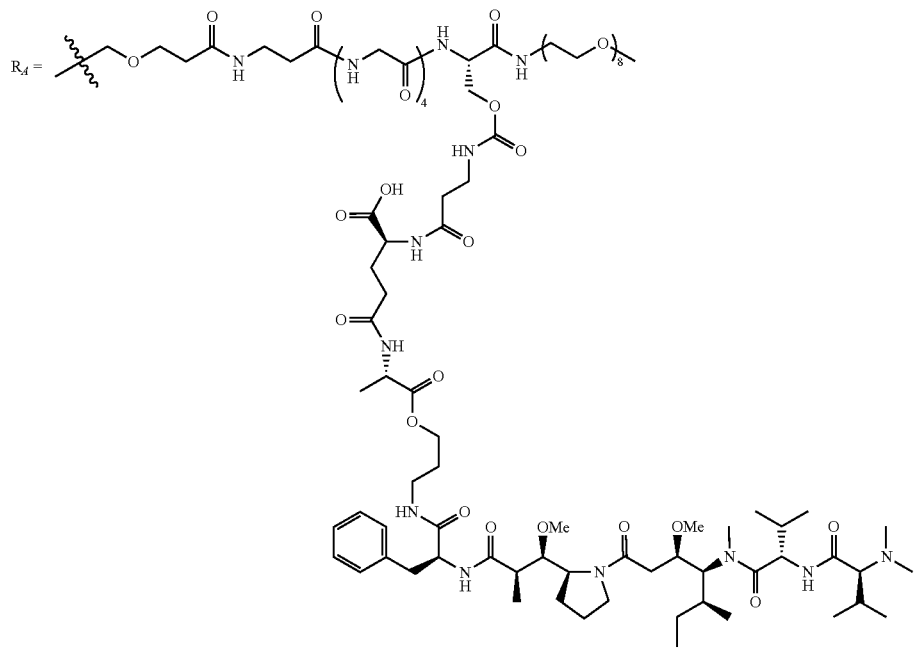
wherein: ■ is GlcNAc; Δ is Fuc; and □ is GalNAc.
Conjugate 9 was as described in Example 2, except azido-modified Trastuzumab (35 mg, 0.239 μmol) was used in Step 2 instead of azido-modified XMT-1535 antibody. The purified Conjugate 9 had a DAR of 7.3 as determined by hydrolysis followed by RP-HPLC.
Example 5: Synthesis of Rituximab Conjugate of Scaffold 6 (Conjugate 10, DAR 6.8)
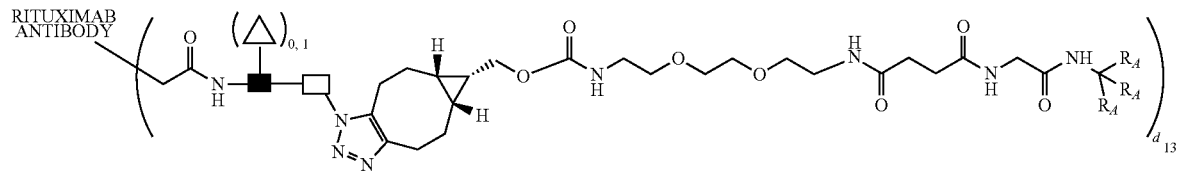

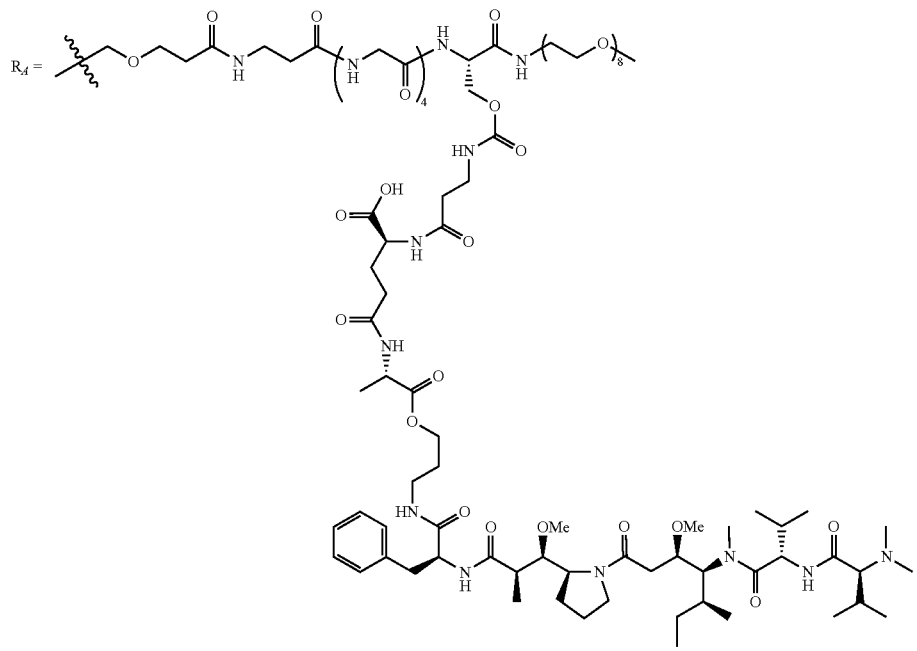
wherein: ■ is GlcNAc; Δ is Fuc; and □ is GalNAc.
Conjugate 10 was prepared as described in Example 2, except azido-modified rituximab (40 mg, 0.28 μmole) was used in Step 2 instead of the azido-modified XMT-1535 antibody. The purified Conjugate 10 had a drug to DAR of 6.8 as determined by hydrolysis followed by RP-HPLC.
Example 6: Synthesis of XMT-1535 Conjugate 11 (DAR 6.5)
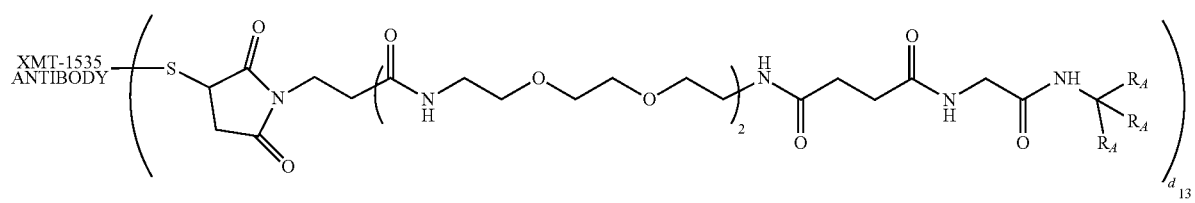

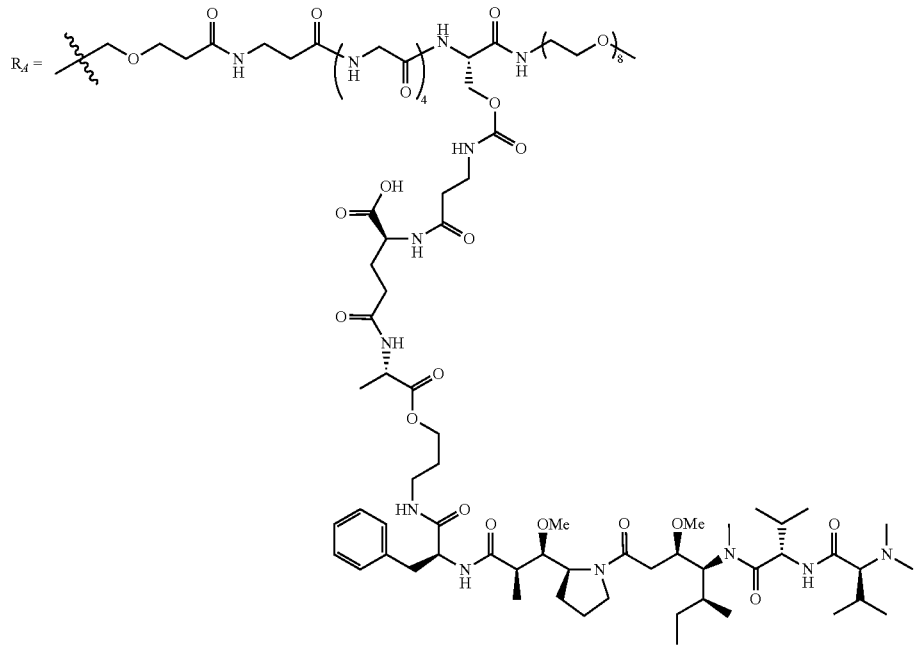

To a solution of XMT-1535 (200 mg, 1.37 μmol) in sodium acetate buffer (25 mM, pH 5.5, 21.1 mL) at +4° C. was added TEAA (aq, 50 mM) and EDTA (1 mM, pH 7.0, 18.95 mL). The pH of the resulting mixture was adjusted to pH 7.0 using NaHCO$_3$(aq, 1.0 M) followed by the addition of TCEP (1.37 mg, 4.77 μmole) in TEAA (aq, 50 mM) and EDTA (1 mM, pH 7.0). After 90 minutes, the pH of the reaction mixture was adjusted to pH 6.0 using acetic acid (aq, 1.0 M). The maleimido scaffold of Scaffold 6, (79.8 mg, 12.3 μmol, prepared as described in U.S. Ser. No. 15/819,650, the entire contents of which are incorporated herein by reference) in TEAA (aq, 50 mM, 9.5 mL) and EDTA (1 mM, pH 7.0) were added and the resulting mixture stirred for 2 hours at +4° C. After 2 hours, the reaction was quenched by the addition of L-cysteine (8.28 mg, 68.3 μmole). The crude product was purified by UF/DF and HIC (75.2 mg, 38% yield) to give the stochastic Conjugate 11. The purified Conjugate 11 had a DAR of 6.5 as determined by hydrolysis followed by RP-HPLC.

Example 7: Synthesis of XMT-1519 Conjugate 12 (DAR 6.6)

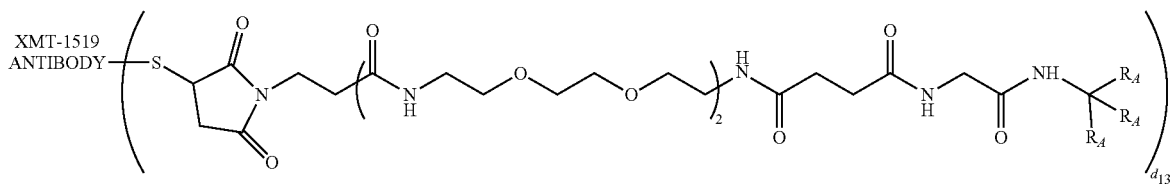

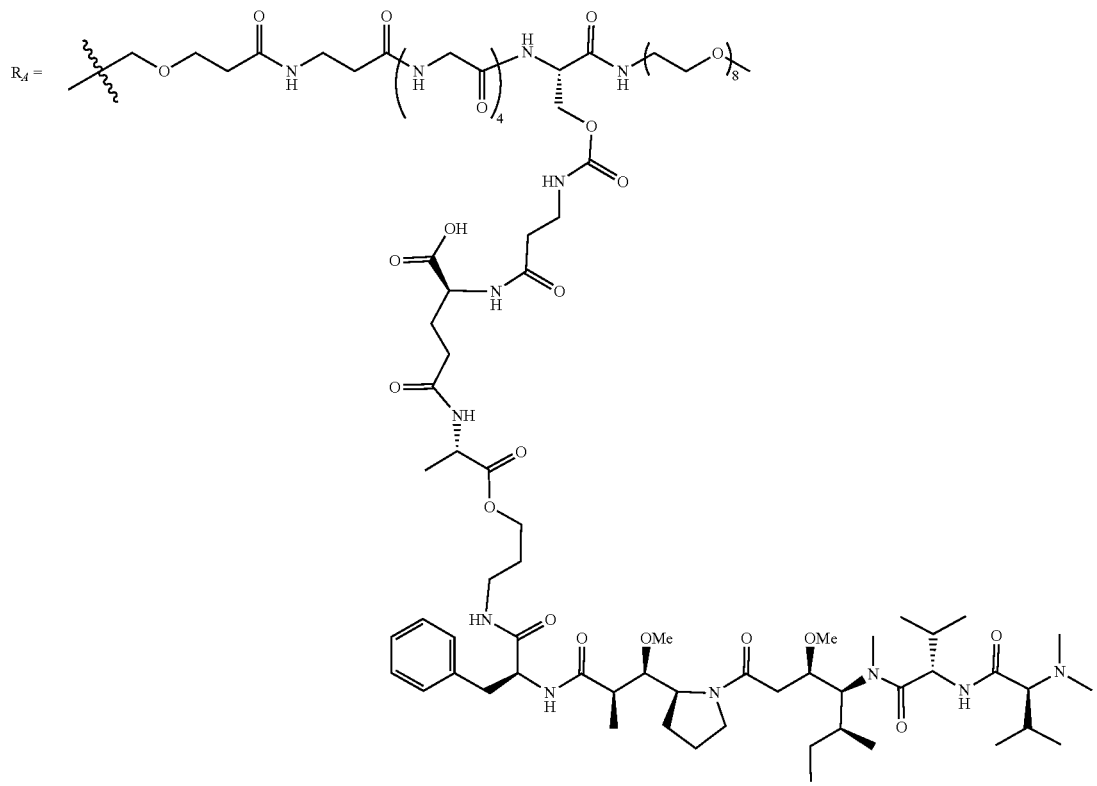
Conjugate 12 was synthesized as described in Example 6, except XMT-1519 antibody (500 mg, 3.47 μmole) was used instead of XMT-1535 antibody. The purified stochastic Conjugate 12 had a DAR of 6.6 as determined by hydrolysis followed by RP-HPLC.
Example 8: Synthesis of Trastuzumab Conjugate 13 (DAR 6.4)
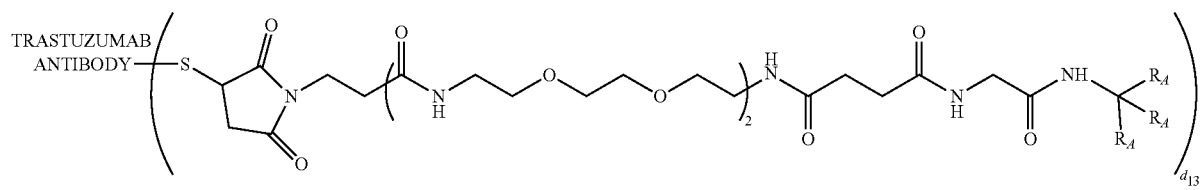

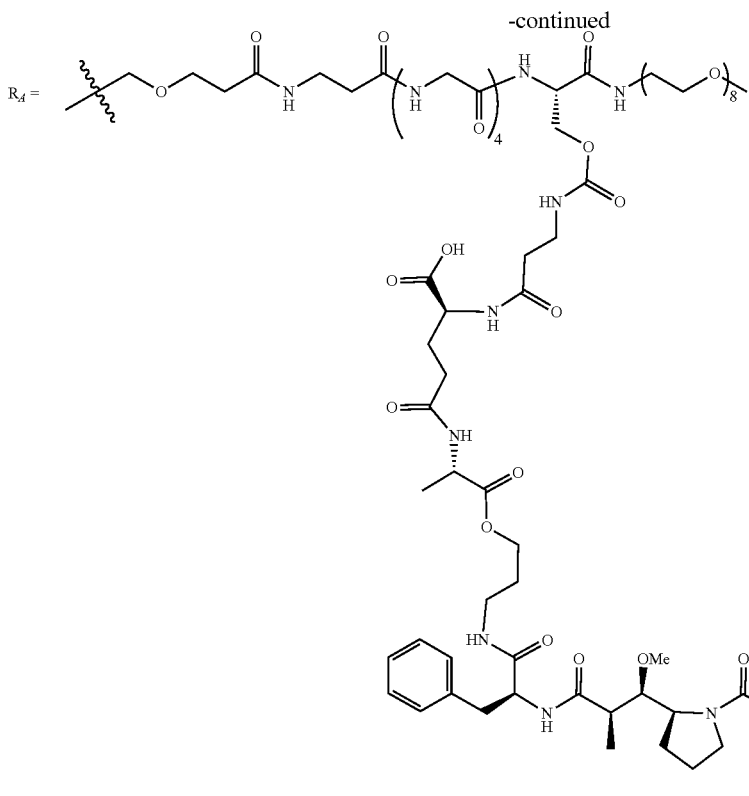

Conjugate 13 was synthesized as described in Example 6, except trastuzumab (40 mg, 0.273 µmole) was used instead of XMT-1535 antibody and the reduction was performed at room temperature. The purified stochastic Conjugate 13 had a DAR of 6.4 as determined by hydrolysis followed by RP-HPLC.

Example 9: Binding of NaPi2b Antibody-Drug Conjugates to NaPi2b Peptide by ELISA Human NaPi2b-derived peptide (QINVTVPSTANCT-SPSLCWTDGIQNWTMKN) was coated onto the surface of each well of a 96-well plate by incubation with the peptide (1p g/mL in PBS), overnight at +4° C. The wells were then blocked by incubation with BSA (3% in PBS, containing 0.1% Tween 20 (PBST)) for 1 hour at room temperature. A range of dilutions (0.017 nM to 1 µM; 3-fold serial dilutions in 3% BSA in PBS) of the test articles (XMT-1535, Conjugate 7, or Conjugate 11) were then added to each well and the plate was incubated for 1 hour at room temperature with gentle rocking. The unbound test article was removed by washing with PBST (3×). A secondary anti-human IgG conjugated to HRP (0.16 µg/mL in PBST) was incubated in each well for 1 hour. The unbound secondary antibody was removed by washing with PBST (3×). The HRP substrate, TMB, was added to each well and incubated until a blue color was visible. The reaction was quenched by the addition of sulfuric acid (0.2 N, 100 µL). The absorbance at 450 nm was measured in a plate reader (Molecular Devices, Spectramax M5). The values were plotted using GraphPad Prism software. $EC_{50}$ values were determined by four-parameter curve fitting. Table I summarizes binding values ($EC_{50}$).

TABLE I

| Test Articles | Mean NaPi2b Binding Values $EC_{50}$ (nM) | Standard Deviation (nM) |
|---|---|---|
| XMT-1535 | 1.77 | N/A |
| Conjugate 7 | 1.44 | 0.55 |
| Conjugate 11 | 1.05 | 0.08 |

As shown in Table I, XMT-1535, Conjugate 7, and Conjugate 11 show comparable $EC_{50}$ values. Results shown are mean $EC_{50}$ values and standard deviations of three replicate experiments for Conjugate 7 and Conjugate 11, and the mean $EC_{50}$ value of two replicate experiments for XMT-1535.

Example 9A: Binding of NaPi2b Antibody-Drug Conjugates to NaPi2b Peptides by ELISA The binding of NaPi2b Antibody-Drug Conjugates to NaPi2b derived-peptides was conducted as described in Example 9 except that NaPi2b-derived peptides derived from human ([Cyc(12,18)]Ac-QINVTVPSTANCT-SPSLCWTDGIQNWTMKN-amide), cynomolgus monkey ([Cyc(12,18)]Ac-QMNVTVPSMANCTSPSLCWTDG-IQIWTMKN-amide), rat ([Cyc(12,18)]Ac-EE-NVTVPSPDNCTSPSYCWTDGIQTWTIQN-amide) or mouse ([Cyc(12,18)]Ac-EMNVTVPSTDNCTS-PSYCWTDGIQTWTIQN-amide) were used. Table IA summarizes binding values ($EC_{50}$).

TABLE IA

| Test Articles | Mean NaPi2b Binding Values EC$_{50}$ (nM) | | | |
|---|---|---|---|---|
| | Human | Cynolmogus Monkey | Rat | Mouse |
| XMT-1535 | 4.43 | 4.04 | 4.71 | 2.77 |
| Compound 7 | 3.70 | 3.83 | 2.48 | 1.79 |
| Compound 11 | 5.00 | 4.19 | 3.72 | 2.26 |

As shown in Table IA, XMT-1535, Conjugate 7, and Conjugate 11 show comparable EC$_{50}$ values for binding to NaPi2b peptides from human, cynomolgus monkey, rat, and mouse. Results shown are mean EC$_{50}$ values of two replicate experiments for each test article.

Example 10: Binding of Her2-Targeted Antibody-Drug Conjugates to Recombinant HER2 Protein by ELISA Recombinant human HER2 (Acro Biosystems) was coated onto the surface of each well of a 96-well plate by incubation at 1 μg/mL in PBS, overnight at +4° C. The wells were then blocked by incubation with PBST for one hour at room temperature. A range of dilutions (9.54×10-5 nM to 100 nM, 4-fold serial dilution in 1% BSA in PBS) of the test articles (XMT-1519, Conjugate 8, or Conjugate 12) were then added to each well and the plate was incubated for 1 hour at room temperature with gentle rocking. The unbound test articles were removed by washing with PBST (3x). A secondary anti-human IgG conjugated to HRP (0.16 μg/ml in PBST) was incubated in each well for 1 hour. The unbound secondary antibody was removed by washing with PBST (3x). The HRP substrate, TMB, was added to each well and incubated until a blue color was visible. The reaction was quenched by the addition of sulfuric acid (0.2 N, 100 μL). The absorbance at 450 nm was measured in a plate reader (Molecular Devices, Spectramax M5). The values were plotted using GraphPad Prism software. EC$_{50}$ values were determined by four-parameter curve fitting. Table II summarizes the mean binding values (EC$_{50}$).

TABLE II

| Test Articles | Mean HER2 Binding Values EC$_{50}$ (nM) |
|---|---|
| XMT-1519 | 0.25 |
| Conjugate 8 | 0.51 |
| Conjugate 12 | 0.47 |

As shown in Table II, XMT-1519, Conjugate 8, and Conjugate 12 show comparable EC$_{50}$ values. Results are mean EC$_{50}$ values of 2 replicate experiments for each test article.

Example 11: Binding Affinity of Antibody-Drug Conjugates to NaPi2b-Derived Peptide The binding kinetics of XMT-1535, Conjugate 7, and Conjugate 11 to immobilized NaPi2b-derived peptide antigen were determined by Biolayer Interferometry (BLI; Octet; ForteBio). Binding constants for XMT-1535, Conjugate 7, and Conjugate 11 were determined using standard Octet procedures (ForteBio). Biotinylated NaPi2b-derived peptide (QINVTVPSTANCTSPSLCWTDGIQNWTMKN-biotin; Genscript) was immobilized to streptavidin octet sensors in kinetics buffer (10x). Sensors were then blocked in kinetics buffer (10x) with biocytin (50 μg/mL). Increasing concentrations of XMT-1535, Conjugate 7, or Conjugate 11 were then associated with immobilized peptide in kinetics buffer (10x).

Table III summarizes the $K_d$ (equilibrium dissociation constant), $k_{on}$ (rate of association), and $k_{off}$ (rate of dissociation) at 25° C. for XMT-1535, Conjugate 7, and Conjugate 11 to the NaPi2b-derived peptide.

TABLE III

| Test Articles | $K_d$ (M) | | $k_{on}$ (M$^{-1}$s$^{-1}$) | | $k_{off}$ (s$^{-1}$) | |
|---|---|---|---|---|---|---|
| | Mean Napi2b binding | Standard Deviation | Mean Napi2b binding | Standard Deviation | Mean Napi2b binding | Standard Deviation |
| Conjugate 7 | 8.28E-11 | 2.36E-11 | 2.00E+05 | 5.84E+04 | 1.81E-05 | 9.97E-06 |
| Conjugate 11 | 8.13E-11 | 3.44E-11 | 1.65E+05 | 2.49E+04 | 1.37E-05 | 7.21E-06 |
| XMT-1535 | 7.29E-11 | 4.36E-11 | 1.70E+05 | 1.50E+04 | 1.27E-05 | 8.61E-06 |

As shown in Table III, XMT-1535, Conjugate 7, and Conjugate 11 show comparable $K_d$ values for their binding to the NaPi2b-derived peptide. Results shown are mean and standard deviation values of four replicate experiments for each test article.

Example 12: Binding Affinity of Antibody-Drug Conjugates to Fc Receptors

The binding kinetics of the XMT-1535, Conjugate 7, and Conjugate 11 to Fc receptors (FcRn, FcγRI, FcγRIIA (H167), and FcγRIIIA (V176) were determined by Biolayer Interferometry (BLI; ForteBio Octet QKe) at 25° C. To test binding to Fcγ receptors, XMT-1535, Conjugate 7, and Conjugate 11 were diluted to 1 μg/mL in kinetics buffer (1x) and captured on anti-human Fab-CH1 (FAB2G) biosensors for 10 minutes. All dilutions and baseline measurements were done in kinetics buffer (1x). Baseline measurements were performed at 61 minutes before and after each capture step. Association measurements to the various Fc receptors were performed at 7 concentrations (from 1 μM to 100 nM, 2-fold serial dilutions) for 5 minutes. Dissociation was performed for 15 minutes. Binding constants were calculated with the global fit averages of the traces using a 1:1 model. Binding constants for XMT-1535, Conjugate 7, and Conjugate 11 to Fc receptors were determined using standard Octet procedures (ForteBio). Kinetic parameters were calculated using Octet software (ForteBio).

To test binding to FcRn receptor, association of XMT-1535, Conjugate 7, and Conjugate 11 to Fab-CH$_1$ (FAB2G) biosensors was performed as described above. After association, sensors were washed for 5 minutes in FcRn binding buffer (Boston Bioproducts; diluted to 100 mM $NaH_2PO_4$, 0.05% Tween 20, pH 6.0). Association and dissociation steps were performed in FcRn binding buffer. Association measurements to FcRn protein (Immunitrack) was measured at 7 concentrations (from 1 μM to 100 nM, 2-fold serial dilutions) for 5 minutes. Dissociation was performed for 15 minutes. Binding constants were calculated with the global fit averages of the traces using a 1:1 model.

Tables IV-VII summarize the $K_d$ (equilibrium dissociation constant), $k_{on}$ (rate of association), and $k_{off}$ (rate of dissociation) for human FcRn (Table IV), FcγRI (Table V), FcγRIIA H167 (Table VI), and FcγRIIIA V167 (Table VII) for each test article.

TABLE IV

| Test Articles | $K_d$ (M) | | $k_{on}$ ($M^{-1}s^{-1}$) | | $k_{off}$ ($s^{-1}$) | |
| --- | --- | --- | --- | --- | --- | --- |
| | Mean | Standard Deviation | Mean | Standard Deviation | Mean | Standard Deviation |
| Conjugate 7 | 5.88E−09 | 2.64E−09 | 8.61E+04 | 2.49E+04 | 4.81E−04 | 1.81E−04 |
| Conjugate 11 | 4.96E−09 | 2.65E−09 | 1.26E+05 | 7.13E+04 | 5.50E−04 | 2.40E−04 |
| XMT-1535 | 2.76E−09 | N/A | 1.60E+05 | N/A | 4.48E−04 | N/A |

As shown in Table IV, XMT-1535, Conjugate 7, and Conjugate 11 show comparable FcRn $K_d$ values. Results shown are mean and standard deviation values of five replicate experiments for Conjugate 7 and Conjugate 11, and mean values of two replicate experiments for the XMT-1535 antibody.

TABLE V

| Test Articles | $K_d$ (M) | | $k_{on}$ ($M^{-1}s^{-1}$) | | $k_{off}$ ($s^{-1}$) | |
| --- | --- | --- | --- | --- | --- | --- |
| | Mean | Standard Deviation | Mean | Standard Deviation | Mean | Standard Deviation |
| Conjugate 7 | 3.05E−09 | 3.00E−09 | 1.13E+06 | 1.44E+05 | 3.73E−03 | 4.06E−03 |
| Conjugate 11 | 1.66E−10 | N/A | 1.26E+06 | N/A | 2.09E−04 | N/A |
| XMT-1535 | 1.50E−10 | 4.09E−11 | 1.28E+06 | 5.33E+05 | 1.92E−04 | 8.49E−05 |

As shown in Table V, Conjugate 7 shows a greater FcγRI $K_d$ and higher $k_{off}$ value compared to Conjugate 11 and XM4T-1535. Results shown are mean and standard deviation values of three replicate experiments for Conjugate 7 and XMT-1535, and mean affinity values for two replicate experiments for Conjugate 11.

TABLE VI

| Test Articles | $K_d$ (M) | | $k_{on}$ ($M^{-1}s^{-1}$) | | $k_{off}$ ($s^{-1}$) | |
| --- | --- | --- | --- | --- | --- | --- |
| | Mean | Standard Deviation | Mean | Standard Deviation | Mean | Standard Deviation |
| Conjugate 7 | Non-Binding | N/A | Non-Binding | N/A | Non-Binding | N/A |
| Conjugate 11 | 1.25E−06 | N/A | 2.73E+05 | N/A | 3.45E−01 | N/A |
| XMT-1535 | 1.74E−06 | 2.74E−07 | 1.75E+05 | 2.72E+04 | 3.08E−01 | 9.91E−02 |

As shown in Table VI, Conjugate 7 does not bind to FcγRIIA whereas the Conjugate 11 and XM4T-1535 have a similar $K_d$ for binding to FcγRIIA. Results shown are mean and standard deviation values of three replicate experiments for Conjugate 7 and XMT-1535, and mean values of two replicate experiments for Conjugate 11.

TABLE VII

| Test Articles | $K_d$ (M) Mean | $K_d$ (M) Standard Deviation | $k_{on}$ (M$^{-1}$s$^{-1}$) Mean | $k_{on}$ (M$^{-1}$s$^{-1}$) Standard Deviation | $k_{off}$ (s$^{-1}$) Mean | $k_{off}$ (s$^{-1}$) Standard Deviation |
|---|---|---|---|---|---|---|
| Conjugate 7 | Non-Binding | N/A | Non-Binding | N/A | Non-Binding | N/A |
| Conjugate 11 | 2.70E−07 | N/A | 2.70E+05 | N/A | 6.71E−02 | N/A |
| XMT-1535 | 6.41E−07 | N/A | 2.16E+05 | N/A | 1.46E−01 | N/A |

As shown in Table VII, Conjugate 7 does not bind to FcγRIIIA, whereas Conjugate 11 and XMT-1535 have a similar $K_d$ for binding to FcγRIIIA. Results shown are the mean values of two replicate experiments for each test article.

Example 13: Cellular Binding Assay for NaPi2b Antibody-Drug Conjugates

The cell surface binding of XMT-1535, Conjugate 7, and Conjugate 11 to cultured OVCAR3 human ovarian carcinoma cells was evaluated using a MACSQuant flow cytometer (Miltenyi Biotec, Bergisch Gladbach, Germany). OVCAR3 cells, grown in RPMI-1640 medium (ATCC) with FBS (20%, ATCC) and 1% penicillin/streptomycin (1%), were detached by treatment with Accutase cell detachment solution (Innovative Cell Technologies). The detached cells were triturated in media, and plated in 96 well U-bottom plates, at a density of 50,000 cells in medium (75 µL). Cells were incubated on ice for 3 hours with a range of concentrations (1 µM to 0.5 nM; 3-fold serial dilutions) of the test articles (XMT-1535, Conjugate 7, or Conjugate 11) in a total volume of 100 µL RPMI-1640 with 6% goat serum. The cells were washed with ice cold PBS (3×), pelleted at 1,000×RCF between each wash step, and resuspended in RPMI-1640 with 2% goat serum (100 µL) and a secondary fluorescently labeled antibody, Alexa Fluor® 647-labelled goat anti-human IgG (5 µg/mL, Life Technologies) for 1 hour on ice. The cells were washed with ice cold PBS (3×), and resuspended in ice cold PBS with 1% paraformaldehyde (100 µL). The fluorescence per cell was determined by analyzing 5,000 cells for each treatment on the flow cytometer. The median fluorescence value for each treatment was plotted, and $EC_{50}$ values were calculated with Graphpad Prism software by four-parameter curve fitting.

Table VIII summarizes the $EC_{50}$ values of XMT-1535, Conjugate 7, and Conjugate 11 for binding to NaPi2b on the cell surface of OVCAR3 cells.

TABLE VIII

| Test Article | Mean OVCAR3 Binding Values $EC_{50}$ (nM) |
|---|---|
| XMT-1535 | 11.20 |
| Conjugate 7 | 8.15 |
| Conjugate 11 | 6.56 |

As shown in Table VIII, XMT-1535, Conjugate 7, and Conjugate 11 show comparable $EC_{50}$ values. Results are mean values for two replicate experiments for each test article.

Example 14: Cellular Binding Assay for HER2 Antibody-Drug Conjugates

The cell surface binding of the antibody-drug conjugates to JIMT-1 cells was evaluated using a MACSQuant flow cytometer (Miltenyi Biotec, Bergisch Gladbach, Germany). JIMT-1 cells, grown in DMEM medium (ATCC) with FBS (10%, ATCC), were detached by treatment with Accutase cell detachment solution (Innovative Cell Technologies, San Diego, Calif.). The detached cells were triturated in media, and plated in 96-well U-bottom plates, at a density of 50,000 cells in 75 µL medium. Cells were incubated on ice for 3 hours with a range of concentrations (1 µM to 0.5 nM; 3-fold serial dilutions) of test article (XMT-1519, Conjugate 8, Conjugate 9, Conjugate 12, or Conjugate 13) in DMEM with 6% goat serum (100 µL). The cells were washed three times with ice cold PBS, pelleted at 1,000×RCF between each wash step, and resuspended in DMEM with 2% goat serum (100 µL) and a secondary fluorescently labeled antibody, Alexa Fluor® 647-labelled goat anti-human IgG (5 µg/mL, Life Technologies) for 1 hour on ice. The cells were washed with ice cold PBS (3×), and resuspended in ice cold PBS with 1% paraformaldehyde (100 µL). The amount of fluorescence per cell was determined by analyzing 5,000 cells for each treatment on the flow cytometer. The median fluorescence value for each treatment was plotted, and $EC_{50}$ values were calculated with Graphpad Prism software by four-parameter curve fitting.

Table IX summarizes the $EC_{50}$ values of the antibody-drug conjugates and the XMT-1519 antibody for binding to HER2 on the cell surface of JIMT-1 cells.

TABLE IX

| Test Article | Mean JIMT-1 Binding Values $EC_{50}$ (nM) |
|---|---|
| XMT-1519 | 0.71 |
| Conjugate 8 | 0.77 |
| Conjugate 9 | 0.11 |
| Conjugate 12 | 0.59 |
| Conjugate 13 | 0.14 |

As shown in Table IX, XMT-1519, Conjugate 8, Conjugate 9, Conjugate 12, and Conjugate 13 show $EC_{50}$ values within a narrow range. Results shown are mean values of two replicate experiments for XMT-1519, Conjugate 8, and Conjugate 12, and $EC_{50}$ values from a single experiment for Conjugate 9 and Conjugate 13.

Example 15: Cytotoxicity Assay for NaPi2b-Antibody-Drug Conjugates

Conjugate 7 and Conjugate 11 were evaluated for their antiproliferation properties in the tumor cell line OVCAR3 in vitro using CellTiter-Glo® (Promega Corp). Cells were plated at a density of 5,000 cells per well in white-walled (volume) 96-well plate and allowed to adhere overnight at 37° C. in a humidified atmosphere of 5% $CO_2$. Cells were incubated with increasing concentrations of the test articles (Conjugate 7 or Conjugate 11, or control Conjugate 10).

Three days later, CellTiter-Glo® reagent was added to the wells at room temperature. The luminescent signal was measured after 10 minutes using a SpectraMax M5 plate reader (Molecular Devices). Dose-response curves were generated using Graphpad Prism software. $EC_{50}$ values were determined from four-parameter curve fitting. Table X summarizes the $EC_{50}$ values of Conjugate 7, Conjugate 11, and control Conjugate 10 after six days of treatment.

TABLE X

| Test Article | Mean $EC_{50}$ (nM) |
| --- | --- |
| Conjugate 7 | 0.39 |
| Conjugate 11 | 0.53 |
| Conjugate 10 | 120.24 |

As shown in Table X, Conjugate 7 and Conjugate 11 showed comparable potency whereas control antibody-drug conjugate, Conjugate 10 was 200-fold less potent than Conjugate 7 and Conjugate 11. Results shown are mean values for two replicate experiments for each test article.

Example 16: Cell Viability Assay for HER2-Antibody-Drug Conjugates

Conjugate 8, Conjugate 10, and Conjuage 12 were evaluated for their anti-proliferation properties in the tumor cell line JIMT-1 and Conjugate 9 and Conjuage 13 were evaluated for their anti-proliferation properties in the tumor cell lines JIMT-1 and SKBR3 in vitro using CellTiter-Glo® (Promega Corp). Cells were plated at a density of 5,000 cells per well in white-walled (volume) 96-well plate and allowed to adhere overnight at 37° C. in a humidified atmosphere of 5% $CO_2$. Cells were incubated with increasing concentrations of the test articles (Conjugate 8, Conjugate 9, Conjugate 10, Conjugate 12, or Conjugate 13). After 3 days for Conjugate 9 and Conjugate 13 or 6 days for Conjugate 8, Conjugate 12, and control antibody-drug conjugate, Conjugate 10, CellTiter-Glo® reagent was added to the wells at room temperature. The luminescent signal was measured after 10 minutes using a SpectraMax M5 plate reader (Molecular Devices). Dose response curves were generated using Graphpad Prism software. $EC_{50}$ values were determined from four-parameter curve fitting.

Table XI summarizes the $EC_{50}$ values of Conjugate 8, Conjugate 12, and control antibody-drug conjugate, Conjugate 10, after 6 days of treatment.

TABLE XI

| Test Articles | JIMT-1 $EC_{50}$ (nM) | Standard Deviation |
| --- | --- | --- |
| Conjugate 8 | 3.18 | 1.08 |
| Conjugate 12 | 4.12 | 1.27 |
| Conjugate 10 | 128.75 | 90.56 |

As shown in Table XI, Conjugate 8 and Conjugate 12 showed comparable potency. Both Conjugate 8 and Conjugate 12 were greater than 25-fold more potent than control antibody-drug conjugate, Conjugate 10. Results are the mean of three replicate experiments for each test article.

Table XII summarizes the $EC_{50}$ values of Conjugate 9 and Conjugate 13 after 3 days of treatment.

TABLE XII

| Test Articles | JIMT-1 $EC_{50}$ (nM) | SKBR3 $EC_{50}$ (nM) |
| --- | --- | --- |
| Conjugate 9 | 0.72 | 0.088 |
| Conjugate 13 | 0.98 | 0.088 |

As shown in Table XII, Conjugate 9 and Conjugate 13 showed comparable potency in both JIMT-1 and SKBR3 cell lines. The results are values of a single experiment for each test article.

Example 17: Plasma Exposure in Mice after Administration of NaPi2b Antibody-Drug Conjugates Female athymic nude mice were inoculated subcutaneously with OVCAR3 cells (n=4 for each group). Conjugate 7, Conjugate 11, or vehicle were dosed intravenously as a single dose on day 1 (mean tumor size of 174-176 $mm^3$ per group; range of 126-257 $mm^3$) at 0.05 mg/kg dose by payload. Plasma was collected at 10 minutes, 24 hours, 96 hours, 168 hours, 336 hours, and 504 hours post dosing. The conjugated AF-HPA concentrations in the plasma were determined by LC-MS/MS analysis as summarized in Table XIII.

TABLE XIII

| Test Articles | $C_{max}$ (ng/mL) | $t_{1/2}$ (day) | $AUC_{inf}$ (day · ng/mL) | $Cl_{obs}$ (mL/day/kg) | $Vol_{ss}$ (mL/kg) |
| --- | --- | --- | --- | --- | --- |
| Conjugate 7 | 1020 | 5.00 | 4150 | 12.0 | 79.4 |
| Conjugate 11 | 1100 | 5.84 | 3680 | 13.6 | 106 |

As shown in Table XIII, Conjugate 7 showed a higher AUC and shorter $t_{1/2}$, and a lower $Cl_{obs}$ and $Vol_{ss}$ (volume of distribution) of conjugated AF-HPA relative to Conjugate 11. $C_{max}$ and $t_{1/2}$ values were nearly equivalent for Conjugate 7 and Conjugate 11.

Example 18: Tissue Distribution in Mice after Administration of NaPi2b Antibody-Drug Conjugates Female athymic nude mice were inoculated subcutaneously with OVCAR3 cells. Thirty-seven tumor-bearing mice (mean tumor volume of 418.5 $mm^3$; range of 204-698 $mm^3$) were administered a single dose of Conjugate 7 at 0.05 mg/kg payload. Plasma, tumor tissue, spleen, lung, liver, and kidney were harvested after 1, 24, 48, 72, 96, 168, 336, 504 (four mice per group) and 672 hours (five mice). In addition, four tumor-bearing mice (mean tumor volume of 653.7 $mm^3$; range of 589-687 $mm^3$) were dosed with vehicle control and harvested after 1 hour. Tissues were homogenized, and then the concentrations of total drug, free AF-HPA and free AF concentrations were determined by LC-MS/MS analysis; the concentration of conjugated drug was calculated by: [Total Drug−(free AF-HPA+free AF)]. The results for the tissue distribution are summarized in Table XIV.

TABLE XIV

| Tissue | Conjugated Drug | | Total Drug | | Free AF-HPA | | Free AF | |
|---|---|---|---|---|---|---|---|---|
| | $C_{max}$ (ng/g) | $AUC_{last}$ (hour*ng/g) | $C_{max}$ (ng/g) | $AUC_{last}$ (hour*ng/g) | $C_{max}$ (ng/g) | $AUC_{last}$ (hour*ng/g) | $C_{max}$ (ng/g) | $AUC_{last}$ (hour*ng/g) |
| Kidney | 43.3 | 2120 | 43.3 | 2750 | NC | NC | 0.564 | 47.3 |
| Liver | 31.7 | 1740 | 24.4 | 1640 | NC | NC | 1.57 | 386 |
| Lung | 30.5 | 3340 | 30.5 | 3880 | NC | NC | 1.02 | 264 |
| Spleen | 47.5 | 3580 | 49.0 | 4940 | 0.512 | 0.256 | 3.45 | 893 |
| Tumor | 187 | 39000 | 300 | 81600 | 21.2 | 5220 | 119 | 34300 |
| Plasma | 831 | 85700 | 831 | 85700 | BQL | NC | 0.501 | 126 |

NC = not calculable.
BQL = below the quantitation limit.

Example 19: Plasma Exposure in Rat after Administration of NaPi2b Antibody-Drug Conjugates Female Sprague-Dawley rats were inoculated by IV bolus into the tail vein with Conjugate 7 or Conjugate 11, at a dose of 0.34 mg/kg by payload (n=4 for each group). Plasma was collected at 10 minutes, 24 hours, 96 hours, 168 hours, 336 hours, and 504 hours post dosing. The conjugated AF-HPA concentrations in the plasma were determined by LC-MS/MS analysis as summarized in Table XV.

TABLE XV

| Test Articles | $C_{max}$ (ng/mL) | $t_{1/2}$ (day) | $AUC_{inf}$ (day · ng/mL) | $Cl_{obs}$ (mL/day/kg) | Volss (mL/kg) |
|---|---|---|---|---|---|
| Conjugate 7 | 6830 | 3.34 | 17600 | 19.3 | 88.4 |
| Conjugate 11 | 7950 | 5.29 | 15600 | 21.8 | 125 |

As shown in Table XV, Conjugate 7 showed a higher $AUC_{inf}$, lower $C_{max}$, shorter $t_2$, lower $Cl_{obs}$, and lower Volss of conjugated AF-HPA relative to Conjugate 11.

Example 20: Plasma Exposure in Cynomolgus Monkey after Administration of NaPi2b Antibody-Drug Conjugates Female cynomolgus monkeys were injected intravenously with Conjugate 7 or Conjugate 11 at 1 mg/kg by antibody by IV infusion over 30 minutes (n=2 for each group). Plasma was collected at 1 hour, 8 hours, 24 hours, 48 hours, 96 hours, 168 hours, 240 hours, 288 hours, 336 hours, 456 hours, and 504 hours post dosing. The conjugated AF-HPA concentrations in the plasma were determined by LC-MS/MS analysis as summarized in Table XVI.

TABLE XVI

| Test Articles | $C_{max}$ (ng/mL) | $t_{1/2}$ (day) | $AUC_{inf}$ (day · ng/mL) | $Cl_{obs}$ (mL/day/kg) | Volss (mL/kg) |
|---|---|---|---|---|---|
| Conjugate 7 | 804 | 6.73 | 4370 | 7.63 | 68.1 |
| Conjugate 11 | 758 | 4.83 | 2140 | 16.8 | 105 |

As shown in Table XVI, Conjugate 7 had a longer $t_{1/2}$, greater $AUC_{inf}$, and lower $Cl_{obs}$ and Volss of conjugated AF-HPA relative to Conjugate 11. $C_{max}$ values were nearly equivalent for the two conjugates.

Example 21: Plasma Exposure in Cynomolgus Monkey after Administration of NaPi2b Antibody-Drug Conjugates Cynomolgus monkeys (n=3 male; n=3 female) were injected intravenously with Conjugate 7 at 1.86, 3.72 or 5.60 mg/kg by antibody by IV infusion over 45 minutes. Plasma was collected pre-dose and at 1 hour, 6 hours, 24 hours, 96 hours, 168 hours, 240 hours, 336 hours, and 504 hours post-dose. The conjugated AF-HPA concentrations in the plasma were determined by LC-MS/MS analysis as summarized in Table XVII.

TABLE XVII

| Conjugate 7 mg/kg (mAb) | Clearance mL/day/kg | $t_{1/2}$ (day) | $AUC_{inf}$ (day · ng/mL) |
|---|---|---|---|
| 1.86 | 8.2 | 6.5 | 7,417 |
| 3.72 | 9.6 | 5.875 | 12,708 |
| 5.60 | 10.8 | 3.48 | 16,917 |

Table XVII summarizes the clearance, half life and $AUC_{inf}$ for Conjugate 7.

Example 22: Tumor Growth Response to the Administration of NaPi2b Antibody-Drug Conjugates in OVCAR3

Female athymic nude mice were inoculated subcutaneously with OVCAR3 cells (n=8 for each group). Conjugate 7, Conjugate 11, control Conjugate 10, or vehicle were dosed intravenously as a single dose on day 1 (mean tumor size of 167-168 mm$^3$ per group; range of 85-297 mm$^3$). Tumor size was measured at the times indicated in FIG. 7 using digital calipers. Tumor volume was calculated and was used to determine the delay in tumor growth. Mice were sacrificed when tumors reached a size of ≥1500 mm$^3$. Tumor volumes are reported as the mean±SEM for each group.

Figure 7:
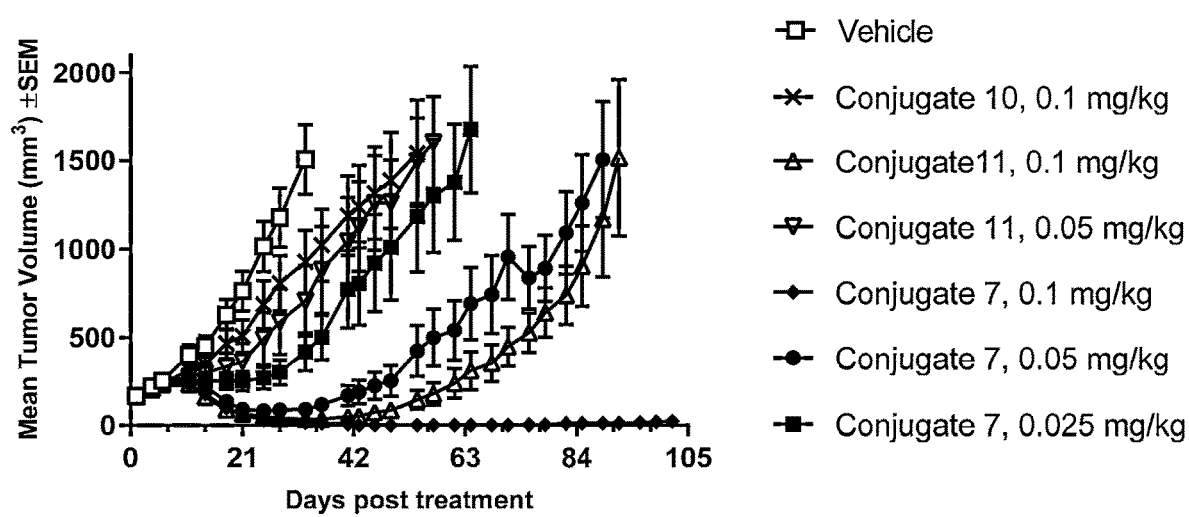
FIG. 7 is a graph showing the anti-tumor efficacy of the XMT-1535 antibody-drug conjugates, Conjugate 11 at 0.05 mg/kg or 0.1 mg/kg by payload, Conjugate 7 at 0.025 mg/kg, 0.05 mg/kg or 0.1 mg/kg by payload, and non-binding control Conjugate 10 at 0.1 mg/kg by payload in an OVCAR3 tumor-bearing mouse model.

FIG. 7 provides the results for the tumor response in mice inoculated subcutaneously with OVCAR3 cells (n=8 for each group) after IV administration as a single dose on day 1 of Conjugate 7, Conjugate 11, or control Conjugate 10 at 0.025 mg/kg, 0.05 mg/kg or 0.1 mg/kg by payload, or vehicle.

All test articles, with the exception of Conjugate 10, resulted in a tumor growth inhibition (TGI) of 60% or greater on Day 33. Conjugate 10 treatment resulted in TGI of 43%. Treatment with Conjugate 7 at 0.1 mg/kg and 0.05 mg/kg and with Conjugate 11 at 0.1 mg/kg, demonstrated the most profound efficacy by resulting in a group mean tumor volume of lower than 100 mm$^3$ and the majority of tumors regressed by Day 33. Treatment with Conjugate 7 at 0.1 mg/kg showed the greatest efficacy against OVCAR3 tumors as evidenced by prolonged tumor growth inhibition through Day 102, the final day of the study, including 3 tumors achieving complete regression. All other groups experienced tumor regrowth as the study progressed.

Example 23: Tumor Growth Response to the Administration of NaPi2b Antibody-Drug Conjugates in CTG-0852

Figure 8:
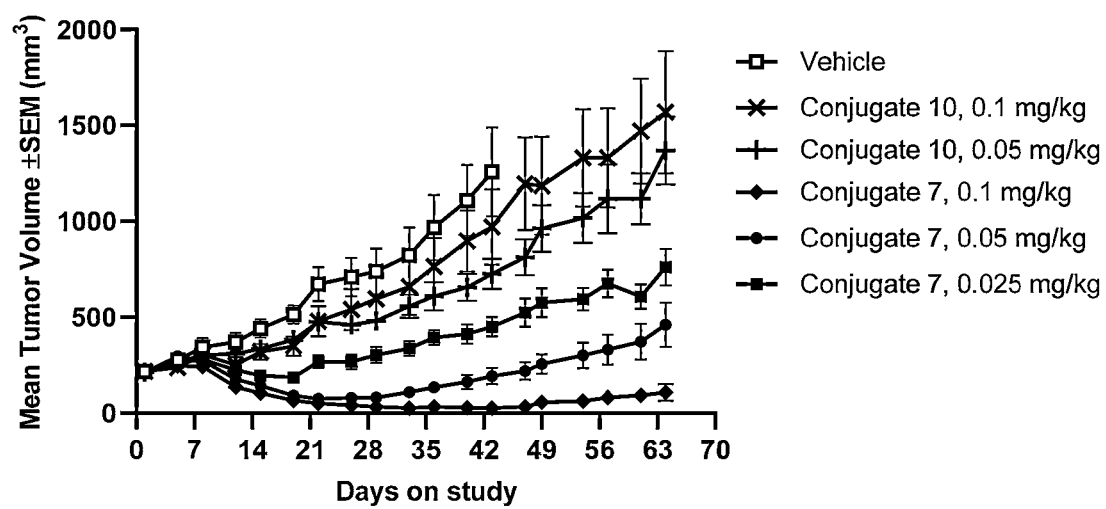
FIG. 8 is a graph showing the anti-tumor efficacy of the XMT-1535 antibody-drug conjugates, Conjugate 7 at 0.025 mg/kg, 0.05 mg/kg or 0.1 mg/kg by payload, and non-binding control Conjugate 10, at 0.05 mg/kg or 0.1 mg/kg by payload in a NSCLC PDX CTG-0852 mouse model.

Athymic mice were inoculated subcutaneously with CTG-0852 lung adenocarcinoma cells (n=8 for each group). Conjugate 7 (at 0.025 mg/kg, 0.05 mg/kg or 0.1 mg/kg by payload), control Conjugate 10 (0.05 mg/kg or 0.1 mg/kg by payload), or vehicle were dosed intravenously as a single dose on day 1 (mean tumor size of 150-300 mm$^3$ per group; range of 85-297 mm$^3$). Tumor volume was calculated and was used to determine the delay in tumor growth. Mice were sacrificed when tumors reached a size of ≥1500 mm$^3$. FIG. 8 shows tumor volumes are reported as the mean±SEM for each group.

FIG. 8 provides the results for the tumor response in mice inoculated subcutaneously with CTG-0852 lung adenocarcinoma cells (n=8 for each group) after IV administration as a single dose on day 1 of Conjugate 7 (at 0.025 mg/kg, 0.05 mg/kg or 0.1 mg/kg by payload), control Conjugate 10 (0.05 mg/kg or 0.1 mg/kg by payload), or vehicle.

Conjugate 7 exhibited dose-dependent, target-dependent tumor growth inhibition (TGI) at all dose levels (FIG. 8). At a dose of 0.1 mg/kg payload, Conjugate 7 showed a TGI of 118%, and elicited sustained tumor regressions to day 49, after which mean tumor volume slowly increased. At 0.05 mg/kg payload, Conjugate 7 showed a TGI of 102% and elicited tumor regressions until day 28, after which mean tumor volume increased. Conjugate 7 elicited tumor growth inhibition at 0.025 mg/kg payload (TGI=77%). Conjugate 10 treatment resulted in a TGI of 28% at a dose of 0.1 mg/kg dose by payload and 51% at 0.05 mg/kg by payload.

Example 24: Tumor Growth Response to Administration of HER2 Antibody-Drug Conjugates Female CB.17 SCID mice were inoculated subcutaneously with JIMT-1 cells. Conjugate 8, Conjugate 9, Conjugate 12, Conjugate 13, Conjugate 10, or vehicle were dosed intravenously as a single dose on day 1 (tumor volume=150-200 mm$^3$). Tumor size was measured at the times indicated in FIGS. 9 and 10 using digital calipers. Tumor volume was calculated and was used to determine the delay in tumor growth. Mice were sacrificed when tumors reached a size of ≥1000 mm$^3$. Tumor volumes are reported as the mean±SEM for each group.

Figure 9:
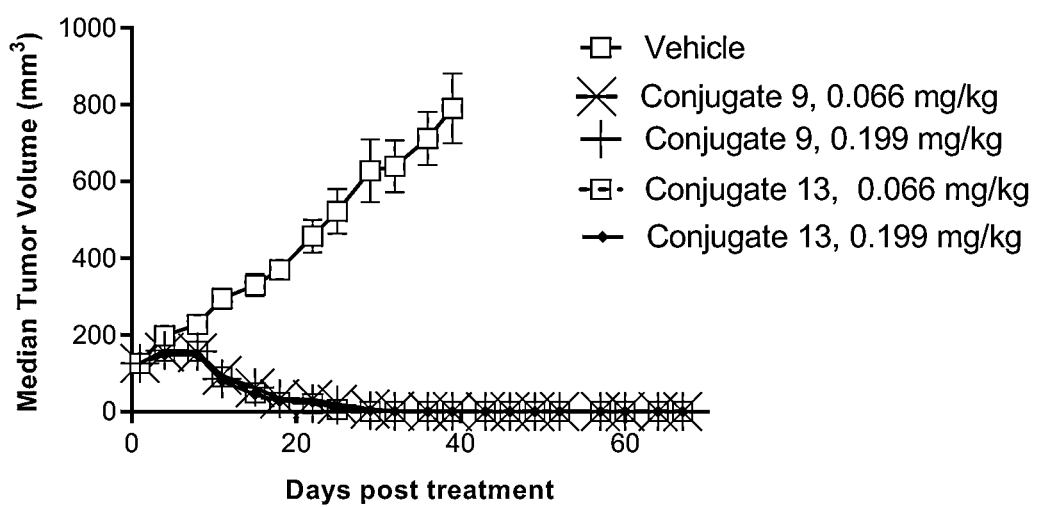
FIG. 9 is a graph showing the anti-tumor efficacy of the HER2 antibody-drug conjugates, Conjugate 9 and Conjugate 13, at 0.067 mg/kg and 0.199 mg/kg by payload in a JIMT-1 tumor-bearing mouse model.

FIG. 9 provides results for the tumor response in JIMT-1 tumor-bearing mice administered with Conjugate 9 or Conjugate 13 (n=10 for each group). All mice treated with Conjugate 9 and Conjugate 13 showed prolonged tumor growth inhibition and no tumor regrowth with both antibody-drug conjugates at both doses tested (0.067 mg/kg and 0.199 mg/kg by payload).

Figure 10:
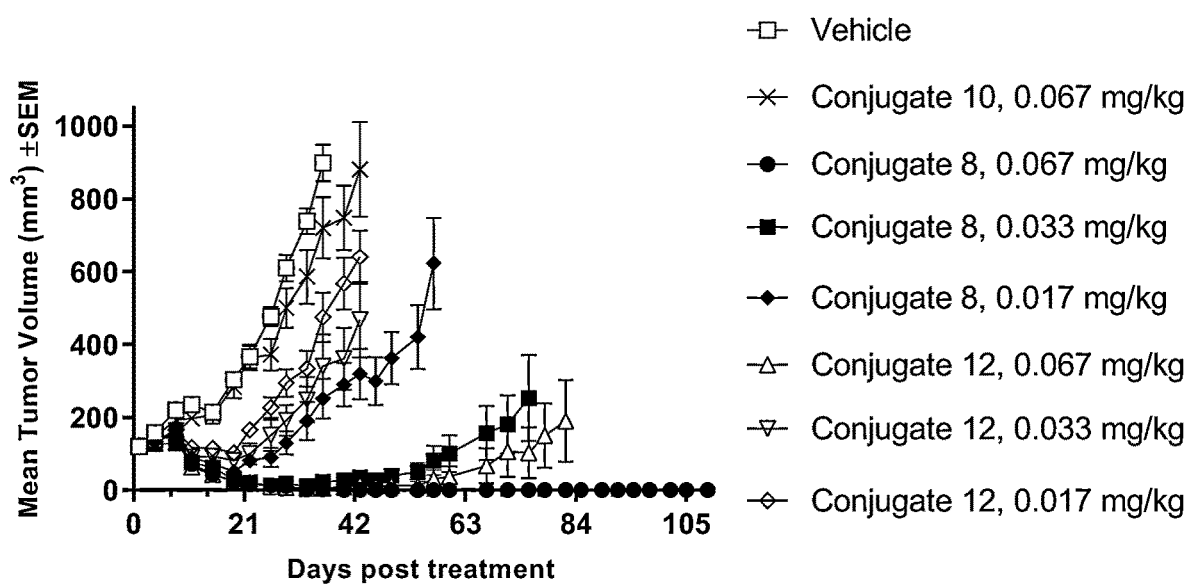
FIG. 10 is a graph showing the anti-tumor efficacy of the HER2 antibody-drug conjugates, Conjugate 8 and Conjugate 12 each at at 0.017 mg/kg, 0.033 mg/kg or 0.067 mg/kg by payload and non-binding control antibody-drug conjugate Conjugate 10, at 0.067 mg/kg by payload in a JIMT-1 tumor-bearing mouse model.
Figure 11:
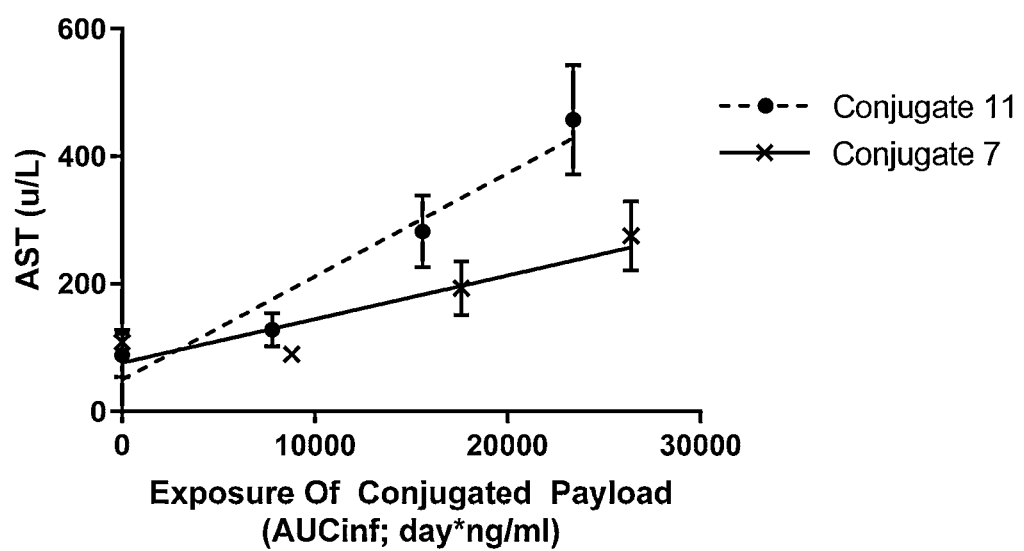
FIGS. 11-18 show elevation of toxicology parameters (AST, ALT, ALP, RBC, WBC, neutrophils, lymphocytes, and hemoglobin respectively) in rats in response to exposure of Conjugate 11 or Conjugate 7.
Figure 12:
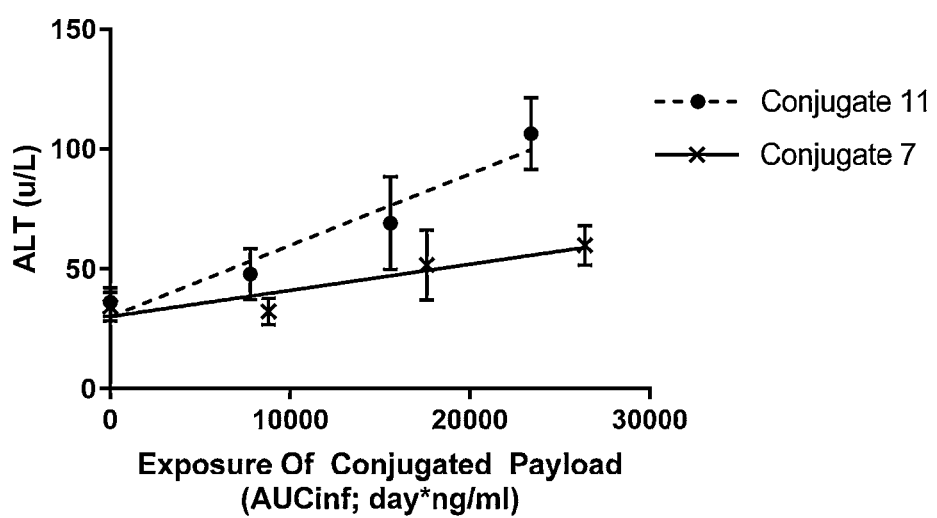
Figure 13:
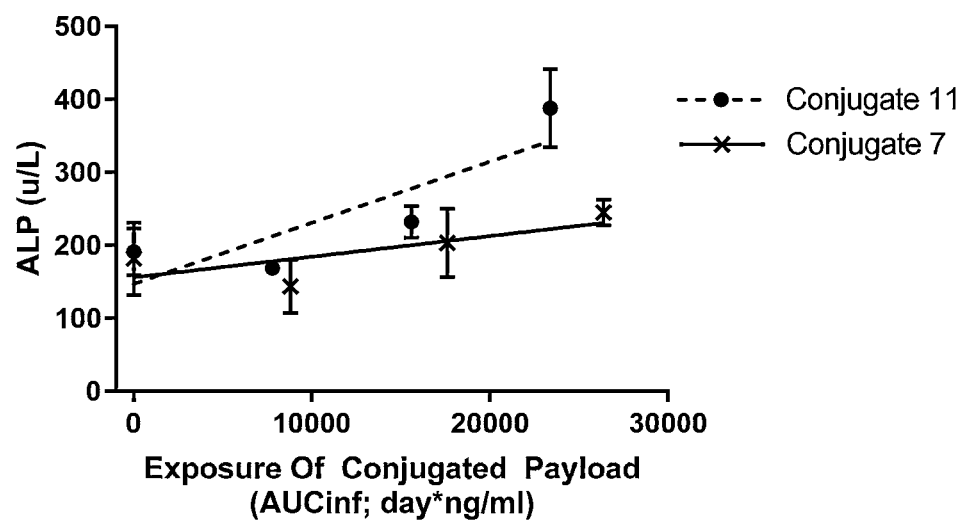
Figure 14:
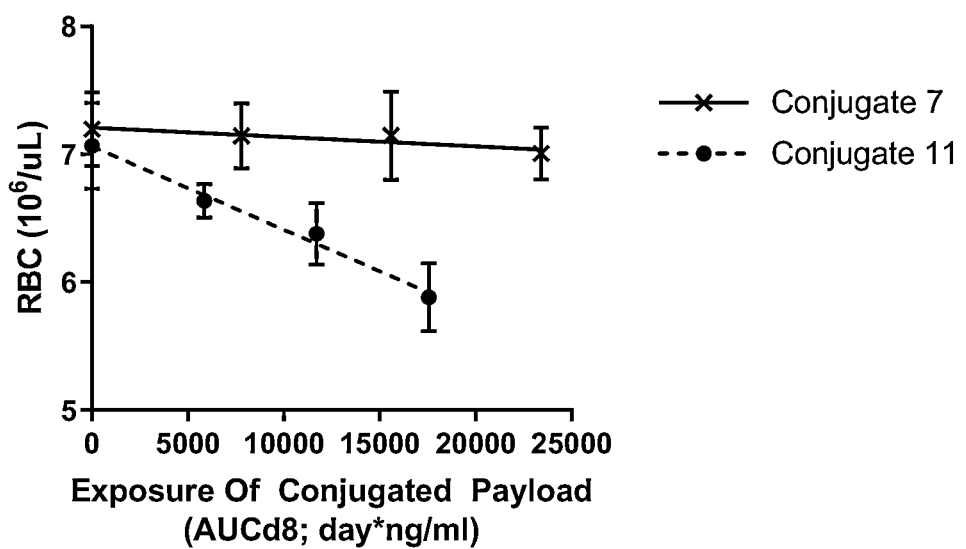
Figure 15:
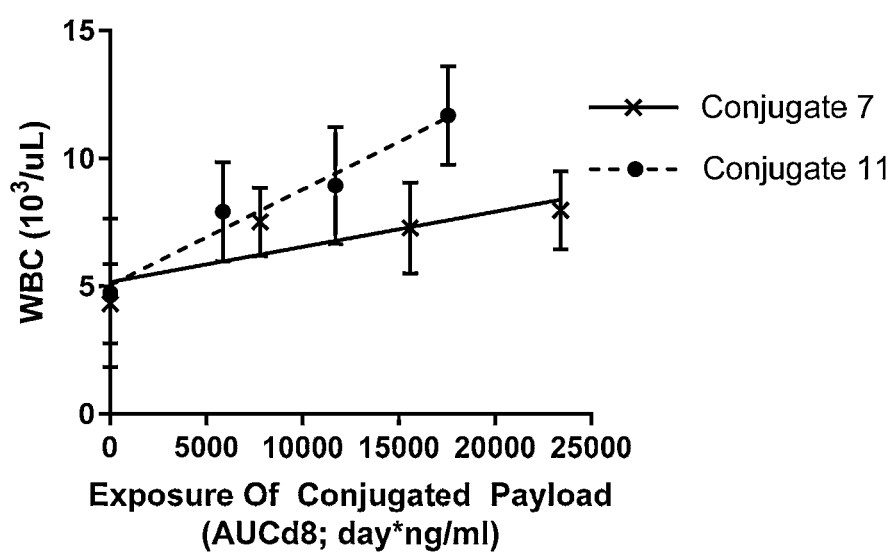
Figure 16:
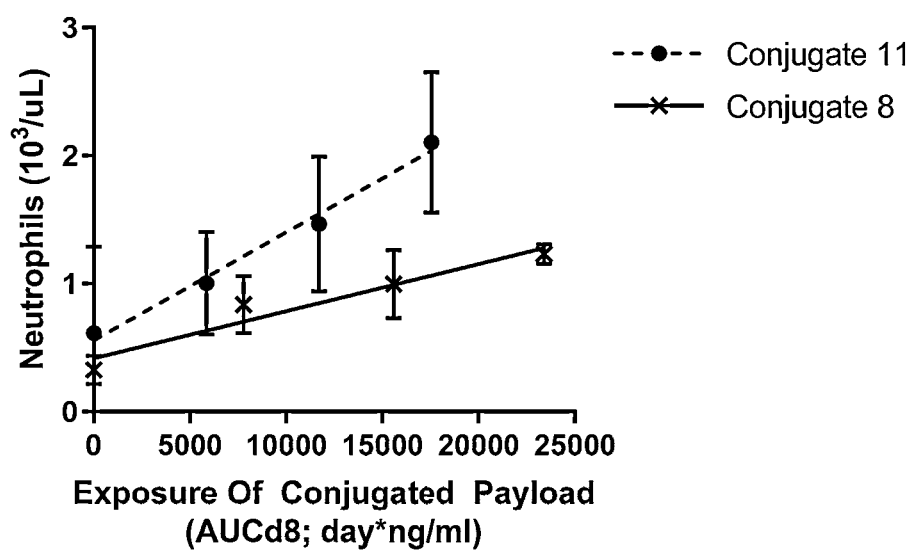
Figure 17:
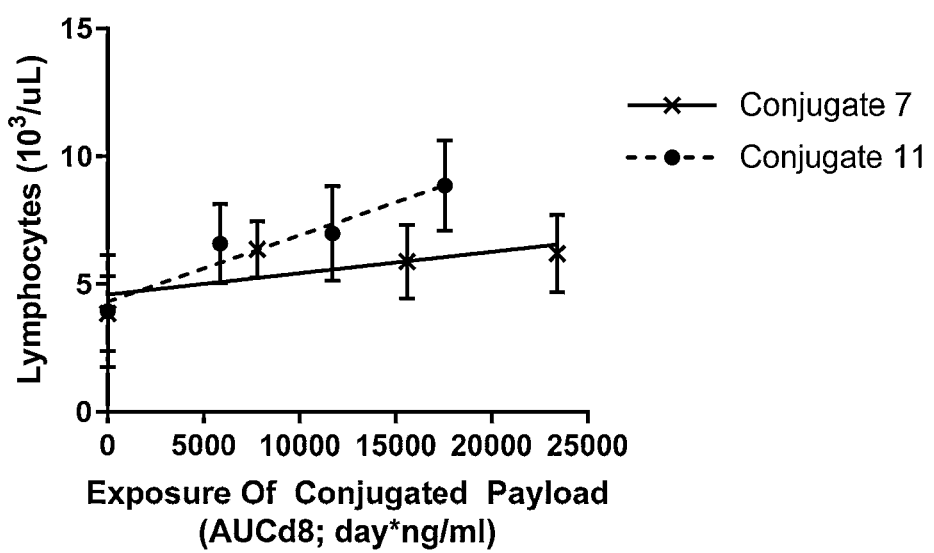
Figure 18:
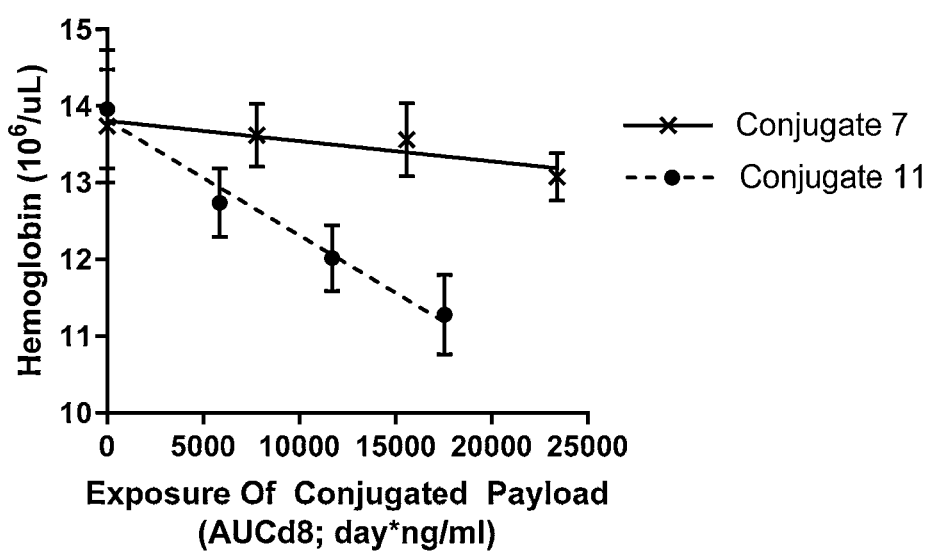

FIG. 10 provides the results for the tumor response in mice inoculated subcutaneously with JIMT-1 cells (n=8 for each group) after IV administration as a single dose on day 1 of vehicle or Conjugate 8, Conjugate 12, or control Conjugate 10 (n=8 for each group) at 0.017 mg/kg, 0.033 mg/kg, or 0.067 mg/kg by payload. Treatment with Conjugate 8 at 0.033 mg/kg and 0.067 mg/kg and Conjugate 12 at 0.067 mg/kg demonstrated the most profound efficacy by resulting in a group mean tumor volume of lower than 50 mm$^3$ and the majority of tumors regressing by Day 19. Treatment with Conjugate 8 at 0.067 mg/kg showed the greatest efficacy against JIMT-1 as evidenced by prolonged tumor growth inhibition through Day 109, the final day of the study, as regression was shown for all tumors. All other groups experienced tumor regrowth as the study progressed.

Example 25: Toxicity Assessment of Antibody-Drug Conjugates In Rats

Toxicity of antibody-drug conjugates were assessed in a rat study. Anti-NaPi2b antibody-drug conjugate (Conjugate 7 or Conjugate 11), or anti-HER2 antibody-drug conjugate (Conjugate 8 or Conjugate 12) at 0.17 mg/kg, 0.34 mg/kg, or 0.51 mg/kg, based on payload, or vehicle was administered into tail veins of female Sprague-Dawley rats (n=5 for each group). Eight days post dosing, blood was collected from each animal for hematology and toxicology analysis.

FIGS. 11-18 show elevation of key toxicology parameters in response to exposure to Conjugate 7 or Conjugate 11, based on results calculated from the study described in Example 18. Conjugate 7 showed lower exposure-dependent elevation of the key toxicology parameters AST, ALT, ALP, WBC, neutrophils, lymphocytes, toxicology parameters RBC and hemoglobin relative to Conjugate 11.

Figure 19:
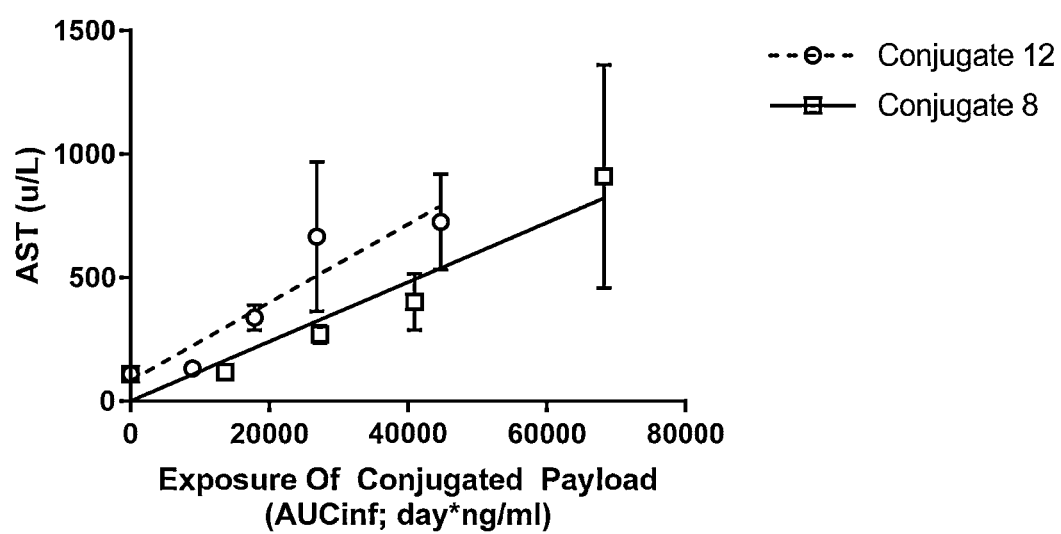
FIGS. 19-21 show elevation of key toxicology parameters (AST, ALT and ALP respectively) in rats in response to exposure of Conjugate 8 or Conjugate 12.
Figure 20:
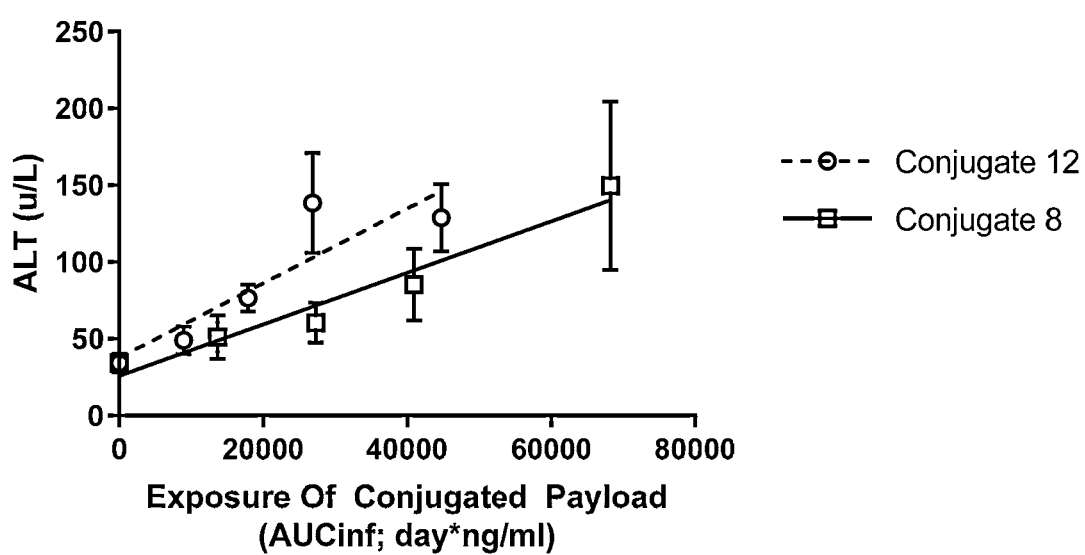
Figure 21:
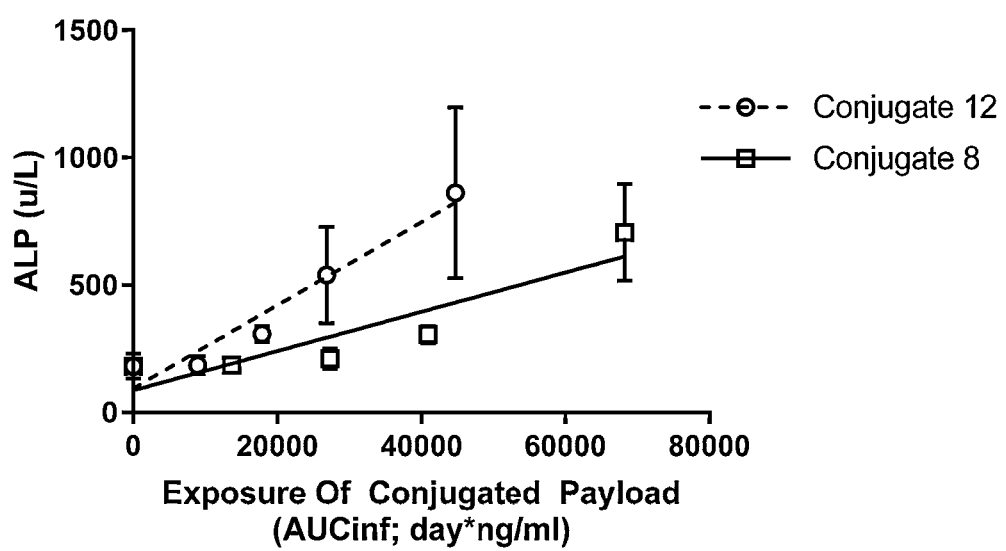

FIGS. 19-21 show elevation of key toxicology parameters in response to exposure of Conjugate 8 or Conjugate 12, based on results calculated from the study described in Example 18. Conjugate 8 showed lower exposure-dependent elevation of the key toxicology parameters AST, ALT, and ALP, relative to Conjugate 12.

EQUIVALENTS

The details of one or more embodiments of the invention are set forth in the accompanying description above. Although any methods and materials similar or equivalent to those described herein can be used in the practice or testing of the present disclosure, the methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

What is claimed is:
1. An antibody-drug conjugate, being of Formula:

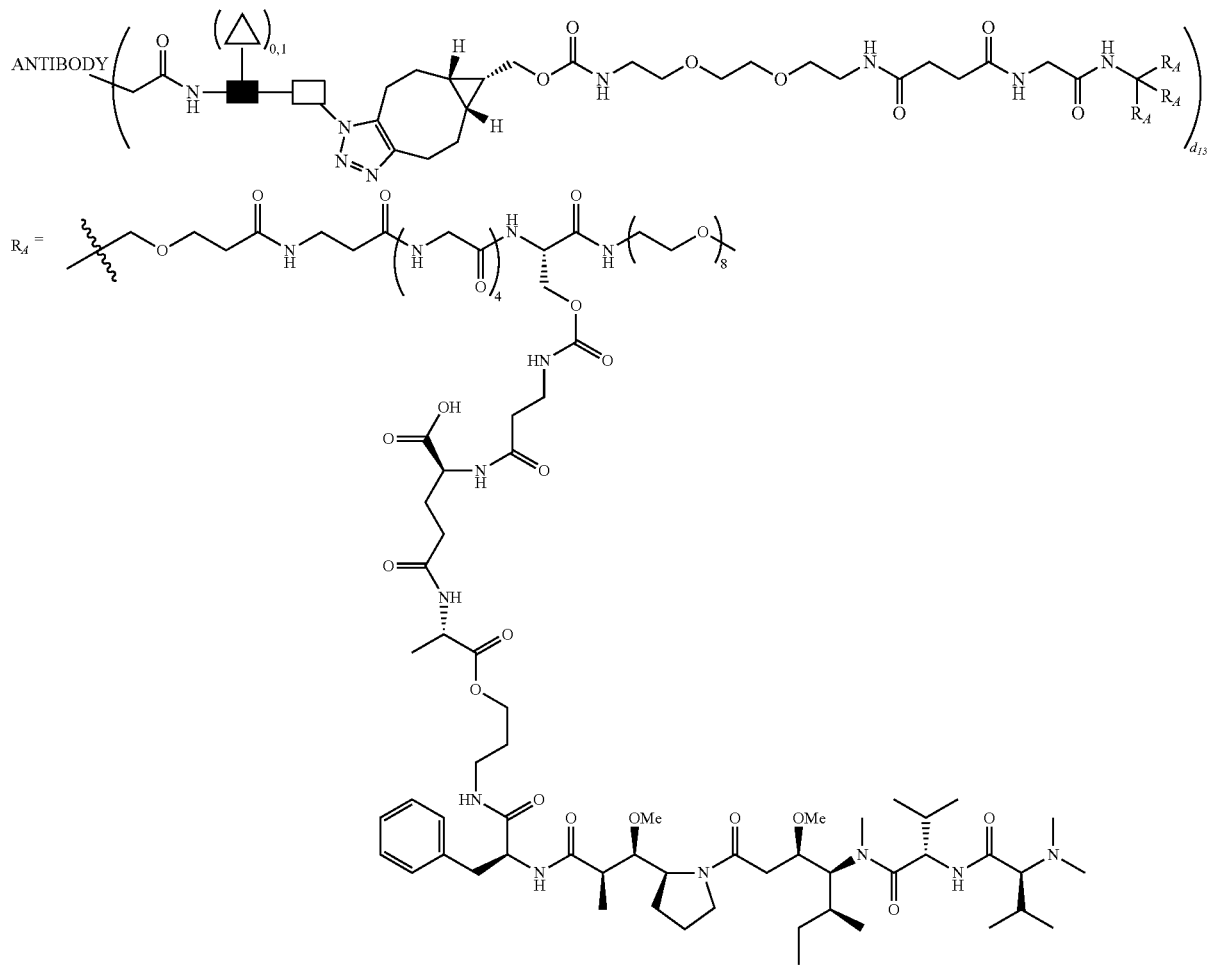

wherein:
- ■ is GlcNAc;
- Δ is Fuc;
- □ is GalNAc;
- $d_{13}$ is 2; and the antibody comprises one or more asparagine group at N297 being connected to the rest of the conjugate.

2. A conjugate of claim 1

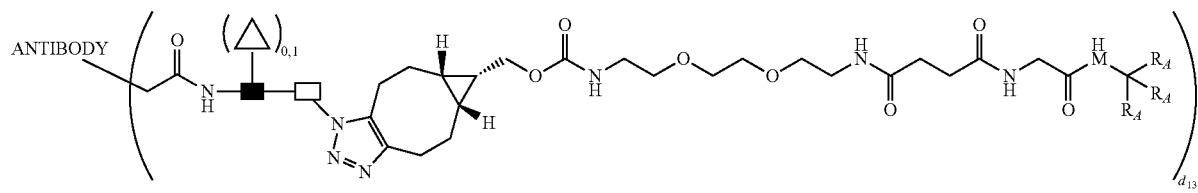

wherein
ANTIBODY is a NaPi2b antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).

3. The conjugate of claim 2, wherein the NaPi2b antibody comprise a heavy chain amino acid sequence of SEQ ID NO: 1 and a light chain amino acid sequence of SEQ ID NO: 2.

4. A method for preparing an antibody-drug conjugate of claim 1, comprising reacting a modified antibody with a scaffold, wherein the scaffold is

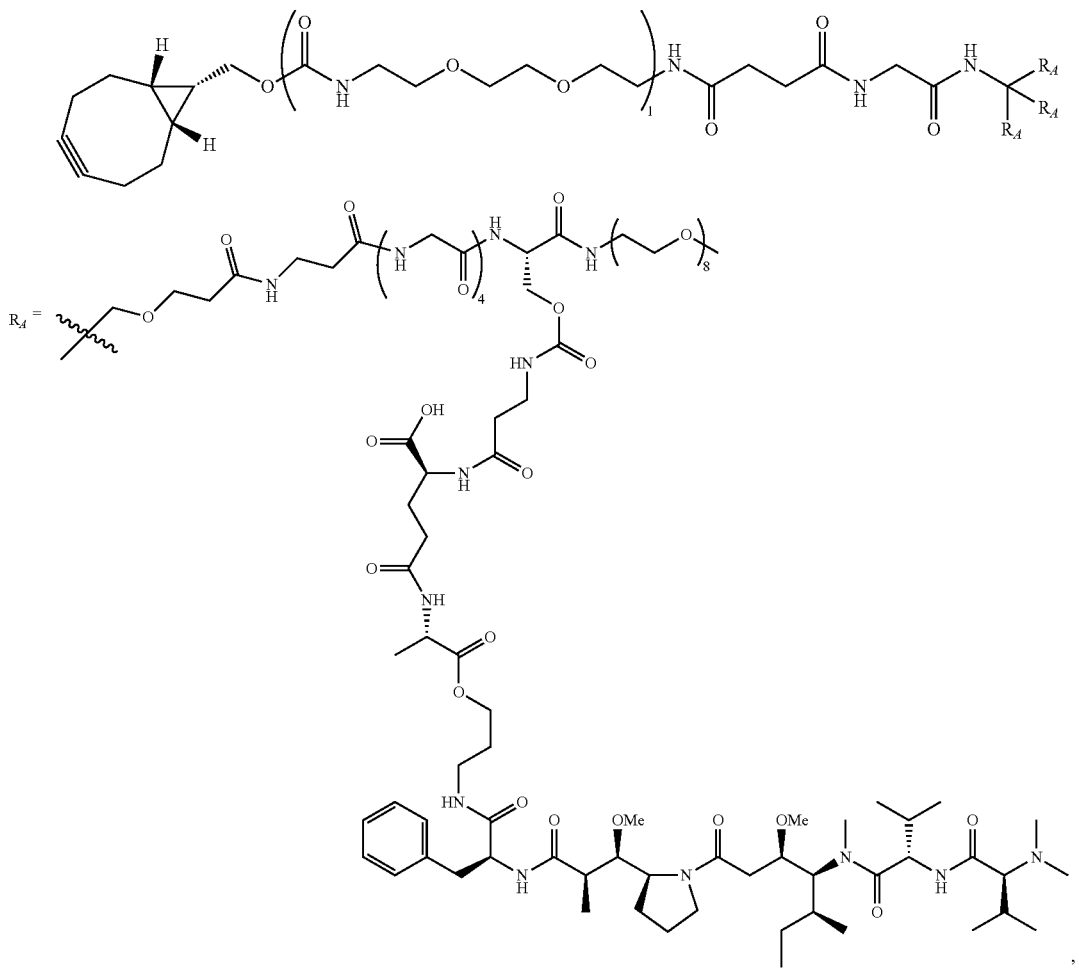

thereby forming a site-specific antibody-drug conjugate, wherein the modified antibody is obtained by contacting a glycoprotein comprising an antibody and core-GlcNAc moiety connected to site N297 of the antibody, with endoglycosidase Endo SH, thereby forming an intermediate antibody comprising a terminal GlcNAc moiety; and contacting the intermediate antibody with 4-AzGalNAc-UDP in the presence of a β-(1,4)-GalNAcT enzyme, thereby forming the modified antibody comprising the modified-GlcNAc moiety; wherein steps (a) and (b) are conducted concurrently.

5. A pharmaceutical composition comprising a conjugate of claim 1 and a pharmaceutically acceptable carrier.

6. A method of treating a cancer in a subject in need thereof, comprising administering to the subject an effective amount of a pharmaceutical composition of claim 5.

7. The method of claim 6, wherein the cancer is a NaPi2b expressing cancers selected from ovarian cancer, non-small cell lung cancer, endometrial cancer, papillary renal cell cancer, salivary duct cancer, papillary thyroid cancer, clear cell renal cancer, breast cancer, kidney cancer, cervical cancer and cholangiocarcinoma.

8. The method of claim 7, wherein the non-small cell lung cancer is sub-typed as adenocarcinoma.

* * * * *

UNITED STATES PATENT AND TRADEMARK OFFICE
CERTIFICATE OF CORRECTION

PATENT NO. : 11,786,605 B2
APPLICATION NO. : 17/144378
DATED : October 17, 2023
INVENTOR(S) : Timothy B. Lowinger et al.

Page 1 of 1

It is certified that error appears in the above-identified patent and that said Letters Patent is hereby corrected as shown below:

In the Claims

Column 309, Claim number 2, Line number 50:
"A conjugate of claim 1

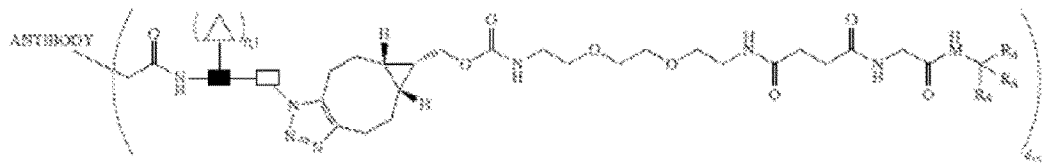

wherein
ANTIBODY is a NaPi2b antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10)."

Should read:
--A conjugate of claim 1
wherein
ANTIBODY is a NaPi2b antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10).--

Signed and Sealed this
Twenty-seventh Day of February, 2024

*Katherine Kelly Vidal*
Katherine Kelly Vidal
*Director of the United States Patent and Trademark Office*

SEQUENCE LISTING

<160> NUMBER OF SEQ ID NOS: 31

<210> SEQ ID NO 1
<211> LENGTH: 449
<212> TYPE: PRT

<213> ORGANISM: Homo sapiens

<400> SEQUENCE: 1

```
Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Ala Pro Gly Gln Gly Leu Glu Trp Ile
        35                  40                  45

Gly Ala Ile Tyr Pro Gly Asn Gly Asp Thr Ser Tyr Lys Gln Lys Phe
    50                  55                  60

Arg Gly Arg Ala Thr Leu Thr Ala Asp Thr Ser Thr Ser Thr Val Tyr
65                  70                  75                  80

Met Glu Leu Ser Ser Leu Arg Ser Glu Asp Ser Ala Val Tyr Tyr Cys
                85                  90                  95

Ala Arg Gly Glu Thr Ala Arg Ala Thr Phe Ala Tyr Trp Gly Gln Gly
            100                 105                 110

Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 2
<211> LENGTH: 215
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Gly Asn Phe
            20                  25                  30

Leu Asn Trp Tyr Gln Gln Lys Pro Gly Lys Thr Val Lys Val Leu Ile
        35                  40                  45

Tyr Tyr Thr Ser Ser Leu Tyr Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Leu
                85                  90                  95

Thr Phe Gly Gln Gly Thr Lys Leu Glu Leu Lys Arg Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 3
<211> LENGTH: 120
<212> TYPE: PRT
<213> ORGANISM: Homo sapiens

<400> SEQUENCE: 3

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Ala Pro Gly Gln Gly Leu Glu Trp Ile
        35                  40                  45

Gly Ala Ile Tyr Pro Gly Asn Gly Asp Thr Ser Tyr Lys Gln Lys Phe
```

```
            50                  55                  60
Arg Gly Arg Ala Thr Leu Thr Ala Asp Thr Ser Thr Ser Thr Val Tyr
 65                  70                  75                  80

Met Glu Leu Ser Ser Leu Arg Ser Glu Asp Ser Ala Val Tyr Tyr Cys
                 85                  90                  95

Ala Arg Gly Glu Thr Ala Arg Ala Thr Phe Ala Tyr Trp Gly Gln Gly
            100                 105                 110

Thr Leu Val Thr Val Ser Ser Gly
            115                 120

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Ser Ala Ser Gln Asp Ile Gly Asn Phe
                 20                  25                  30

Leu Asn Trp Tyr Gln Gln Lys Pro Gly Lys Thr Val Lys Val Leu Ile
             35                  40                  45

Tyr Tyr Thr Ser Ser Leu Tyr Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Lys Leu Pro Leu
                 85                  90                  95

Thr Phe Gly Gln Gly Thr Lys Leu Glu Leu Lys Arg
            100                 105

<210> SEQ ID NO 5
<211> LENGTH: 10
<212> TYPE: PRT
<213> ORGANISM: Homo sapiens

<400> SEQUENCE: 5

Gly Tyr Thr Phe Thr Gly Tyr Asn Ile His
  1               5                  10

<210> SEQ ID NO 6
<211> LENGTH: 17
<212> TYPE: PRT
<213> ORGANISM: Homo sapiens

<400> SEQUENCE: 6

Ala Ile Tyr Pro Gly Asn Gly Asp Thr Ser Tyr Lys Gln Lys Phe Arg
  1               5                  10                  15

Gly

<210> SEQ ID NO 7
<211> LENGTH: 10
<212> TYPE: PRT
<213> ORGANISM: Homo sapiens

<400> SEQUENCE: 7

Gly Glu Thr Ala Arg Ala Thr Phe Ala Tyr
  1               5                  10
```

```
<210> SEQ ID NO 8
<211> LENGTH: 11
<212> TYPE: PRT
<213> ORGANISM: Homo sapiens

<400> SEQUENCE: 8

Ser Ala Ser Gln Asp Ile Gly Asn Phe Leu Asn
1               5                   10

<210> SEQ ID NO 9
<211> LENGTH: 7
<212> TYPE: PRT
<213> ORGANISM: Homo sapiens

<400> SEQUENCE: 9

Tyr Thr Ser Ser Leu Tyr Ser
1               5

<210> SEQ ID NO 10
<211> LENGTH: 9
<212> TYPE: PRT
<213> ORGANISM: Homo sapiens

<400> SEQUENCE: 10

Gln Gln Tyr Ser Lys Leu Pro Leu Thr
1               5

<210> SEQ ID NO 11
<211> LENGTH: 329
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 357
<212> TYPE: DNA
<213> ORGANISM: Homo sapiens

<400> SEQUENCE: 13
caagttcagc tggttcagtc tggcgccgag gttgtgaaac tggcgcctc tgtgaagatg      60 agctgcaagg ccagcggcta caccttcacc ggctacaaca tccactgggt caagcaggcc     120
cctggacagg gactcgaatg gatcggagcc atctatcccg caacggcga caccagctac     180 aagcagaagt tccggggcag agccacactg accgccgata aagcaccag caccgtgtac     240 atggaactga gcagcctgag aagcgaggac agcgccgtgt actattgcgc cagaggcgaa     300
acagccagag ccacctttgc ctattggggc cagggaaccc tggtcaccgt tagctct        357

<210> SEQ ID NO 14
<211> LENGTH: 321
<212> TYPE: DNA
<213> ORGANISM: Homo sapiens
```

<400> SEQUENCE: 14

```
gatattcaga tgacacagag ccccagcagc ctgtctgcct ctgtgggaga cagagtgacc      60
atcacctgta gcgccagcca ggatatcggc aacttcctga actggtatca gcagaaaccc     120
ggcaagaccg tgaaggtgct gatctactac acctccagcc tgtacagcgg cgtgcccagc     180
agatttctg gcagcggctc tggcaccgac tacaccctga ccatatctag cctgcagcct     240
gaggacttcg ccacctacta ctgccagcag tacagcaagc tgcccctgac atttggccag     300
ggcaccaagc tggaactgaa g                                               321
```

<210> SEQ ID NO 15
<211> LENGTH: 690
<212> TYPE: PRT
<213> ORGANISM: Homo sapiens

<400> SEQUENCE: 15

| | | | | | | | | | | | | | | |
|---|---|---|---|---|---|---|---|---|---|---|---|---|---|---|
| Met | Ala | Pro | Trp | Pro | Glu | Leu | Gly | Asp | Ala | Gln | Pro | Asn | Pro | Asp | Lys |
| 1 | | | | 5 | | | | | 10 | | | | | 15 | |
| Tyr | Leu | Glu | Gly | Ala | Ala | Gly | Gln | Gln | Pro | Thr | Ala | Pro | Asp | Lys | Ser |
| | | | 20 | | | | | 25 | | | | | 30 | | |
| Lys | Glu | Thr | Asn | Lys | Thr | Asp | Asn | Thr | Glu | Ala | Pro | Val | Thr | Lys | Ile |
| | | 35 | | | | | 40 | | | | | 45 | | | |
| Glu | Leu | Leu | Pro | Ser | Tyr | Ser | Thr | Ala | Thr | Leu | Ile | Asp | Glu | Pro | Thr |
| 50 | | | | | 55 | | | | | 60 | | | | | |
| Glu | Val | Asp | Asp | Pro | Trp | Asn | Leu | Pro | Thr | Leu | Gln | Asp | Ser | Gly | Ile |
| 65 | | | | | 70 | | | | | 75 | | | | | 80 |
| Lys | Trp | Ser | Glu | Arg | Asp | Thr | Lys | Gly | Lys | Ile | Leu | Cys | Phe | Phe | Gln |
| | | | | 85 | | | | | 90 | | | | | 95 | |
| Gly | Ile | Gly | Arg | Leu | Ile | Leu | Leu | Leu | Gly | Phe | Leu | Tyr | Phe | Phe | Val |
| | | | 100 | | | | | 105 | | | | | 110 | | |
| Cys | Ser | Leu | Asp | Ile | Leu | Ser | Ser | Ala | Phe | Gln | Leu | Val | Gly | Gly | Lys |
| | | | 115 | | | | | 120 | | | | | 125 | | |
| Met | Ala | Gly | Gln | Phe | Phe | Ser | Asn | Ser | Ser | Ile | Met | Ser | Asn | Pro | Leu |
| | 130 | | | | | 135 | | | | | 140 | | | | |
| Leu | Gly | Leu | Val | Ile | Gly | Val | Leu | Val | Thr | Val | Leu | Val | Gln | Ser | Ser |
| 145 | | | | | 150 | | | | | 155 | | | | | 160 |
| Ser | Thr | Ser | Thr | Ser | Ile | Val | Val | Ser | Met | Val | Ser | Ser | Ser | Leu | Leu |
| | | | | 165 | | | | | 170 | | | | | 175 | |
| Thr | Val | Arg | Ala | Ala | Ile | Pro | Ile | Ile | Met | Gly | Ala | Asn | Ile | Gly | Thr |
| | | | 180 | | | | | 185 | | | | | 190 | | |
| Ser | Ile | Thr | Asn | Thr | Ile | Val | Ala | Leu | Met | Gln | Val | Gly | Asp | Arg | Ser |
| | | | 195 | | | | | 200 | | | | | 205 | | |
| Glu | Phe | Arg | Arg | Ala | Phe | Ala | Gly | Ala | Thr | Val | His | Asp | Phe | Phe | Asn |
| | 210 | | | | | 215 | | | | | 220 | | | | |
| Trp | Leu | Ser | Val | Leu | Val | Leu | Leu | Pro | Val | Glu | Val | Ala | Thr | His | Tyr |
| 225 | | | | | 230 | | | | | 235 | | | | | 240 |
| Leu | Glu | Ile | Ile | Thr | Gln | Leu | Ile | Val | Glu | Ser | Phe | His | Phe | Lys | Asn |
| | | | | 245 | | | | | 250 | | | | | 255 | |
| Gly | Glu | Asp | Ala | Pro | Asp | Leu | Leu | Lys | Val | Ile | Thr | Lys | Pro | Phe | Thr |
| | | | 260 | | | | | 265 | | | | | 270 | | |
| Lys | Leu | Ile | Val | Gln | Leu | Asp | Lys | Lys | Val | Ile | Ser | Gln | Ile | Ala | Met |
| | | | 275 | | | | | 280 | | | | | 285 | | |
| Asn | Asp | Glu | Lys | Ala | Lys | Asn | Lys | Ser | Leu | Val | Lys | Ile | Trp | Cys | Lys |
| | 290 | | | | | 295 | | | | | 300 | | | | |

```
Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365

Leu Ile Leu Ser Leu Leu Val Leu Cys Gly Cys Leu Ile Met Ile Val
    370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
        435                 440                 445

Ile Thr Ile Glu Arg Ala Tyr Pro Leu Thr Leu Gly Ser Asn Ile Gly
    450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Phe Asn Ile
                485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
        515                 520                 525

Ala Val Phe Tyr Leu Ile Ile Phe Phe Leu Ile Pro Leu Thr Val
    530                 535                 540

Phe Gly Leu Ser Leu Ala Gly Trp Arg Val Leu Gly Val Gly Val
545                 550                 555                 560

Pro Val Val Phe Ile Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
        595                 600                 605

Lys Phe Thr Gly Cys Phe Gln Met Arg Cys Cys Cys Cys Cys Arg Val
    610                 615                 620

Cys Cys Arg Ala Cys Cys Leu Leu Cys Asp Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
        675                 680                 685

Ala Leu
    690

<210> SEQ ID NO 16
<211> LENGTH: 1255
<212> TYPE: PRT
```

<213> ORGANISM: Homo sapiens

<400> SEQUENCE: 16

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
```

```
                820             825             830
Met Ser Tyr Leu Glu Asp Val Arg Leu Val His Arg Asp Leu Ala Ala
            835             840             845
Arg Asn Val Leu Val Lys Ser Pro Asn His Val Lys Ile Thr Asp Phe
850             855             860
Gly Leu Ala Arg Leu Leu Asp Ile Asp Glu Thr Glu Tyr His Ala Asp
865             870             875             880
Gly Gly Lys Val Pro Ile Lys Trp Met Ala Leu Glu Ser Ile Leu Arg
            885             890             895
Arg Arg Phe Thr His Gln Ser Asp Val Trp Ser Tyr Gly Val Thr Val
            900             905             910
Trp Glu Leu Met Thr Phe Gly Ala Lys Pro Tyr Asp Gly Ile Pro Ala
            915             920             925
Arg Glu Ile Pro Asp Leu Leu Glu Lys Gly Arg Leu Pro Gln Pro
            930             935             940
Pro Ile Cys Thr Ile Asp Val Tyr Met Ile Met Val Lys Cys Trp Met
945             950             955             960
Ile Asp Ser Glu Cys Arg Pro Arg Phe Arg Glu Leu Val Ser Glu Phe
            965             970             975
Ser Arg Met Ala Arg Asp Pro Gln Arg Phe Val Val Ile Gln Asn Glu
            980             985             990
Asp Leu Gly Pro Ala Ser Pro Leu Asp Ser Thr Phe Tyr Arg Ser Leu
            995             1000            1005
Leu Glu Asp Asp Asp Met Gly Asp Leu Val Asp Ala Glu Glu Tyr
    1010            1015            1020
Leu Val Pro Gln Gln Gly Phe Phe Cys Pro Asp Pro Ala Pro Gly
    1025            1030            1035
Ala Gly Gly Met Val His His Arg His Arg Ser Ser Ser Thr Arg
    1040            1045            1050
Ser Gly Gly Gly Asp Leu Thr Leu Gly Leu Glu Pro Ser Glu Glu
    1055            1060            1065
Glu Ala Pro Arg Ser Pro Leu Ala Pro Ser Glu Gly Ala Gly Ser
    1070            1075            1080
Asp Val Phe Asp Gly Asp Leu Gly Met Gly Ala Ala Lys Gly Leu
    1085            1090            1095
Gln Ser Leu Pro Thr His Asp Pro Ser Pro Leu Gln Arg Tyr Ser
    1100            1105            1110
Glu Asp Pro Thr Val Pro Leu Pro Ser Glu Thr Asp Gly Tyr Val
    1115            1120            1125
Ala Pro Leu Thr Cys Ser Pro Gln Pro Glu Tyr Val Asn Gln Pro
    1130            1135            1140
Asp Val Arg Pro Gln Pro Pro Ser Pro Arg Glu Gly Pro Leu Pro
    1145            1150            1155
Ala Ala Arg Pro Ala Gly Ala Thr Leu Glu Arg Pro Lys Thr Leu
    1160            1165            1170
Ser Pro Gly Lys Asn Gly Val Val Lys Asp Val Phe Ala Phe Gly
    1175            1180            1185
Gly Ala Val Glu Asn Pro Glu Tyr Leu Thr Pro Gln Gly Gly Ala
    1190            1195            1200
Ala Pro Gln Pro His Pro Pro Ala Phe Ser Pro Ala Phe Asp
    1205            1210            1215
Asn Leu Tyr Tyr Trp Asp Gln Asp Pro Pro Glu Arg Gly Ala Pro
    1220            1225            1230
```

```
Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 17
<211> LENGTH: 117
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly His Gly Tyr Phe Asp Leu Trp Gly Arg Gly Thr Leu
            100                 105                 110

Val Thr Val Ser Ser
        115

<210> SEQ ID NO 18
<211> LENGTH: 329
<212> TYPE: PRT
<213> ORGANISM: Homo sapiens

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 446
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly His Gly Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
```

```
            210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 20
<211> LENGTH: 9
<212> TYPE: PRT
<213> ORGANISM: Homo sapiens

<400> SEQUENCE: 20

Phe Thr Phe Ser Ser Tyr Ser Met Asn
1               5

<210> SEQ ID NO 21
<211> LENGTH: 17
<212> TYPE: PRT
<213> ORGANISM: Homo sapiens

<400> SEQUENCE: 21

Tyr Ile Ser Ser Ser Ser Ser Thr Ile Tyr Tyr Ala Asp Ser Val Lys
1               5                   10                  15

Gly

<210> SEQ ID NO 22
<211> LENGTH: 8
<212> TYPE: PRT
<213> ORGANISM: Homo sapiens

<400> SEQUENCE: 22

Gly Gly His Gly Tyr Phe Asp Leu
1               5
```

<210> SEQ ID NO 23
<211> LENGTH: 351
<212> TYPE: DNA
<213> ORGANISM: Homo sapiens

<400> SEQUENCE: 23
gaggtgcagc tggtggagtc tgggggaggc ttggtacagc ctggggggtc cctgagactc        60
tcctgtgcag cctctggatt caccttcagt agctatagca tgaactgggt ccgccaggct       120
ccagggaagg ggctggagtg ggtttcatac attagtagta gtagtagtac catatactac       180
gcagactctg tgaagggccg attcaccatc tccagagaca tgccaagaa ctcactgtat        240 ctgcaaatga acagcctgag agctgaggac acggcggtgt actactgcgc cagaggtgga       300
cacggatatt tcgacctatg ggggagaggt accttggtca ccgtctcctc a                351

<210> SEQ ID NO 24
<211> LENGTH: 108
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys
            100                 105

<210> SEQ ID NO 25
<211> LENGTH: 106
<212> TYPE: PRT
<213> ORGANISM: Homo sapiens

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

```
<210> SEQ ID NO 26
<211> LENGTH: 215
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 12
<212> TYPE: PRT
<213> ORGANISM: Homo sapiens

<400> SEQUENCE: 27

Arg Ala Ser Gln Ser Val Ser Ser Ser Tyr Leu Ala
1               5                   10

<210> SEQ ID NO 28
<211> LENGTH: 7
<212> TYPE: PRT
<213> ORGANISM: Homo sapiens

<400> SEQUENCE: 28

Gly Ala Ser Ser Arg Ala Thr
1               5

<210> SEQ ID NO 29
<211> LENGTH: 9
<212> TYPE: PRT
<213> ORGANISM: Homo sapiens

<400> SEQUENCE: 29
```

Gln Gln Tyr His His Ser Pro Leu Thr
1               5

<210> SEQ ID NO 30
<211> LENGTH: 324
<212> TYPE: DNA
<213> ORGANISM: Homo sapiens

<400> SEQUENCE: 30
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtaccacc acagtcctct cacttttggc   300
ggagggacca aggttgagat caaa                                          324

<210> SEQ ID NO 31
<211> LENGTH: 630
<212> TYPE: PRT
<213> ORGANISM: Homo sapiens

<400> SEQUENCE: 31

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

-continued

```
Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
        290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
        370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
        450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
        530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
        610                 615                 620

Arg Ala Ser Pro Leu Thr
625                 630
```